United States Patent
Genovese et al.

(10) Patent No.: US 11,708,587 B2
(45) Date of Patent: *Jul. 25, 2023

(54) COMPOSITIONS AND METHODS FOR INCREASING THE EFFICIENCY OF CELL CULTURES USED FOR FOOD PRODUCTION

(71) Applicant: Upside Foods, Inc., Berkeley, CA (US)

(72) Inventors: Nicholas J. Genovese, Hayward, CA (US); Eric N. Schulze, San Francisco, CA (US); Danielle Nicole Desmet, Berkeley, CA (US)

(73) Assignee: UPSIDE FOODS, INC., Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/929,646

(22) Filed: Sep. 2, 2022

(65) Prior Publication Data

US 2023/0002789 A1    Jan. 5, 2023

Related U.S. Application Data

(63) Continuation of application No. 16/630,404, filed as application No. PCT/US2018/042187 on Jul. 13, 2018, now Pat. No. 11,479,792.

(60) Provisional application No. 62/532,345, filed on Jul. 13, 2017.

(51) Int. Cl.
| | |
|---|---|
| A23L 35/00 | (2016.01) |
| C12N 15/87 | (2006.01) |
| C07K 14/65 | (2006.01) |
| C07K 14/76 | (2006.01) |
| C12N 5/071 | (2010.01) |
| C12N 9/12 | (2006.01) |
| C12N 9/00 | (2006.01) |

(52) U.S. Cl.
CPC .............. *C12N 15/87* (2013.01); *C07K 14/65* (2013.01); *C07K 14/76* (2013.01); *C12N 5/0602* (2013.01); *C12N 9/1276* (2013.01); *C12N 9/93* (2013.01); *A23L 35/00* (2016.08); *C12N 2501/60* (2013.01); *C12Y 603/01002* (2013.01)

(58) Field of Classification Search
CPC ........ C07K 14/65; C07K 14/76; C12N 15/87; A23L 35/00
See application file for complete search history.

(56) References Cited

U.S. PATENT DOCUMENTS

| | | | |
|---|---|---|---|
| 5,624,840 | A | 4/1997 | Naughton et al. |
| 6,593,275 | B1 | 7/2003 | Unkefer et al. |
| 6,767,719 | B1 | 7/2004 | Morin et al. |
| 6,835,390 | B1 | 12/2004 | Vein |
| 7,033,744 | B2 | 4/2006 | Kobayashi et al. |
| 7,147,871 | B2 | 12/2006 | Harbin et al. |
| 7,270,829 | B2 | 9/2007 | Van Eelen |
| 8,105,575 | B2 | 1/2012 | Kim et al. |
| 8,703,216 | B2 | 4/2014 | Forgacs et al. |
| 8,883,502 | B2 | 11/2014 | Zhang et al. |
| 9,102,739 | B2 | 8/2015 | Lazar et al. |
| 11,479,792 | B2 * | 10/2022 | Genovese .............. C07K 14/76 |
| 2002/0068706 | A1 | 6/2002 | Gyuris et al. |
| 2005/0260748 | A1 | 11/2005 | Chang et al. |
| 2006/0121006 | A1 | 6/2006 | Chancellor et al. |
| 2007/0248716 | A1 | 10/2007 | Kruse et al. |
| 2010/0319079 | A1 | 12/2010 | Kruse et al. |
| 2011/0091604 | A1 | 4/2011 | Miller |
| 2011/0191871 | A1 | 8/2011 | Walsh et al. |
| 2011/0225664 | A1 | 9/2011 | Smith |
| 2011/0301249 | A1 | 12/2011 | Challakere |
| 2013/0004466 | A1 | 1/2013 | Tremblay et al. |
| 2013/0029008 | A1 | 1/2013 | Forgacs et al. |
| 2013/0171731 | A1 | 7/2013 | Ivashchenko et al. |
| 2013/0224855 | A1 | 8/2013 | Gupta et al. |
| 2013/0255003 | A1 | 10/2013 | Forgacs et al. |
| 2014/0093618 | A1 | 4/2014 | Forgacs et al. |
| 2014/0242155 | A1 | 8/2014 | Ramunas et al. |
| 2014/0370537 | A1 | 12/2014 | Sakurai et al. |
| 2015/0025128 | A1 | 1/2015 | Cain et al. |
| 2015/0079238 | A1 | 3/2015 | Marga et al. |
| 2015/0087532 | A1 | 3/2015 | Brown et al. |
| 2015/0133520 | A1 | 5/2015 | Czech et al. |
| 2015/0216216 | A1 | 8/2015 | Marga |
| 2015/0231209 | A1 | 8/2015 | Hsueh et al. |
| 2015/0289541 | A1 | 10/2015 | Brown et al. |
| 2015/0296834 | A1 | 10/2015 | Geistlinger |
| 2015/0296835 | A1 | 10/2015 | Anderson et al. |
| 2015/0305361 | A1 | 10/2015 | Holz-Schietinger et al. |

(Continued)

FOREIGN PATENT DOCUMENTS

| | | |
|---|---|---|
| CA | 2333966 C | 12/1999 |
| CA | 2780087 A1 | 12/2012 |

(Continued)

OTHER PUBLICATIONS

Good Food Institute. Downloaded Oct. 25, 2022; Deep dive: Cultivated meat cell lines. On the web at gfi.org/science/the-science-of-cultivated-meat/deep-dive-cultivated-meat-cell-lines/. pp. 1-13.*
Li. 2021; Cultured meat: Growing meat in the lab. Berkley Scientific Journal. Fall 2021; pp. 67-70.*
ADDGENE. "pBABE-hygro-hTERT." Plasmid #1773, Dec. 1998, 6 pages, [Online] [Retrieved Dec. 3, 2020], Retrieved from the Internet <UR: https://www.addgene.org/1773/>.
ADDGENE. "pBABE-neo-hTERT." Plasmid #1774, Dec. 1998, 5 pages, [Online] [Retrieved Dec. 4, 2020], Retrieved from the Internet <URL: https://www.addgene.org/1774/>.

(Continued)

*Primary Examiner* — Karen Cochrane Carlson
(74) *Attorney, Agent, or Firm* — Fenwick & West LLP

(57) ABSTRACT

Provided herein are compositions and methods to make and use engineered cells, for the purpose of increasing the cell density of a culture comprising metazoan cells and for the production of a cultured edible product.

17 Claims, 12 Drawing Sheets

Specification includes a Sequence Listing.

(56) References Cited

U.S. PATENT DOCUMENTS

| | | |
|---|---|---|
| 2015/0305390 A1 | 10/2015 | Vrljic et al. |
| 2016/0227830 A1 | 8/2016 | Genovese et al. |
| 2016/0251625 A1 | 9/2016 | Genovese et al. |
| 2017/0101629 A1 | 4/2017 | Minshull et al. |
| 2017/0114382 A1 | 4/2017 | Follit et al. |
| 2017/0369849 A1 | 12/2017 | Hanson et al. |
| 2019/0024079 A1 | 1/2019 | Genovese et al. |
| 2020/0190524 A1 | 6/2020 | Minshull et al. |
| 2021/0106032 A1 | 4/2021 | Leung et al. |
| 2021/0145031 A1 | 5/2021 | Leung et al. |

FOREIGN PATENT DOCUMENTS

| | | |
|---|---|---|
| CN | 1942576 A | 4/2007 |
| CN | 101624570 A | 1/2010 |
| EP | 0435617 A1 | 7/1991 |
| EP | 1037966 B1 | 5/2003 |
| JP | 2013-81783 | 5/2013 |
| WO | WO 1993/009236 A1 | 5/1993 |
| WO | WO 1999/031222 A1 | 6/1999 |
| WO | WO 1999/031223 A1 | 6/1999 |
| WO | WO 2006/041429 A2 | 4/2006 |
| WO | WO 2007/071339 A1 | 6/2007 |
| WO | WO 2010/068897 A2 | 6/2010 |
| WO | WO 2012/095514 A1 | 7/2012 |
| WO | WO 2012/170995 A2 | 12/2012 |
| WO | WO 2012/176023 A1 | 12/2012 |
| WO | WO 2013/007656 A1 | 1/2013 |
| WO | WO 2013/016547 A2 | 1/2013 |
| WO | WO 2013/073246 A1 | 5/2013 |
| WO | WO 2015/038988 A1 | 3/2015 |
| WO | WO 2015/066377 A1 | 5/2015 |
| WO | WO 2015/120174 A1 | 8/2015 |
| WO | WO 2015/167959 A1 | 11/2015 |
| WO | WO 2016/052472 A1 | 4/2016 |
| WO | WO 2017/019125 A1 | 2/2017 |
| WO | WO 2017/120089 A1 | 7/2017 |
| WO | WO 2017/124100 A1 | 7/2017 |
| WO | WO 2018/208628 A1 | 11/2018 |
| WO | WO 2019/014652 A1 | 1/2019 |

OTHER PUBLICATIONS

Albini, S. et al., "Epigenetic Reprogramming of Human Embryonic Stem Cells into Skeletal Muscle Cells and Generation of Contractile Mvospheres," Cell Reports 3:661-670 (2013).

Animal Sake Farm Animals List, downloaded May 24, 2022; on the web at animalsake.com/farm-animals-list. pp. 1-10.

Baquero-Perez et al., "A Simplified but Robust Method for the Isolation of Avian and Mammalian Satellite cells," BMC Cell Biology 13(16): Jan. 2011-Nov. 2011 (2012).

Barberi, T., et al., "Derivation of engraftable skeletal myoblasts from human embryonic stem cells," Nature Medicine 13(5):642-648(2007).

Barnes, et al., Advances in animal cell recombinant protein production: GS-NSO expression system, Cytotechnology 2000, vol. 32, pp. 109-123.

Bartholet, J., "Inside the Meat Lab a Handful of Scientists Aim to Satisfy the World's Growing Appetite for Steak Without Wrecking The Planet. The First Step: Grab a Petri Dish," Scientific American, pp. 65-69 (2011).

Bell et al., "Understanding TERT Promoter Mutations: A Common Path to Immortality," Mol Cancer Res 14:315-323 (2016). Published Online First Mar. 3, 2016, retrieved Jul. 6, 2017, from mcr.aacrjournals.org, 10 pages.

Benjaminson, M., et al., "In Vitro Edible Muscle Protein Production System (MPPS): Stage 1, FISH," Acta Astronautica 51 (12):879-889 (2002).

Bentzinger, C., et al., "Building Muscle: Molecular Regulation of Myogenesism," Cold Spring Harb Perspect Biol 4(2): 1-16 (2012).

Bhagavati and Xu., "Generation of Skeletal Muscle from Transplanted Embryonic Stem Cells in Dystrophic Mice," Biochemical and Biophysical Research Communications 333:644-649 (2005).

Bhat and Bhat, "Animal-Free Meat Biofabrication," American Journal of Food Technology 6(6):441-459, (2011).

Bhat, Z.F. et al., "Prospectus of cultured meat—Advancing meat alternatives," Journal of Food Science and Technology 48(2), Apr. 2010, pp. 125-140.

Black, Brian L., and Eric N. Olson. "Transcriptional control of muscle development by myocyte enhancer factor-2 (MEF2) proteins" Annual review of cell and developmental biology 14.1 (1998): 167-196.

Blomberg et al. Twenty years of embryonic stem cell research in farm animals. Reproduction in Domestic Animals, vol. 47, Suppl. 4, pp. 80-85, Aug. 2012.

Boonen and Post, "The Muscle Stem Cell Niche: Regulation of Satellite Cells During Regeneration," Tissue Engineering—Part B: Reviews 14(4):419-431 (2008).

Canizo et al., "Exogenous human OKSM factors maintain pluripotency gene expression of bovine and porcine iPS-like cells obtained with STEMCCA delivery system," BMC Research Notes vol. 11, Article No. 509, Jul. 2018, 8 pages.

Cenciarelli et al., "Critical Role Played by Cyclin D3 in the Myod-Mediated Arrest of Cell Cycle During Myoblast Differentiation," Molecular and Cellular Biology 19(7):5203-5217 (1999).

Chang, et al., "Generation of Transplantable, Functional Satellite-Like Cells from Mouse Embryonic Stem Cells," Faseb J. 23, 1907-1919 (2009).

Chen et al. DNA methyltransferase inhibitor CDA-11 inhibits myogenic differentiation. Biochemical and Biophysical Research Communications, vol. 422, pp. 522-526, May 22, 2012.

Chen et al., "Potentiation of MyoD1 Activity By 5-Aza-2'-Deoxycytidine," Cell Growth & Differentiation, 1:383-392 (1990).

Chen, et al., Homeostatic control of Hippo signaling activity revealed by an endogenous activating mutation in YAP, Genes & Development, 29, Jun. 2015, 1285-1297.

Chiu and Blau,"5-5Azacytidine Permits Gene Activation in a Previously Noninducible Cell Type," Cell, vol. 40, 417-424 (1985).

Choi, Sang-Woon, and Simonetta Friso. "Epigenetics: a new bridge between nutrition and health" Advances in nutrition 1.1 (2010): 8-16.

Cox et al., "Yap reprograms glutamine metabolism to increase nucleotide biosynthesis and enable liver growth," Nat. Cell. Biol. 18(8), Jan. 18, 2017, pp. 886-896.

Darabi, R., et al., "Perspective Lineage-Specific Reprogramming as a Strategy for Cell Therapy," Cell Cycle 7(12):1732-1737 (2008).

Darabi, R., et al., "Assessment of the Myogenic Stem Cell Compartment Following Transplantation of Pax3/Pax7-lnduced Embryonic Stem Cell-Derived Progenitors," Lillehei Heart Institute, Department of Medicine, University of Minnesota, Minneapolis, MN, USA, 27 pages (2011).

Darabi, R., et al., Functional Skeletal Muscle Regeneration from Differentiating Embryonic Stem Cells, Nature and Medicine 14(2):134-143 (2008).

Datar and Betti, "Possibilities for an In Vitro Meat Production System," Innovative Food Science & Emerging Technologies 11(1):13-22(2010).

Davis, R., et al., "Expression of a Single Transfected cDNA Converts Fibmblasts to Myoblasts," Cell, vol. 51. 987-1000 (1987).

Dekel, I., et al., "Conditional Conversion of ES Cells to Skeletal Muscle by an Exogenous MyoDI Gene," (1992).

Delany, M. E. et al. "Telomeres in the Chicken: Genome Stability and Chromosome Ends." Poultry Science, vol. 82, No. 6, Jun. 1, 2003, pp. 917-926.

Desbois-Mouthon, Christele, et al. "Insulin and IGF-1 stimulate the.beta.-catenin pathway through two signalling cascades involving GSK-3.beta, inhibition and Ras activation" Oncogene 20.2 (2001): 252-259.

Ding, Vanessa MY, et al. "FGF-2 modulates Wnt signaling in undifferentiated hESC and iPS cells through activated PI3-K/GSK3. beta. signaling" Journal of cellular physiology 225.2 (2010): 417-428.

(56) References Cited

OTHER PUBLICATIONS

Dominguez et al., "Beyond editing: repurposing CRISPR-Cas9 for precision genome regulation and interrogation," Nature Reviews Molecular Cell Biology 17:5-15, Dec. 16, 2015.
Dong, J. et al. "Elucidation of a Universal Size-Control Mechanism in Drosophila and Mammals," Cell, vol. 130, No. 6, pp. 1120-1133, Sep. 21, 2007.
Edelman, P., et al., "In Vitro-Cultured Meat Production," Tissue Engineering 11 (5/6):659-662 (2005).
European Patent Office, Extended European Search Report and Opinion, EP Patent Application No. 18797874.7, dated May 21, 2021, 15 pages.
European Patent Office, Extended European Search Report and Opinion, EP Patent Application No. 18832585.6, dated Apr. 9, 2021, nine pages.
Extended European Search Report dated May 19, 2017, from the European patent Office for Application No. 14858383.4, filed Oct. 30, 2014, 10 pages.
Fan, L. et al., "The use of glutamine synthetase as a selection marker: recent advances in Chinese hamster ovary cell line generation processes," Pharmaceutical Bioprocessing 1(15), 2013, pp. 487-502.
Final Office Action dated Jul. 13, 2017, from The United States Patent and Trademark Office for U.S. Appl. No. 15/134,252, filed Apr. 30, 2016, 28 pages.
Final Office Action dated Nov. 27, 2018, from The United States Patent and Trademark Office for U.S. Appl. No. 15/134,252, filed Apr. 30, 2016, 24 pages.
Garrels et al. Ectopic expression of human telomerase KNA component results 1n increased telomerase activity and elongated telomeres in bovine blastocysts. Biol Reprod. 2012, 87(4):95, 1-7.
GENBANK. "Bos Taurus Cyclin-Dependent Kinase 4, mRNA (cDNA Clone MGC:133903 IMAGE:8041087), Complete CDS." NCBI, GenBank: BC109858.1, Nov. 2005, 2 pages, [Online] [Retrieved Dec. 7, 2020], Retrieved from the Internet <URL:https://www.ncbi.nlm.nih.gov/nuccore/BC109858>.
GENBANK. "Gallus Gallus Gallus Telomerase Reverse Transcriptase (IbRT) mRNA, Complete CDS." GenBank: NCBI, AY502592.1,2004, 3 pages, [Online] [Retrieved Dec. 7, 2020], Retrieved from the Internet <URL:https://www.ncbi.nlm.nih.gov/nuccore/AY502592>.
Genovese et al., "Enhanced Development of Skeletal Myotubes from Porcine Induced Pluripotent Stem Cells," Scientific Reports, vol. 7, Feb. 6, 2017, 12 pages.
George et al. "Exploiting Expression of Hippo Effector, Yap, for Expansion of Functional Islet Mass," Molecular Endocrinology. Sep. 2015, vol. 29, Iss. 11, pp. 1594-1607.
Gianakopoulos, P., et al., "MyoD Directly Up-regulates Premyogenic Mesoderm Factors during Induction of Skeletal Myogenesis in Stem Cells," The Journal of Biological Chemistry 286(4):2517-2525 (2011).
Goudenege, S., et al., "Myoblasts Derived From Normal hESCs and Dystrophic hiPSCs Efficiently Fuse With Existing Muscle Fibers Following Transplantation," Molecular Therapy 20(11):2153-2167 Nov. 2012 (2012).
Hanas et al. Potentiation of myogenesis by 5-azacytidine. Journal of Cell Biology, vol. 91, No. 2, p. 27, Abstract 1051, Nov. 1981.
Harley, "Telomerase is not an oncogene," Oncogene 2002, 21(4):494-502.
He Rong et al., "Expression and clinical significance of p15 protein, mRNA in nasopharyngeal carcinoma," Chinese Journal of Laboratory Diagnosis, vol. 13, No. 5, Jun. 19, 2009, pp. 618-622, (with English abstract).
Hollenberg, S., et al., "Use of a conditional MyoD transcription factor in studies of MyoD trans- activation and muscle determination," Proc. Natl. Acad. Sci. USA vol. 90, pp. 8028-8032 (1993).
Hopkins and Dacey, "Vegetarian meat: Could Technology Save Animals and Satisfy Meat Eaters?" Journal of Agricultural and Environmental Ethics 21(6):579-596 (2008).

Hu, Yang "Exercise molecule biology," Beijing Sport University press, pp. 152-157 (2013) (with the English translation of paragraph 2 on p. 152 to paragraph 1 on p. 157).
Huang et al. "Zfp423 Promotes Adipogenic Differentiation of Bovine Stromal Vascular Cells," PLOS ONE, Oct. 2012, vol. 7, Issue 10, 10 pages.
Hupkes et al. Epigenetics: DNA demethylation promotes skeletal myyotube maturation. The FASEB Journal, vol. 25, No. 11, pp. 3861-3872, Nov. 2011.
Hupkes, Marlinda, et al. "DNA methylation restricts spontaneous multi-lineage differentiation of mesenchymal progenitor cells, but is stable during growth factor-induced terminal differentiation" Biochimica et Biophysica Acta (BBA)-Molecular Cell Research 1813.5 (2011): 839-849.
Hwang, Y., et al., "Directed In Vitro Myogenesis of Human Embryonic Stem Cells and Their In Vivo Engraftment," PLOS ONE e72023 8(8):1-10 (2013).
Iacovino, M., et al., "Inducible Cassette Exchange: A Rapid and Efficient System Enabling Conditional Gene Expression in Embryonic Stem and Primary Cells," Stem Cells 2011;29:1580-1587 (2011).
Iemata, M., et al., "Suppression by Glutamate of Proliferative Activity Through Glutathione Depletion Mediated by the Cystine/Glutamate Anti porter in Mesenchymal C3H10T1/2 Stem Cells," Journal of Cellular Physiology 213:721-729 (2007).
International Preliminary Report on Patentability in corresponding PCT Application No. PCT/US2014/063250, dated May 3, 2016.
International Search Report and Written Opinion issued by The International Searching Authority for Application No. PCT/US14/63250, dated Jan. 21, 2015, 9 pages.
International Search Report and Written Opinion issued by the International Searching Authority for Application No. PCT/US2017/13782, dated Apr. 10, 2017, 7 pages.
International Search Report and Written Opinion issued by The International Searching Authority for Application No. PCT/US2018/031276, dated Sep. 10, 2018, 10 pages.
International Search Report and Written Opinion issued by the International Searching Authority for Application No. PCT/US2018/042187, dated Nov. 1, 2018, 15 pages.
Jesus et al., "The telomerase activator TA-65 elongates short telomeres and increases health span of adult/old mice without increasing cancer incidence," Aging Cell 10:604-621 (2011).
Jones, N., "A Taste of Things to Come?" Nature 468:752-753 (2010).
Kadim, I.T. et al., "Cultured meat from muscle stem cells: A review of challenges and prospects," Journal of Integrative Agriculture 14(2), Feb. 2015, pp. 222-233.
Kanzaki et al. 2002; Telomerase rescues the expression levels of keratinocyte growth factor and insulin-like growth factor-II in senescent human fibroblasts. Environmental Cell Research. 279: 321-329.
Knox et al., "A streamlined implementation of the glutamine synthetase-based protein expression system," BMC Biotechnol. Sep. 24, 2013;13:74, 10 pages.
Kucharczak, J. et al., "R-Cadherin Expression Inhibits Myogenesis and Induces Myoblast Transformation via Rac1 GTPase," Cancer Research, vol. 68, No. 16, Aug. 15, 2008, pp. 6559-6568.
Langelaan, et al., "Meet The New Meat: Tissue Engineered Skeletal Muscle," Trends in Food Science & Technology 21(2):59-66 (2010).
Lassar, A., et al., "Transfection of a DNA Locus That Mediates the Conversion of IOTV2 Fibroblasts to Myoblasts," Cell 47:649-656 (1986).
Lavial et al., "Chicken Embryonic Stem Cells as a Non-Mammalian Embryonic Stem Cell Model," Development, Growth & Differentiation 52:101-1114 (2010).
Lee et al. "Establishment of an immortal chicken embryo liver-derived cell line," 2013 Poultry Science, vol. 92, No. 6, 9 pages.
Lei, et al., TAZ promotes cell proliferation and epithelial-mesenchymal transition and is inhibited by the hippo pathway, Molecular and Cellular Biology, 28(7): 2426-2436. (Year: 2008).
Leung, M., et al., "Nanofiber-Based in Vitro System for High Myogenic Differentiation of Human Embryonic Stem Cells," Biomacromolecules 14:4207-4216 (2013).

(56) References Cited

OTHER PUBLICATIONS

Li et al., "Short-Term Serum-Free Culture Reveals That Inhibition of Gsk3beta Induces the Tumor-Like Growth of Mouse Embryonic Stem Cells," 6(6):Jan. 10-Oct. 10 (2011).

Lian et al., Directed Cardiomyocyte Differentiation From Human Pluripotent Stem Cells by Modulating WnVBeta-Catenin Signaling Under Fully Defined Conditions. Nature Protocols, 8(1 ): 162-175 (2013).

Liu et al., "Linking Telomere Regulation to Stem Cell Pluripotency," Trends in Genetics 33(1), Jan. 2017, 16-33.

Maak et al., "Identification and Analysis of Putative Regulatory Sequences for the MYF5/MYF6 Locus in Different Vertebrate Species," Gene, 379: 141-147 (2006).

Mahmood, A., Enhanced Differentiation of Human Embryonic Stem Cells to Mesenchymal Progenitors by Inhibition of TGF-beta/Activin/Nodal Signaling Using SB-431542 Journal of Bone and Mineral Research 25(6):1216-1233 (2010).

Mannaerts et al. The Hippo pathway effector YAP controls mouse hepatic stellate cell activation, Journal of Hepatology, 63, Sep. 2015, 679-688.

McFarlane et al., "Myostatin Signals Through Pax? To Regulate Satellite Cell Self-Renewal," Experimental Cell Research 314:317-329 (2008), available online Sep. 2007.

McKinnon, T et al., "Kras activation in p53-deficient myoblasts results in high-grade sarcoma formation with impaired myogenic differentiation," Oncotarget, vol. 6, No. 16, Jun. 10, 2015, pp. 14220-14232.

Minniti, C.P. et al., "Insulin-like growth factor II overexpression in myoblasts induces phenotypic changes typical of the malignant phenotype," Cell Growth & Differentiation, vol. 6, Mar. 1995, pp. 263-269.

Minzuno, Y., et al., "Generation of Skeletal Muscle Stem/Progenitor Cells from Murine Induced Pluripotent Stem Cells," The FASEB Journal 24:2245-2243 (2010).

Miranda, A.F. et al., "Transformation of human skeletal muscle cells by simian virus 40," PNAS, vol. 80, Nov. 1983, pp. 6581-6585.

Molkentin et al. Cooperative activation of muscle gene expression by MEF2 and myogenic bHLH proteins. Cell, vol. 83, pp. 1125-1136, Dec. 1995.

Munro, et al. Histone deacetylase inhibitors induce a senescence-like state in human cells by a p16-dependent mechanism that is independent of a mitotic clock. Exp Cell Res. 2004 295(2):525-538.

Nagashima et al., "The Hippo Pathway as Drug Targets in Cancer Therapy and Regenerative Medicine," Current Drug Targets, vol. 18, Mar. 2017, pp. 447-454.

Nguyen, H.T. et al., "Viral Small T Oncoproteins Transform Cells by Alleviating Hippo-Pathway-Mediated Inhibition of the YAP Proto-oncogene," Cell Reports, vol. 8, No. 3, Aug. 7, 2014, pp. 707-713.

Noh et al., "Reduction of ammonia and lactate through the coupling of glutamine synthetase selection and downregulation of lactate dehydrogenase-A in CHO cells," Appl Microbial Biotechnol. Feb. 2017; 101(3): 1035-1045.

Non-Final Office Action dated Dec. 13, 2016, from The United States Patent and Trademark Office for U.S. Appl. No. 15/134,252, filed Apr. 30, 2016, 28 pages.

Non-Final Office Action dated Mar. 12, 2018, from The United States Patent and Trademark Office for U.S. Appl. No. 15/134,252, filed Apr. 20, 2016, 28 pages.

Nowak-Lmialek et al. Pluripotent cells in farm animals: state of the art and future perspectives. Reproduction, Fertility and Development, vol. 25, No. 1, pp. 103-108, 2012. (Year: 2012).

Overholtzer, M. et al., "Transforming properties of YAP, a candidate oncogene on the chromosome 11a22 amplicon," PNAS, vol. 103, No. 33, Aug. 15, 2006, pp. 12405-12410.

Ozasa et al., "Efficient Conversion Of ES Cells into Myogenic Lineage Using the Gene-Inducible System," Biochemical and Biophysical Research Communications 357: 957-963 (2007).

Pandurangan, et al. A novel approach for in vitro meat production. Appl Microbial Biotechnol. Jul. 2015; 99(13):5391-5395. doi: 10.1007/s00253-015-6671-5. Epub May 14, 2015.

Paredes, C. et al., "Modification of glucose and glutamine metabolism in hybrid om a cells through metabolic engineering," Cytotechnology, vol. 30, Jul. 1999, pp. 85-93.

Park et al. "Generation of porcine induced pluripotent stem cells and evaluation of their major histocompatibility complex protein expression in vitro." Veterinary Research Communications, vol. 37, No. 4, pp. 293-301, Dec. 2013, published online Aug. 23, 2013. (Year: 2013).

Poon et al., The sterile 20-like kinase Tao-1 controls tissue growth by regulating the Salvador-Warts-Hippo pathway, Developmental Cell, 21, Nov. 15, 2011, pp. 896-906.

Post, M., "Cultured beef: Medical Technology to Produce Food," Journal of the Science of Food and Agriculture 94(6), Apr. 2014, pp. 1039-1041.

Post, M., "Cultured Meat from Stem Cells: Challenges and Prospects," Meat Sci. 92(3), Nov. 2012, pp. 297-301.

Rao, L., et al., "Highly Efficient Derivation of Skeletal Myotubes from Human Embryonic Stem Cells," Stem Cell Rev and Rep 8:1109-1119 (2012).

Rezanejad et al., Induced pluripotent stem cells: Progress and future perspectives in the stem cell world. Cellular Reprogramming 14(6), Dec. 2012, pp. 459-470.

Rinkevich, B. Cell cultures from marine invertebrates: New insights for capturing endless sternness. Marine Biotechnology (New York, N.Y.), vol. 13, No. 3, pp. 345-354, Jun. 2011, Epub Jan. 7, 2011.

Rohwedel, J., et al., "Muscle Cell Differentiation of Embryonic Stem Cells Reflects Myogenesis in Vivo Developmentally Regulated Expression of Myogenic Determination Genes and Functional Expression of Ionic Currents.," Dev Biol. 164(1):87-101 (1994). (Abstract).

Rommel, C., "Mediation of IGF-1-Induced Skeletal Myotube Hypertrophy by PI(3)K/AkVmTOR and PI(3)K/AkVGSK3 Pathways," Nature Cell Biology 3:1009-1013 (2001).

Ryan, T., "Retinoic Acid Enhances Skeletal Myogenesis in Human Embryonic Stem Cells by Expanding the Premyogenic Progenitor Population," Stem Cell Rev and Rep 8, Jun. 2012, pp. 482-493.

Sakurai, H., et al., "Bidirectional Induction Toward Paraxial Mesodermal Derivatives from Mouse ES Cells in Chemically Defined Medium," Stem Cell Research 3:157-169 (2009).

Sakurai, H., et al., "Paraxial Mesodermal Progenitors Derived from Mouse Embryonic Stem Cells Contribute to Muscle Regeneration via Differentiation into Muscle Satellite Cells," Stem Cells 26:1865-1873 (2008).

Salani, S., et al., "Generation of Skeletal Muscle Cells from Embryonic and Induced Pluripotent Stem Cells as an in Vitro Model and for Therapy of Muscular Dystrophies," J. Cell. Mol. Med. 16(7), Jul. 2012, pp. 1353-1364.

Sasaki, T., et al., "Generation of a Multi-Layer Muscle Fiber Sheet from Mouse ES Cells by the Spermine Action at Specific Timing and Concentration," Differentiation 76, Dec. 2008, pp. 1023-1030.

Schnapp, Esther, et al. "Induced early expression of mrf4 but not myog rescues myogenesis in the myod/myf5 double-morphant zebrafish embryo" Journal of Cell Science 122.4, Feb. 15, 2009, pp. 481-488.

Schutte, U. et al., "Hippo Signaling Mediates Proliferation, Invasiveness, and Metastatic Potential of Clear Cell Renal Cell Carcinoma," Translational Oncology, vol. 7, Iss. 2, Apr. 2014, pp. 309-321.

Sharpless, et al. Forging a signature of in vivo senescence. Nature Reviews Cancer, Jul. 2015, 15(7):397-408.

Stadler, G. et al. "Establishment of Clonal Myogenic Cell Lines from Severely Affected Dystrophic Muscles—CDK4 Maintains the Myogenic Population." Skeletal Muscle, vol. 1, Article 12, Mar. 2011, pp. 1-10.

Tako, E. et al. "Using the Domestic Chicken (Gallus gallus) as an in Vivo Model for Iron Bioavailability." Poultry Science, vol. 89, No. 3, Mar. 1, 2010, pp. 514-521.

Tan et al., "Efficient Derivation of Lateral Plate and Paraxial Mseoderm Subtypes From Human Embryonic Stem Cells Through GS Kimediated Differentiation," Stem Cells and Development 22(13), Jul. 2013, pp. 1893-1906.

(56) References Cited

OTHER PUBLICATIONS

Tanaka, et al., "Efficient and Reproducible Myogenic Differentiation from Human iPS Cells: Prospects for Modeling Miyoshi Myopathy In Vitro," PLOS ONE e61540 8(4), Apr. 23, 2013, pp. 1-14.

Taylor et al. "Multiple new phenotypes induced in 10T 1/2 and 3T3 cells treated with 5-azacytidine," Cell 17:771-779 (1979).

Telugu, B., et al., "Leukemia Inhibitory Factor (LIF)-dependent, Pluripotent Stem Cells Established from Inner Cell Mass of Porcine Embryos," Journal of Biological Chemistry, Aug. 2011, 286(33):28948-28953.

Telugu, B., et al., "Lit-Dependent, Pluripotent Stem Cells Established from Inner Cell Mass of Porcine Embryos," The American Society for Biochemistry and Molecular Biology, Inc., Downloaded from www.jbc.org at University of Missouri-Columbia, on Jul. 15, 2011.

Tseng et al. The GSK-3 inhibitor BIO promotes proliferation in mammalian cardiomyocytes. Chemistry & Biology, vol. 13, pp. 957-963, Sep. 2006.

Tuomisto, et al., "Environmental Impacts of Cultured Meat Production," Environ. Sci. Technol. 45(14):6117-6123 (2011).

United States Office Action, U.S. Appl. No. 15/134,252, dated Dec. 13, 2016, 31 pages.

United States Office Action, U.S. Appl. No. 15/134,252, dated Jul. 13, 2017, 43 pages.

United States Office Action, U.S. Appl. No. 15/134,252, dated Mar. 12, 2018, 28 pages.

United States Office Action, U.S. Appl. No. 15/134,252, dated Mar. 3, 2020, 18 pages.

United States Office Action, U.S. Appl. No. 15/134,252, dated Nov. 27, 2018, 21 pages.

United States Office Action, U.S. Appl. No. 16/070,251, dated Jan. 8, 2021, 31 pages.

United States Office Action, U.S. Appl. No. 16/070,251, dated Jul. 9, 2021, 21 pages.

Van Der Schaft, D., et al., "Engineering Skeletal Muscle Tissues from Murine Myoblast Progenitor Cells and Application of Electrical Stimulation," J. Vis. Exp. 73:1-6 (Mar. 2013).

Van Der Velden, J., et al., "Inhibition of Glycogen Synthase Kinase-3beta-activity is Sufficient to Stimulate Myogenic Differentiation," Am J Physiol Cell Physiol 290: C453-C462, (2006).

Van Der Weele et al. Cultured meat: every village its own factory?, Trends in Biotechnology, Jun. 2014, vol. 32, No. 6, 3 pages.

Van Der Weele, C., "In Vitro Meat," Encyclopedia of Food and Agricultural Ethics, Oct. 2014, pp. 1-8.

Van Der Weele, C., "In Vitro Meat: Promises and Responses: Cooperation Between Science, Social Research and Ethics," Global Food Security: Ethical and Legal Challenges: EurSafe 2010 Bilbao, Spain Sep. 16-18, 2010, pp. 507-512.

Vyas, D., et al., "GSK-3 Negatively Regulates Skeletal Myotube Hypertrophy," Am J Physiol Cell Physiol 283: C545-C551 (2002).

Wagers, A., "Want Not, Waste Not," Cell Stem Cell 2:6-7 (2008).

Wang et al., "Immortalization of chicken preadipocytes by retroviral transduction of chicken TERT and TR," (2017), PLoS ONE 12(5): e0177348. retrieved May 9, 2017 at https://doi.org/10.1371/journal.pone.0177348.

Watt et al. "Regulation of Tissue Growth by the Mammalian Hippo Signaling Pathway," Frontiers in Physiology. Nov. 24, 2017 (Nov. 24, 2017), vol. B, Article 942, pp. 1-12.

Weintraub et al. Activation of muscle-specific genes in pigment, nerve, fat, liver and fibroblast cell lines by forced expression of MyoD. Proceedings of the National Academy of Sciences, USA, 86:5434-5438 (1989).

West et al. Porcine induced pluripotent stem cells produce chimeric offspring. Stem Cells and Development, vol. 19, No. 8, 2010, pp. 1211-1220, 2010. (Year: 2010).

Wilschut, K., et al., "Alpha 6 Integrin is Important for Myogenic Stem Cell Differentiation," Stem Cell Research 7:112-123 (2011).

Wilschut, K., et al., "Extracellular Matrix Components Direct Porcine Muscle Stem Cell Behavior," Experimental Cell Research 316:341-352 (2010).

Wilschut, K., et al., "Isolation and Characterization of Porcine Adult Muscle-Derived Progenitor Cells," Journal of Cellular Biochemistry 105: 1228-1239 (2008).

Wooton et al. "Telomerase Alone Extends the Replicative Life Span of Human Skeletal Muscle Cells Without Compromising Genomic Stability," Human Gene Therapy, vol. 14, No. 15, Oct. 10, 2003, 15 pages.

Wu, G., et al., "Production and Supply of High-Quality Food Protein for Human Consumption: Sustainability, Challenges, and Innovations," Annals of the New York Academy of Sciences 1321 (1), Aug. 2014, pp. 1-19.

Xu et al., "Effects of glutamine and asparagine on recombinant antibody production using CHO-GS cell lines," Biotechnol Prog. Nov.-Dec. 2014;30(6):1457-68.

Yokoyama et al., "The Myogenic Transcriptional Network," Cellular and Molecular Life Sciences 68: 1843-1849 (2011).

Yu et al., "Chinese Disease Signal Pathway and Targeted Therapy," Anhui Science and Technology Press, p. 372 (2013) (with the English translation of paragraphs 4-8 on p. 372).

Zeng, Q. et al., "The Emerging Role of the Hippo Pathway in Cell Contact Inhibition, Organ Size Control, and Cancer Development in Mammals," Cancer Cell, vol. 13, Mar. 2008, pp. 188-192.

Zhao, B. et al., "Cell detachment activates the Hippo pathway via cytoskeleton reorganization to induce anoikis," Genes & Development, vol. 26, Jan. 2012, pp. 54-68.

Zheng, J., K., et al., "Skeletal Myogenesis by Human Embryonic Stem Cells," Cell Research 713-722 (2006).

Zhu, C-H. et al. "Cellular Senescence in Human Myoblasts is Overcome by Human Telomerase Reverse Transcriptase and Cyclin-Dependent Kinase 4: Consequences in Aging Muscle and Therapeutic Strategies for Muscular Dystrophies." Aging Cell, vol. 6, No. 4, Aug. 2007, pp. 515-523.

\* cited by examiner

US 11,708,587 B2

COMPOSITIONS AND METHODS FOR INCREASING THE EFFICIENCY OF CELL CULTURES USED FOR FOOD PRODUCTION

CROSS-REFERENCE TO RELATED APPLICATIONS

The present application is a continuation of co-pending U.S. patent application Ser. No. 16/630,404, filed on Jan. 10, 2020, which is the 371 National Stage application of PCT Application No. PCT/US2018/042187, filed on Jul. 13, 2018, which claims the benefit of and priority to U.S. Provisional Application No. 62/532,345, filed Jul. 13, 2017, all of which are hereby incorporated by reference in their entireties for all purposes.

REFERENCE TO SEQUENCE LISTING

The instant application contains a Sequence Listing with 58 sequences, which has been submitted in XML format and is hereby incorporated herein by reference in its entirety. Said XML copy, created on Sep. 2, 2022, is named 39028-53374-Seqeunce-Listing.xml, and is 125 kilobytes (KB) in size.

BACKGROUND OF THE INVENTION

The mass production of cells for biomass production remains limited by several factors, thus limiting final yields. Examples of such factors include (1) accumulation of extracellular metabolic waste products such as ammonia/ammonium hydroxide, in the cell culture medium to toxic levels, (2) depletion of necessary nutrients, such as glutamine, in the cell culture medium, requiring a constant supply and supplementation of such nutrients, incurring both expense and additional manipulation of the cells, and the (3) requirement for supplemented proteins, such as growth factors, which support the productivity of a cultivation process.

Provided herein are compositions and methods that address this need.

BRIEF SUMMARY OF THE INVENTION

Provided herein are compositions and methods to make and use modified cells, for the purpose of increasing the efficiency of cell cultures, increasing the cell density of metazoan cell cultures, and for making a cultured edible product for human or non-human consumption.

In one aspect, provided herein is a method for increasing the cell density of a culture comprising metazoan cells, the method comprising: (a) introducing into the cells one or more polynucleotide sequences encoding glutamine synthetase (GS), insulin-like growth factor (IGF), and albumin; and (b) culturing the cells in a cultivation infrastructure.

In another aspect, provided herein is a method for increasing the cell density of a culture comprising metazoan cells, the method comprising: (a) introducing into the cells one or more polynucleotide sequences encoding glutamine synthetase (GS), insulin-like growth factor (IGF), albumin or a combination thereof; and (b) culturing the cells in a cultivation infrastructure.

In yet another aspect, provided herein is a method for increasing the cell density of a culture comprising metazoan cells, the method comprising: (a) introducing into the cells one or more polynucleotide sequences encoding glutamine synthetase (GS), insulin-like growth factor (IGF), albumin or a combination thereof; (b) introducing into the cells a polynucleotide sequence encoding a telomerase reverse transcriptase (TERT); and (c) culturing the cells in a cultivation infrastructure.

In one aspect provided herein is a method of decreasing the concentration of ammonia and/or ammonium hydroxide in the medium of cells in culture comprising increasing the expression of glutamine synthetase (GS) protein in the cells, wherein the cells are of livestock, poultry, game or aquatic animal species, and wherein the concentration of ammonia (i.e. ammonium hydroxide) in the medium is decreased by at least 2.5%.

In another aspect, provided herein is a method of increasing the production of glutamine in cells comprising increasing the expression of glutamine synthetase (GS) protein in the cells, wherein the cells are of livestock, poultry, game or aquatic animal species, and wherein the concentration of glutamine in the cells is increased by at least 2.5%.

In another aspect, provided herein, is a method of increasing the concentration of Insulin-like growth factor (IGF) in the medium of cells in culture comprising increasing the expression of IGF protein in the cells, wherein the cells are of livestock, poultry, game or aquatic animal species, and wherein the concentration of IGF in the medium is increased by at least 2.5% or is increased to at least 0.001 ng/mL.

In another aspect, provided herein is a method of increasing the concentration of albumin in the medium of cells in culture comprising increasing the expression of albumin in the cells, wherein the cells are of livestock, poultry, game or aquatic animal species, and wherein the concentration of albumin in the medium is increased at least 2.5% or is increased to at least 0.1 μg/mL.

In one aspect, provided herein is an in vitro method for producing a cultured edible product, the method comprising: (a) introducing one or more polynucleotide sequences encoding glutamine synthetase (GS), insulin-like growth factor (IGF), albumin or a combination thereof into myogenic cells; (b) optionally introducing a polynucleotide sequence encoding a telomerase reverse transcriptase (TERT) into the cells; (c) inducing myogenic differentiation of the cells expressing GS, IGF, albumin or combinations thereof and optionally TERT, wherein the differentiated cells form myocytes and multinucleated myotubes; and (d) culturing the myocytes and myotubes to generate skeletal muscle fibers, thereby producing a cultured edible product.

In another aspect, provided herein is an in vitro method for producing a cultured edible product, the method comprising: (a) overexpressing GS, IGF, albumin, or a combination thereof in a self-renewing cell line, wherein the cell line is a myogenic transcription factor-modified cell line, and wherein the cell line is of a livestock, poultry, game or aquatic animal species; (b) inducing myogenic differentiation of the cell line, wherein the differentiated cell line forms myocytes and multinucleated myotubes; and (c) culturing the myocytes and myotubes to generate skeletal muscle fibers, thereby producing a cultured edible product. In another aspect provided herein is a cultured edible product produced by the in vitro method.

In one aspect, provided herein is a method for increasing the secretion of glutamine by cells into a culture medium, the method comprising increasing the expression of a glutamine synthetase (GS) protein in the cells, wherein the cells are from livestock, poultry, game or aquatic animal species, and wherein the concentration of glutamine secreted into the culture medium is increased by at least 2.5%.

In one aspect, provided herein is a method for increasing the rate of proliferation of cells in a cultivation infrastructure, comprising: (a) introducing into the cells one or more polynucleotide sequences encoding glutamine synthetase (GS), insulin-like growth factor (IGF), albumin or a combination thereof; and (b) culturing the cells in a cultivation infrastructure, wherein the cells are from livestock, poultry, game or aquatic animal species.

In another aspect, provided herein is a method for decreasing death of cells in a cultivation infrastructure, comprising: (a) introducing into the cells one or more polynucleotide sequences encoding glutamine synthetase (GS), insulin-like growth factor (IGF), albumin or a combination thereof; and (b) culturing the cells in a cultivation infrastructure, wherein the cells are from livestock, poultry, game or aquatic animal species.

In another aspect, provided herein is a method for increasing protein production in cells in a cultivation infrastructure, comprising: (a) introducing into the cells a polynucleotide sequence encoding insulin-like growth factor (IGF); and (b) culturing the cells in a cultivation infrastructure, wherein the cells are from livestock, poultry, game or aquatic animal species.

In another aspect provided herein is a cultured edible product comprising cells having increased expression of GS, increased expression of IGF, increased expression of albumin, increased expression of telomerase reverse transcriptase (TERT), loss-of-function mutations in cyclin-dependent kinase inhibitor (CKI) proteins, increased expression of YAP, increased expression of TAZ, and/or increased expression of myogenic transcription factors.

In another aspect provided herein is a construct comprising any one of the sequences selected from Tables 1A and 1B.

In another aspect provided herein is an expression vector comprising any one of the sequences selected from Tables 1A and 1B.

In another aspect provided herein is a cell comprising an expression vector comprising any one of the sequences selected from Tables 1A and 1B. In some embodiments, the cell is from a livestock, poultry, game, or aquatic species.

BRIEF DESCRIPTION OF THE DRAWINGS

FIG. 2A shows fibroblasts transfected with vehicle-only and grown in media with supplemented glutamine. FIG. 2B shows fibroblasts transfected with mouse GS and grown in media with supplemented glutamine. FIG. 2C shows fibroblasts transfected with vehicle-only and grown in media without supplemented glutamine.

FIG. 2D shows fibroblasts transfected with a mouse GS gene and grown in media without supplemented glutamine.

FIG. 5A shows myoblasts transfected with vehicle-only and grown in medium with supplemented glutamine. FIG. 5B shows myoblasts transfected with mouse GS and grown in media with supplemented glutamine. FIG. 5C shows myoblasts transfected with vehicle-only and grown in media without supplemented glutamine. FIG. 5D shows myoblasts transfected with a mouse GS gene and grown in media without supplemented glutamine.

FIG. 10A shows fibroblasts transfected with vehicle-only. FIG. 10B shows fibroblasts transfected with a human IGF-1 gene.

FIG. 10C Fibroblasts transfected with a mouse albumin gene. FIG. 10D shows fibroblasts transfected with a human albumin gene.

FIG. 11A shows myoblasts transfected with vehicle-only. FIG. 11B shows myoblasts transfected with a human IGF-1 gene. FIG. 1C shows myoblasts transfected with a mouse albumin gene. FIG. 11D shows myoblasts transfected with human albumin gene.

DETAILED DESCRIPTION OF THE INVENTION

Figure 1:
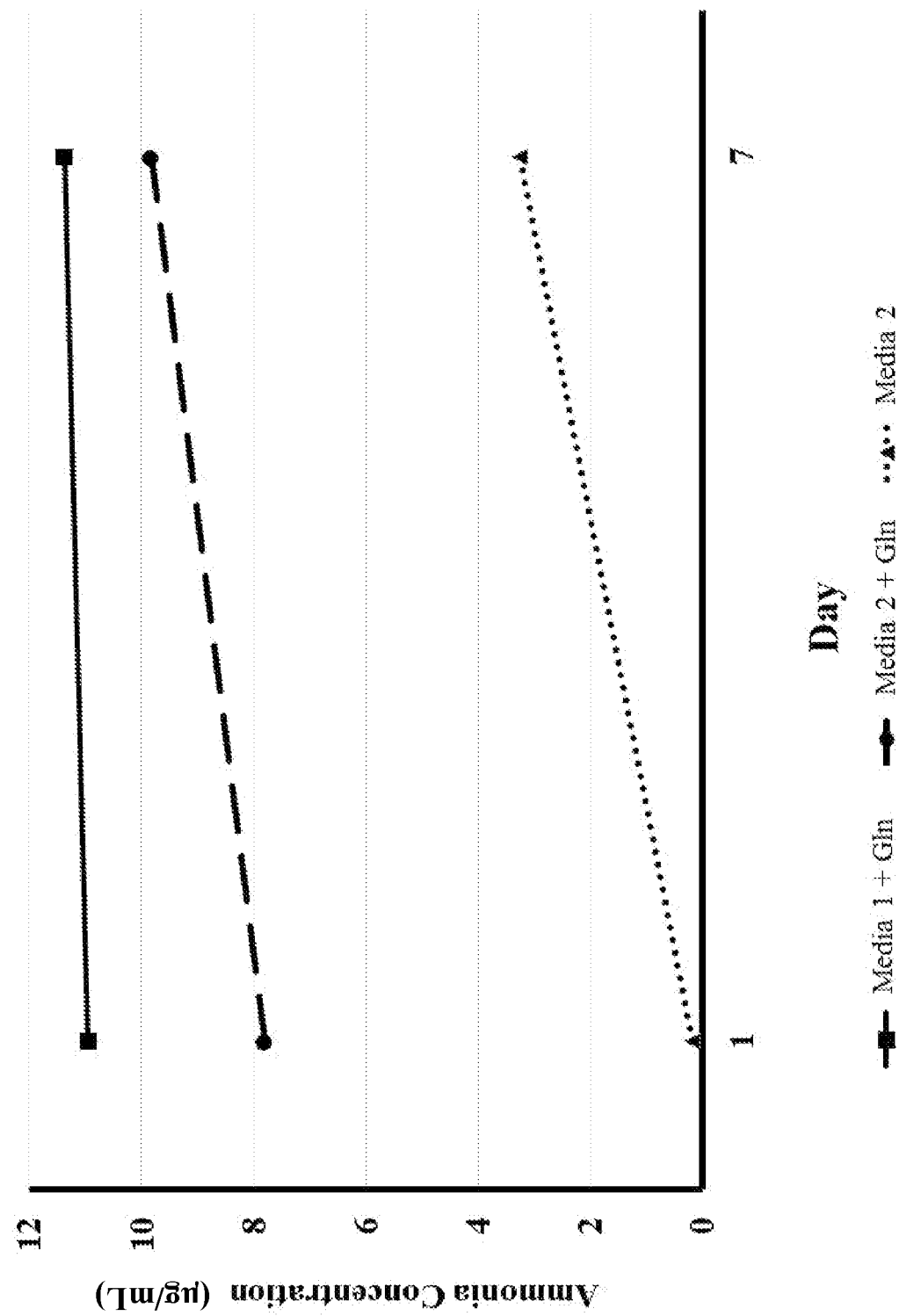
FIG. 1 shows a spontaneous increase in ammonia concentration in various cell culture media.

Provided herein are compositions and methods to make and use engineered cells, for the purpose of increasing the efficiency of cell cultures. Specifically, provided herein are exemplary methods of increasing culture density (e.g. cell density of metazoan cells in culture) and methods for producing cultured edible product. Also provided are methods of making and using cells with reduced requirements for glutamine supplementation, and reduced supplementation with certain animal-cell secreted components such as insulin-like growth factor (IGF) and albumin.

Before describing certain embodiments in detail, it is to be understood that this invention is not limited to particular compositions or biological systems, which can vary. It is also to be understood that the terminology used herein is for the purpose of describing particular illustrative embodiments only, and is not intended to be limiting. The terms used in this specification generally have their ordinary meaning in the art, within the context of this invention and in the specific context where each term is used. Certain terms are discussed below or elsewhere in the specification, to provide additional guidance to the practitioner in describing the compositions and methods of the invention and how to make and use them. The scope and meaning of any use of a term will be apparent from the specific context in which the term is used. As such, the definitions set forth herein are intended to provide illustrative guidance in ascertaining particular embodiments of the invention, without limitation to particular compositions or biological systems.

As used in the present disclosure and the appended claims, the singular forms "a," "an" and "the" include plural references unless the content clearly dictates otherwise.

Throughout the present disclosure and the appended claims, unless the context requires otherwise, the word "comprise", or variations such as "comprises" or "comprising", will be understood to imply the inclusion of a stated element or group of elements but not the exclusion of any other element or group of elements.

Standard techniques may be used for recombinant DNA, oligonucleotide synthesis, and tissue culture and transduction (e.g., electroporation, transfection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well-known and commonly used in the art. Standard techniques may be used for recombinant technology, molecular biological, microbiological, chemical syntheses, chemical analyses, pharmaceutical preparation, production, and delivery.

Cells

Provided herein are methods for modifying cells to overexpress and/or inhibit certain gene products, for the purpose of achieving increased cell density and in some embodiments, for the purpose of providing a cultured edible product. For example, in certain aspects, cells modified as described herein may be cultivated for food production, e.g. production of cultured chicken, cultured beef, and cultured fish.

The cells used in the methods of the present disclosure can be primary cells, or cell lines. The methods provided herein are applicable to any metazoan cell in culture. In various embodiments, methods of the present disclosure may use any one of the cell populations described herein.

In some embodiments, the cells are harvested for the production of cell-based food products, such as cultured edible product from an animal (e.g. cultured poultry, cultured livestock, cultured game, cultured fish). Thus in some embodiments, the methods utilize cells with the potential to differentiate into skeletal muscle. In certain embodiments, the cells are from livestock such as domestic cattle, pigs, sheep, goats, camels, water buffalo, rabbits and the like. In certain embodiments, the cells are from poultry such as domestic chicken, turkeys, ducks, geese, pigeons and the like. In certain embodiments, the cells are from game species such as wild deer, gallinaceous fowl, waterfowl, hare and the like. In certain embodiments, the cells are from aquatic species or semi-aquatic species harvested commercially from wild fisheries or aquaculture operations, or for sport, including certain fish, crustaceans, mollusks, cephalopods, cetaceans, crocodilians, turtles, frogs and the like. In certain embodiments, the cells are from exotic, conserved or extinct animal species. In certain embodiments, the cells are from any metazoan species demonstrating the capacity for skeletal muscle tissue specification. In certain embodiments, the cells are modifiable by a genetic switch to induce rapid and efficient conversion of the cells to skeletal muscle for cultured food production (e.g. cultured poultry, cultured livestock, cultured game, and cultured fish).

In some embodiments, the cells are from *Gallus gallus, Bos taurus, Sous scrofa, Meleagris gallopavo, Anas platyrynchos, Salmo salar, Thunnus thynnus, Ovis aries, Coturnix coturnix, Capra aegagrus hircus,* or *Homarus americanus.*

In some embodiments, the cells are from any animal species intended for human or non-human dietary consumption.

In some embodiments, the cells are from livestock, poultry, game, or aquatic species. In other embodiments, the cells are from humans, primates (e.g. monkeys), rodents, including rats and mice, and companion animals such as dogs, cats, horses, and the like.

In some embodiments, the cells are self-renewing stem cell lines.

In some embodiments, the cells are satellite cells, myoblasts, myocytes, fibroblasts, induced pluripotent stem cells, hepatocytes, vascular endothelial cells, pericytes, embryonic stem cells, mesenchymal stem cells, extraembryonic cell lines, somatic cell lines, adipocytes, embryonic stem cells or chondrocytes.

In some embodiments, the cells are myogenic cells. In some embodiments, the myogenic cells are natively myogenic (e.g. are myogenic cells that are cultured in the cultivation infrastructure). Natively myogenic cells include, but are not limited to, myoblasts, myocytes, satellite cells, side population cells, muscle derived stem cells, mesenchymal stem cells, myogenic pericytes, or mesoangioblasts. In other embodiments, the myogenic cells are not natively myogenic (e.g. are non-myogenic cells that are specified to become myogenic cells in the cultivation infrastructure). In some embodiments, non-myogenic cells include embryonic stem cells, induced pluripotent stem cells, extraembryonic cell lines, and somatic cells other than muscle cells.

In some embodiments, non-myogenic cells are modified to become myogenic cells through the expression of one or more myogenic transcription factors. In exemplary embodiments, the myogenic transcription factor is MYOD1, MYOG, MYF5, MYF6, PAX3, PAX7, paralogs, orthologs, or genetic variants thereof.

In some embodiments, cells are modified to extend their renewal capacity through inactivation of cyclin-dependent kinase inhibitor (CKI) proteins and/or activation of Telomerase reverse transcriptase (TERT). Accordingly, in some embodiments, cells used in the methods of the present disclosure comprise a polynucleotide sequence expressing TERT. In some embodiments, cells used in the methods of the present disclosure comprise one or more loss-of-function mutations in the endogenous genes encoding CKI proteins. In some embodiments, cells comprise loss-of-function mutations in CKI proteins p15, p16, paralogs, orthologs, or genetic variants thereof. In some embodiments, cells used in the methods of the present disclosure comprise a polynucleotide sequence expressing TERT and one or more loss-of-function mutations in the endogenous genes encoding CKI proteins. The loss-of-function mutation may partially or completely inhibit the activity of CKI proteins.

In some embodiments, the process of extending the renewal capacity of the cells comprises activating Telomerase reverse transcriptase (TERT) activity in the cells and/or inactivating CKI proteins.

In some embodiments, the process of extending the renewal capacity of the cells comprises ectopic expression of TERT. In some embodiments, the process of extending the renewal capacity of the cells comprises introducing targeted mutations in the TERT promoter. In some embodiments, the process of extending the renewal capacity of the cells comprises activating endogenous TERT expression by an engineered transcriptional activator. In some embodiments, the process of extending the renewal capacity of the cells comprises transient transfection of TERT mRNA. In some embodiments, induction of endogenous pluripotency-associated telomerase activity in stem cells such as ESC and iPSC supports extended and indefinite cell renewal. In some embodiments, maintenance endogenous pluripotency-associated telomerase activity in stem cells such as ESC and iPSC supports extended and indefinite cell renewal.

In some embodiments, the process of extending the renewal capacity of the cells comprises inactivating one or more CKI proteins. In some embodiments, inactivating CKI proteins comprises introducing loss-of-function mutations in one or more genes encoding CKI proteins. In some embodiments, the loss-of-function mutation partially inhibits the activity of one or more CKI proteins. In some embodiments, the loss-of-function mutation completely inhibits the activity of one or more CKI proteins.

In some embodiments, the inactivation of CKI proteins and/or activation of TERT in the cells extend their renewal capacity for at least 25 population-doublings, at least 50 population-doublings, at least 60 population-doublings, at least 70 population-doublings, at least 80 population-doublings, at least 90 population-doublings, at least 100 population-doublings, at least 110 population-doublings, at least 120 population-doublings, at least 130 population-doublings, at least 140 population-doublings, at least 150 population-doublings, at least 160 population-doublings, at least 170 population-doublings, at least 180 population-doublings, at least 190 population-doublings, or at least 200 population-doublings. In some exemplary embodiments, the cells are primary myoblasts of a livestock, game, aquatic, or poultry species, whose renewal capacity is further extended.

In some embodiments, the cells are modified to inhibit HIPPO signaling, for example, by activating Yes-Associated Protein 1 (YAP1), Transcriptional co-Activator with PDZ-binding motif (TAZ), or a combination thereof in the cells.

In some embodiments, the cells are somatic cells. In some embodiments, the cells are not somatic cells.

In some embodiments, the cells are anchorage-dependent cells and are cultivated in on a substrate. In some embodiments, the cells are anchorage independent cells and are cultivated in a suspension culture. In some embodiments, the cells are cultivated in a suspension culture and form a self-adherent aggregate.

It is noted that the cells can be cultivated for any downstream application, not just limited to food production.

Cellular Modifications

Provided herein are compositions and methods to modify any one of the cells provided herein with a gene of interest in order to increase cell density of metazoan cells in a culture medium, decrease waste products, such as ammonia or ammonium hydroxide, decrease dependency on exogenous addition of factors such as glutamine, albumin, and IGF to the media and to provide a cultured edible product.

Glutamine Synthetase (GS)

Provided herein are cells that overexpress a GS protein.

Provided herein is a method of increasing the production of glutamine in cells or by cells, increasing glutamine secretion into culture medium, and/or decreasing the concentration of extracellular ammonia (to be used interchangeably with ammonium hydroxide where ammonium hydroxide is the form of ammonia present in an aqueous solution) in the medium of cells in culture, comprising increasing the expression of a glutamine synthetase (GS) protein in cells. Also provided herein is a method of increasing the cell density of metazoan cell in culture, comprising increasing the expression of GS in the cells in combination with other modifications described herein and culturing the cells in a cultivation infrastructure. Also provided is an in vitro method for producing a cultured edible product comprising increasing the expression of GS in the cells in combination with other modifications described herein.

In some embodiments, the cells are modified to overexpress a gene encoding a GS protein. In some embodiments, cells ectopically express a GS gene. In some embodiments, the cells are genetically modified and carry stable integrations of one or more copies of a GS gene. In some embodiments, the cells overexpress the gene encoding the GS protein at levels sufficient to decrease the ammonia production, increase the production of glutamine, or any combination thereof. In some embodiments, methods described herein to overexpress GS comprise introducing into the cells a polynucleotide sequence from Table 1B comprising a GS gene.

Increase of GS expression may be achieved using different approaches. In some embodiments, the expression is inducible. In some embodiments, the method comprises expressing nucleotides that encode the GS gene. In some embodiments, the nucleotides are ectopically expressed from constructs that are introduced into the cells, for example expressed from a plasmid, or other expression vector. In some embodiments, the constructs are integrated into the cell's genome, and the expression is driven in that manner (e.g. homologous recombination, introduction mediated by CRISPR-based technology). In some embodiments, expression of the GS gene involves electroporating a DNA, delivering a DNA complexed with a transfection vehicle, using a viral vector (e.g. retrovirus, lentivirus, adenovirus, adeno-associated virus, herpes simplex virus), and the like, or combinations thereof. In some embodiments, the expression is constitutive. In some embodiments, the expression is conditional, e.g. inducible, e.g. under the control of an inducible promoter, e.g. an inducible Tet construct. In some embodiments, the expression of GS is constitutive, but the expression of additional genes of interest is inducible. In some embodiments, the expression of GS is inducible, but the expression of additional genes of interest is constitutive.

In the methods described herein, a polynucleotide sequence encoding the GS gene may encode any homolog of GS, including GS paralogs, or a GS protein translated from any splice variants of a GS gene, or may comprise any mutations in the GS gene sequence including, but not limited to nucleotide deletions, truncations, fusions, or substitutions. Mutations may be synthetic or naturally occurring.

The GS gene can be from of any organism. The GS gene can be from bacteria, plants, fungi, and archaea. The GS gene can be from any animal, such as vertebrate and invertebrate animal species. The GS gene can be from any vertebrate animal species such as mammals, reptiles, birds, amphibians, and the like. The GS gene can be from any mammalian species such as a human, murine, bovine, porcine, and the like.

In some embodiments, the cells are of a livestock, poultry, game or aquatic animal species. In an exemplary embodiment, the renewal capacity of the primary duck myoblasts are extended, and the myoblasts are engineered to stably overexpress GS. In another exemplary embodiment, the renewal capacity of the primary duck myoblasts are extended, and the myoblasts are engineered to transiently overexpress GS. In another exemplary embodiment, the renewal capacity of the primary duck myoblasts are extended and are engineered to ectopically overexpress GS.

In some embodiments, the synthesis of glutamine by the cells is increased by at least 2.5%, by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, at least 160%, at least 170%, at least 180%, at least 190%, at least 200%, at least 225%, at least 250%, at least 275%, at least 300%, at least 325%, at least 350%, at least 375% at least 400%, at least, 425%, at least 450%, at least 475%, at least 500%, at least 550%, at least 600%, at least 650%, at least 700%, at least 750%, at least 800%, at least 850%, at least 900%, at least 950% at least 1,000%, at least 1,100%, at least 1,200%, at least 1,300%, at least 1,400%, at least 1,500%, at least 1,600%, at least 1,700%, at least 1,800%, at least 1,900%, at least 2,000%, at least 2,250%, at least 2,500%, at least 2,750%, at least 3,000%, at least 3,500%, at least 4,000%, at least 4,500%, at least 5,000%, at least 6,000%, at least 7,000%, at least 8,000%, at least 9,000%, or even by at least 10,000%, including values and ranges therebetween, compared to cultures of cells in which glutamine synthesis is not increased by expression of GS as described herein.

In some embodiments, increased expression of GS using the methods described herein increases the concentration of glutamine in the culture medium to at least 0.001 mM, to at least 0.0025 mM, to at least 0.005 mM, to at least 0.0075 mM, to at least 0.01 mM, to at least 0.025 mM, to at least 0.05 mM, to at least 0.075 mM, to at least 0.1 mM, at least 0.25 mM, to at least 0.50 mM, to at least 0.75 mM, to at least 1.0 mM, to at least 1.5 mM, to at least 2.0 mM, to at least 3.0 mM, to at least 5.0 mM, to at least 10 mM, or even to at least 20 mM, including values and ranges therebetween, compared to cultures of cells in which the expression of GS is not increased.

Methods to measure the increase in the concentration of intracellular glutamine production include, but are not limited to assessment of the glutamine concentration in lysates of cell biomass or the ambient culture medium by HPLC (Chorili et. al., 2012. Validation of a HPLC Method for Determination of Glutamine in Food Additives Using Post-Column Derivatization, AJAC Vol. 3 No. 2) commercially available kits for absolute glutamine determination kits (Sigma-Aldrich #GLN1 and #GLN2), and trace-labeled ($H^3$ radiolabeled) glutamine monitoring.

In some embodiments, the protein synthesis in the cells is increased by at least 2.5%, by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or even by at least 95%.

In some embodiments, the concentration of ammonia is decreased by at least 2.5%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or even at least 95%. Methods to measure the decrease of extracellular ammonia concentrations in the cell media include, but are not limited to commercially available absolute ammonia detection kits such as (Sigma-Aldrich #AA0100), diffuse reflectance-based fiberoptic ammonia sensors (Non-enzymatic reversible colorimetric method such as diffuse reflectance-based fiberoptics (Spear, S. K., Rhiel, M., Murhammer, D. W. et al. Appl Biochem Biotechnol (1998) 75: 175), and use of a biochemistry analyzer (e.g. YSI Biochemistry Analyzer 2700).

In some embodiments, there is a delay in time for the cells to reach the ammonia concentration of otherwise not manipulated cultures (the wild-type cell ammonia concentration). For example, cells overexpressing GS may demonstrate at least a 1.5-fold, 2-fold, 3-fold, 4-fold, 5-fold, 6-fold, 7-fold, 8-fold, 9-fold, 10-fold, 15-fold, 20-fold, 25-fold, 30-fold, 40-fold, or even at least a 50-fold delay in time to achieve the wild type cell ammonia concentration.

In some embodiments, provided herein is a method of increasing the cell density of a culture comprising metazoan cells, comprising increasing the expression of glutamine synthetase (GS) protein by the cells, wherein the cells are of livestock, poultry, game or aquatic animal species. The culture density of cells may reach about $10^5$ cells/mL, about $10^6$ cells/mL, about $10^7$ cells/mL, about $10^8$ cells/mL, about $10^9$ cells/mL, or about $10^{10}$ cells/mL (cells in the cellular biomass/mL of cultivation infrastructure), including values and ranges therebetween.

In some embodiments, provided herein is a method of decreasing cell death comprising increasing the expression of glutamine synthetase in the cells. In some embodiments, the decrease in cell death is about 2.5%, about 5%, about 10%, about 20%, about 30%, about 40%, about 50%, about 60%, about 70%, about 80%, about 90%, or about 100%, including values and ranges therebetween, compared to the methods where the expression of GS is not increased.

Insulin-Like Growth Factor (IGF)

Provided herein are cells that overexpress an IGF protein.

Provided herein is a method of increasing the production and secretion of IGF by cells comprising increasing the expression of an IGF protein in cells. Also provided herein is a method of increasing the cell density of a culture comprising metazoan cells comprising increasing the expression of IGF in the cells in combination with other modifications described herein and culturing the cells in a cultivation infrastructure. Also provided is an in vitro method for producing a cultured edible product comprising increasing the expression of GS in the cells in combination with other modifications described herein.

In some embodiments, the cells are modified to overexpress the gene encoding an IGF protein. In some embodiments, cells ectopically express the IGF gene. In some embodiments, the cells are genetically modified and carry stable integrations of one or more copies of an IGF gene. In some embodiments, the cells overexpress the gene encoding the IGF protein at levels sufficient to increase production and/or secretion of IGF into the cell medium. The IGF gene can be of any metazoan species.

Increase of IGF expression may be achieved using different approaches. In some embodiments, the expression is inducible. In some embodiments, the method comprises expressing nucleotides that encode the IGF gene. In some embodiments, the nucleotides are ectopically expressed from constructs that are introduced into the cells, for example expressed from a plasmid, or other expression vector. In some embodiments, the constructs are integrated into the cell's genome, and the expression is driven in that manner (e.g. homologous recombination, introduction mediated by CRISPR-based technology). In some embodiments the expression of the IGF gene involves electroporating a DNA, delivering a DNA complexed with a transfection vehicle, using a viral vector (e.g. retrovirus, lentivirus, adenovirus, adeno-associated virus, herpes simplex virus), and the like, or combinations thereof. In some embodiments, the expression is constitutive. In some embodiments, the expression is conditional, e.g. inducible, e.g. under the control of an inducible promoter, e.g. an inducible Tet construct. In some embodiments, the expression of IGF is constitutive, but the expression of additional genes of interest is inducible. In some embodiments, the expression of IGF is inducible, but the expression of additional genes of interest is constitutive.

The IGF gene can be from any animal, such as vertebrate and invertebrate animal species. The IGF gene can be from any vertebrate animal species such as mammals, reptiles, birds, amphibians, and the like. The IGF gene can be from any mammalian species such as a human, murine, bovine, porcine, poultry, and the like.

In the methods described herein, a polynucleotide sequence encoding the IGF gene may encode any homolog of IGF, including IGF paralogs, such as IGF-1, IGF-2 or any other IGF paralogs, or an IGF protein translated from any splice variants of an IGF gene, or may comprise any mutations in the IGF gene sequence including, but not limited to nucleotide deletions, truncations, fusions, or substitutions. Mutations may be synthetic or naturally occurring. In one embodiment, the methods described herein comprise introducing into the cells a polynucleotide sequence encoding IGF-1. In another embodiment, the methods described herein comprise introducing into the cells a polynucleotide sequence encoding IGF-2. In some embodiments, methods described herein to overexpress IGF comprise introducing into the cells a polynucleotide sequence from Table 1B comprising an IGF gene.

In some embodiments, the cells are of a livestock, poultry, game or aquatic animal species. In an exemplary embodiment, the renewal capacity of the primary duck myoblasts is extended, and the myoblasts are engineered to stably overexpress IGF. In another exemplary embodiment, the renewal capacity of the primary duck myoblasts is extended, and the myoblasts are engineered to transiently overexpress IGF. In another exemplary embodiment, the renewal capacity of the primary duck myoblasts is extended, and the myoblasts are engineered to ectopically overexpress IGF.

In some embodiments, the concentration of IGF in the cell culture medium is increased by at least 0.001%, 0.005%, 0.01%, at least 0.02%, at least 0.03%, at least 0.04%, at least 0.05%, at least 0.075%, at least 0.1%, at least 0.5%, at least 0.75%, at least 1%, at least 1.25%, at least 1.5%, at least 1.75%, at least 2%, at least 2.5%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, at least 160%, at least 170%, at least 180%, at least 190%, at least 200%, at least 225%, at least 250%, at least 275%, at least 300%, at least 325%, at least 350%, at least 375% at least 400%, at least, 425%, at least 450%, at least 475%, at least 500%, at least 550%, at least 600%, at least 650%, at least 700%, at least 750%, at least 800%, at least 850%, at least 900%, at least 950% at least 1,000%, at least 1,100%, at least 1,200%, at least 1,300%, at least 1,400%, at least 1,500%, at least 1,600%, at least 1,700%, at least 1,800%, at least 1,900%, at least 2,000%, at least 2,250%, at least 2,500%, at least 2,750%, at least 3,000%, at least 3,500%, at least 4,000%, at least 4,500%, at least 5,000%, at least 6,000%, at least 7,000%, at least 8,000%, at least 9,000%, or even by at least 10,000% including values and ranges therebetween, compared to cultures of cells in which the expression of IGF is not increased as described herein.

In some embodiments, increased expression of IGF using the methods described herein increases the concentration of IGF in the culture medium by at least 0.00001 ng/mL, to at least 0.000025 ng/mL, to at least 0.000075 ng/mL, to at least 0.0005 ng/mL, to at least 0.001 ng/mL, to at least 0.0025 ng/mL, to at least 0.005 ng/mL, to at least 0.0075 ng/mL, to at least 0.01 ng/mL, to at least 0.025 ng/mL, to at least 0.05 ng/mL, to at least 0.1 ng/mL, to at least 0.25 ng/mL, to at least 0.5 ng/mL, to at least 1 ng/mL, to at least 2.5 ng/mL, to at least 5 ng/mL, to at least 7.5 ng/mL, to at least 10 ng/mL, to at least 25 ng/mL, to at least 50 ng/mL, to at least 75 ng/mL, to at least 125 ng/mL, to at least 250 ng/mL, to at least 500 ng/mL, to at least 750 ng/mL, to at least 1,000 ng/mL, to at least 1,500 ng/mL, to at least 2,000 ng/mL, to at least 2,500 ng/mL, to at least 3,000 ng/mL, to at least 3,500 ng/mL, to at least 4,000 ng/mL, to at least 4,500 ng/mL, to at least 5,000 ng/mL to at least 6,000 ng/mL, to at least 7,000 ng/mL, to at least 8,000 ng/mL, to at least 9,000 ng/mL, or even to at least 10,000 ng/mL including values and ranges therebetween, compared to cultures of cells in which the expression of IGF is not increased as described herein.

Methods to measure the increase in the concentration of IGF include, but are not limited to, antibody-based methods such as immunoprecipitation, co-immunoprecipitation, Western blotting, Enzyme-linked immunosorbent assay (ELISA), and amino-acid based tagging, isolation, and separation (e.g., FLAG, GST, GFP, etc.).

In some embodiments, the rate of synthesis of IGF by cells is increased by about 0.000001 $\mu g/10^6$ cells/day, by about 0.00001 $\mu g/10^6$ cells/day, by about 0.0001 $\mu g/10^6$ cells/day, 0.001 $\mu g/10^6$ cells/day, by about 0.01 $\mu g/10^6$ cells/day, by about 0.1 $\mu g/10^6$ cells/day, by about 1.0 $\mu g/10^6$ cells/day, by about 10 $\mu g/10^6$ cells/day, by about 100 $\mu g/10^6$ cells/day, by about 10 $\mu g/10^6$ cells/day, by about 100 $\mu g/10^6$ cells/day, by about 1,000 $\mu g/10^6$ cells/day, or by even about 10,000 $\mu g/10^6$ cells/day, including values and ranges therebetween, compared to cells wherein the rate of IGF synthesis is not increased as described herein.

In some embodiments, provided herein is a method of increasing the proliferation rate of cells comprising increasing the expression of Insulin-like Growth Factor (IGF) protein by the cells, wherein the cells are of livestock, poultry, game or aquatic animal species. In some embodiments, the population doubling time of the cells is decreased by about by about 5%, by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95%, or by more than 95%, including values and ranges therebetween, compared to cells wherein the expression of IGF is not increased.

In some embodiments, provided herein is a method of increasing protein production in the cells comprising increasing the expression of Insulin-like Growth Factor (IGF) protein by the cells, wherein the cells are of livestock, poultry, game or aquatic animal species. In some embodiments, the protein produced by the cells in culture is measured as total cell protein per cell nucleus. In some embodiments, the total cell protein per nucleus is increased by about 5%, by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95%, by about 100%, by about 110%, by about 120%, by about 130%, by about 140%, by about 150%, by about 160%, by about 170%, by about 180%, by about 190%, by about 200%, by about 225%, by about 250%, by about 275%, by about 300%, by about 350%, by about 400%, by about 450%, by about 500%, by about 550%, by about 600%, by about 650%, by about 700%, by about 750%, by about 800%, by about 850%, by about 900%, by about 950%, by about 1,000%, by about 1,100%, by about 1,200%, by about 1,300%, by about 1,400%, by about 1,500%, by about 1,600%, by about, 1,700%, by about 1,800%, by about 1,900%, by about 2,000%, by about 2,100%, by about 2,200%, by about 2,300%, by about 2,400%, by about 2,500%, by more than 2,500%, including values and ranges therebetween, compared to the total cell protein production where the expression of IGF is not increased.

In some embodiments, the total cell protein per nucleus is increased by about 5 pg/nucleus; by about 10 pg/nucleus; by about 15 pg/nucleus; by about 20 pg/nucleus; by about 25 pg/nucleus; by about 30 pg/nucleus; by about 35 pg/nucleus; by about 40 pg/nucleus; by about 45 pg/nucleus, by about 50 pg/nucleus; by about 55 pg/nucleus, by about 60 pg/nucleus, by about 65 pg/nucleus, by about 70 pg/nucleus, by about 75 pg/nucleus, by about 80 pg/nucleus, by about 85 pg/nucleus, by about 90 pg/nucleus, by about 95 pg/nucleus, by about 100 pg/nucleus, by about 110 pg/nucleus, by about 120 pg/nucleus, by about 130 pg/nucleus, by about 140 pg/nucleus, by about by about 150 pg/nucleus, by about, by about 160 pg/nucleus, by about 170 pg/nucleus, by about 180 pg/nucleus, by about 190 pg/nucleus, by about 200 pg/nucleus, by about 225 pg/nucleus, by about 250 pg/nucleus, by about 275 pg/nucleus, by about 280 pg/nucleus, by about 290 pg/nucleus, by about 300 pg/nucleus, by about 350 pg/nucleus, by about 400 pg/nucleus, by about 450 pg/nucleus, by about 500 pg/nucleus, by about 550 pg/nucleus, by about 600 pg/nucleus, by about 650 pg/nucleus, by about 700 pg/nucleus, by about 750 pg/nucleus, by about 800 pg/nucleus, by about 850 pg/nucleus, by about 900 pg/nucleus, by about 950 pg/nucleus, by about 1000 pg/nucleus, by about 1,100 pg/nucleus, by about 1,200 pg/nucleus, by about 1,300 pg/nucleus, by about 1,400 pg/nucleus, by about 1,500 pg/nucleus, by about 1,600 pg/nucleus, by about 1,700 pg/nucleus, by about 1,800 pg/nucleus, by about 1,900 pg/nucleus, by about 2,000 pg/nucleus, by about 2,100 pg/nucleus, by about 2,200 pg/nucleus, by about 2,300 pg/nucleus, by about 2,400 pg/nucleus, by about 2,500 pg/nucleus, by more than 2,500 pg/nucleus, including values and ranges therebetween.

In some embodiments, provided herein is a method for increasing the rate of proliferation of cells in a cultivation infrastructure, comprising increasing the expression of Insulin-like Growth Factor (IGF) protein in the cells, wherein the cells are of livestock, poultry, game or aquatic animal species. In some embodiments, increasing the expression of IGF comprises introducing a polynucleotide sequence encoding IGF into the cells. In some embodiments, the polynucleotide sequence encodes IGF1. In some embodiments, the polynucleotide sequence encodes IGF2. In some embodiments, the polynucleotide sequence comprises an IGF coding sequence from Tables 1A and 1B.

Albumin

Provided herein are cells that overexpress an albumin protein.

Provided herein is a method of increasing the production and secretion of albumin by cells comprising increasing the expression of an albumin protein in the cells. Also provided herein is a method of increasing the cell density of a culture comprising metazoan cells, comprising increasing the expression of albumin in the cells in combination with other modifications described herein and culturing the cells in a cultivation infrastructure. Also provided is an in vitro method for producing a cultured edible product comprising increasing the expression of albumin in the cells in combination with other modifications described herein.

In some embodiments, the cells are modified to overexpress the gene encoding albumin. In some embodiments, cells ectopically express the albumin gene. In some embodiments, the cells are genetically modified and carry stable integrations of one or more copies of the albumin gene. In some embodiments, the cells overexpress the gene encoding the albumin protein at levels sufficient to increase production and/or secretion of albumin into the cell culture medium.

Increase of albumin expression may be achieved using different approaches. In some embodiments, the expression is inducible. In some embodiments, the method comprises expressing nucleotides that encode the albumin gene. In some embodiments, the nucleotides are ectopically expressed from constructs that are introduced into the cells, for example expressed from a plasmid, or other expression vector. In some embodiments, the constructs are integrated into the cell's genome, and the expression is driven in that manner (e.g. homologous recombination, introduction mediated by CRISPR-based technology). In some embodiments, expression of the albumin gene involves electroporating a DNA, delivering a DNA complexed with a transfection vehicle, using a viral vector (e.g. retrovirus, lentivirus, adenovirus, adeno-associated virus, herpes simplex virus), and the like, or combinations thereof. In some embodiments, the expression is constitutive. In some embodiments, the expression is conditional, e.g. inducible, e.g. under the control of an inducible promoter, e.g. an inducible Tet construct. In some embodiments, the expression of albumin is constitutive, but the expression of additional genes of interest is inducible. In some embodiments, the expression of albumin is inducible, but the expression of additional genes of interest is constitutive.

The albumin gene can be from any animal, such as vertebrate and invertebrate animal species. In some embodiments, the albumin gene can be from any vertebrate animal species such as mammals, reptiles, birds, amphibians, and the like. In some embodiments, the albumin gene can be from any mammalian species, such as a human, murine, bovine, porcine, livestock, and the like.

In the methods described herein, a polynucleotide sequence encoding the albumin gene may encode any homolog of albumin, including any albumin paralogs, or an albumin protein translated from any splice variants of an albumin gene, or may comprise any mutations in the albumin gene sequence including, but not limited to nucleotide deletions, truncations, fusions, or substitutions. Mutations may be synthetic or naturally occurring. In some embodiments, methods described herein to overexpress albumin comprise introducing into the cells a polynucleotide sequence from Table 1B comprising an albumin gene.

In some embodiments, the cells are of a livestock, poultry, game or aquatic animal species. In an exemplary embodiment, the renewal capacity of the primary duck myoblasts is extended, and the myoblasts are engineered to stably overexpress albumin. In another exemplary embodiment, the renewal capacity of the primary duck myoblasts is extended, and the myoblasts are engineered to transiently overexpress albumin. In another exemplary embodiment, the renewal capacity of the primary duck myoblasts is extended, and the myoblasts are engineered to ectopically overexpress albumin.

In some embodiments, an increased expression of albumin using the methods described herein increases the concentration of albumin in the culture medium by at least 0.0010%, 0.005%, 0.01%, at least 0.02%, at least 0.03%, at least 0.04%, at least 0.05%, at least 0.075%, at least 0.1%, at least 0.5%, at least 0.75%, at least 1%, at least 1.25%, at least 1.5%, at least 1.75%, at least 2%, at least 2.5%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, at least 160%, at least 170%, at least 180%, at least 190%, at least 200%, at least 225%, at least 250%, at least 275%, at least 300%, at least 325%, at least 350%, at least 375% at least 400%, at least, 425%, at least 450%, at least 475%, at least 500%, at least 550%, at least 600%, at least 650%, at least 700%, at least 750%, at least 800%, at least 850%, at least 900%, at least 950% at least 1,000%, at least 1,100%, at least 1,200%, at least 1,300%, at least 1,400%, at least 1,500%, at least 1,600%, at least 1,700%, at least 1,800%, at least 1,900%, at least 2,000%, at least 2,250%, at least 2,500%, at least 2,750%, at least 3,000%, at least 3,500%, at least 4,000%, at least 4,500%, at least 5,000%, at least 6,000%, at least 7,000%, at least 8,000%, at least 9,000%, or even by at least 10,000% including values and ranges therebetween, compared to cultures of cells in which the albumin expression is not increased as described herein.

In some embodiments, an increased expression of albumin using the methods described herein increases the concentration of albumin in the culture medium to at least 0.0001 mg/mL, to at least 0.0002 mg/mL, to at least 0.0004 mg/mL, to at least 0.0005 mg/mL, to at least 0.0006 mg/mL, to at least 0.0007 mg/mL, to at least 0.0008 mg/mL, to at least 0.0009 mg/mL, to at least 0.001 mg/mL, to at least 0.002 mg/mL, to at least 0.003 mg/mL, to at least 0.004 mg/mL, to at least 0.005 mg/mL, to at least 0.006 mg/mL, to at least 0.007 mg/mL, to at least 0.008 mg/mL, to at least 0.009 mg/mL, to at least 0.01 mg/mL, to at least 0.05 mg/mL, to at least 0.075 mg/mL, to at least 0.1 mg/mL, to at least 0.25 mg/mL, to at least 0.5 mg/mL, to at least 0.75 mg/mL, to at least 1 mg/mL, to at least 1.25 mg/mL, to at least 1.5 mg/mL, to at least 1.75 mg/mL, to at least 2 mg/mL, to at least 3 mg/mL, to at least 5 mg/mL, to at least 10 mg/mL, to at least 20 mg/mL, to at least 25 mg/mL, to at least 50 mg/mL, to at least 75 mg/mL, or even to at least 100 mg/mL, including values and ranges therebetween, compared to cultures of cells in which the albumin expression is not increased as described herein.

Methods to measure the increase in the concentration of albumin include commercial kits, such as the BCG Albumin Assay Kit (Sigma-Aldrich #MAK124), BCP Albumin Assay Kit (Sigma-Aldrich #MAK125), and antibody-based methods, such as immunoprecipitation, co-immunoprecipitation, Western blotting, Enzyme-linked immunosorbent assay (ELISA), and amino-acid based tagging, isolation, and separation (e.g., FLAG, GST, GFP, etc.).

In some embodiments, provided herein is a method of increasing the rate of proliferation of cells in a cultivation infrastructure, comprising increasing the expression of albumin in the cells, wherein the cells are of livestock, poultry, game or aquatic animal species. In some embodiments, the population doubling time of the cells is decreased by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95%, by more than 95%, including values and ranges therebetween, compared to cells in which the expression of albumin is not increased.

In one embodiment, provided herein is a method of decreasing cell death comprising increasing the expression of albumin in the cells. In some embodiments, the decrease in cell death provided is about 2.5%, about 5%, about 10%, about 20%, about 30%, about 40%, about 50%, about 60%, about 70%, about 80%, about 90%, or about 100%, including values and ranges therebetween, compared to the methods wherein the expression of albumin is not increased.

In some embodiments, provided herein are cells that overexpress any combination of GS, IGF, and albumin. For example, in one embodiment, provided herein are cells that overexpress a GS protein and an IGF protein. In one embodiment, provided herein are cells that overexpress an albumin protein and a GS protein. In one embodiment, provided herein are cells that overexpress an albumin protein and an IGF protein. In one embodiment, provided herein are cells that overexpress an albumin protein, a GS protein, and an IGF protein.

TERT and CKI Proteins

Provided herein are cells whose renewal capacity is extended, for e.g., by overexpressing a TERT protein and/or by inhibiting the activity of CKI proteins. Exemplary methods to overexpress TERT and inhibit the activity of CKI proteins are disclosed in U.S. Provisional Application No. 62/278,869, filed on Jan. 14, 2016, and 62/361,867, filed on Jul. 13, 2016, and a PCT Application No. PCT/US2017/013782, filed on Jan. 17, 2017, all of which are incorporated herein by reference in their entirety.

In some embodiments, provided herein is a method for increasing the density of cells in a culture or an in vitro method for producing a cultured edible product comprising increasing the expression of a TERT protein in the cells in combination with increasing the expression of GS, IGF, albumin, or a combination thereof. In some embodiments, provided herein is a method for increasing the density of cells in a culture or an in vitro method for producing a cultured edible product comprising inhibiting the activity of CKI proteins in the cells in combination with increasing the expression of GS, IGF, albumin, or a combination thereof. In some embodiments, provided herein is a method for increasing the density of cells in a culture or an in vitro method for producing a cultured edible product comprising increasing the expression of a TERT protein in the cells, inhibiting the activity of CKI proteins in the cells, and increasing the expression of GS, IGF, albumin, or a combination thereof.

In some embodiments, the cells are modified to overexpress a polynucleotide sequence encoding TERT. In some embodiments, cells ectopically express the TERT polynucleotide. In some embodiments, the cells are genetically modified and carry stable integrations of one or more copies of the TERT polynucleotide.

Increased expression of TERT may be achieved using different approaches. In some embodiments, increased expression of TERT may be achieved by ectopically expressing TERT. In some embodiments, increased expression of TERT may be achieved by introducing targeted mutations in the TERT promoter. In some embodiments, increased expression of TERT may be achieved by activating endogenous TERT expression by an engineered transcriptional activator. In some embodiments, increased expression of TERT may be achieved by transiently transfecting TERT mRNA.

In some embodiments, the expression of TERT is inducible. In some embodiments, the method comprises expressing nucleotides that encode the TERT protein. In some embodiments, the nucleotides are ectopically expressed from constructs that are introduced into the cells, for example expressed from a plasmid, or other expression vector. In some embodiments, the constructs are integrated into the cell's genome, and the expression is driven in that manner (e.g. homologous recombination, introduction mediated by CRISPR-based technology). In some embodiments, the expression of the TERT gene involves electroporating a DNA, delivering a DNA complexed with a transfection vehicle, using a viral vector (e.g. retrovirus, lentivirus, adenovirus, adeno-associated virus, herpes simplex virus), and the like, or combinations thereof. In some embodiments, the expression is constitutive. In some embodiments, the expression is conditional, e.g. inducible, e.g. under the control of an inducible promoter, e.g. an inducible Tet construct. In some embodiments, the expression of TERT is constitutive, but the expression of additional genes of interest is inducible. In some embodiments, the expression of TERT is inducible, but the expression of additional genes of interest is constitutive.

The polynucleotide encoding TERT can be from of any organism. The TERT polynucleotide can be from bacteria, plants, fungi, and archaea. The TERT polynucleotide can be from any animal, such as vertebrate and invertebrate animal species. The TERT polynucleotide can be from any vertebrate animal species such as mammals, reptiles, birds, amphibians, and the like. The TERT polynucleotide can be from any mammalian species, such as a human, murine, bovine, porcine, and the like.

In some embodiments, the methods of inhibiting CKI proteins comprise introducing loss-of-function mutations, e.g., INDEL (insertion or deletion) mutations, into one or more genes encoding CKI proteins in the cells. This can be accomplished using any gene based technologies, for example, using CRISPR-Cas (Clustered Regularly Interspersed Short Palindromic Repeats) based technology or TALEN based technology. In an exemplary embodiment, the genes encoding CKI proteins are the genes encoding CKI proteins p15, p16, paralogs, orthologs, or genetic variants thereof. In an exemplary embodiment, the methods of inhibiting CKI proteins comprise introducing loss-of-function mutations in CDKN2B gene (p15) and/or in CDKN2A gene (p16).

In some embodiments, inhibiting the activity of CKI proteins comprises activating a CDK4 protein, paralogs, orthologs or genetic variants thereof.

In some embodiments, the methods of inhibiting the CKI function comprise introducing into the cells a vector expressing a polynucleotide that encodes a dominant negative mutant of one or more CKI proteins. In some embodiments, the polynucleotide is ectopically expressed from a construct that is introduced into the cells of the biomass, for example expressed from a plasmid, or other vector. In some embodiments, the construct is integrated into the cell's genome, and the expression is driven in that manner (e.g. introduction mediated by CRISPR-based technology). In some embodiments, the expression of the polynucleotide involves electroporating a DNA, delivering a DNA complexed with a transfection vehicle, using a viral vector (e.g. retrovirus, lentivirus, adenovirus, adeno-associated virus, herpes simplex virus), and the like, or combinations thereof. In some embodiments, the expression is constitutive. In some embodiments, the expression is conditional, e.g. inducible, e.g. under the control of an inducible promoter, e.g. an inducible Tet construct.

In some embodiments, the methods of inhibiting comprise delivering dominant negative mutants of one or more CKI proteins directly, e.g. purified proteins, synthetic proteins, or recombinantly expressed proteins, or combinations thereof, to the cells.

In some embodiments, the methods of inhibiting comprise transcriptional repression of the endogenous genes encoding one or more CKI proteins in the cells. This can be accomplished, for example, by using nucleic acid sequence-directed transcriptional repressors. For example, an endonuclease-defective Cas9, dCas9, can be combined with a guide RNA that targets the promoter region of the genes encoding one or more CKI proteins and reduces the transcriptional activation and concomitant gene expression.

In some embodiments, the cells are of a livestock, poultry, game or aquatic animal species. In an exemplary embodiment, the renewal capacity of the primary duck myoblasts is extended, and the myoblasts are engineered to stably overexpress GS, IGF, albumin, or any combination thereof. In another exemplary embodiment, the renewal capacity of the primary duck myoblasts is extended, and the myoblasts are engineered to transiently overexpress GS, IGF, albumin, or any combination thereof. In another exemplary embodiment, the renewal capacity of the primary duck myoblasts is extended, and the myoblasts are engineered to ectopically overexpress GS, IGF, albumin, or any combination thereof.

In some embodiments, provided herein are cells that overexpress a GS protein and an IGF protein. The cells may optionally be modified to extend renewal capacity, and may comprise activated TERT and/or inactivated CKI protein, may comprise an antagonized HIPPO signaling pathway, e.g., activated YAP/TAZ, may be further differentiated, and the like.

In some embodiments, provided herein are cells that overexpress an albumin protein and a GS protein. The cells may optionally be modified to extend renewal capacity, and may comprise activated TERT and/or inactivated CKI protein, may comprise an antagonized HIPPO signaling pathway, e.g., activated YAP/TAZ, may be further differentiated, and the like.

In some embodiments, provided herein are cells that overexpress an albumin protein and an IGF protein. The cells may optionally be modified to extend renewal capacity, and may comprise activated TERT and/or inactivated CKI protein, may comprise an antagonized HIPPO signaling pathway, e.g., activated YAP/TAZ, may be further differentiated, and the like.

In some embodiments, provided herein are cells that overexpress an albumin protein, a GS protein, and an IGF protein. The cells may optionally be modified to extend renewal capacity, and may comprise activated TERT and/or inactivated CKI protein, may comprise an antagonized HIPPO signaling pathway, e.g., activated YAP/TAZ, may be further differentiated, and the like.

Tables 1A and 1B show exemplary sequences used for ectopic overexpression in some exemplary embodiments provided herein. The cells may optionally be modified to extend renewal capacity, and may comprise activated TERT and/or inactivated CKI protein, may comprise an antagonized HIPPO signaling, e.g., activated YAP/TAZ, may be further differentiated, and the like.

Table 1C shows exemplary amino acid sequences for GS, albumin, and IGF proteins that may be expressed in cells according to the methods described here.

TABLE 1A

| Gene | Species | NCBI # | Vendor | Eukaryotic selection marker | Prokaryotic selection marker | Tag | Backbone |
|---|---|---|---|---|---|---|---|
| Glutamine Synthetase (GS) | mouse | NM_008131 | Genscript OMu19897D | Neo | Amp | C terminal DYKDDDDK (SEQ ID NO: 57) tags | pcDNA3.1+/C-(K)DYK (SEQ ID NO: 58) |
| IGF-1 | human | NM_000618.2 | Origene RG212527 | Neo | Kan | Myc-DDK | pCMV6-Entry |
| Albumin | human | NM_000477 | Genscript OHu18744 | Neo | Amp | C terminal DYKDDDDK (SEQ ID NO: 57) tags | |
| Albumin | Mouse | NM_009654 | Genscript OMu21640 | Neo | Amp | C terminal DYKDDDDK (SEQ ID NO: 57) tags | |

TABLE IB

| Gene | Species | NCBI # | DNA Sequence |
|---|---|---|---|
| IGF1 + porcine albumin signal peptide | bovine | | ATGAAGTGGGTGACTTTTATTTCCCTTCTCTTTCTCTTC AGCTCTGCTTATTCCTTCTTGAAGCAGGTGAAGATGC CCATCACATCCTCCTCGCATCTCTTCTATCTGGCCCTG TGCTTGCTCGCCTTCACCAGCTCTGCCACGGCGGGAC CCGAGACCCTCTGCGGGGCTGAGTTGGTGGATGCTCT CCAGTTCGTGTGCGGAGACAGGGGCTTTTATTTCAAC AAGCCCACGGGGTATGGCTCGAGCAGTCGGAGGGCG CCCCAGACAGGAATCGTGGATGAGTGCTGCTTCCGGA GCTGTGATCTGAGGAGGCTGGAGATGTACTGCGCGCC TCTCAAGCCCGCCAAGTCGGCCCGCTCAGTCCGTGCC CAGCGCCACACCGACATGCCCAAGGCTCAGAAGGAA GTACATTTGAAGAACACAAGTAGAGGGAGTGCAGGA AACAAGAACTACAGAATGTAG (SEQ ID NO: 1) |
| IGF1 + porcine albumin signal peptide | chicken | | ATGAAGTGGGTGACTTTTATTTCCCTTCTCTTTCTCTTC AGCTCTGCTTATTCCTTCTTGAAGGTGAAGATGCACA CTGTGTCCTACATTCATTTCTTCTACCTTGGCCTGTGTT TGCTTACCTTAACCAGTTCTGCTGCTGCCGGCCCAGA AACACTGTGTGGTGCTGAGCTGGTTGATGCTCTTCAGT TCGTATGTGGAGACAGAGGCTTCTACTTCAGTAAGCC TACAGGGTATGGATCCAGCAGTAGACGCTTACACCAC AAGGGAATAGTGGATGAATGCTGCTTCCAGAGTTGTG ACCTGAGGAGGCTGGAGATGTACTGTGCTCCAATAAA GCCACCTAAATCTGCACGCTCTGTACGTGCTCAGCGC CACACTGATATGCCAAAAGCACAAAAGGAAGTGCAT TTGAAGAATACAAGTAGAGGGAACACAGGAAACAGA AACTACAGAATGTAA (SEQ ID NO: 2) |
| IGF1 + porcine albumin signal peptide | porcine | | ATGAAGTGGGTGACTTTTATTTCCCTTCTCTTTCTCTTC AGCTCTGCTTATTCCTTGGCCCTGTGCTTGCTCTCCTT CACCAGCTCTGCCACGGCTGGACCTGAGACCCTCTGT GGGGCTGAGCTGGTGGACGCTCTTCAGTTCGTGTGCG GAGACAGGGGCTTTTATTTCAACAAGCCCACAGGGTA CGGCTCCAGCAGTCGGAGGGCGCCACAGACGGGCAT CGTGGATGAGTGCTGCTTCCGGAGCTGTGATCTGAGG AGGCTGGAGATGTACTGTGCACCCCTCAAGCCTGCCA AGTCGGCCCGCTCCGTCCGTGCCCAGCGCCACACGGA CATGCCCAAGGCTCAGAAGGAAGTACATTTGAAGAA CACAAGTAGAGGGAGTTCAGGAAACAAGAACTACAG AATGTAG (SEQ ID NO: 3) |
| Wild Type IGF1 | chicken | NM_001004384 | ATGGAAAAAATCAACAGTCTTTCAACACAATTAGTTA AGTGCTGCTTTTGTGATTTCTTGAAGGTGAAGATGCAC ACTGTGTCCTACATTCATTTCTTCTACCTTGGCCTGTG TTTGCTTACCTTAACCAGTTCTGCTGCTGCCGGCCCAG AAACACTGTGTGGTGCTGAGCTGGTTGATGCTCTTCA GTTCGTATGTGGAGACAGAGGCTTCTACTTCAGTAAG CCTACAGGGTATGGATCCAGCAGTAGACGCTTACACC |

TABLE IB-continued

| Gene | Species | NCBI # | DNA Sequence |
|---|---|---|---|
| | | | ACAAGGGAATAGTGGATGAATGCTGCTTCCAGAGTTG<br>TGACCTGAGGAGGCTGGAGATGTACTGTGCTCCAATA<br>AAGCCCACCTAAATCTGCACGCTCTGTACGTGCTCAGC<br>GCCCACACTGATATGCCAAAAGCACAAAAGGAAGTGC<br>ATTTGAAGAATACAAGTAGAGGGAACACAGGAAACA<br>GAAACTACAGAATGTAA (SEQ ID NO: 4) |
| Wild Type IGF1 | bovine | NM_<br>001077828 | ATGGGAAAAATCAGCAGTCTTCCAACCCAATTATTTA<br>AGTGCTGCTTTTGTGATTTCTTGAAGCAGGTGAAGAT<br>GCCCATCACATCCTCCTCGCATCTCTTCTATCTGGCCC<br>TGTGCTTGCTCGCCTTCACCAGCTCTGCCACGGCGGG<br>ACCCGAGACCCTCTGCGGGGCTGAGTTGGTGGATGCT<br>CTCCAGTTCGTGTGCGGAGACAGGGGCTTTTATTTCA<br>ACAAGCCCACGGGGTATGGCTCGAGCAGTCGGAGGG<br>CGCCCCAGACAGGAATCGTGGATGAGTGCTGCTTCCG<br>GAGCTGTGATCTGAGGAGGCTGGAGATGTACTGCGCG<br>CCTCTCAAGCCCGCCAAGTCGGCCCGCTCAGTCCGTG<br>CCCAGCGCCACACCGACATGCCCAAGGCTCAGAAGG<br>AAGTACATTTGAAGAACACAAGTAGAGGGAGTGCAG<br>GAAACAAGAACTACAGAATGTAG (SEQ ID NO: 5) |
| Wild Type IGF1 | porcine | NM_<br>214256 | ATGCACATCACATCCTCTTCGCATCTCTTCTACTTGGC<br>CCTGTGCTTGCTCTCCTTCACCAGCTCTGCCACGGCTG<br>GACCTGAGACCCTCTGTGGGGCTGAGTGGTGGACGC<br>TCTTCAGTTCGTGTGCGGAGACAGGGGCTTTTATTTCA<br>ACAAGCCCACAGGGTACGGCTCCAGCAGTCGGAGGG<br>CGCCACAGACGGGCATCGTGGATGAGTGCTGCTTCCG<br>GAGCTGTGATCTGAGGAGGCTGGAGATGTACTGTGCA<br>CCCCTCAAGCCTGCCAAGTCGGCCCCGCTCCGTCCGTG<br>CCCAGCGCCACACGGACATGCCCAAGGCTCAGAAGG<br>AAGTACATTTGAAGAACACAAGTAGAGGGAGTTCAG<br>GAAACAAGAACTACAGAATGTAG (SEQ ID NO: 6) |
| Albumin + porcine albumin signal peptide | bovine | | ATGAAGTGGGTGACTTTTATTTCCCTTCTCTTTCTCTTC<br>AGCTCTGCTTATTCCAGGGGTGTGTTTCGTCGAGATAC<br>ACACAAGAGTGAGATTGCTCATCGGTTTAAAGATTTG<br>GGAGAAGAACATTTTAAAGGCCTGGTACTGATTGCCT<br>TTTCTCAGTATCTCCAGCAGTGTCCATTTGATGAGCAT<br>GTAAAATTAGTGAACGAACTAACTGAGTTTGCAAAAA<br>CATGTGTTGCTGATGAGTCCCATGCCGGCTGTGAGAA<br>GTCACTTCACACTCTCTTTGGAGATGAATTGTGTAAAG<br>TTGCATCCCTTCGTGAAACCTATGGTGACATGGCTGA<br>CTGCTGTGAGAAACAAGAACCTGAGAGAAATGAATG<br>CTTCTTGTCACACAAAGATGATAGCCCTGATCTACCT<br>AAACTCAAACCTGACCCCAATACTTTGTGTGACGAGT<br>TTAAGGCCGATGAAAAGAAGTTTTGGGGAAAATACCT<br>ATACGAAATTGCTAGAAGACATCCCTACTTTTATGCA<br>CCAGAACTCCTTTACTATGCTAATAAATATAATGGAG<br>TTTTTCAAGAATGCTGCCAAGCTGAAGATAAAGGTGC<br>CTGCCTGCTACCAAAGATTGAAACTATGAGGGAAAG<br>GTACTGACTTCATCTGCCAGACAGAGACTCAGGTGTG<br>CCAGTATTCAAAAATTTGGAGAAAGAGCTTTAAAAGC<br>ATGGTCAGTAGCTCGCCTGAGCCAGAAATTTCCCAAG<br>GCTGAGTTTGTAGAAGTTACCAAGCTAGTGACAGATC<br>TCACAAAAGTGCACAAGGAATGCTGCCATGGAGACCT<br>ACTTGAATGCGCAGATGACAGGGCGGACCTTGCCAAG<br>TACATATGTGATAATCAAGATACAATCTCCAGTAAAC<br>TGAAGGAATGCTGTGATAAGCCTTTGTTGGAAAAATC<br>CCACTGCATTGCTGAGGTAGAAAAAGATGCCATACCT<br>GAAAACTTGCCCCCATTAACTGCTGACTTTGCTGAAG<br>ATAAGGATGTATGCAAAAACTATCAAGAAGCAAAGG<br>ATGCCTTCCTGGGCTCATTTCTTTATGAATATTCAAGA<br>AGGCATCCTGAATATGCTGTCTCAGTGCTATTGAGAC<br>TTGCCAAGGAATATGAAGCCACACTGGAGGAATGCTG<br>TGCCAAAGATGATCCACATGCATGCTATTCCACAGTG<br>TTTGACAAACTTAAGCATCTTGTGGATGAGCCTCAGA<br>ATTTAATTAAACAAACTGTGACCAATTCGAAAAACT<br>TGGAGAGTATGGATTCCAAAATGCGCTCATAGTTCGT<br>TACACCAGGAAAGTACCCCAAGTGTCAACTCCAACTC<br>TCGTGGAGGTTTCAAGAAGCCTAGGAAAAGTGGGTAC<br>TAGGTGTTGTACAAAACCGGAATCAGAAAGAATGCCC<br>TGTACAGAAGACTATCTGAGCTTGATCCTGAACCGGT<br>TGTGCGTGCTGCATGAGAAGACACCAGTGAGTGAAA<br>AAGTCACCAAGTGCTGCACAGAGTCATTGGTGAACAG<br>ACGGCCATGTTTCTCTGCTCTGACACCTGATGAAACA<br>TATGTACCCAAAGCCTTTGATGAGAAATTGTTCACCTT<br>CCATGCAGATATATGCACACTTCCCGATACTGAGAAA<br>CAAATCAAGAAACAAACTGCACTTGTTGAGCTGTTGA |

TABLE IB-continued

| Gene | Species | NCBI # | DNA Sequence |
|---|---|---|---|
| | | | AACACAAGCCCAAGGCAACAGAGGAACAACTGAAAA<br>CCGTCATGGAGAATTTTGTGGCTTTTGTAGACAAGTG<br>CTGCGCAGCTGATGACAAAGAAGCCTGCTTTGCTGTG<br>GAGGGTCCAAAACTTGTTGTTTCAACTCAAACAGCCT<br>TAGCCTAA (SEQ ID NO: 7) |
| Albumin +<br>porcine<br>albumin<br>signal<br>peptide | chicken | | ATGAAGTGGGTGACTTTTATTTCCCTTCTCTTTCTCTTC<br>AGCTCTGCTTATTCCAGGAATCTGCAAAGATTTGCTC<br>GTGATGCAGAGCACAAGAGTGAAATTGCCCATCGCTA<br>CAATGATTTGAAAGAAGAAACATTTAAGGCAGTTGCC<br>ATGATCACATTTGCCCAGTATCTCCAGAGGTGCTCTTA<br>TGAAGGACTGTCTAAGCTTGTGAAGGATGTTGTTGAT<br>CTGGCACAAAAATGTGTAGCCAATGAAGATGCTCCTG<br>AATGCTCAAAACCACTGCCTTCCATTATCCTGGATGA<br>AATCTGCCAAGTGGAAAAGCTCCGTGACTCTTATGGT<br>GCAATGGCCGACTGCTGTAGCAAAGCTGATCCTGAAA<br>GAAATGAGTGTTTCCTGTCATTTAAAGTTTCCCAACCA<br>GACTTCGTTCAGCCATACCAAAGACCAGCTTCTGATG<br>TGATATGCCAGGAATACCAGGACAACAGAGTGTCATT<br>TCTGGGACATTTCATCTATTCTGTTGCAAGAAGACAC<br>CCCTTCTTGTATGCCCCTGCAATCCTTAGTTTTGCTGT<br>TGATTTTGAACATGCACTTCAAAGCTGTTGCAAAGAG<br>AGTGATGTCGGTGCTTGCCTGGACACCAAGGAAATTG<br>TTATGAGAGAAAAAGCCAAGGGAGTAAGTGTGAAGC<br>AGCAGTATTTTGTGGAATCTTGAAGCAGTTCGGAGA<br>TAGAGTTTTCCAAGCACGACAACTTATTTACCTAAGC<br>CAAAAATACCCCAAGGCTCCATTCTCAGAGGTTTCTA<br>AATTTGTACATGATTCTATCGGCGTCCACAAAGAGTG<br>CTGTGAAGGGGACATGGTGGAGTGCATGGATGACATG<br>GCACGTATGATGAGCAATCTGTGCTCTCAACAAGATG<br>TTTTCTCAGGTAAAATCAAAGACTGCTGTGAGAAGCC<br>TATTGTGGAACGAAGCCAGTGCATTATGGAGGCAGAA<br>TTTGATGAGAAACCTGCAGATCTTCCTTCATTAGTTGA<br>AAAGTACATAGAAGATAAGGAAGTGTGTAAAAGTTTT<br>GAAGCAGGCCACGATGCATTCATGGCAGAGTTCGTTT<br>ATGAATACTCACGAAGACACCCTGAGTTCTCCATACA<br>GCTTATTATGAGAATTGCCAAAGGATATGAATCACTT<br>CTGGAAAAGTGCTGCAAAACTGATAACCCTGCTGAGT<br>GCTACGCAAATGCTCAAGAGCAACTGAACCAACATAT<br>CAAAGAAACTCAGGATGTTGTGAAGACAAACTGTGAT<br>CTTCTCCATGACCATGGCGAGGCAGACTTCCTCAAGT<br>CCATCCTGATCCGCTACACTAAGAAAATGCCTCAAGT<br>ACCAACTGATCTCCTGCTTGAAACTGGAAAGAAAATG<br>ACAACTATTGGTACTAAGTGCTGCCAGCTTCCTGAAG<br>ACAGACGCATGGCTTGTTCTGAGGGTTATCTGAGCAT<br>TGTGATTCATGATACGTGCAGGAAACAGGAGACCACA<br>CCTATAAATGACAACGTTTCACAATGCTGCAGCAGCT<br>CCTATGCTAACAGAAGACCATGTTTCACTGCTATGGG<br>AGTAGATACCAAATATGTTCCTCCACCATTTAATCCTG<br>ATATGTTCAGCTTTGATGAAAAATTGTGCAGTGCTCCT<br>GCTGAAGAACGAGAAGTAGGCCAGATGAAATTGCTA<br>ATCAACCTCATTAAACGCAAGCCCCAGATGACAGAAG<br>AACAAATAAAGACAATTGCTGATGGTTTCACTGCCAT<br>GGTTGACAAGTGCTGCAAGCAGTCGGACATCAATACA<br>TGCTTTGGAGAAGAGGGTGCCAACCTAATAGTCCAAA<br>GCAGAGCCACATTAGGAATTGGTGCTTAA (SEQ ID<br>NO: 8) |
| Wild Type<br>Albumin | porcine | NM_<br>001005208 | ATGAAGTGGGTGACTTTTATTTCCCTTCTCTTTCTCTTC<br>AGCTCTGCTTATTCCAGGGGTGTGTTCGTCGAGATAC<br>ATACAAGAGTGAAATTGCTCATCGGTTTAAAGATTTG<br>GGAGAACAATATTTCAAAGGCCTAGTGCTGATTGCCT<br>TTTCTCAGCATCTCCAGCAATGCCCATATGAAGAGCA<br>TGTGAAATTAGTGAGGGAAGTAACTGAGTTTGCAAAA<br>ACATGTGTTGCTGATGAGTCAGCTGAAAATTGTGACA<br>AGTCAATTCACACTCTCTTTGGAGATAAATTATGTGCA<br>ATTCCATCCCTTCGTGAACACTATGGTGACTTGGCTGA<br>CTGCTGTGAAAAGAAGAGCCTGAGAGAAACGAATG<br>CTTCCTCCAACACAAAAATGATAACCCCGACATCCCT<br>AAATTGAAACCAGACCCTGTTGCTTTATGCGCTGACT<br>TCCAGGAAGATGAACAGAAGTTTTGGGGAAAATACCT<br>ATATGAAATTGCCAGAGACATCCCTATTTCTACGCC<br>CCAGAACTCCTTTATTATGCCATTATATATAAAGATGT<br>TTTTTCAGAATGCTGCCAAGCTGCTGATAAAGCTGCC<br>TGCCTGTTACCAAAGATTGAGCATCTGAGAGAAAAG<br>TACTGACTTCCGCCGCCAAACAGAGACTTAAGTGTGC<br>CAGTATCCAAAAATTCGGAGAGAGAGCTTTCAAAGCA<br>TGGTCATTAGCTCGCCTGAGCCAGAGATTTCCCAAGG |

TABLE IB-continued

| Gene | Species | NCBI # | DNA Sequence |
|---|---|---|---|
| | | | CTGACTTTACAGAGATTTCCAAGATAGTGACAGATCT<br>TGCAAAAGTCCACAAGGAATGCTGCCATGGTGACCTG<br>CTTGAATGTGCAGATGACAGGGCGGATCTTGCCAAAT<br>ATATATGTGAAAATCAAGCACAATCTCCACTAAACT<br>GAAGGAATGCTGTGATAAGCCTCTGTTGGAAAAATCC<br>CACTGCATTGCTGAGGCAAAAAGAGATGAATTGCCTG<br>CAGACCTGAACCCATTAGAACATGATTTTGTTGAAGA<br>TAAGGAAGTTTGTAAAAACTATAAAGAAGCAAAGCA<br>TGTCTTCCTGGGCACGTTTTTGTATGAGTATTCAAGAA<br>GGCACCCAGACTACTCTGTCTCATTGCTGCTGAGAAT<br>TGCCAAGATATATGAAGCCACACTGGAGGACTGCTGT<br>GCCAAAGAGGATCCTCCGGCATGCTATGCCACAGTGT<br>TTGATAAATTTCAGCCTCTTGTGGATGAGCCTAAGAA<br>TTTAATCAAACAAAACTGTGAACTTTTTGAAAAACTT<br>GGAGAGTATGGATTCCAAAATGCGCTCATAGTTCGTT<br>ACACCAAGAAAGTACCCCAAGTGTCAACTCCAACTCT<br>TGTGGAGGTCGCAAGAAAACTAGGACTAGTGGGCTCT<br>AGGTGTTGTAAGCGTCCTGAAGAAGAAAGACTGTCCT<br>GTGCTGAAGACTATCTGTCCCTGGTCCTGAACCGGTT<br>GTGCGTGTTGCACGAGAAGACACCAGTGAGCGAAAA<br>AGTTACCAAATGCTGCACAGAGTCCTTGGTGAACAGA<br>CGGCCTTGCTTTTCTGCTCTGACACCAGACGAAACAT<br>ACAAACCCAAAGAATTTGTTGAGGGAACCTTCACCTT<br>CCATGCAGACCTATGCACACTTCCTGAGGATGAGAAA<br>CAAATCAAGAAGCAAACTGCACTCGTTGAGTTGTTGA<br>AACACAAGCCTCATGCAACAGAGGAACAACTGAGAA<br>CTGTCCTGGGCAACTTTGCAGCCTTTGTACAAAAGTG<br>CTGCGCCGCTCCTGACCATGAGGCCTGCTTTGCTGTG<br>GAGGGTCCGAAATTTGTTATTGAAATTCGAGGGATCT<br>TAGCCTAA (SEQ ID NO: 9) |
| Wild Type<br>Albumin | chicken | NM_<br>205261 | ATGAAGTGGGTAACATTAATTTCATTCATTTTCCTCTT<br>CAGTTCAGCAACATCCAGGAATCTGCAAAGATTTGCT<br>CGTGATGCAGAGCACAAGAGTGAAATTGCCCATCGCT<br>ACAATGATTTGAAAGAAGAAACATTTAAGGCAGTTGC<br>CATGATCACATTTGCCCAGTATCTCCAGAGGTGCTCTT<br>ATGAAGGACTGTCTAAGCTTGTGAAGGATGTTGTTGA<br>TCTGGCACAAAAATGTGTAGCCAATGAAGATGCTCCT<br>GAATGCTCAAAACCACTGCCTTCCATTATCCTGGATG<br>AAATCTGCCAAGTGGAAAAGCTCCGTGACTCTTATGG<br>TGCAATGGCCGACTGCTGTAGCAAAGCTGATCCTGAA<br>AGAAATGAGTGTTTCCTGTCATTTAAAGTTTCCCAACC<br>AGACTTCGTTCAGCCATACCAAAGACCAGCTTCTGAT<br>GTGATATGCCAGGAATACCAGGACAACAGAGTGTCAT<br>TTCTGGGACATTTCATCTATTCTGTTGCAAGAAGACAC<br>CCCTTCTTGTATGCCCCTGCAATCCTTAGTTTTGCTGT<br>TGATTTTGAACATGCACTTCAAAGCTGTTGCAAAGAG<br>AGTGATGTCGGTGCTTGCCTGGACACCAAGGAAATTG<br>TTATGAGAGAAAAAGCCAAGGGAGTAAGTGTGAAGC<br>AGCAGTATTTTGTGGAATCTTGAAGCAGTTCGGAGA<br>TAGAGTTTTCCAAGCACGACAACTTATTTACCTAAGC<br>CAAAAAATACCCCAAGGCTCCATTCTCAGAGGTTTCTA<br>AATTTGTACATGATTCTATCGGCGTCCACAAAGAGTG<br>CTGTGAAGGGGACATGGTGGAGTGCATGGATGACATG<br>GCACGTATGATGAGCAATCTGTGCTCTCAACAAGATG<br>TTTTCTCAGGTAAAATCAAAGACTGCTGTGAGAAGCC<br>TATTGTGGAACGAAGCCAGTGCATTATGGAGGCAGAA<br>TTTGATGAGAAACCTGCAGATCTTCCTTCATTAGTTGA<br>AAAGTACATAGAAGATAAGGAAGTGTGTAAAAGTTTT<br>GAAGCAGGCCACGATGCATTCATGGCAGAGTTCGTTT<br>ATGAATACTCACGAAGACACCCCTGAGTTCTCCATACA<br>GCTTATTATGAGAATTGCCAAAGGATATGAATCACTT<br>CTGGAAAAGTGCTGCAAAACTGATAACCCTGCTGAGT<br>GCTACGCAAATGCTCAAGAGCAACTGAACCAACATAT<br>CAAAGAAACTCAGGATGTTGTGAAGACAAACTGTGAT<br>CTTCTCCATGACCATGGCGAGGCAGACTTCCTCAAGT<br>CCATCCTGATCCGCTACACTAAGAAAATGCCTCAAGT<br>ACCAACTGATCTCCTGCTTGAAACTGGAAAGAAAATG<br>ACAACTATTGGTACTAAGTGCTGCCAGCTTCCTGAAG<br>ACAGACGCATGGCTTGTTCTGAGGGTTATCTGAGCAT<br>TGTGATTCATGATACGTGCAGGAAACAGGAGACCACA<br>CCTATAAATGACAACGTTTCACAATGCTGCAGCAGCT<br>CCTATGCTAACAGAAGACCATGTTTCACTGCTATGGG<br>AGTAGATACCAAATATGTTCCTCCACCATTTAATCCTG<br>ATATGTTCAGCTTTGATGAAAATTGTGCAGTGCTCCT<br>GCTGAAGAACGAGAAGTAGGCCAGATGAAATTGCTA<br>ATCAACCTCATTAAACGCAAGCCCCAGATGACAGAAG<br>AACAAATAAAGACAATTGCTGATGGTTTCACTGCCAT |

TABLE IB-continued

| Gene | Species | NCBI # | DNA Sequence |
|---|---|---|---|
| | | | GGTTGACAAGTGCTGCAAGCAGTCGGACATCAATACA<br>TGCTTTGGAGAAGAGGGTGCCAACCTAATAGTCCAAA<br>GCAGAGCCACATTAGGAATTGGTGCTTAA (SEQ ID<br>NO: 10) |
| Wild Type<br>Albumin | Bovine | NM_<br>180992 | ATGAAGTGGGTGACTTTTATTTCTCTTCTCCTTCTCTTC<br>AGCTCTGCTTATTCCAGGGGTGTGTTTCGTCGAGATAC<br>ACACAAGAGTGAGATTGCTCATCGGTTTAAAGATTTG<br>GGAGAAGAACATTTTAAAGGCCTGGTACTGATTGCCT<br>TTTCTCAGTATCTCCAGCAGTGTCCATTTGATGAGCAT<br>GTAAAATTAGTGAACGAACTAACTGAGTTTGCAAAAA<br>CATGTGTTGCTGATGAGTCCCATGCCGGCTGTGAGAA<br>GTCACTTCACACTCTCTTTGGAGATGAATTGTGTAAAG<br>TTGCATCCCTTCGTGAAACCTATGGTGACATGGCTGA<br>CTGCTGTGAGAAACAAGAACCTGAGAGAAATGAATG<br>CTTCTTGTCACACAAAGATGATAGCCCTGATCTACCT<br>AAACTCAAACCTGACCCCAATACTTTGTGTGACGAGT<br>TTAAGGCCGATGAAAAGAAGTTTTGGGGAAAATACCT<br>ATACGAAATTGCTAGAAGACATCCCTACTTTTATGCA<br>CCAGAACTCCTTTACTATGCTAATAAATATAATGGAG<br>TTTTTCAAGAATGCTGCCAAGCTGAAGATAAAGGTGC<br>CTGCCTGCTACCAAAGATTGAAACTATGAGGGAAAAG<br>GTACTGACTTCATCTGCCAGACAGAGACTCAGGTGTG<br>CCAGTATTCAAAAATTTGGAGAAAGAGCTTTAAAAGC<br>ATGGTCAGTAGCTCGCCTGAGCCAGAATTTCCCAAG<br>GCTGAGTTTGTAGAAGTTACCAAGCTAGTGACAGATC<br>TCACAAAAGTGCACAAGGAATGCTGCCATGGAGACCT<br>ACTTGAATGCGCAGATGACAGGGCGGACCTTGCCAAG<br>TACATATGTGATAATCAAGATACAATCTCCAGTAAAC<br>TGAAGGAATGCTGTGATAAGCCTTTGTTGGAAAAATC<br>CCACTGCATTGCTGAGGTAGAAAAAGATGCCATACCT<br>GAAAACTTGCCCCCATTAACTGCTGACTTTGCTGAAG<br>ATAAGGATGTATGCAAAAACTATCAAGAAGCAAAGG<br>ATGCCTTCCTGGGCTCATTTCTTTATGAATATTCAAGA<br>AGGCATCCTGAATATGCTGTCTCAGTGCTATTGAGAC<br>TTGCCAAGGAATATGAAGCCACACTGGAGGAATGCTG<br>TGCCAAAGATGATCCACATGCATGCTATTCCACAGTG<br>TTTGACAAACTTAAGCATCTTGTGGATGAGCCTCAGA<br>ATTTAATTAAACAAAACTGTGACCAATTCGAAAAACT<br>TGGAGAGTATGGATTCCAAAATGCGCTCATAGTTCGT<br>TACACCAGGAAAGTACCCCAAGTGTCAACTCCAACTC<br>TCGTGGAGGTTTCAAGAAGCCTAGGAAAAGTGGGTAC<br>TAGGTGTTGTACAAAACCGGAATCAGAAAGAATGCCC<br>TGTACAGAAGACTATCTGAGCTTGATCCTGAACCGGT<br>TGTGCGTGCTGCATGAGAAGACACCAGTGAGTGAAA<br>AAGTCACCAAGTGCTGCACAGAGTCATTGGTGAACAG<br>ACGGCCATGTTTCTCTGCTCTGACACCTGATGAAACA<br>TATGTACCCAAAGCCTTTGATGAGAAATTGTTCACCTT<br>CCATGCAGATATATGCACACTTCCCGATACTGAGAAA<br>CAAATCAAGAAACAAACTGCACTTGTTGAGCTGTTGA<br>AACACAAGCCCAAGGCAACAGAGGAACAACTGAAAA<br>CCGTCATGGAGAATTTTGTGGCTTTTGTAGACAAGTG<br>CTGCGCAGCTGATGACAAAGAAGCCTGCTTTGCTGTG<br>GAGGGTCCAAAACTTGTTGTTTCAACTCAAACAGCCT<br>TAGCCTAA (SEQ ID NO: 11) |
| TERT | chicken | Modified<br>NM_<br>001031007.1<br>(substitution<br>made at<br>position<br>2667 T to C) | ATGGAGCGCGGGGCTCAGCCGGGAGTCGGTGTGCGG<br>CGGCTCCGCAATGTAGCGCGGGAGGAGCCCTTCGCCG<br>CGGTCCTGGGCGCGCTGCGGGCTGCTACGCCGAGGC<br>CACGCCGCTGGAGGCCTTCGTCCGGCGGCTGCAGGAG<br>GGTGGCACCGGGGAGGTCGAGGTGCTGCGAGGCGAC<br>GACGCTCAGTGCTACCGGACCTTCGTGTCGCAGTGCG<br>TGGTGTGCGTCCCCCGCGGTGCTCGCGCCATCCCCCG<br>GCCCATCTGCTTCCAGCAGTTATCCAGTCAGAGCGAA<br>GTCATCACAAGAATCGTTCAGAGGCTGTGTGAAAAGA<br>AAAGAAGAACATCCTTGCGTATGGATACTCCTTGCT<br>GGATGAGAACAGTTGTCACTTCAGAGTTTTGCCATCTT<br>CGTGTATATACAGCTATCTGTCCAATACTGTAACAGA<br>AACGATTCGCATCAGTGGCCTCTGGGAGATACTGCTG<br>AGTAGGATAGGGGACGACGTGATGATGTACCTGCTGG<br>AGCACTGTGCACTCTTCATGCTGGTTCCCCCAAGTAA<br>CTGTTACCAGGTCTGCGGGCAACCAATTTATGAACTT<br>ATTTCGCGTAACGTAGGGCCATCCCCAGGGTTTGTTA<br>GACGACGGTACTCAAGGTTTAAACATAATAGCTTGCT<br>TGACTATGTGCGAAAAAGGCTTGTGTTTCACAGGCAC<br>TATCTTTCCAAGTCGCAGTGGTGGAAGTGCAGGCCGA<br>GACGTCGAGGTCGTGTCTCCAGCAGGAGAAAAAGAA<br>GGAGCCATAGGATACAAAGCCTAAGGTCTGGTTATCA |

TABLE IB-continued

| Gene | Species | NCBI # | DNA Sequence |
|------|---------|--------|--------------|
| | | | GCCTTCTGCAAAAGTGAACTTTCAAGCAGGTAGGCAG
ATCAGCACAGTTACTGCACGTCTGGAAAAACAGAGCT
GCTCCAGTTTATGTTTGCCAGCTAGAGCACCATCTTTA
AAAAGGAAGCGTGATGGAGAACAGGTTGAAATCACA
GCTAAGAGAGTGAAAATAATGGAGAAAGAGATAGAG
GAACAGGCTTGTAGTATCGTTCCTGATGTAAACCAAA
GTAGCTCCCAGAGGCATGGAACCTCCTGGCATGTAGC
ACCACGTGCTGTAGGTCTTATTAAAGAACATTACATTT
CTGAAAGAAGTAACAGTGAGATGTCTGGTCCTTCTGT
AGTTCACAGATCTCACCCTGGGAAGAGGCCTGTGGCA
GACAAAAGCTCTTTTCCACAAGGAGTTCAGGGTAACA
AACGCATAAAGACCGGTGCAGAAAAACGAGCAGAAT
CCAATAGAAGGGGCATAGAGATGTATATAAACCCAA
TCCATAAACCCAATAGAAGGGGCATAGAGAGGCGTA
TAAATCCAACCCACAAACCTGAGTTGAATTCTGTACA
AACTGAACCAATGGAAGGTGCTTCTTCAGGGGACAGA
AAGCAGGAAAATCCCCCAGCTCATTTGGCAAAGCAGT
TACCAAATACATTGTCGCGCTCTACAGTGTACTTTGA
GAAGAAATTTCTTCTGTATTCCCGCAGTTACCAAGAA
TATTTTCCTAAATCGTTCATACTGAGCCGCCTGCAGGG
TTGTCAGGCAGGTGGAAGGCGGCTTATAGAAACTATA
TTCTTAAGCCAAAACCCATTAAAGGAACAGCAGAACC
AAAGCCTACCACAGCAAAAGTGGCGAAAGAAGAGGT
TGCCCAAACGCTACTGGCAAATGAGAGAGATATTTCA
GAAGCTGGTAAAGAACCATGAGAAGTGCCCTTATTTA
GTTTTCTTGAGGAAAAATTGCCCTGTTTTGCTTTCTGA
AGCATGTTTGAAAAAGACGGAGCTGACCTTGCAGGCG
GCTCTGCCTGGGGAAGCAAAGGTTCACAAGCACACA
GAACATGGGAAAGAGTCCACTGAGGGTACTGCACCG
AACAGCTTCCTCGCTCCTCCCTCAGTGCTAGCATGTGG
GCAGCCAGAGAGAGGGGAACAGCACCCTGCAGAGGG
GAGTGATCCGCTCCTCAGGGAGCTGCTCAGGCAGCAC
AGCAGCCACTGGCAGGTGTATGGCTTTGTGAGGGAGT
GCCTGGAGCGGGTGATCCCTGCTGAGCTGTGGGGTTC
AAGCCATAACAAATGCCGGTTCTTTAAAAACGTGAAA
GCATTCATTTCCATGGGAAGTATGCTAAGCTTTCATT
GCAGCAGCTGATGTGGAAGATGAGAGTGAATGACTG
CGTATGGCTTCGTCTGGCCAAAGGTAATCACTCTGTTC
CTGCCTATGAACATTGTTACCGTGAAGAAATTCTGGC
AAAATTCCTATACTGGCTGATGGATTCCTATGTTATCG
AGTTGCTCAAATCATTTTTCTATATCACCGAGACCATG
TTCCAGAAAAACATGCTTTTCTACTACCGAAAGTTTAT
CTGGGGCAAGTTACAGAACATTGGAATTAGAGACCAT
TTTGCCAAAGTACATCTACGTGCCTTGTCTTCAGAGG
AGATGGAAGTGATCCGTCAAAAAAAGTATTTTCCTAT
TGCATCAAGGCTCCGGTTCATTCCTAAAATGAATGGT
TTAAGACCCGTAGTAAGACTAAGCCGTGTTGTTGAAG
GACAGAAACTCAGCAAGGAAAGCAGAGAAAAGAAG
ATACAGCGCTATAACACTCAGCTAAAAAATCTATTTA
GTGTTTTAAACTATGAACGAACTGTAAACACCAGTAT
CATTGGCTCCTCAGTATTCGGGAGAGATGATATCTAC
AGGAAGTGGAAGGAGTTTGTTACAAAGGTTTTTGAAT
CAGGTGGTGAAATGCCTCATTTCTACTTTGTAAAGGG
TGATGTATCCAGAGCTTTTGATACCATTCCTCACAAG
AAACTTGTGGAAGTGATATCACAGGTCTTGAAACCTG
AGAGCCAAACTGTCTATGGAATAAGGTGGTATGCAGT
GATTATGATTACCCCAACTGGAAAAGCCAGGAAACTC
TATAAGAGACATGTTTCTACTTTCGAGGATTTTATTCC
AGACATGAAGCAGTTTGTGTCCAAGCTTCAAGAGAGA
ACTTCATTACGAAATGCAATAGTAGTTGAACAGTGCT
TAACTTTTAATGAGAACAGTTCCACCCTGTTTACTTTC
TTTCTTCAAATGTTACATAATAACATCCTGGAGATTGG
GCACAGGTACTATATACAGTGCTCTGGAATCCCACAG
GGCTCCATTTTGTCAACCTTACTTTGCAGCTTATGCTA
CGGAGACATGGAAAACAAATTACTCTGTGGGATCCAG
AAGGATGGAGTCCTAATACGTCTTATTGATGACTTTTT
GCTGGTTACGCCACATTTAATGCAGGCAAGAACTTTT
CTAAGGACTATAGCAGCAGGTATTCCTGAGTATGGCT
TTTTAATAAATGCCAAGAAGACTGTGGTGAATTTTCCT
GTTGATGATATCCCGGGATGTTCCAAGTTCAAACATC
TGCCAGATTGTCGTTTGATCTCATGGTGTGGTTTATTA
TTGGATGTGCAGACACTTGAGGTTTATTGTGATTACTC
CAGTTATGCCTTTACTTCTATCAGATCAAGTCTTTCCT
TCAATTCAAGTAGAATAGCTGGGAAAAACATGAAATG
CAAATTGACTGCAGTCCTCAAACTGAAATGCCATCCT
TTACTTCTTGACTTAAAGATCAACAGCCTTCAGACAG
TTCTAATTAACATCTACAAGATATTTTTACTTCAGGCT
TACAGGTTCCATGCCTGTGTTCTTCAGCTTCCATTCAA |

TABLE IB-continued

| Gene | Species | NCBI # | DNA Sequence |
|---|---|---|---|
| | | | CCAGAAAGTTAGGAATAATCCTGATTTCTTCCTAAGG<br>ATCATCTCTGATACTGCTTCATGCTGCTATTTTATCCT<br>GAAAGCTAAAAATCCAGGAGTTTCTTTAGGTAGCAAA<br>GATGCATCTGGCATGTTCCCTTTTGAGGCAGCAGAAT<br>GGCTGTGCTACCATGCCTTCATTGTCAAACTGTCCAAC<br>CACAAAGTTATTTACAAATGCTTACTTAAGCCCCTTA<br>AAGTCTATAAGATGCATCTGTTTGGGAAGATCCCAAG<br>GGATACTATGGAACTGCTGAAGACGGTGACGGAACC<br>ATCGCTTTGTCAAGATTTCAAAACTATACTGGACTAA<br>(SEQ ID NO: 12) |
| cMyoDER | chicken | | ATGGACTTACTGGGCCCCATGGAAATGACGGAGGGCT<br>CCCTCTGCTCCTTCACGGCCGCCGATGACTTCTATGAC<br>GACCCGTGCTTCAACACGTCGGACATGCACTTCTTCG<br>AGGACCTGGACCCCCGGCTGGTGCACGTGGGCGGGCT<br>GCTGAAGCCCGAGGAGCACCCGCACCACCACGGGCA<br>CCACCACGGGAACCCACACGAGGAGGAGCACGTGCG<br>GGCGCCCAGTGGGCACCACCAGGCCGGCCGCTGCCTG<br>CTGTGGGCGTGCAAGGCCTGCAAGAGGAAGACCACC<br>AACGCTGACCGCCGCAAAGCCGCCACCATGAGGGAA<br>CGGCGGCGGCTCAGCAAGGTCAACGAGGCCTTCGAG<br>ACCCTCAAGCGCTGCACTTCCACCAACCCCAACCAGC<br>GCCTGCCCAAGGTGGAGATCCTGCGCAACGCCATCCG<br>CTACATCGAGAGCCTGCAGGCCCTGCTGCGTGAGCAG<br>GAGGGCGATTCTTCTACAGAGCTGCGAGCTCCAACCC<br>TTTGGACAAGTCCACTGGTGGTTAAACATAACAAGAA<br>GAACAGTCCGGCTCTGTCTCTGACAGCAGAACAGATG<br>GTCAGTGCCTTGCTGGAAGCTGAGCCACCTATAGTTT<br>ATTCTGAATATGACCCCAATAGACCATTCAACGAAGC<br>ATCTATGATGACCCTGTTGACCAACCTTGCAGACAGA<br>GAATTAGTGCACATGATCAACTGGGCAAAGAGAGTTC<br>CAGGATTTGTGGATTTAACACTCCATGATCAGGTCCA<br>TCTGCTGGAATGTGCCTGGTTAGAGATATTGATGATC<br>GGCTTAGTCTGGCGCTCCATGGAACACCCAGGAAAGC<br>TTTTATTTGCACCTAATCTATTACTGGACAGGAATCAA<br>GGGAAATGTGTAGAGGGCATGGTGGAAATCTTTGACA<br>TGCTACTGGCTACTGCTGCTCGGTTTCGGATGATGAA<br>CCTTCAAGGGGAGGAATTTGTGTGCCTTAAGTCCATC<br>ATCCTGCTCAATTCTGGTGTGTACACTTTTCTTTCTAG<br>CACCTTGAAATCTCTGGAAGAGAGGGACTATATCCAC<br>CGTGTTCTGGACAAAATCACAGATACTCTGATACACC<br>TAATGGCAAAGTCAGGTCTTTCTCTGCAGCAGCAACA<br>CCGGCGACTAGCTCAGCTCCTCCTTATCCTCTCTCACA<br>TCAGGCATATGAGCAACAAAGGAATGGAGCACCTGT<br>ACAATATGAAGTGTAAAAATGTAGTTCCGCTCTACGA<br>CCTCTTACTGGAGATGCTGGACGCTCACCGCCTACAT<br>GCACCGGCAGCCAGGAGTGCTGCACCAATGGAAGAG<br>GAGAACCGAAACCAACTGACAACCGCACCAGCTTCAT<br>CTCATTCCCTGCAGTCCTTTTACATTAACAGCAAAGA<br>AGAGGAGAGTATGCAGAATACAGCTATCGCCGATGC<br>ATACTACCCAGTGCTGGAGCACTACAGCGGGGAGTCA<br>GATGCCTCCAGCCCTCGCTCCAACTGCTCCGACGGCA<br>TGATGGAGTACAGCGGGCCGCCCTGTAGCTCTCGCAG<br>GAGAAACAGCTACGACAGCAGCTACTACACGGAATC<br>ACCAAATGACCCAAAGCATGGGAAGAGTTCTGTTGTT<br>TCCAGCCTCGACTGCCTCTCAAGCATTGTGGAGAGGA<br>TTTCCACAGACAACTCCACATGTCCCATACTGCCTCCA<br>GCTGAAGCTGTAGCTGAAGGGAGTCCCTGTTCCCCCC<br>AGGAAGGAGCAAACCTGAGTGACAGTGGAGCCCAGA<br>TTCCTTCCCCCACCAACTGCACCCCTCTTCCCCAGGAA<br>AGCAGCAGCAGCAGCAGCAGCAATCCAATCTACCAA<br>GTGCTATAA (SEQ ID NO: 13) |
| IGF2 | Cow<br>[Bos<br>Taurus] | NM_<br>174087.3 | ATGGGGATCACAGCAGGAAAGTCGGTGCTGGTGCTTC<br>TTGCCTTCTTGGCCTTCGCCTCGTGCTGCTATGCTGCT<br>TACCGCCCCAGCGAGACTCTGTGCGGCGGGGAGCTGG<br>TGGACACCCTCCAGTTTGTCTGTGGGGACCGCGGCTT<br>CTACTTCAGCCGACCATCCAGCCGCATAAACCGACGC<br>AGCCGTGGCATCGTGGAAGAGTGTTGCTTCCGAAGCT<br>GCGACCTGGCCCTGCTGGAGACTTACTGTGCCACCCC<br>CGCCAAGTCCGAGAGGGATGTGTCTGCCTCTACGACC<br>GTGCTTCCGGACGACGTCACCGCATACCCCGTGGGCA<br>AGTTCTTCCAATATGACATCTGGAAGCAGTCCACCCA<br>GCGCCTGCGCAGGGGCCTGCCCGCCTTCCTGCGAGCA<br>CGCCGGGGTCGCACGCTCGCCAAGGAGCTGGAGGCG<br>CTCAGAGAGGCCAAGAGTCACCGTCCGCTGATCGCCC<br>TGCCCACCCAGGACCCTGCCACCCACGGGGGCGCCTC<br>TTCCAAGGCATCCAGCGATTAG (SEQ ID NO: 15) |

TABLE IB-continued

| Gene | Species | NCBI # | DNA Sequence |
|---|---|---|---|
| IGF1 | Zebrafish [*Danio rerio*] | NM_131825.2 | ATGTCTAGCGGTCATTTCTTCCAGGGGCATTGGTGTGA TGTCTTTAAGTGTACCATGCGCTGTCTCCCGAGTACCC ACACCCTCTCACTGGTGCTGTGCGTCCTCGCGTTGACT CCCGCGACTCTGGAGGCGGGGCCGGAGACGCTGTGC GGGGCGGAGCTTGTAGACACGCTGCAGTTTGTGTGTG GAGACAGGGGCTTTTATTTCAGCAAACCGACAGGATA TGGACCTAGTTCAAGAAGGTCACACAACCGTGGCATC GTGGACGAATGCTGCTTTCAGAGCTGTGAGCTACGGC GCCTCGAGATGTATTGTGCGCCTGTGAAGACAGGCAA ATCTCCACGATCTCTACGAGCACAACGACACACAGAT ATTCCCAGGACACCAAAGAAACCTATATCTGGGCATA GCCACTCTTCCTGTAAGGAGGTTCATCAGAAGAACTC GAGCCGAGGAAACACAGGGGGCAGAAACTATCGCAT GTAG (SEQ ID NO: 16) |
| serum albumin 1 | Rainbow trout [*Oncorhynchus mykiss*] | XM_021614654.1 | ATGAGGAGACCCTGTATCCTGGCCATCCAGCCTGACA CGGAGTTCATGCCCCCAGAGCTGGATGCCAGCAACTT CCACATGGGCCCTGAGCTCTGCACCAAGGACAGCAAG GAGCTGCTGCTCTCTGGGAAGAAACTACTGTATGGTG TGGTCAGACATAAGACCACCATCACTGAGGAGCAGCT GAAGTCCATCTCTACTAAATATCACAGTATGAAGGAG AAGTGCTGTGCTGCTGAGGACCAAGCAGCATGCTTCA CTGAGGAGGCACCCAAGCTGGTTGCTGAGAGTGCAG AGCTGGTCAAGGCTTAA (SEQ ID NO: 17) |
| GLUL | Tilapia [*Oreochromis niloticus*] | NM_001279668.1 | ATGGCTACATCCGCCAGCGCCAGCTTGAGTAAAGCTG TCAAGCAGCAGTACATGGAGCTCCCTCAGGGGGACA AAGTCCAGGCCATGTACATCTGGATCGACGGAACCGG AGAGGGGCTCCGATGCAAAACCAGGACGCTTGATTCT GAGCCCAAAAGCATCGAAGATCTTCCTGAATGGAACT TTGACGGATCCAGTACCTACCAGTCCGAAGGCTCCAA CAGCGACATGTATCTGATCCCCTCAGCCATGTTCCGC GATCCATTCCGCAAAGACCCCAACAAGCTGGTGCTGT GTGAAGTCCTGAAGTACAACCGTAAACCTACAGAAAC CAACCTTCGGCTCACCTGTAAGAAAGTGATGGATATG GTGGCGGATCAGCATCCTTGGTTTGGCATGGAGCAGG AGTACACCATCCTTGGAACGGACGGGCATCCATTTGG CTGGCCATCTAATGGTTTCCCCGGACCACAGGGGCCG TACTACTGTGGTGTTGGAGCTGACAAAGCCTATGGCA GGGACGTAGTCGAGGCCCATTACAAAGCTTGTTTGTA CGCTGGAGTCCAGATTTGTGGCACAAATGCTGAAGTA ATGCCTGCTCAGTGGGAGTTCCAGGTCGGACCTTGCG AAGGCATTGACATGGGCGATCATTTGTGGGTAGCGCG CTTCATCCTGCACCGTGTCTGTGAGGATTTTGGCGTCG TCGCCTCATTTGATCCCAAGCCAATCCCTGGAAACTG GAACGGTGCTGGCTGCCATACAAACTTCAGCACGAAA GAGATGAGGGAAGACGGTGGATTGAAAGCTATTGAG GATTCCATTGAGAAGCTTGGAAAGAGGCACAGCTACC ACATTCGTGCCTACGACCCCAAAGGGGGGCTCGACAA CGCCCGCCGTCTCACTGGCCGCCATGAAACCTCAAAC ATCAACGAATTCTCTGCTGGTGTGGCCAACCGTGGTG CCAGCATTCGCATTCCTCGTAATGTTGGTCAGGAGAA GAAAGGCTACTTCGAAGACCGTCGCCCTTCAGCCAAC TGTGACCCGTACAGTGTGACCGAGGCCCTGATCCGCA CCTGTCTGCTGAACGAGGAAGGAGATGAACCCGCGG ATTACTAA (SEQ ID NO: 18) |
| IGF2 | Rainbow trout [*Oncorhynchus mykiss*] | NM_001124697.1 | ATGGAAACCCAGAAAAGACACGAATACCACTCAGTTT GTCACACCTGCCGGAGAACGGAAAACACAAGAATGA AGGTCAAGATGATGTCTTCGTCAAATCGAGTGCTGGT CATTGCGCTGGCACTTACTCTGTACATTGTTGAAGTGG CTTCGGCAGAAACGCTATGTGGAGGAGAACTGGTGG ACGCGCTGCAGTTCGTCTGTGAAGATAGAGGATTCTA TTTCAGTAGGCCAACCAGCAGGTCTAACAGCAGACGC TCCCAGAACCGTGGTATCGTGGAGGAGTGTTGTTTCC GTAGCTGTGACCTCAACCTGTTGGAGCAGTACTGTGC CAAACCTGCCAAGTCAGAGAGGGACGTGTCGGCCAC CTCTCTACAGATCATTCCCATGGTGCCCACAATCAAA CAGGATGTCCCAAGAAAACATGTGACTGTGAAGTATT CCAAATATGAGGCGTGGCAGAGGAAGGCTGCTCAGC GGCTCCGGAGGGCGTCCCGGCCATCCTCAGGGCCCG GAAGTTCCGGAGGCAGGCGGTGAAGATCAAGGCCCA AGAGCAGGCGATGTTCCACCGGCCTCTGATCACCCTG CCCAGCAAGCTTCCCCCAGTCCTGCCCCCACGGACA ACTACGTCAGCCACAATTGA (SEQ ID NO: 19) |

TABLE IB-continued

| Gene | Species | NCBI # | DNA Sequence |
|---|---|---|---|
| IGF1 | Tropical clawed frog [Xenopus tropicalis] | XM_00293 6829.4 | ATGGAAAAAAACAACAGTCTTTCAACACAATTATTTA<br>AGTGCTACTTTTGTGATTTCTTAAAGCTGAAGATGCAC<br>AAAATGTCCTACATTCATCTGCTCTACCTGGCTTTGTG<br>TTTCCTGACTTTAACCCATTCAGCAGCTGCTGGACCAG<br>AGACCCTCTGTGGAGCCGAACTGGTAGACACTCTTCA<br>GTTTGTATGTGGAGACAGAGGCTTCTATTTTAGCAAG<br>CCAACAGGGTACGGATCCAGCAATCGAAGATCGCATC<br>ACAGAGGAATAGTAGATGAGTGCTGTTTCCAAAGCTG<br>TGATTTCAGAAGGCTGGAGATGTACTGCGCTCCTGCC<br>AAGCCAGCCAAATCAGCACGTTCTGTACGTGCTCAAC<br>GTCACACTGACATGCCAAAAGCCCAGAAGGAAGTAC<br>ACCTAAAGAATGCAAGTCGAGGAAACACAGGGAGTC<br>GAGGATTCCGAATGTAA (SEQ ID NO: 20) |
| GLUL | Tropical clawed00491 frog [Xenopus tropicalis] | XM_ 4038.3 | ATGGCAACCTCCGCCAGTGCTCAGTTGAGTAAGGCCA<br>TAAAGCAGATGTATCTGGAACTGCCACAGGGAGATA<br>AGGTGCAGGCTATGTACATCTGGGTTGATGGGACCGG<br>GGAGGGTCTTCGCTGCAAGACTCGCACTCTGGACAGT<br>GAACCCAAGACCATAGAAGATCTTCCTGAATGGAACT<br>TCGATGGATCTAGCACATACCAATCCGAGGGTTCCAA<br>CAGTGACATGTACCTGATTCCAGTTGCAATGTTTAGA<br>GACCCTTTTCGAAGGGACCCCAACAAGCTGGTACTCT<br>GCGAGGTGCTCAAATACAACCGAAAAACAGCTGAAA<br>CAAACTTGCGTCATACATGTAACCAGATAATGGACAT<br>GATGGCCAATGAGCATCCATGGTTTGGCATGGAACAG<br>GAATACACATTGCTGGGTATGGATGGACACCCTTTTG<br>GCTGGCCTTCAAATGGCTTCCCAGGACCACAAGGTCC<br>CTATTACTGTGGAGTGGGTGCAGATAAGGCATATGGT<br>CGGGATATTGTGGAGGCTCATTATCGGGCTTGCCTTTA<br>TGCTGGTGTGAAAATTGCAGGAACAAATGCAGAAGTT<br>ATGCCAGCACAGTGGGAGTTCCAAATTGGGCCATGTG<br>AGGGAATAGAAATGGGAGATCACCTTTGGATTGCTCG<br>ATTTATACTGCATAGAATTTGTGAGGATTTTGGGATCA<br>TTGTTTCGTTTGACCCAAAGCCCATAACTGGAAACTG<br>GAATGGAGCTGGATGTCACACCAATTTCAGCACAAAG<br>TCAATGCGTGAAGAAGGAGGCCTTAAGGACATAGAA<br>GAATCCATTGAACGTCTAAGCAAACGTCATGATTATC<br>ACATCAGAATGTATGACCCAAGGGGTGGTAAAGACA<br>ATGCCCGTCGTCTCACAGGTTTCCATGAGACCTCCAG<br>CATCCATGAGTTCTCTGCAGGAGTGGCAAACCGTGGT<br>GCCAGTATCCGCATTCCCCGCAGTGTAGGCCAGGAGA<br>AGAAAGGCTATTTTGAAGATCGTCGTCCATCAGCCAA<br>CTGTGATCCCTATGCTGTGACAGAAGCTATGATCAGA<br>ACCTGCCTACTGAATGAAACTGGAGACGAACCTCTTG<br>AATACAAGAACTAA (SEQ ID NO: 21) |
| ALB | Tropical clawed frog [Xenopus tropicalis] | BC075287.1 | ATGAACGCGTTGATGCGGCGTGCCTGCTGCGGGGCGC<br>TATTCCCCCTCTCATTCCGACTGGCCGCGCTGAGCCCT<br>ATGAAGGGAGCTAGTAACTTTAGCTGCGGTAACGTGT<br>GCGCCTCTCCTGCCGGATGTTGGGCGCCACCAAGTGG<br>ACACGACACGGGGATAAAAGTGTACAACAGCCTTACT<br>AGGAGGAAGGATCCACTTATTCTGGCAGATCCGACAG<br>TAGCGACATGGTATAGCTGTGGACCTACAGTTTATGA<br>CCATGCACATCTTGGACATGCATGTTCTTATGTTAGAT<br>TTGACATAATTCGAAGGATTCTGCTCAAGGTTTTTGGG<br>ATTGATACAGTCGTGGTGATGGTAGTCACAGACATTG<br>ATGATAAGATAATCAAGAGAGCAAAGGAGCTCAATA<br>TATCTCCTGTGGCCTTAGCTCGTACTTACGAACAGGAT<br>TTTAAACAAGACATGACTGCGTTGAAGGTCCTTCCAC<br>CAACAGTATACATGAGAGTTACTGAAAATATTCCACA<br>GATCATATCATTTATTGAACACATAATTGCCAATGGA<br>TATGCATATGCTACCTCACAAGGAAATGTTTATTTTGA<br>TGTTCAGTCGATTGGAGAGCGATATGGGAAATTTAAT<br>GATTCTTTCAGTGTGATACAGCCAGCGAATCAGCATCAC<br>AAGATAAAAGGCATATCCGAGATTTTGCTTTGTGGAA<br>AACATCCAAGCCTGAGGAGCCTTACTGGGCTTCTCCT<br>TGGGGCAAGGGAAGACCTGGCTGGCACATAGAGTGT<br>TCCACAATTGCAAGTTCTGTATTTGGCAAACATCTAG<br>ACATTCACACTGGTGGGATTGACCTTGCTTTCCCTCAT<br>CATGAAAATGAAATTGCTCAGTGTGAGGCATATCACC<br>AGAGCACACAGTGGGGAAACTATTTCCTTCATACTGG<br>ACATTTACATTTGAAAGGGAATGAAGAAAAAATGTCA<br>AAATCCCTGAGAAACTATCTGACAGTTAAGGAGTTTT<br>TAAAGTCCTTTTCCCCTGACCAGTTTAGAATGTTTTGT<br>CTGCGCTCAAAATATAAATCAGCCGTGGAATACAGCA<br>ACGGGTCCATGCATGATGCAGTAAATACCCTACACAC<br>CATCTCTTCGTTTGTCGATGATGCAAAAGCCTATATGA |

TABLE IB-continued

| Gene | Species | NCBI # | DNA Sequence |
|---|---|---|---|
| | | | AAGGTCAGCTGATTTGCCAACCAGTGCAGGAGGCTTT<br>ACTCTGGCAAAGGCTGAATGAAACAAAAGTAAATGTT<br>AAGGCTGCGTTTTCAGATGACTTTGACACCCCACGAG<br>CAGTTGATGCAGTTATGGACCTCATTCACCATGGCAA<br>CAGACAGCTTAAGGCTGTTTCCAAGGAGTCAAACTCT<br>CCCAGGAGCTCTGTAGTTTATGGTGCCATGATCTCTTA<br>CATTGAACAATTTCTGGAGATATTGGGAATTTCCTTGA<br>GCCAAAACCAGGTCGCTGCAGAAGATAGACACTCGG<br>CTGTTCTCTTTAATGTAGTAGAAGAAATGATCAGTTTT<br>AGAAGTAAGGTGCGGAATTACGCCCTGGCTGCAGATG<br>AATCACCAAATGCAATAGGACAAGAGGAAAAACAGC<br>AATACAAGGAGAGGAGAAGGCAGTTGTTACTGGAAA<br>GGGAACCACTCCTACAGGCTTGTGACATAATGCGCCA<br>ACATCTGGCTGTATATGGCATAAATGTAAAGGATCGT<br>GGAAATACATCAACATGGGAACTACTTTGACCGCAAA<br>GAAGAAACCTAG (SEQ ID NO: 22) |
| IGF2 | Tropical clawed frog [*Xenopus tropicalis*] | NM_001113672.1 | ATGAGGCATCTCCTCCTCCTCTCTATCACCTTCCTGGT<br>ATACACGCTAGACTCTGCTAAAGCCTATGGAGCAACG<br>GAGACCCTGTGCGGTGGGGAGCTGGTGGACACCCTGC<br>AGTTTGTTTGTGGAGACAGGGGCTTCTATTTCAGCAG<br>GAATAATGGCCGCTCCAACCGCAGGGCTAACAGGGG<br>GATTGTGGAAGAATGTTGCTTCCGGAGCTGTGATTTG<br>GAACTGTTGGAAACGTACTGCGCAAAGCCAGCTAAG<br>AACGAGAGGGATGTCTCCACTGCACCCTCCACAGCAA<br>TACCACCACTGAACAAGCAGGACCTGTACCACAAACA<br>TCACCACACAAAGAGCTCCAAGTATGACATTTGGCAG<br>AGGAAGTCTATCCATCGGCTGCGGAGAGGAGTCCCTG<br>CCATTGTACGTGCTAGGCAGTATCGATTGCTAATGCA<br>GCAGGCTGAAGAATCAGAGCAGGCACTATCACATCG<br>GCCCCTTACCACCTTACCCATAACGCGGCCTCTCCATC<br>TGCAACAAACCTCAGAACCTTCCCTCAATTGA (SEQ ID NO: 23) |
| GLUL | Chicken [*Gallus gallus*] | NM_205493.1 | ATGGCCACCTCGGCGAGCTCCCACCTGAGCAAAGCCA<br>TCAAGCACATGTACATGAAGCTGCCGCAGGGTGAGA<br>AGGTCCAAGCCATGTACATCTGGATCGACGGGACTGG<br>GGAGCACCTCCGCTGCAAAACCCGCACTCTGGACCAC<br>GAACCCAAGAGCCTGGAAGATCTCCCCGAGTGGAACT<br>TTGATGGCTCCAGCACCTTCCAAGCCGAAGGCTCCAA<br>CAGCGACATGTACCTGCGACCTGCTGCCATGTTCCGG<br>GACCCTTTTCGCAAGGATCCCAACAAATTAGTTCTCT<br>GTGAGGTCTTCAAATACAACCGCCAGTCTGCAGACAC<br>AAATCTTCGGCACACCTGTAGGCGGATTATGGATATG<br>GTGTCCAACCAGCACCCCTGGTTTGGGATGGAGCAGG<br>AGTACACCCTTCTGGGAACAGATGGTCATCCGTTTGG<br>CTGGCCTTCCAATTGCTTCCCTGGACCCCAAGGTCCGT<br>ACTACTGCGGTGTAGGAGCTGACAAAGCCTATGGCAG<br>AGACATTGTGGAGGCCCACTACCGAGCGTGCCTGTAT<br>GCTGGTGTGAAAATTGGAGGAACCAACGCAGAAGTG<br>ATGCCAGCCCAGTGGGAGTTCCAGGTGGGACCGTGCG<br>AAGGGATTGAGATGGGGGATCACCTCTGGATAGCAC<br>GTTTCATCCTCCACCGGGTGTGCGAAGACTTTGGTGTC<br>ATTGTGTCCTTCGATCCCAAACCCATCCCTGGGAACT<br>GGAACGGTGCTGGCTGTCACACCAACTTCAGCACCAA<br>GAACATGAGGGAAGATGGAGGTCTCAAGCACATCGA<br>GGAGGCCATCGAGAAGCTGAGCAAGCGCCACCAGTA<br>CCACATCCGTGCCTACGACCCCAAAGGAGGGCTGGAC<br>AACGCCCGGCGCCTGACGGGCTTCCACGAGACGTCCA<br>GCATCCACGAGTTCTCCGCCGGCGTGGCCAACCGCGG<br>CGCCAGCATCCGCATCCCACGCAACGTGGGCCATGAG<br>AAGAAAGGCTACTTCGAGGACCGCGGGCCTTCAGCCA<br>ACTGCGATCCCTACGCCGTGACGGAGGCCCTGGTCCG<br>TACGTGTCTCCTCAACGAAACCGGGGACGAGCCTTTT<br>GAGTACAAGAACTAa (SEQ ID NO: 24) |
| IGF2 | Chicken [*Gallus gallus*] | NM_001030342 | ATGTGTGCTGCCAGGCAGATACTGCTGCTACTGCTGG<br>CCTTCCTGGCCTATGCGTTGGATTCAGCTGCGGCGTAT<br>GGCACGGCGGAGACCCTCTGCGGTGGGGAGCTGGTG<br>GACACACTGCAGTTCGTCTGTGGGGACAGGGGCTTCT<br>ACTTCAGTAGACCAGTGGGACGAAATAACAGGAGGA<br>TCAACCGTGGCATTGTGGAGGAGTGCTGCTTTCGGAG<br>CTGTGACCTGGCTCTGCTGGAAACCTACTGTGCCAAG<br>TCCGTCAAGTCAGAGCGTGACCTCTCCGCCACCTCCC<br>TCGCGGGCCTCCCAGCCCTCAACAAGGAGAGCTTCCA<br>GAAGCCATCTCATGCCAAGTACTCCAAGTACAACGTG<br>TGGCAGAAGAAGAGCTCGCAGCGGCTGCAGCGGGAG<br>GTGCCAGGCATCCTGCGTGCCCGTCGGTACCGGTGGC |

TABLE IB-continued

| Gene | Species | NCBI # | DNA Sequence |
|---|---|---|---|
| | | | AGGCGGAGGGGCTGCAAGCAGCTGAGGAAGCCAGGG<br>CGATGCATCGTCCCCTCATCTCCTTGCCCAGTCAGCGG<br>CCCCCAGCGCCGCGGGCATCCCCTGAAGCGACCGGCC<br>CCCAGGAATGA (SEQ ID NO: 25) |
| TERT | Cow<br>[*Bos taurus*] | NM_<br>001046242.1 | ATGCCGCGCGCGCCCAGGTGCCGGGCCGTGCGCGCCC<br>TTCTGCGGGCCAGCTACCGGCAGGTGCTGCCCCTGGC<br>CGCCTTCGTACGGCGCCTGCGGCCCCAGGGCCACCGG<br>CTTGTGCGGCGCGGGGACCCGGCGGCCTTCCGCGCGC<br>TGGTGGCTCAGTGCTTGGTGTGCGTGCCCTGGGACGC<br>GCAGCCGCCCCTGCCGCCCCGTCCTTCCGCCAGGTG<br>TCCTGCCTGAAGGAGCTGGTGGCCAGAGTCGTGCAGA<br>GGCTCTGCGAGCGCGGCGCGAGGAACGTGCTGGCCTT<br>CGGCTTCACGCTGCTGGCCGGGGCCCGCGGCGGGCCG<br>CCCGTGGCCTTCACGACCAGCGTACGCAGCTACCTGC<br>CCAACACGGTAACCGACACGCTGCGCGGCAGCGGCG<br>CCTGGGGGCTGCTGCTGCACCGCGTGGGCGACGACGT<br>GCTCACCCACCTGCTGTCGCGCTGCGCGCTCTACCTGC<br>TGGTGCCCCCGACCTGCGCCTACCAGGTGTGTGGGCC<br>GCCGCTCTATGACCTCCGCGCCGCCGCCGCCGCCGCT<br>CGTCGGCCCACGCGGCAAGTGGGCGGGACCCGGGCG<br>GGCTTCGGACTCCCGCGCCCGGCCTCGTCGAACGGCG<br>GCCACGGGAGGCCGAAGGACTCCTGGAGGCGCGGG<br>CCCAGGGCGCGAGGCGGCGTCGCAGTAGCGCGCGGG<br>GACGACTGCCTCCAGCCAAGAGGCCCAGGCGCGGCCT<br>GGAGCCCGGGCGGGATCTCGAAGGGCAGGTGGCCCG<br>CAGCCCGCCCCGCGTGGTGACACCTACCCGAGACGCT<br>GCGGAAGCCAAGTCTCGGAAGGGCGACGTGCCCGGG<br>CCCTGCCGCCTCTTCCCGGGCGGCGAGCGGGGTGTCG<br>GCTCCGCGTCCTGGCGGCTGTCACCCTCGGAGGGCGA<br>GCCGGGTGCCGGAGCTTGCGCTGAGACCAAGAGGTTC<br>CTTTACTGCTCCGGCGGTGGCGAACAGCTGCGCCGCT<br>CCTTCCTGCTCTGCTCCCTGCCTCCCAGCCTGGCCGGG<br>GCGCGGACACTCGTGGAAACCATCTTTCTGGACTCGA<br>AGCCCGGGCCGCCAGGGGCTCCCCGCCGGCCGCGCCG<br>CCTGCCCGCGCGCTACTGGCAGATGCGGCCCCTGTTC<br>CGGAAACTGCTTGGGAACCACGCGCGGAGCCCCTATG<br>GCGCGCTGCTCAGGGCGCACTGCCCGCTGCCGGCCTC<br>TGCGCCCCGGGCGGGGCCAGACCATCAGAAGTGCCCT<br>GGTGTTGGGGGCTGCCCCTCTGAGAGGCCGGCCGCTG<br>CCCCCGAGGGCGAGGCGAACTCAGGGCGCCTGGTCC<br>AGCTGCTCCGCCAGCACAGCAGCCCCTGGCAGGTGTA<br>CGGGCTCCTGCGGGCCTGTCTTCGCCGCCTGGTGCCC<br>GCCGGCCTCTGGGGCTCCCGGCACAACGAGCGGCGCT<br>TCCTGCGGAACGTGAAGAAGCTCCTCTCCCTGGGGAA<br>GCACGGCAGGCTCTCGCAGCAGGAGCTCACGTGGAA<br>GATGAAGGTGCAGGACTGCGCCTGGCTGCGCGCGAG<br>CCCAGGGGCTCGCTGCGTGCCCGCCGCGGAGCACCGC<br>CAGCGCGAGGCCGTCCTGGGTCGCTTCCTGCACTGGC<br>TGATGGGCGCCTACGTGGTGGAGCTGCTCAGGAGCTT<br>CTTCTACGTCACAGAGACCACGTTCCAGAAGAACCGG<br>CTCTTCTTCTTCCGGAAGCGCATCTGGAGCCAGCTGC<br>AGCGCCTGGGCGTCAGACAACACTTAGACCGTGTGCG<br>GCTTCGAGAACTGTCAGAAGCAGAGGTCAGGCAGCA<br>CCAGGAGGCCAGGCCGGCTCTGCTGACATCCAGGCTC<br>CGTTTCGTCCCCAAGCCCGGCGGGCTGCGGCCCATCG<br>TGAACGTGGGCTGTGTTGAGGGCGCCCCGGCACCGCC<br>CAGAGACAAGAAGGTGCAGCATCTCAGCTCACGGGT<br>CAAGACGCTGTTCGCGGTGCTGAACTACGAGCGAGCT<br>CGGCGGCCTGGCCTCCTGGGGGCCTCGGTGCTGGGCA<br>TGGACGACATCCACAGGGCCTGGCGGGCCTTCGTGCT<br>GCCCCTGAGGGCCCGGGGCCCAGCCCCCCCGCTCTAC<br>TTCGTCAAGGTGGACGTGGTGGGGGCTACGATGCCC<br>TCCCCCAGGATAAGCTGGCAGAGGTGATCGCTAACGT<br>GCTGCAGCCGCAGGAGAATACGTACTGCGTGCGCCAC<br>TGCGCCATGGTCCGGACTGCGCGCGGGCGCATGCGCA<br>AGTCCTTCAAGAGACACGTGTCCACCTTCTCGGACTT<br>CCAGCCGTACCTGAGGCAGCTCGTGGAGCATCTGCAG<br>GCGATGGGCTCCCTGAGGGACGCCGTGGTCATCGAGC<br>AGAGCTGCTCCCTGAACGAGCTGGCAGCAGCCTCTT<br>CAACCTCTTCCTGCACCTGGTCCGCAGCCACGTCATC<br>AGGATCGGGGCAGGTCCTACATCCAGTGTCAGGGG<br>ATCCCCCAGGGCTCCATCCTGTCTCACCCTGCTCTGCAG<br>CTTCTGCTATGGGACATGGAGAACAAGCTCTTCCCT<br>GGAGTCCAGCAGGACGGGGTGCTTCTGCGCCTGGTGG<br>ACGACTTCCTGCTGGTCACCCCACACCTGACGCGGGC<br>CAGAGACTTCCTCAGGACGCTGGTGCGCGGTGTGCCT<br>GAGTATGGCTGCCAGGTGAACCTGCGGAAGACGGTG |

TABLE IB-continued

| Gene | Species | NCBI # | DNA Sequence |
|---|---|---|---|
| | | | GTGAACTTCCCCGTGGAGCCCGGGGCCCTGGGCGGCG<br>CGGCGCCCCTGCAGCTGCCGGCCCACTGCCTGTTCCC<br>CTGGTGCGGCCTGCTGCTGGATACCCGCACCCTGGAG<br>GTGCATGGCGACCACTCCAGTTATGCCCGGACGTCCA<br>TCAGAGCGAGTCTCACCTTCACCCAGGGCTTCAAGCC<br>CGGGAGGAACATGCGTCGCAAGCTGTTGGCGGTCTTG<br>CAGCTCAAGTGCCATGGGCTCTTCCTGGACCTGCAGG<br>TGAACAGTCTGCAGACGGTCTTCACAAACGTTTACAA<br>GATATTCCTGCTGCAGGCCTACAGGTTCCACGCCTGC<br>GTGCTGCAGCTGCCCTTCAGCCAGCCGGTCAGGAGCA<br>GCCCCGCGTTCTTTCTCCAGGTCATCGCCGACACCGC<br>ATCCCGCGGCTACGCCCTCCTGAAAGCCAGGAACGCA<br>GGGGCGTCACTGGGGGCCAGGGGCGCCGCCGGCCTG<br>TTCCCGTCTGAAGCTGCGCAGTGGCTGTGTCTCCACG<br>CCTTCCTGCTCAAGCTGGCTCGCCACCGTGTCACCTAC<br>AGCCGCCTGCTGGGGGCCCTCCGGACAGCCCGAGCAC<br>GGCTGCACCGGCAGCTCCCGGGGCCCACACGGGCCGC<br>CCTGGAGGCGGCGGCCGACCCCGCCCTGACCGCAGAC<br>TTCAAGACCATCTTGGACTGA (SEQ ID NO: 39) |
| TERT | Porcine<br>[Sus<br>scrofa] | NM_<br>001244300.2 | ATGCCGCGCGCGCCCCGGTGCCGGGCCGTGCGCTCCC<br>TGCTCCGGGACCGCTACAGGCAGGTGCTGCCGCTGGC<br>CACCTTCGTGCGGCGCGCCTGGGCCCTGAGGGCCGCGG<br>CTTGTTCGGCGCGGGGACCCGGCGGCTACCGCGCGC<br>TGGTGGCGCAGTGCCTGGTGTGCGTGCCCTGGGACGC<br>GCAGCCGCCTCCTGCCTCCCCGTCCTTCCGCCAGGTGT<br>CCTGCCTGAAGGAGCTGGTGGCCAGGGTCGTGCAGAG<br>GCTCTGCGAGCGCGGCGCGAGGAACGTGCTGGCCTTT<br>GGCTTCGCGCTGCTGGACGGGGCTCGCGGCGGGCCGC<br>CCGTGGCCTTCACGACCAGCGTGCGCAGCTACCTGCC<br>CAACACCGTGACCGACACACTGCGCGGGAGCGGCGC<br>GTGGGGGCTGCTGCTGCGCCGCGTGGGCGACGACGTG<br>CTCACCCACCTGTTGGCGCGCTGCGCGCTGTACCTGCT<br>GGTGCCCCCGAGTTGCGCCTACCAGGTGTGCGGGCCG<br>CCACTCTATGACCTCTACACCGCAGCGGAGGCTCGGC<br>CCATGCGACACAAGGGCCAGACCCCGACTGGCCTCGG<br>ACTCACGCGCCCCGTTTGCAATGGGGAAGCCGGGCGA<br>CCCCAGGAGCAGAGGGCGCAAGGTGTGAGGCGACGT<br>CGGGGCAGAGCGGGGGACATCCACTTCCAGCCAAG<br>AGGCCCAGGCACGTCCCGGAGCCTGAACAGGGTCCC<br>GAAGGGCAGGCGTCCCGGGCCCACCAGGGCAGGGCG<br>CCTGGGCCGAGCGACAGCGACCCCCCCGTGATGACAC<br>CTACCAGAGCCGCTGCGAAAGCCAAGTCTCGGGAGG<br>GTGAGGCGCCCGGAACCCGGCCACCTTTCCCCTCAAGC<br>AGGCGGTGCGCGGGGTACCTGCCCCCATCCTGGTGG<br>CAGCCACACCTCCAGGGCAAGCCCAGTCCTCATGTGT<br>GCGCTGCCGAGACCAAGCGCTTCCTCTACTGCTCGGG<br>GAGCAAGGAAGGGCTGCGCCGCTCGTTCCTGCTCTGC<br>TCCCTGCCGCCCAGCCTGGCGGGGGCCGGGAGGCTCG<br>TGGAGGTCATCTTTCTGGCCTCAAAGCCCGGGCAGCC<br>AGGGGCGCGCCGCGTGCCCGCACGCTACTGGCGGATG<br>AGGCCCCTGTTCCGGGAGCTGCTTAAGAACCACGCGC<br>GGTGCCCCTACAAGGCGCTTCTCAGGGCGCACTGCCC<br>GTTGCGGGCTGCGGCGACCCTCTCGGGGTCCGGCGGT<br>CAGGTGTGCGACCACAAAGTGGGCCCCCTCGCTCCAG<br>AGCGGCTGGCAGCGGCCGCCGAGGGGACTCGGCCT<br>CGAGGCGCCTAGTCCAGCTGCTCCGCCAGCACAGCAG<br>CCCCTGGCAGGTGTACCGCCTCCTGCGGGCCTGTCTTC<br>ACCGGCTGGTGCCCCGGGCCTCTGGGGCTCCCCGCA<br>CAACAAGCGGCGCTTTCTGAAGAATGTGAAGAAGCTC<br>GTCTCCCTGGGGAAGCACGCCAGGCTCTCGCTGCAGG<br>AGCTGATGTGGAAGATGAAAGTGCAAGACTGCATCTG<br>GCTGCGCCGGAGCCCGACGCTCGCCATGTCCAGGCC<br>GCCGAGCACCGTCTGAGAGAGGCCATTCTGGCCAAGT<br>TCCTGCGCTGGTTGATGGGCACGTACGTGGTCGAGCT<br>GCTCAGGTCGTTTTTTTATGTCACGGAGACCACGTTTC<br>AGAAGAACCGGCTCTTCTTCTTCCGGAAGCGCATCTG<br>GAGCCGGCTGCAGAGCGCAGGCATCAGGCAACACTT<br>AGATCGTGTGCGGCTTCGAGAACTGTCGGAAGCAGAG<br>ATCAGGCGACGCCGGGAGGCCAGGCCCGCTGTACTG<br>ACCTCCAAGCTCCGCTTCGTCCCCAAACCCGACGGGC<br>TGCGGCCCATCGTGAACATGGCGAACGTCGTGCGAGC<br>CAGGACAGGCCCCGGAGACAAGAAGGTCCGGCGTCT<br>CACGGGGCAGGTCAAGACGCTGTTTGCTGTGCTGAAC<br>TACGAGCGGGCGCGGCGCCCGCGCCTCCTGGGGGCCT<br>CCGTGCTGGGCGTGGGTGACATCCACAGGGCCTGGCG<br>GGCCTTTGTGCTGCCCCTGCGGGCCCAGGACCCGGCC<br>CCCCCGCTGTACTTTGTCAAGGTGGACGTGACGGGGG |

TABLE IB-continued

| Gene | Species | NCBI # | DNA Sequence |
|---|---|---|---|
| | | | CCTACGACGCCCTCCCTCAGGACAGGCTGCTGGAGGT<br>GGTCGCCAACGTGATCCGGCCCCACGAGAGCACGTAC<br>TGCGTGCGCCAGTGCGCCGTGCTCCGGAGGACCGCCC<br>GCGGGCACGTGCGCAAGTCCTTCCAAACCCACGTGTC<br>CACCTTCGCAGACCTCCAGCCTTACATGAGACAGTTT<br>GTGGCACACCTGCAGGCAACCGGCCCGCTGAGGGAC<br>GCCGTGGTCATCGAGCAGAGCTGCTCTCTGAACGAGG<br>CCGGCAGCCGTCTCCTGGAGCTTTTCCTGAGCCTGCTG<br>CGAAACCACGTCATCCGGATCGGGGGCAGGTCCTACG<br>TCCAGTGTCAGGGGATCCCACAGGGCTCCATTCTGTC<br>CACGCTGCTCTGCAGCCTGTGCTACGGGGACATGGAA<br>AACAGACTCTTCCCCGGGATCCAGCGTGACGGGGTGC<br>TCCTGCGCTTGGTGGACGACTTCCTGCTGGTGACCCCT<br>CACCTGACACGAGCCAAAGCCTTTCTCAGGACCCTGG<br>TCCGCGGCGTGCCCGAGTACGGCTGCCTGGCCAACTT<br>GCGGAAGACGGCCGTGAACTTCCCTGTGGAGGACGG<br>CGCCCGGGGCGGCCCGGCCCCACTGCAGCTGCCGGCA<br>CACTGCCTGTTCCCCTGGTGCGGGCTGCTGCTGGACA<br>CCCGCACGCTGGAGGTGCACTGCGACTATGCCAGTTA<br>CGCCCGGACCTCGATCAGAGCGAGTCTCACCTTCAAC<br>CAGGGCTTCAAGCCCGGGAGGAACATGCGCCGCAAG<br>CTCTTGGCGGTCTTGCGGCTAAAGTGCCACGGGATCC<br>TTCTGGACCTGCAGGTGAACAGTCTTCCGACGGTGCT<br>CGCCAACGTTTACAAGATCTTCCTGCTGCAGGCCTAC<br>AGGTTCCACGCGTGTGCTGCAGCTGCCCTTCCGTC<br>AGCCGCTTGCGAGGAACCCCTCATTTTCCTCCGGCTT<br>GTCTCCGACACCGCGTCCTGCTGCTACTCGCTCCTGAA<br>AGCCAGAAACGCAGGGATGTCCCTGGGAGCCAGGGG<br>CGCCTCCGGCCCGTTTCCCTCTGAAGCCGCAGAGTGG<br>CTCTGCCTCCACGCCTTCCTGCTCAAGCTGGTTCGTCA<br>CCGCGTTACCTACAGCTGTCTTCTGGGGCCGCTCCGG<br>GCAGCCAGAGAGCGATTGTGCCAGCGGCTCCCTGGGG<br>CCACACTGGCCGCCCTCGAGGCCGCCGCCGACCCAGC<br>CCTGACTACAGACTTCCGGACCATCCTGGACTGA<br>(SEQ ID NO: 40) |
| TERT | Zebrafish<br>[Danio<br>rerio] | NM_<br>001083866.1 | ATGTCTGGACAGTACTCGACAGATGGCGGATTTAGGC<br>CGGTTTTGGAGATTCTGCGCTCCTTATATCCGGTCGTG<br>CAGACTTTGGAGGAGTTCACCGACGGACTGCAATTCC<br>CTGACGGCCGAAAGCCGGTTCTGCTGGAGGAAACAG<br>ACGGCGCGCGCTTTAAAAAGCTCCTCAGTGGACTTAT<br>TGTATGTGCGTACACGCCGCCGCAGCTGCGCGTCCCC<br>GCCCAGCTCAGCACCCTGCCGGAGGTCTTGGCGTTCA<br>CTCTGAACCACATTAAACGTAAGAAACTGAGGAACGT<br>CCTGGGCTTCGGTTATCAATGCAGCGACGTGACGACC<br>AGTTCGGATCCCTTCCGTTTCCATGGCGACGTTTCGCA<br>GACGGCTGCCTCCATCAGCACCAGCGAGGTCTGGAAG<br>CGTATCAACCAGCGTCTGGGCACGGAGGTAACGCGGT<br>ACCTGCTGCAGGACTGTGCCGTTTTCACCACCGTCCC<br>GCCATCGTGTGTTCTGCAGGTGTGCGGAGAACCTGTT<br>TACGACTTGCTGATGCCGCGCTCATGGTCTGGCTTTTT<br>CCTCAGTAACTCAGATAATGAACGAATCAGCGGCGCG<br>ATGCGGAAATTCCCTGCTGTCCAGAAGACAGTCGCAA<br>TTTCCAAAAAGAGAACAAGAGATAACGAAAAATATA<br>TTTCGGTAAAGCGGCGGAGGGTAAAGGAAACTGTGA<br>ATAATAATAACGGAAATTACAGATCTCTGTGTTTTGC<br>AATTTCTAAAAAGAGAGCGATAGATAATGAAGAAAA<br>TATTTCGTTAAAGCGACGGAGGATGGAGGAAACTGAC<br>CAAGTAGCGAAAATACGTAATGAAAATCACGAATCTC<br>AGAGTTTCGCAATTTCTAAAAAGAGAGCGAGAGATAA<br>TGAAGAAATATTTCGTTAAAGCGACAAAGGATGGA<br>GGAAATTGACCAAGTAGCGAAAATACGTAACGAAAA<br>TCATGGATCTCAGAGTTGGAAACCAGCAGATCAGCGT<br>CCTCCTCGACCCTCGCAATGTTCAATACGCGTTCTGAG<br>CATGCTCTACAATGGGCGGGGCATGAAGAACTTCCTG<br>CTCAACAGGAAGTTGAAAGGAGTGGGCGGGGCCAGG<br>CGCATGCAAGGGGAGGATCTTGTCCGCATGATTTTCC<br>TCCAATCAGAATCCAACGACAGCAAACCGAAAAAAC<br>TTCCCAAACGATTCTTCGCAATGGTGCCGCTATTCAGT<br>CGGCTGTTGCGGCAGCACAGGAAGTGTCCGTATCGGC<br>TGTTCCTGCAGAGGAAGTGTGCAGGAAATCCAGACGT<br>GAAGGATATGGAGTCTCTGCTGAAGTCACACTCGTCT<br>CCATATAGAGTTTATCTGTTCGTCAGGGAGTGTCGCG<br>CCATATTATTCCCCACGAGCTCTGGGGCTGCCAGGAA<br>AACCAGCTCCACTTCCTGTCTAATGTAAAGAACTTCCT<br>GCTTCTGGGGAAGTTTGAGCGCCTCACGCTGGTCCAG<br>CTGATGTGGAGGATGAAGGTTCAGGCCTGCCATTGGC<br>TGGGGCCCAAGAAACGTCAGTGTGCGAGCGAGCACC |

TABLE IB-continued

| Gene | Species | NCBI # | DNA Sequence |
|---|---|---|---|
| | | | GCTACCGTGAGTGGATGTTGGGTCAGTGTATGGGCTG<br>GATGTTGAGTGGTTTTGTGGTCGGTCTGGTCAGAGCTC<br>AGTTCTACATCACGGAGAGTATGGGCCACAAACACAC<br>ACTGCGCTTCTACAGGGGAGATGTCTGGAGCAGACTG<br>CAGGACCAGGCCTTCAGGGCTCATCTGTGTAAGGGCC<br>AGTGGAGGCCCCTGTCTCCATCCCAGGCGCTGAAGGT<br>CCCCAATAGTGCAGTGACATCCCGCATCCGCTTTATTC<br>CCAAAACCAGCAGCATGAGGCCCATCACACGCCTCAG<br>CGGCAGCAGAGACACACTGCAGTATTTTCAGAGCTGT<br>GTGCGTGTGCTGCAGAATGTGTTGAGTGTGTGTGTGC<br>GTGAGGCCCCGGGGCCCATGGGCTCCACCGTCTGGGG<br>TTGGCAGGACATTCACAGACGCCTGCAAGACTTCAGC<br>CCTCAGCAGAAGAGCTCGCCACGACCGCTCTACTTCG<br>TCAAGGTGGATGTGAGCGGAGCGTATGACAGTCTCCC<br>GCACCTGAAGCTGGTGGAGGTGCTGAAGGAAGTGTTG<br>GGTCCGTTTGCAGAGCAGAGCTTCTTCCTGCGTCAGT<br>ACAGCAGTGTGTGGAGCGACCCGACCCGCGGCCTGCG<br>CAAACGCTTCTGCACCAAAGCTGAGATGTCAGAGCCG<br>CTCAACATGAAGGGGTTTGTTGTGGATGAACAGGTCA<br>GCGGGCGCCTGCATGACGCTATATTAGTGGAGCGGCA<br>CTCGTCTGAGGTCAGAGGTGGAGACGTCTTCCAGTTC<br>TTCCAGAAGATGCTCTGCAGTTACGTCATCCATTACG<br>ACCAGCAGATGTTCCGGCAGGTGTGTGGGATCCCGCA<br>GGGCTCTTCAGTGTCTTCTCTGCTGTGTAATCTGTGTT<br>ACGGACACATGGAGAAAGCCCTGCTGAAGGACATCG<br>CTAAAGGAGGGTGTCTGATGAGGCTGATTGATGATTT<br>TTTGCTCATTACTCCTCATCTGAGTAAAGCCACAGAGT<br>TCCTGACCACTCTTCTGTCTGGAGTTCCAGATTACGGT<br>TGCCAGATTAACCCTCAGAAGGTGGCGGTGAACTTCC<br>CCGTGTGTGTGTCCTGGGTAAACTCGGGCGTCTCTGT<br>GCTGCCGTCCAGCTGCCTGTTCCCCTGGTGCGGCTTGA<br>TGATACACACACACACGCTGGACGTCTATAAAGACTA<br>CTCACGGTATGACGGCCTATCACTGCGCTACAGCCTG<br>ACTCTTGGCTCCGCCCACTCTCCATCTACAGTCATGAA<br>GAAGCTGCTGTCGGTGCTCAGCATCAAAAGCACGGAC<br>ATCTTCTTAGACCTCAGGCTGAACTCTGTGGAGGCCG<br>TTTACAGGAGTCTGTATAAGCTGATTCTGCTGCAGGC<br>GCTCAGGTTTCATGCGTGCGTGAGGAGTCTGCCGTTG<br>GGTCAGAGTGTGAACAGAAACCCGTCGTTCTTCCTGA<br>AGATGATCTGGAGAATGACTCGAGTCACCAATAAACT<br>CCTCACACACATTAACAAAGGTCTGCCTGTGTGTTCT<br>GTGGACAGTGGTGGTGTTCTGCAGTCTGAGGCGGTTC<br>AGCTTTTATTCTGTTTGGCCTTCGAGACGCTTTTCAGA<br>CGGTTTCGCTCGGTTTACCACTGCCTGATCCCTGCACT<br>GCACAAACGGAAGCGTGCTCTTCAGCGTGAGCTCTGC<br>GGGATCACTCTGGCTCGGGTCCGTCAAGCTTCCTCTCC<br>CAGAATCCCCCTGGATTTCAGCATGCGGGTGTAA<br>(SEQ ID NO: 41) |
| TERT | Tilapia<br>[*Oreochromis<br>niloticus*] | XM_<br>003458511.4 | ATGACGCGGGCCCTTAAAAGGTCAAACATAGCTAAAT<br>CCCAGTGTAAAGTAGCTAACCTCCGTCCAAGTGCTCC<br>GAACACAGTCGGTATGTCTGCGACTGATATGTCCGGT<br>GTGCTGGATATCCTTCGGTTACTGTACCGGCACACGC<br>AGACACTGGAGGAGTTTTCGGACAGCATCGTGTTCAG<br>AGAAGGACAGAAAGCAGCTCTCATTGAGCAGACAGA<br>TACAAACCGATTCAAATCTTTCGTTAGGAGTGTTTTTG<br>TGTGCTTTGACAAGGAGCTACAGCAGGTAGCGAGCTG<br>TAAACAGATCTGCAGTCTGCCTGAACTACTGGCGTTT<br>GTTCTCAACACTCTAAAAAGAAAAAGAAAAAGGAAT<br>GTCTTGGCACATGGCTATAACTTTCAGACCCTGGCTC<br>AGGAGGATCGGGATGCAGACTTCCTCAAATTCCAAGG<br>CGACGTAACACAGAGTGCTGCCTACATCCACGGCAGT<br>GACCTGTGGAAAAAAGTCACAATGCGTCTGGGCACA<br>GACATCACGCAATATCTTCTGGAGAGCTGCTCTGTGT<br>TTGTGGCAGTTCCTCCTTCGTGTGTTTTCCAGGTGTGC<br>GGCCCTCCAGTCTATGACAGGGTGTCCATGACCATGG<br>CCTCGAGTGGGTTTTTCTCCAGCCTGGAGTCAGGAA<br>ACATAATCGTACCAAGATTGAGAGCTGTCGAGGGTCA<br>GTGAGTTTGAAACAGAAACGCACAGTTGTGAATCCTG<br>CTGCAAGCAAGAAGATGAAAAGAAGGAATAAAGGAG<br>GGAAAAAGGGAAAAGAAAACGGGAAACTGGTGAA<br>GAGGAGGAGGTGGCGGTTTGTTCAAGAAAGAGGCGG<br>CGAGTAGCGTCTATAGAACATCAACAGGCGATCCAAC<br>CAGTTGGCTCTGAAAAGGAAGGACAGGTTGTGCCTGT<br>GGAATCAGCACCGCCTGCAGCTTTCAAACAGCCTGTT<br>GAAATGCCAACATTGGAGGGCGGTCCTAGTTGGAGAT<br>CAGGGATTTTCCCCCCTTTACCACCCTCGCAATGTTTT<br>ATCCGCACCCTGGGATTCCTGTATGGGGGCAGGGGCA |

TABLE IB-continued

| Gene | Species | NCBI # | DNA Sequence |
|---|---|---|---|
| | | | TGCGTGGCTTTCTTCTTAACAGGAGGAAGAAGACTGC<br>TCATGGATCCAGAAGGCTTCAAGGACAAGATCTGGTA<br>AGAATAGTCTTCTTCGAGGGACTAGCGTATTTGAATG<br>GAGTAGAGAGGAAGCCTAAAAAACTCCCCCAGAGGT<br>TCTTTGGCATGGTCCCCCTGTTTAGGCAGCTCTTACAA<br>CAACACAGGAGCTGTTCCTACACCAAAATACTACAGA<br>GGTTATGTCCATCAATAGAGGAGAGCAATGCAGGAC<br>AGGGAGAACTAAACTCACTCTTACCTCAGCACTGTGC<br>ACCGCACAGGGTTTACCTGTTTGTCCGGGAATGCCTC<br>TCTTCTGTGATCCCGCAAGAACTGTGGGGCTCTGATC<br>AAAACCGGCTGCATTTCTTTGCCAGGGTCAGGACTTT<br>CTTGCGAAGTGGCAAGTTTGAGAGGCTCTCACTGGCT<br>GAACTGATGTGGAAGATAAAGGTGAATGACTGTGATT<br>GGTTGAAGAGGAGTAAAACAGGCTGTTTTCCACCCAG<br>CGAGCTTGCGTATCGGACACAGGTCCTGGGTCAGTTC<br>TTGGCTTGGCTTCTGGATGGATATGTTACAGGCCTTGT<br>GAGAGCCTGTTTCTATGCAACAGAGAGTATTGGGCAA<br>AAAAACGCCATCAGGTTCTACAGGCAGGAAGTCTGG<br>GCCAAACTGCAAGACTTGGCCTTCAGAGGTCACCTTT<br>CCAAAGGCCAGATGGAAGAGCTGACTCCAGCTCAGG<br>TGGCATCCCTGCCCAAAGGCACCGTCATCTCCCGCCT<br>TCGCTTTATTCCCAAGACTGATGGCATGAGGCCCATC<br>ACACGAGTCATAGGAGCAGATGCCAAAACAAGGCTC<br>TACCGAGGCCGTGTCAGGGACTTGCTGGATATGCTGC<br>GGGCCTGTGTGCGTGCCACTCCATCACTGCTGGGGTC<br>CACAGTGTGGGGATGACTGACATCCACAAGGTTTTG<br>TGCTCTTTGGCACCAGCGCAGAAGGAAAAACCACAAC<br>CCCTCTATTTTGTTAAGGTGGACGTGAGTGGAGCCTAT<br>GAGAGTTTGCCGCATGACAAACTCATAGAGGTGATTG<br>GCCAAGCCCTGTCACCTGTCCACGATGAACTCTTTAC<br>CATCCGCCGCTATGCCAAGATCTGGGCGGACTCCCAC<br>GAAGGCCTGAAAAAGGCCTTTGTCAGACAGGCAGATT<br>TCCTGGAGGATAACATGGGATCCACCAACATGAAGG<br>GCTTTTTGACGTCACTGCAGAGAAAAGGCAAAGTTCA<br>TCACGCCATCCTGGTTGAGCAGCACTTTTGCTCAGATC<br>TTCATGGCAGAGAGGCATTGCAGTTCTTTACCCAAAT<br>GCTAACTGGCAGTGTTGTTCAGTATGGGAAAAAGACG<br>TACCGTCAGTGCCGGGGATTCCTCAGGGATCGGTTG<br>TGTCTAGTCTGCTCTGCTGCCTTTGCTACGGCCACATG<br>GAGAATCTCCTGTTTAAAGATATTCCTGGACACAAAG<br>GGTGTTTGATGAGACTGGTGGATGACTTCCTTCTGATC<br>ACACCAGACCAACATGAAGCACAAGCTTTTCTCAAGA<br>TCTTGCTGGCCGGAGTGCCACAGTATGGTCTGGCGGT<br>CAACCCGCAGAAGGTGGTTTTGAACTTTCAGGTATCG<br>GGAAGCGTGGCCTCCTGTCCCGACATTCGCATCCTGC<br>CCCCTCACTGCCTCTTCCCCTGGTGTGGACTGCTGCTG<br>GACACCCACAAGCTGGACGTCTATAAAGACTATTCCA<br>GCTATGCTGGACTGTCTCTGCGCTACAGCCTTACTCTG<br>GGTTCATCCCACTCTGCAGGACAGCAGATGAAAAGGA<br>AACTAATGGCTATCCTCAGGCTCAAGTGTCATGCCCT<br>GTTCTTCGACTTGAAGACTAATTCTCTTGAAGCGGTCT<br>ACAAGAACATCTACAAGCTGGTGCTGCTGCATGCGTG<br>CAGGTTTCATGTCTGTGCCCAAAGCTTGCCCTTTGGTC<br>AGACCGTTTCCAAGAACCCCGTCTTCTTTCTGCAGTTG<br>ATATGGGAGATGGCCCAGTACTGCAACAAGCTCATCA<br>GACGCAGCAACAAAGGACTGATTTTAGGTGATAAGG<br>CCCAGACGGGGATCGTGCAGTACGAAGCAGTGGAGC<br>TGCTTTTCTGTCTGTGCTTCTTGCTGGTGCTGTCACAA<br>CATCGTCTTCTCTATAAAGATCTGCTCGCACACTTGCA<br>CAAGCGAAAGCGCAGTCTGGAGCGGCGTCTGGGGGA<br>CCTGAGGCTGGCCAGGGTGCGGCAGGCTGCTAGCCCC<br>AGGACTCCAGTCGACTTCTTGGCCATTCAGACATAA<br>(SEQ ID NO: 42) |
| TERT | Rainbow<br>trout<br>[Oncorhynchus<br>mykiss] | XM_<br>021559758.1 | ATGCCCAGTGGCGATATGACACGTGTGCTCGGCATAC<br>TCGGCTCTCTGTATCGGCACGTCGAGACCCTGGAGGA<br>GTTTGCAGACCATATTGTATTCAGAGAGGGACAGAGA<br>GCGGTGCTCATCGAACCGACAGATACAACGCGCTTCA<br>TATCGTTTGTCCGGGGAGTGTTGGTCTGCACGGATAA<br>AACCCTACAGGACGTCCCCAGCTGCAATCAGATCAGC<br>ACCGTGCCTGAGCTGTTGGCGTTCGTGTTGAACAACA<br>TCAAGAGGAAAAGAAAAGGAATGTCCTGGCGCACG<br>GTTACGGTTACACGTTCCAGGACCGCGACGCAGACCA<br>GTTTAAGTTTCATGGCGAGATCACTCAGAGTGCCATG<br>TACATCCACTGCAGCGACTTATGGAAGAGGGCCTGCC<br>AGCGCCTCGGCACGGACATCTCCAAGTACCTCCTGGA<br>GAGCTGTTCTTTGTTCGTGACGGTGCCGCCGTCGTCCG<br>CGTTCCAGGTGTGCGGCGTGCCTGTGTACGACCGCGT |

TABLE IB-continued

| Gene | Species | NCBI # | DNA Sequence |
|---|---|---|---|
| | | | TTCCATGTCAACGGGTATCTCTAGGTTCCACCTGGGAT |
| | | | ACAAACGGAATGGTACTACTAGGAACAGCAGAGGGA |
| | | | GAAGTAAGGAGGTCAGAAATGGGGGATGGGAATTTC |
| | | | AGGGTTCTGCTGGGAGAAATAGGAGAAAGGATGGAG |
| | | | GTAGAGACACTGGGAAAAGGAAGGGAGACGAGGTCA |
| | | | GTTTGGGAGGGAAGAGGAAGAGGGAGAGGGAGGAG |
| | | | GTGGAAGGAGATGTGTGTTTGCCTGGAAAAAGGAGAT |
| | | | GCACTCAAAGAGAAGCTCCCACAGTCTCCAGTGGGAC |
| | | | TAGCGATCGTAAGCACAGAACACTGGAAACAAATGG |
| | | | GGTCAAGAGACCAGTGGAGGTCATTTCTCTCACCAAG |
| | | | GGACCCACACAGAGCCTACAGGTTTTCAATGGTTCTA |
| | | | GCAATGTGGAACAGGTGTCAGCAGAAATGGAACGTC |
| | | | TCAGGAAGCCAGTGGAGAAACTGGCTGGACCCGGAA |
| | | | GACCATTGGAGGCTGTGATGGTCACCATAGCACCCGC |
| | | | TGAGAGCTCTAAACAGGTCTCCAACGGCACAGGTAAT |
| | | | ATCGAGCAGATGTCAATGAAAACAGGACATAGAAGG |
| | | | CCAGCGGCTGTAGTCCCAAGACCAGTAGAAGAACAG |
| | | | TCTGGACCTGTATCGGCCACCGTCCATGTAGAGGGGG |
| | | | GCCCTAGTTGGAGAACAGGGTCGTTCCCACCGCTTCC |
| | | | CCACTCCCAGTGTTTCATCCGCACCCTGGGCATGCTCT |
| | | | ACGGAGGGCGGGGCATGCGCCGCTTCCTACTAAACAG |
| | | | GAAGAGGAAAAGTAGGGACGAGGGGCCCAGGCGTCT |
| | | | GCAGGGGCGAGACTTAGTGAGACTGGTCTTCTTTGAA |
| | | | GGCGTGGCCTATCTGAACGGAACAGAAAGGAAGCCT |
| | | | GAGAGACTTCCCAGAAGATTTTTCACCTTGGTGCCTCT |
| | | | GTTTTGTCAGTTGTTACGTCGACACAGGAGGTGTCCCT |
| | | | ATTCTAAGATACTGCAGAGGGTTTGTCCAGCAGTGGG |
| | | | ACAGGGGATATGGCCTCCCTCCTGCCCCAGCACAGT |
| | | | GCACCTCACCGGGTGTACCTCTTTGTCAGAGAGTGCC |
| | | | TCAACGCGGTGGTCCCCTCGGAGTTCTGGGGGTCGGA |
| | | | CCATAACCGATTCAAATTCCTGTCCGCAGTCAGGAAC |
| | | | TTCCTGTCCATGGGCAAGTTTGAGAGGATGTCATTGG |
| | | | CTGAGCTGATGTGGAAGATGAAGGTGAATGACTGTGA |
| | | | TTGGCTGAAGATCAGCAAGACAGGCCGCTGCCCGCCC |
| | | | AGTGAGCTGTCGTATCGGACGCGGGTGCTAGGCCAGC |
| | | | TCCTGGCTTGGCTGCTGGATGGCTATGTGCTAGGCCT |
| | | | GGTGAGAGCTATGTTCTACGTCACAGAGAGCATGGGA |
| | | | CAGAAGAACGCACTGCGCTTCTACAGATACCAGGTCT |
| | | | GGGCCAAGCTGCAGGAGCTGGCTTTCAGTGGTCACCT |
| | | | CTCTAAAGGTCAGATGTCAGAGTTGACCCTGGCCCAG |
| | | | GTGACGTCGCTCCCCAAAACCACTGTCCCCTCCCGCC |
| | | | TCCGCTTCATCCCCAAGACCGAAGGGATGAGACCCAT |
| | | | CACACGGGTCATAGGGGCTGACGCCAAAACAAGGTT |
| | | | GTTCCAGACCCGTGTGAAGGAGCTGTTAGATGTGCTA |
| | | | GGTGTCTGTGTACGGTCCTCTCCCTCTCTCCTGGGCTC |
| | | | TACAGTGTGGGGGTTGACCGACATCCACAGAGTCCTC |
| | | | TCTTCCATCACCCCTGCTCAGAAAGACAAACCACAGC |
| | | | GGCTCTACTTTGTCAAGGTGGATGTGAGTGGGGCCTA |
| | | | TGACAGTCTACCCCACACTCAGCTCTTGGAGGTGATT |
| | | | GGTCAGGTCCTGTCACATGTGCAGCAAGAGCTTTTCT |
| | | | CGGTGCGACGCTATGCCAAGGTGTGGGCCGACACCCA |
| | | | CGAGGGCCTCAAGAAGACCTTTGTCAGACAGGCAGA |
| | | | CTTCACGGAAGACACTGTGTCGTCCACCAACATGAAA |
| | | | GGCTTTGTGATGTCACTGCAGAGAGAGGGCAAAGTTC |
| | | | ACGATGCCATACTGGTGGAGCAGCATTTCTCCACAGA |
| | | | TATTCATGGCAAAGACGTCTTGGAGTTCTTCACCCAG |
| | | | ATGCTCTCTAGCTGTGTTGTCCAGTTTGGGAAGAAATC |
| | | | GTTCCGTCAGTGTCAGGGGATTCCTCAGGGTTCCGCG |
| | | | GTGTCGTCTCTGCTGTGCTGCCTCTGTTACGGCCACAT |
| | | | GGAGAACCTTCTGTTTCCTAACGTCAGTCGGCGAGGA |
| | | | GGGTGTCTGATGAGACTGGTTGACGATTTCCTCCTCAT |
| | | | CACTCCTGACCTGAGCCAGGCACAGACCTTCCTCAAG |
| | | | ACCCTGATGGCGGGGGTACCACGGTACGGGTGTGTGG |
| | | | TGAACCCCCAGAAGGTGGCTGTTAACTTCCCTTTGGG |
| | | | TGAGTGGGGGTCCTGTCCTGCTGGGGTACGCCTGCTG |
| | | | CCTTTACACTGTCTGTTCCCCTGGTGTGGACTATTGCT |
| | | | GAATACACACACCCTGGACGTCCACAACAACTACGCC |
| | | | AGCTACGCTGGCCTATCCCTGCGCTACAGCCTGACGC |
| | | | TAGGCTCCGCCCACTGCGCGGGGCAGCAAATGAAGA |
| | | | GGAAGCTCATGTCCATCCTTAGATTCAAGTGCCACGC |
| | | | CCTCTTCCTGGACCTCAAAACCAACTCCCTGGAGGCT |
| | | | GTCTATAGCAACGTCTACAAGTTAGTGTTGCTGCAGG |
| | | | CGTTCAGGTTCCATGCCTGTGCACAGAGTTTGCCGTTT |
| | | | GGTCAGAAAGTGGGCGGAAACCACTCGTACTTCCTCA |
| | | | ATCTGATCTGGGACTTGCGGAGTACACCAACCATCT |
| | | | AGTCAGACTCTGCAACAAAGGTGTGTCTCTAGGCTGT |
| | | | AAGGCTTTAACAGGTAGCCTTCAGTATGAGGCAGTAG |
| | | | AACTGATATACTGTCTGGCCTTCCTGTTGGTTCTGTCC |

TABLE IB-continued

| Gene | Species | NCBI # | DNA Sequence |
|---|---|---|---|
| | | | CGTCATCGCCCCCTCTACTACCATCTCCTCGCTCCGCT ACGCACACGTAAGAGGAAGCTGGAGGGGAAGCTGGA GGGTTTGAGATTGGCCCGAATCAGACAGGCTGCCACA CCCAAAATGCCTGAAGACTTCAAGGCCATCCAGGCCT AG (SEQ ID NO: 43) |
| TERT | Tropical clawed frog [*Xenopus tropicalis*] | XM_ 018094976.1 | ATGACTCTGTGTACCGGAGGAGCTGAACTACTGAGCA TTTTGCACAGCCTTTATGGCCAGGTCCTTGGGATTGTG GAATATATCGACTCACTGCATGTTCCCGGCGGCATTA AGGTGCCTGTGCTGCGAGAGGGAGACCCGGAGAAGT TCAAGTCATTTGTTGCGGAACTGATGCTGTGCATTCCA AGAGGAACAAAGTCGCTTCCGTCCCCTGTCTCCTTTCT TCAGCTATCAACTCAGAGAGAAGTAGTGGCGCGAGTA ATTCAGCGGATTTGTGAAAAGAAAAGAAAAAATGTTC TTGCTTTTGGTTATGGCTTAGTTGATGAAAAAGCTCT CTGAATATTCGATTGACTCCAAATATTTGCAGTTATTT TCCTAATTCCACAACAACAACAATCAGCACAAGTATT CTTTGGGAAACTCTGCTTACTAGAGTAGGTGATGATG TTATGATGTATTGGCTGGAACAATGCTCAGTTTTTGTA TTTGTGCCACCTAGTTGTTGTTATCAAATCAGTGGGCA GCCAATCTACACTTTACCCTATGATAGTATGTGTTCAT TTCGATCTCAGTCATTTATGCATAGCAATGTTTTGTTG CAGTACATTAAAAGAAATGCCTTTTCTTGCGGAAAA AATATCTGAAGCCAAAAAAGTGGTGGAAAACGGTGTT AAACAGCAAAGTAGAAAACATTCAAAGACTTCTCA AATGCTAACATGGCAAAATAAAAAGTCCACATCAGC ATTGCCTATTTGTAGTGAGTCATCTATGAAAGTTACCA CAAAAATACATTCCAAAAGGAAGATGTGTACTACAG ATATTTGTGACATTCCAACTAAGAAACGCAGAGTCAA CTTGGACAAAGATGATAAAATGGACCACGTTTCCTTT ACGTCTGCATGTCTTTCTTCCTTCTCAAATGTGTGCCC TGAAGCTAAAGTACAAGCAACGGAATTTATTACCTCA AGATATGGAAAAAAAACAAAAATTCAATGTCCAAAA TCGACTTCATACTCAGTTGATGGTGAATTTAATGTAAC TCTTCAAAATAATGCTAATACGTTTATTACCAATGCTT CTGTCCCTACAATACAAAGCAAAACTTCATTTTCAAA TATTTTTATTGAAATTGGAAGAACATTGTATTCAAGTA TTAGTTTCAAGAAGGGCTTCTCTGAAAGTTTTATACTT AACAGTTTAGACTGTACCCCTTCTGGGAGCCAAAAT TAGTGGAAACCATATTTCTAAACAACTTTTTAACTGA GCAAAATTTTGACCAGCCAAAACGGGATGAAAACTTT AGATCTAAACTTCCCAAACGTTATTGGAGAATGAGAA AATATTTCCAAGAATTAATACAGAACCATAAGAATTT CCCTTATCTGGTATATTTGAATAAACACTGCCCTGTTA GGCCTTCAATGGCTTGTTCACACAAACTGGCGTTGCA GAAAAAGAATAAATGTAAAATGGATAAATCAATTTGT GACTTAAGTAATACCTCAGTTATGAAAACAAAATTG TAAATGATGAAAGCCGCTAAAACATGTTACAGCCGA AGCAACTTTTTTACCTCTTCTTAAACAACACAGCAGC AGTTGGCAAGTGTACATGTTTGTTAGAGAATGTTTAA ATAGTTTAGTGCCTGATTTCATATGGGGCTCCAGTCAC AACAAGTGCCGTTTCCTTAGAAATGTAAAATCTTTTCT TTTTTTTGTGGCAAATTTGGCAAGGTGTGTTTATTAG AGCTTATGTGGAAGATGAAAGTAGAAGACTGCTCTTG GATTCGTCTACGAAAAAGTGATCACTTTGTTCCTGCTT CAGAACACTTGCTACGAGAGAGAATCCTTGCCAAATT TATCTTTTGGCTAATGGACACCTATGTCATACAGTTGC TGAAATCATTTTTTTTTGTCACGGAAACCATGTTTCAG AAGAATAGACTTTTGTTCTACAGAAAAAGAATTTGGA AGAAACTTCAAAATTTAGGTCTAAGAAAACATCTAGA GAAGGTGAAATTGCGTCCATTGTCCTGCGATGAACTA GAAAAGATGCAACAATGGAAAAACATTCCACTGGTTT CCAGGCTCAGATTCATACCAAAACAAATGGACTACG TCCAATATCTAGAGTATCCAGTACTTTGGGTAGCCAA CAAAGCAAAGAAAACCAAGAAGAAGATTCAACAT TTTACCTCTCGGGTTCGAAACCTTTTTAGTGTTCTTAA CTATGAATGGAATAGAAATTGCAGCCTAATTGGCTCA TCTGTTTTTGGCATGGATGATATATACAAACAGTGGA AAAAATTTGTGCTAGATTTTGAAAAATCGAGAGCTGA AAAAGGCAAATTTTACTTTGTGAAGACAGATGTTAAG GGAGCATATGATACCATTCCACATTCAAAGCTCGATG AAGTGATCTTAAAAGTAATTAATCCAAATGCAAATGA AGTATATTGCATACGACGTTATGCCTCAGTTTCAGTGG ATTCAACTGGACGCATTATAAAAATCTTTCAAAAGACA TGTATCTGCATTAGCAGATGTTCTTCCAAATATGAAAC AGTTTGTTTCAAATCAACAAGAAAAAAACTTGACACG TAACACAATTCTAGTGGAACAGAGCCTTTTATTGAAT GAGAGCTCTGTCAAACTTCTTGCTGTTTTTCAACAAAT |

TABLE IB-continued

| Gene | Species | NCBI # | DNA Sequence |
|---|---|---|---|
| | | | GATCAGATCCCATATTTTAAGAATAGAAGATCGATAT<br>TACATGCAGTGCTGTGGAATACCACAGGGTTCAATGT<br>TATCTACAATCCTATGCAGTTTATGCTATGGAGACATG<br>GAAAATAAACTGTTTGGCGGAATACAGCAAAATGGG<br>GTACTAATGCGATTGATTGATGATTTTTTGTTTGTAAC<br>ACCTCATCTTAACCAGGCAAAAACATTTTTAAGGACT<br>CTGGCAGAAGGAATTCCCCAATATGGGTGCTCCATCA<br>GCCCTCAAAAAACAGTGGTAAACTTTCCTGTTGATGA<br>CATCCCAGCATGCTCTGAGGTGGAACAATTACCAGTT<br>CACTGCTTGTTCCGGTGGTGTGGTCTTTTGCTGGACAC<br>TCAGACTTTGGATGTTTACTATGATTATTCAAGCTATG<br>CCTGTACCTCAATCCGATCAAGTATGACATTTTGTCAC<br>AGTTCTGCAGCAGGAAAAAACATGAAACAAAAACTT<br>CTAAGAGTCCTTAAATTGAAGTGCCACAGTCTCTTTCT<br>TGATTTACAGGTAAACAGTTTAAGGACAGTTTTCATC<br>AATACTTATAAGATATTCTTACTTCAAGCTTACAGATT<br>CCATGCTTGTGTTGTTCAGCTTCCATTTGGCCAGCGTG<br>TAATGAATAATCCACCTTTTTTTCTTACTGTGATTTCT<br>GATATGGCACCTTGCTTTTACACTACTTTTAAGTCCAA<br>AAACAAAGATGTCACACGTGGGTACAAGGATGTGAG<br>CTGCCAGTTTAACTTTGAAGCAGTCCAGTGGCTCAGT<br>TATCAAGCTTTTCTTACTAAGCTTCGCAATCACAAAAT<br>ATTATACAAATGTCTTATTGGGCCACTGCAGAACTGT<br>AAAATGCAGTTATCTAGAAGACTTTCGCAGTATACTA<br>TTGATCTTCTAAAAGCTGTCACAGATTCTTCCCTTCAC<br>AAAGACTTTTCATGTATAATGGATTAG (SEQ ID NO: 44) |
| TERT | Chicken<br>[*Gallus gallus*] | NM_001031007.1 | ATGGAGCGCGGGGCTCAGCCGGGAGTCGGCGTGCGG<br>CGGCTCCGCAATGTAGCGCGGGAGGAGCCCTTCGCCG<br>CGGTCCTGGGCGCGCTGCGGGGCTGCTACGCCGAGGC<br>CACGCCGCTGGAGGCCTTCGTCCGGCGGCTGCAGGAG<br>GGTGGCACCGGGGAGGTCGAGGTGCTGCAGGCGAC<br>GACGCTCAGTGCTACCGGACCTTCGTGTCGCAGTGCG<br>TGGTGTGCGTCCCCCGCGGTGCTCGCGCCATCCCCCG<br>GCCCATCTGCTTCCAGCAGTTATCCAGTCAGAGCGAA<br>GTCATCACAAGAATCGTTCAGAGGCTGTGTGAAAAGA<br>AAAAGAAGAACATCCTTGCGTATGGATACTCCTTGCT<br>GGATGAGAACAGTTGTCACTTCAGAGTTTTGCCATCTT<br>CGTGTATATACAGCTATCTGTCCAATACTGTAACAGA<br>AACGATTCGCATCAGTGGCCTCTGGGAGATACTGCTG<br>AGTAGGATAGGGGACGACGTGATGATGTACCTGCTGG<br>AGCACTGTGCACTCTTCATGCTGGTTCCCCCAAGTAA<br>CTGTTACCAGGTCTGCGGGCAACCAATTTATGAACTT<br>ATTTCGCGTAACGTAGGGCCATCCCCAGGGTTTGTTA<br>GACGACGGTACTCAAGGTTTAAACATAATAGCTTGCT<br>TGACTATGTGCGAAAAAGGCTTGTGTTTCACAGGCAC<br>TATCTTTCCAAGTCACAGTGGTGGAAGTGCAGGCCGA<br>GACGTCGAGGTCGTGTCTCCAGCAGGAGAAAAAGAA<br>GGAGCCATAGGATACAAAGCCTAAGGTCTGGTTATCA<br>GCCTTCTGCAAAAGTGAACTTTCAAGCAGGTAGGCAG<br>ATCAGCACTGTTACTGCACGTCTGGAAAAACAGAGCT<br>GCTCCAGTTTATGTTTGCCAGCTAGAGCACCATCTTTA<br>AAAAGGAAGCGTGATGGAGAACAGGTTGAAATCACA<br>GCTAAGAGAGTGAAAGTAATGGAGAAAGAGATAGAG<br>GAACAGGCTTGTAGTATCGTTCCTGATGTAAACCAAA<br>GTAGCTCCCAGAGGCATGGAACCTCCTGGCATGTAGC<br>ACCACGTGCTGTAGGTCTTATTAAAGAACATTACATTT<br>CTGAAAGAAGTAACAGTGAGATGTCTGGTCCTTCTGT<br>AGTTCGCAGATCTCACCCTGGGAAGAGGCCTGTGGCA<br>GACAAAAGCTCTTTTCCACAAGGAGTTCAGGGTAACA<br>AACGCATAAAGACCGGTGCAGAAAAACGAGCAGAAT<br>CCAATAGAAGGGGCATAGAGATGTATATAAACCCAA<br>TCCATAAACCCAATAGAAGGGGCATAGAGAGGCGTA<br>TAAATCCAACCCACAAACCTGAGTTGAATTCTGTACA<br>AACTGAACCAATGGAAGGTGCTTCTTCAGGGGACAGA<br>AAGCAGGAAAATCCCCAGCTCATTTGGCAAAGCAGT<br>TACCAAATACATTGTCGCGCTCTACAGTGTACTTTGA<br>GAAGAAATTTCTTCTGTATTCCCGCAGTTACCAAGAA<br>TATTTTCCTAAATCGTTCATACTGAGCCGCCTGCAGGG<br>TTGTCAGGCAGGTGGAAGGCGGCTTATAGAAACTATA<br>TTCTTAAGCCAAAACCCATTAAAGGAACAGCAGAACC<br>AAAGCCTACCACAGCAAAAGTGGCGAAAGAAGAGGT<br>TGCCCAAACGCTACTGGCAAATGAGAGAGATATTTCA<br>GAAGCTGGTAAAGAACCATGAGAAGTGCCCTTATTTA<br>GTTTTCTTGAGGAAAAATTGCCCTGTTTTGCTTTCTGA<br>AGCATGTTTGAAAAAGACGGAGCTGACCTTGCAGGCG<br>GCTCTGCCTGGGGAAGCAAAGGTTCACAAGCACACA |

TABLE IB-continued

| Gene | Species | NCBI # | DNA Sequence |
|---|---|---|---|
| | | | GAACATGGGAAAGAGTCCACTGAGGGTACTGCACCG<br>AACAGCTTCCTCGCTCCTCCCTCAGTGCTAGCGTGTGG<br>GCAGCCAGAGAGAGGGGAACAGCACCCTGCAGAGGG<br>GAGTGATCCGCTCCTCAGGGAGCTGCTCAGGCAGCAC<br>AGCAGCCACTGGCAGGTGTATGGCTTTGTGAGGGAGT<br>GCCTGGAGCGGGTGATCCCTGCTGAGCTGTGGGGTTC<br>AAGCCATAACAAATGCCGGTTCTTTAAAAACGTGAAA<br>GCATTCATTTCCATGGGGAAGTATGCTAAGCTTTCATT<br>GCAGCAGCTGATGTGGAAGATGAGAGTGAATGACTG<br>CGTATGGCTTCGTCTGGCCAAAGGTAATCACTCTGTTC<br>CTGCCTATGAACATTGTTACCGTGAAGAAATTCTGGC<br>AAAATTCCTATACTGGCTGATGGATTCCTATGTTATCG<br>AGTTGCTCAAATCATTTTTCTATATCACCGAGACCATG<br>TTCCAGAAAAACATGCTTTTCTACTACCGAAAGTTTAT<br>CTGGGGCAAGTTACAGAACATTGGAATTAGAGACCAT<br>TTTGCCAAAGTACATCTACGTGCCTTGTCTTCAGAGG<br>AGATGGAAGTGATCCGTCAAAAAAGTATTTTCCTAT<br>TGCATCAAGGCTCCGGTTCATTCCTAAAATGAATGGT<br>TTAAGACCCGTAGTAAGACTAAGCCGTGTTGTTGAAG<br>GACAGAAACTCAGCAAGGAAAGCAGAGAAAAGAAG<br>ATACAGCGCTATAACACTCAGCTAAAAAATCTATTTA<br>GTGTTTTAAACTATGAACGAACTGTAAACACCAGTAT<br>CATTGGCTCTTCAGTATTCGGGAGAGATGATATCTAC<br>AGGAAGTGGAAGGAGTTTGTTACAAAGGTTTTTGAAT<br>CAGGTGGTGAAATGCCTCATTTCTACTTTGTAAAGGG<br>TGATGTATCCAGAGCTTTTGATACCATTCCTCACAAG<br>AAACTTGTGGAAGTGATATCACAGGTCTTGAAACCTG<br>AGAGCCAAACTGTCTATGGAATAAGGTGGTATGCAGT<br>GATTATGATTACCCCAACTGGAAAAGCCAGGAAACTC<br>TATAAGAGACATGTTTCTACTTTCGAGGATTTTATTCC<br>AGACATGAAGCAGTTTGTGTCCAAGCTTCAAGAGAGA<br>ACTTCATTACGAAATGCAATAGTAGTTGAACAGTGCT<br>TAACTTTTAATGAGAACAGTTCCACCCTGTTTACTTTC<br>TTTCTTCAAATGTTACATAATAACATCCTGGAGATTGG<br>GCACAGGTACTATATACAGTGCTCTGGAATCCCACAG<br>GGCTCCATTTTGTCAACCTTACTTTGCAGCTTATGCTA<br>CGGAGACATGGAAAACAAATTACTCTGTGGGATCCAG<br>AAGGATGGAGTCCTAATACGTCTTATTGATGACTTTTT<br>GCTGGTTACGCCACATTTAATGCAGGCAAGAACTTTT<br>CTAAGGACTATAGCAGCAGGTATTCCTGAGTATGGCT<br>TTTTAATAAATGCCAAGAAGACTGTGGTGAATTTTCCT<br>GTTGATGATATCCCGGGATGTTCCAAGTTCAAACATC<br>TGCCAGATTGTCGTTTGATCTCATGGTGTGGTTTATTA<br>TTGGATGTGCAGACACTTGAGGTTTATTGTGATTACTC<br>CAGTTATGCCTTTACTTCTATCAGATCAAGTCTTTCCT<br>TCAATTCAAGTAGAATAGCTGGAAAAAACATGAAATG<br>CAAATTGACTGCAGTCCTCAAACTGAAATGCCATCCT<br>TTACTTCTTGACTTAAAGATCAACAGCCTTCAGACAG<br>TTCTAATTAACATCTACAAGATATTTTTACTTCAGGCT<br>TACAGGTTCCATGCCTGTGTTCTTCAGCTTCCATTCAA<br>CCAGAAAGTTAGGAATAATCCTGATTTCTTCCTAAGG<br>ATCATCTCTGATACTGCTTCATGCTGCTATTTTATCCT<br>GAAAGCTAAAAATCCAGGAGTTTCTTTAGGTAGCAAA<br>GATGCATCTGGCATGTTCCCTTTTGAGGCAGCAGAAT<br>GGCTGTGCTACCATGCCTTCATTGTCAAACTGTCCAAC<br>CACAAAGTTATTTACAAATGCTTACTTAAGCCCCTTA<br>AAGTCTATAAGATGCATCTGTTTGGGAAGATCCCAAG<br>GGATACTATGGAACTGCTGAAGACGGTGACGGAACC<br>ATCGCTTTGTCAAGATTTCAAAACTATACTGGACTAA<br>(SEQ ID NO: 45) |
| TERT | Turkey<br>[*Meleagris<br>gallopavo*] | XM_<br>019613879.1 | ATGTCTGGGGCTCGGGGGCTCGTCTGGTGCGACGAGC<br>GAGCGTGGCTGTTATCCAGTCAGAGCGAAGTCATCAC<br>AAGAATCGTTCAGAGACTATGTGAAAAGAAAAAGAA<br>GAACATCCTTGCGTATGGATACTCCTTGCTGGATGAA<br>AACAGTTGTCACTTCAGGATTTTGCCATCTTCGTGCAT<br>ATACAGCTATCTGCCCAATACTGTAACAGAAACGATT<br>CGCATCAGTGGCCTCTGGGAGATACTGCTGAGCAGGA<br>TAGGGGACGATGTGATGATGTACCTGCTGGAGCACTG<br>TGCACTCTTCATGCTGGTTCCCCCAAGTAACTGTTACC<br>AGGTCTGCGGGCAACCAATTTATGAACTTATTTCGCG<br>TAACATAGGGCCGTCCCCAGGGTTCGTTAGACGACGA<br>TATTCAAGGTTTAAACATAATAACTTGCTTAACTATGT<br>GCGAAAAAGACTTGTGTTTCATAGGCACTATCTTTCC<br>AAGTCACAGTGGTGGAAGTGCGGGCCGAGACGTCAA<br>GGTCGTGTCTCCAGCAGAAGAAAAGAAGGACCCAT<br>AGGATACAAAGCCCAAGGTCTGGTTACCAGTCTTCTG<br>CAAAAGTGAACTTTCAAGCAGGCATGCGGATCAGCAC |

TABLE IB-continued

| Gene | Species | NCBI # | DNA Sequence |
|---|---|---|---|
| | | | AGTTACTGCACATCTGGAAAAACAGAACTGCTCCAGT
TTATGTTTGCCAGCTAGAACACCATCTTTAAAAAGGA
AGCGTGATGGAGAACAGGTTGAAACCACAGCTAAGA
GAGTGAAAGTAATGGAGAGAGAGGAACAGGCTTGTA
GTATCGTTCCTGATGTAAATCGAAGTAGCTCCCGGAG
GCATGGAGTTTGGCATGTAGCACCACGTGCTGTAGGT
CTTATTAAAGAACGTTACGTTTCTGAAAGAAGTTACA
GTGAGATGTCTGGTCCTTCTGTAGTTCACAGATCTCAC
CCTGGGAAGAGGCCTGTAGCAGACAAAAGCTCTTTTC
CAAGAGGAGTTCAGGGTAACAAACACATAAAGACCG
GTGCAGAAAAACGAGCAGAATCCAATAAAAGGGGCA
TAGAGATGTATATAAACCCAATCTGTAAACCCAATAG
AAGGGGTATAGAGAGGCATATAAATCCAACCCATAA
ACCTGGGTTGAATTCTGTACAAACTGAACCAATGGAA
AGTGCTTCTTCGGGGGACAGAAAGCAGGAAAATCCCC
CAGCTCATTTGGCAAAGCAGTTACCAAATACATTCTT
GCGCTCTGCAGTGTACTTTGAGAAGAAATTTCTTCTGT
ATTCCCGTAGTTACCAAGAATATTTTCCTAAATCGTTC
ATACTGAGCCGCCTGCAGGGTTGTCAGGCAGGTGGAA
GGCAGCTTATAGAAACTATATTTTTAAGCCAAAACCC
ATTAAAGGAAAAGCAGAACCAAAGCCTAAAACAGCA
AAAGTGGAGAAAGAAGAGGTTGCCCAAACGCTACTG
GCAAATGAGAGAGATATTTCAGAAGCTGTTAAAAAAC
CACGAGAAGTGCCCTTATTTAGTTTTCTTGAGAAAAA
ATTGCCCTGTTTTGCTTTCTGAAGCATGTTTGAAAAAA
ACGGAGCTGACCTTGCAGGCAGCTCTGCCTGGGGAAG
CAAAGGTTCACAAGCACACAGAACATGGGGAAGAGA
CCACTGAGGGTACTGCACCGAACAGCTTCTACACTCC
TCCCTCAATGCCATTGTGTGGGCAGACAGAGAGAGAG
GAGCAGCACCTTGCAGAGGGGAGTGATCCGCTCCTCA
GGGAGCTGCTCAGGCAGCACAGCAGCCACTGGCAGG
TGTATGGCTTTGTGAGGGAGTGCCTGGAGCGGGTGAT
TCCTGCCGAGCTGTGGGGTTCAAGCCATAACAAATGC
CGGTTCTTTAAAAACGTGAAAGCATTCATTTCCATGG
GGAAGTATGCTAAGCTTTCATTGCAGCAGCTGATGTG
GAAGATGAGAGTGAATGACTGCGTATGGCTTCGTCTG
GCCAAAGGTAATCATTCTGTTCCTGCCTATGAACATT
GTTACCGTGAAGAAATTTTGGCAAAATTCCTATACTG
GCTGATGGATTCCTATGTTATCGAGTTGCTCAAATCAT
TTTTCTATATCACCGAGACCATGTTCCAGAAAAACAT
GCTTTTCTACTACCGAAAGTTTATCTGGGCAAGTTAC
AGAACATTGGAATTAGAAACCATTTTGCCAAAGTACA
TCTACGTGCTTTATCTTCAGAGGAGATGGAAGTGATC
CATCAAAAAAAGTATTTTCCTATTGCATCAAGGCTCC
GGTTCATTCCTAAAATCAATGGTTTAAGACCCGTAGT
AAGACTAAGCCGTGTTGTTGAAGGACAGAAACTCAGC
AAGGAAAGCAGAGAAAAGAAGATACAGCGCTATAAC
ACTCAGCTAAAAAATCTATTTAGTGTGTTAAATTATG
AACGAACTGTAAACACCAGTATCATTGGCTCTTCAGT
ATTCGGGAGAGATGATATCTACAGGAAGTGGAAGGA
GTTTGTTACAAAGGTTTTTGAATCAGGTGGTGAAATG
CCTCATTTCTACTTTGTGAAGGGTGATGTGTCCAGAGC
TTTTGATACTATTCCTCACAAGAAACTTGTGGAAGTG
ATCTCACAGGTCTTGAAACCTGAGAGCCAAACTGTAT
ATGGAATAAGGTGGTATGCTGTGATTATGATTACCCC
AACTGGAAAAGCCAGGAAGCTCTATAAGAGACACGT
TTCTACTTTTGAGGATTTTATTCCAGACATGAAGCAGT
TTGTGTCCAAGCTTCAAGAGAGAACTTCATTACGAAA
TGCAATAGTAGTTGAACAGTGCTTAACTTTTAATGAG
AACAGTTCCACCCTGTTTACTTTCTTTCTTCAAATGTT
ACATAATAACATCCTGGAGATTGGGCACAGGTACTAT
ATACAGTGCTCTGGAATCCCACAGGGCTCCATTTTGT
CAACCTTACTTTGCAGCTTATGCTATGGAGACATGGA
AAACAAATTACTTTGTGGAATCCAGAAGGATGGAATC
CTAATACGTCTTATTGATGACTTTTTGCTGGTTACACC
ACATTTAATGCAGGCAAAAACTTTTCTAAGGACTATA
GCAGCAGGTATTCCTGAGTATGGCTTTTTAATAAATG
CCAAGAAGACAGTGGTGAATTTTCCTGTTGATGATAT
TCCGGGATGTTCTAAGTTCAAACAGCTGCCAGATTGT
CGTTTGATCTCATGGTGCGGTTTATTACTGGATATGCA
GACACTTGAGGTTTATTGTGATTACTCCAGTTATGCCT
TTACTTCTATCAGATCAAGTCTTTCCTTCAATTCAAGT
AGAATAGCTGGAAAAAACATGAAATGCAAATTGACT
GCAGTCCTCAAACTGAAATGCCATCCTTTATTTCTTGA
CTTAAAGATCAACGCCTTAAAACAGTTTTAATTAAC
ATCTACAAGATATTTTTACTTCAGGCTTACAGATTCCA
TGCCTGTGTTCTTCAGCTTCCATTCAACCAGAAAGTTA
GGAATAATCCTTATTTCTTTGTAAGGATCATCTCTGAT |

TABLE IB-continued

| Gene | Species | NCBI # | DNA Sequence |
|---|---|---|---|
| | | | ACTGCTTCATGCTGCTATTTTATCCTGAAAGCTAAAAA<br>TCCAGGGGTTTGTTTAGGTTGCAAAGATGCATCTGGC<br>ATGTTCCCTTTTGAGGCAGCAGAATGGCTCTGCTACC<br>ATGCTTTCATTGTCAAACTGTCCAACCACAAAGTTATT<br>TACAAATGCTTACTTAAGCCCCTTAAAGTCTATAAGA<br>TGCATCTGTTTGGGAAGATACCAAGGGATACTATGGT<br>ACTGCTGAAGACAGTGACGGAACCATCTCTTTGTCAA<br>GATTTCAAAACTATACTGGACTAA (SEQ ID NO: 46) |
| TERT | Duck<br>[*Anas<br>platyrhynchos*] | XM_<br>013104503.2 | ATGCAGAGGCTGTGTGGGAAAAAGAAGAAGAACATC<br>CTCACGTATGGATACTCCTTGCTGGATGAAAACAGTT<br>CTCACTTCCAAATCATGCCGCTCTCAAACGTGTACAG<br>CTACCTGCCCAACACCGCAACAGAAACCATGCGTATC<br>AGTGGCCTCTGGGAAACGCTGCTGAGCAGGATAGGG<br>GATGACGTGATGATGTATTTATTGGAACACTGTGCGA<br>TCTTTATGCTGGTTCCCCCTAGTAACTGTTACCAAGTC<br>TGTGGGCAACCAATTTATGAACTTATTTCGCAAAATG<br>TAGAATCAGCCCCAGCGTTTGTTAAACAACGGCTTTC<br>AAAGCACAAACGTAGTAGCTTGCTTAAGTATACCCAG<br>AAAAGGCTAACGTTTCACAGACAGTATCTTTCAAAGT<br>CACGTCAGTCGAAACGCAGGCAAAGACTTGAAGCTA<br>ATGTCTCCAGCGTGAGAAATAAAACCAGCAATAATAT<br>ACAAAGCCTAGGGTCCGCTGCTCTGGAAAAACAGAGT<br>AGCTCCAATGCAGGTTTGTCAGCTACAGCACCGTCCT<br>TAAAAAGGAAGCTTGCTAGGGAGCAACTGGAAGTCA<br>CGGCTAAGAGAGCAAGATTAGAAGAGAAAGAGAGGG<br>AGGAACAGGCATGTAATACTGCTCCTAATGTAAACCA<br>GAGCATTCCCAAGAGGTATGGAACCGGCTGTGTAGCA<br>TCACGTTCTGTAAGTCTGACTAAAGAAAAAAACATTT<br>CTCAAAGAAGTAACAGTGATATGCCTCGTCCTCTTT<br>AGTTCACAATTCTCATCGCGGGAAGAAGTCTGTGGCA<br>GACAAAAGCTCTTTCCTGCAAGGAGCTGAGAGTAACA<br>GACATTTAAAGCCCAGCATTGAAATGCAAGCAGGATC<br>CAGCAGGAAGGGAGTGGAGACACGCAGGCCTATACC<br>TCGGTTGGATTGGGTACCAATCGAACCGGCGGAAAGT<br>AGTTCTTCAGGACACAAAAAGCAGGAAGGTCCCCTAG<br>CTCATCTGGCAGAGGAGGTACCAAATAGGGTTTTGCC<br>ATCTACAATATACATTGACAGGAAGTTTCTGTATTCTC<br>GCAGATACTGGGGGAGCGTTTCCCGAAATCCTTCCT<br>ATTGAATCGCCTGAAGGGTAGCCAGGCAGGTGTAAA<br>GCGGCTAATAGAAACGATATTCTTAAGCCAAAATCCG<br>TTTGGGCAAAAGTGCAACCAAGGTCTGCCACAGAAA<br>AAACGGAGAAAGAAGAAGCTTCCCAAACGCTTCTGG<br>AGAATGAGAAGTATATTTCAACAACTCTTAAAGAATC<br>ATGGAAAGTTCCCTTACGTAGCTTTCTTGAGACAAAA<br>TTGCCCTCTTCGGATATCTGACACCATTTTGGGAAAA<br>GCCAAGCTGCTCAGTCGGGCACCTTTGCCTGGGCAAG<br>CAGAGGCTCGCAAGCAAGCAGAACAGCTTGGGAAGG<br>AGCCTGCTGAGCGTGTGGCAAGCAGCAGATGTGAATC<br>TGGTCACACCAACGTGCCCAGCAGCGTACGCGCTCCT<br>CTCGCAGCATCTGCGTGTGGGGAGCCGGGGGGTGAG<br>GAGCAGATCCCTGCAGAGGCGTCTGATTCAGTCCTCA<br>GGGAGCTTCTCAAGGAGCACTGCAGCCACTTCCAGGT<br>GTACCTCTTTGTGAGGGAGTGCGTGGAGAGGGTGATC<br>CCCACCGAGCTCTGGGGTTCAAACCATAACAAGCGCC<br>GGTTCTTCAAGAACGTGAAAGCGTTCATTTCCATGGG<br>GAAGTACGCTAAGCTTTCCTTGCAGGTGTTGATGTGG<br>AAGATGAGAGTAAATGACTGCATGTGGCTTCGTCTGG<br>CCAAAGGTAATCACTTTGTTCCTGCCTCTGAACACCTT<br>TACCGTGAAGAAATTTTGGCTAAATTCCTATACTGGCT<br>GATGGATACGTATGTTGTTCAGTTGCTCAGATCATTTT<br>TCTATGTCACCGAGACCATGTTCCAGAAAAACATGCT<br>CTTCTACTACCGAAAGTGTATTTGGGCAAGTTACAG<br>GACATTGGAATTAGAAAGCATTTTTCCAAAGTGAAGC<br>TACGTCCTTTAACTGCAGAGGGAGATGGAAGCGATCCA<br>TCAAAAAAAATACCTTCCTATGGCGTCAAAGCTCCGT<br>TTCATTCCCAAAGTCACTGGACTAAGACCCATCGTCA<br>GAATGAGCGGTGTTGTTGAAGCACAAACGTTGAGCAA<br>GGAAAGCAGAGCAAAGAAGGCCGATGTGTCCAGGGC<br>TTTTGATAGCATTCCTCACAATAAACTTGTGGAAGTG<br>ATTTCACAGGTCTTAAAACCCGAGAAAAAAACTGTCT<br>ACTGCATACGGCGCTATGCAGTGGTTATGATCACTGG<br>AAGTGGAAAAACCAGGAAGTTATATAAGAGACATGT<br>TTCTACTTTCAAGGATTTTATGCCAGACATGAAGCAGT<br>TTGTGTCCCGGCTTCATGAGAGTACCTCATTGCGAGA<br>TGCAATAATAGTTGAACAGAGCCTAACTTTCAATGAG<br>ACAAGTGCCAGTCTATTTAATTTTTTTCTTCAAATGCT<br>AAATAATAACATCCTGGAAATTGAGCGCAGTTACTAC |

TABLE IB-continued

| Gene | Species | NCBI # | DNA Sequence |
|---|---|---|---|
| | | | TTACAGTGCTCTGGAATTCCACAGGGCTCCCTTTTGTC
AACCTTGCTTTGCAGCTTGTGCTATGAGACATGGAA
AACAAATTATTCAGTGGGGTACAGAAGGATGGAGTCC
TGATCCGTCTCATTGATGACTTTTTGCTGGTTACACCA
CATTTAATGCATGCAAGAACTTTTCTAAGGACTCTAG
CAATGGGCATTCCTGAGTATGGCTTTTTGATAAACCC
CAAAAAGACAGTGGTGAATTTTTCTGCTGACGATATC
CCAGAATGTTCTGAATTTAAACAGCTGCCAAACTGTC
GTTTGATCCATGGTGTGGCTTATTATTGGATACACAG
ACACTTGAGGTTTACTGCGATTACTCCAGCTATTCTG
TACTTCTATCAGATCAAGTCTTTCCTTCAATTCAAACA
GAACAGCTGGGAAAAACATGAAACACAAATTGCTTG
CAGTCCTTAAACTGAAATGCCATGGCTTGTTTCTCGAT
TTACAGATCAATAGCCTTAAAACAGTTTTCATTAACGT
CTACAAGATATTTTACTTCAGGCTTACAGGTTCCATG
CCTGTGTTATTCAACTTCCATTCAACCAGAAAGTTAG
GAACAATCCTGATTTCTTCCTCAGAGTCATCGCTGAG
AATGCATCGTGCTGCTATTCTATGCTAAAAGCTAAAA
ATCCAGGGTTTACTTTAGGTAACAGAGGTGCATCTGG
CATGTTTCCTTCTGAGGCAGCAGAGTGGCTCTGCTATC
ATGCCTTCACTGTCAAACTGTCAAACCACAAAGTTGT
TTACAAATGCTTGCTGAAGCCCCTGAAGTTCTGTATG
ATGCAGCTATTCCGGAAGATCCCAAAGGATACTAAGG
CACTACTGAAGACAGTGACAGAACCATCTATTTGTAA
AGATTTCAAATCTATCCTGGACTGA (SEQ ID NO: 47) |

TABLE 1C

| Gene | Species | NCBI # | Amino Acid Sequence |
|---|---|---|---|
| IGF2 | Cow [Bos Taurus] | NP_776512.2 | MGITAGKSVLVLLAFLAFASCCYAAYRPSETL
CGGELVDTLQFVCGDRGFYFSRPSSRINRRSR
GIVEECCFRSCDLALLETYCATPAKSERDVSA
STTVLPDDVTAYPVGKFFQYDIWKQSTQRLR
RGLPAFLRARRGRTLAKELEALREAKSHRPLI
ALPTQDPATHGGASSKASSD (SEQ ID NO: 26) |
| IGF1 | Zebrafish [Danio rerio] | NP_571900.1 | MSSGHFFQGHWCDVFKCTMRCLPSTHTLSLV
LCVLALTPATLEAGPETLCGAELVDTLQFVCG
DRGFYFSKPTGYGPSSRRSHNRGIVDECCFQS
CELRRLEMYCAPVKTGKSPRSLRAQRHTDIPR
TPKKPISGHSHSSCKEVHQKNSSRGNTGGRNY
RM (SEQ ID NO: 27) |
| serum albumin 1 | Rainbow trout [Oncorhynchus mykiss] | XP_021470329.1 | MRRPCILAIQPDTEFMPPELDASNFHMGPELC
TKDSKELLLSGKKLLYGVVRHKTTITEEQLKSI
STKYHSMKEKCCAAEDQAACFTEEAPKLVAE
SAELVKA (SEQ ID NO: 28) |
| GLUL | Tilapia [Oreochromis niloticus] | NP_001266597.1 | MATSASASLSKAVKQQYMELPQGDKVQAMY
IWIDGTGEGLRCKTRTLDSEPKSIEDLPEWNFD
GSSTYQSEGSNSDMYLIPSAMFRDPFRKDPNK
LVLCEVLKYNRKPTETNLRLTCKKVMDMVA
DQHPWFGMEQEYTILGTDGHPFGWPSNGFPG
PQGPYYCGVGADKAYGRDVVEAHYKACLYA
GVQICGTNAEVMPAQWEFQVGPCEGIDMGD
HLWVARFILHRVCEDFGVVASFDPKPIPGNW
NGAGCHTNFSTKEMREDGGLKAIEDSIEKLGK
RHSYHIRAYDPKGGLDNARRLTGRHETSNINE
FSAGVANRGASIRIPRNVGQEKKGYFEDRRPS
ANCDPYSVTEALIRTCLLNEEGDEPADY (SEQ ID NO: 29) |
| IGF2 | Rainbow trout [Oncorhynchus mykiss] | NP_001118169.1 | METQKRHEYHSVCHTCRRTENTRMKVKMMS
SSNRVLVIALALTLYIVEVASAETLCGGELVD
ALQFVCEDRGFYFSRPTSRSNSRRSQNRGIVEE
CCFRSCDLNLLEQYCAKPAKSERDVSATSLQII
PMVPTIKQDVPRKHVTVKYSKYEAWQRKAA
QRLRRGVPAILRARKFRRQAVKIKAQEQAMF
HRPLITLPSKLPPVLPPTDNYVSHN (SEQ ID NO: 30) |

TABLE 1C-continued

| Gene | Species | NCBI # | Amino Acid Sequence |
|---|---|---|---|
| IGF1 | Tropical clawed frog [*Xenopus tropicalis*] | XP_002936875.1 | MEKNNSLSTQLFKCYFCDFLKLKMHKMSYIH LLYLALCFLTLTHSAAAGPETLCGAELVDTLQ FVCGDRGFYFSKPTGYGSSNRRSHHRGIVDEC CFQSCDFRRLEMYCAPAKPAKSARSVRAQRH TDMPKAQKEVHLKNASRGNTGSRGFRM (SEQ ID NO: 31) |
| GLUL | Tropical clawed frog [*Xenopus tropicalis*] | XP_004914095.1 | MATSASAQLSKAIKQMYLELPQGDKVQAMYI WVDGTGEGLRCKTRTLDSEPKTIEDLPEWNF DGSSTYQSEGSNSDMYLIPVAMFRDPFRRDPN KLVLCEVLKYNRKTAETNLRHTCNQIMDMM ANEHPWFGMEQEYTLLGMDGHPFGWPSNGF PGPQGPYYCGVGADKAYGRDIVEAHYRACLY AGVKIAGTNAEVMPAQWEFQIGPCEGIEMGD HLWIARFILHRICEDFGIIVSFDPKPITGNWNGA GCHTNFSTKSMREEGGLKDIEESIERLSKRHD YHIRMYDPRGGKDNARRLTGFHETSSIHEFSA GVANRGASIRIPRSVGQEKKGYFEDRRPSANC DPYAVTEAMIRTCLLNETGDEPLEYKN (SEQ ID NO: 32) |
| ALB | Tropical clawed frog [*Xenopus tropicalis*] | AAH75287.1 | MNALMRRACCGALFPLSFRLAALSPMKGASN FSCGNVCASPAGCWAPPSGHDTGIKVYNSLTR RKDPLILADPTVATWYSCGPTVYDHAHLGHA CSYVRFDIIRRILLKVFGIDTVVVMVVTDIDDK IIKRAKELNISPVALARTYEQDFKQDMTALKV LPPTVYMRVTENIPQIISFIEHIIANGYAYATSQ GNVYFDVQSIGERYGKFNDSFSDTASESASQD KRHIRDFALWKTSKPEEPYWASPWGKGRPG WHIECSTIASSVFGKHLDIHTGGIDLAFPHHEN EIAQCEAYHQSTQWGNYFLHTGHLHLKGNEE KMSKSLRNYLTVKEFLKSFSPDQFRMFCLRSK YKSAVEYSNGSMHDAVNTLHTISSFVDDAKA YMKGQLICQPVQEALLWQRLNETKVNVKAA FSDDFDTPRAVDAVMDLIHHGNRQLKAVSKE SNSPRSSVVYGAMISYIEQFLEILGISLSQNQVA AEDRHSAVLFNVVEEMISFRSKVRNYALAAD ESPNAIGQEEKQQYKERRQLLLEREPLLQAC DIMRQHLAVYGINVKDRGNTSTWELLDRKEE T (SEQ ID NO: 33) |
| IGF2 | Tropical clawed frog [*Xenopus tropicalis*] | NP_001107144.1 | MRHLLLLSITFLVYTLDSAKAYGATETLCGGE LVDTLQFVCGDRGFYFSRNNGRSNRRANRGI VEECCFRSCDLELLETYCAKPAKNERDVSTAP STAIPPLNKQDLYHKHHHTKSSKYDIWQRKSI HRLRRGVPAIVRARQYRLLMQQAEESEQALS HRPLTTLPITRPLHQQTSEPSLN (SEQ ID NO: 34) |
| GLUL | Chicken [*Gallus gallus*] | NP_990824.1 | MATSASSHLSKAIKHMYMKLPQGEKVQAMYI WIDGTGEHLRCKTRTLDHEPKSLEDLPEWNF DGSSTFQAEGSNSDMYLRPAAMFRDPFRKDP NKLVLCEVFKYNRQSADTNLRHTCRRIMDMV SNQHPWFGMEQEYTLLGTDGHPFGWPSNCFP GPQGPYYCGVGADKAYGRDIVEAHYRACLY AGVKIGGTNAEVMPAQWEFQVGPCEGIEMGD HLWIARFILHRVCEDFGVIVSFDPKPIPGNWNG AGCHTNFSTKNMREDGGLKHIEEAIEKLSKRH QYHIRAYDPKGGLDNARRLTGFHETSSIHEFS AGVANRGASIRIPRNVGHEKKGYFEDRGPSAN CDPYAVTEALVRTCLLNETGDEPFEYKN(SEQ ID NO: 35) |
| ALB | Chicken [*Gallus gallus*] | NP_990592.2 | MKWVTLISFIFLFSSATSRNLQRFARDAEHKSE IAHRYNDLKEETFKAVAMITFAQYLQRCSYEG LSKLVKDVVDLAQKCVANEDAPECSKPLPSII LDEICQVEKLRDSYGAMADCCSKADPERNEC FLSFKVSQPDFVQPYQRPASDVICQEYQDNRV SFLGHFIYSVARRHPFLYAPAILSFAVDFEHAL QSCCKESDVGACLDTKEIVMREKAKGVSVKQ QYFCGILKQFGDRVFQARQLIYLSQKYPKAPF SEVSKFVHDSIGVHKECCEGDMVECMDDMA RMMSNLCSQQDVFSGKIKDCCEKPIVERSQCI MEAEFDEKPADLPSLVEKYIEDKEVCKSFEAG HDAFMAEFVYEYSRRHPEFSIQLIMRIAKGYE SLLEKCCKTDNPAECYANAQEQLNQHIKETQ DVVKTNCDLLHDHGEADFLKSILIRYTKKMP |

TABLE 1C-continued

| Gene | Species | NCBI # | Amino Acid Sequence |
|------|---------|--------|---------------------|
| | | | QVPTDLLLETGKKMTTIGTKCCQLPEDRRMA CSEGYLSIVIHDTCRKQETTPINDNVSQCCSSS YANRRPCFTAMGVDTKYVPPPFNPDMFSFDE KLCSAPAEEREVGQMKLLINLIKRKPQMTEEQ IKTIADGFTAMVDKCCKQSDINTCFGEEGANL IVQSRATLGIGA (SEQ ID NO: 36) |
| IGF1 | Chicken [*Gallus gallus*] | NP_001004384.1 | MEKINSLSTQLVKCCFCDFLKVKMHTVSYIHF FYLGLCLLTLTSSAAAGPETLCGAELVDALQF VCGDRGFYFSKPTGYGSSSRRLHHKGIVDECC FQSCDLRRLEMYCAPIKPPKSARSVRAQRHTD MPKAQKEVHLKNTSRGNTGNRNYRM (SEQ ID NO: 37) |
| IGF2 | Chicken [*Gallus gallus*] | NP_001025513 | MCAARQILLLLLAFLAYALDSAAAYGTAETL CGGELVDTLQFVCGDRGFYFSRPVGRNNRRIN RGIVEECCFRSCDLALLETYCAKSVKSERDLS ATSLAGLPALNKESFQKPSHAKYSKYNVWQK KSSQRLQREVPGILRARRYRWQAEGLQAAEE ARAMHRPLISLPSQRPPAPRASPEATGPQE (SEQ ID NO: 38) |

Provided herein are expression vectors comprising any one of the sequences selected from Tables 1A and 1B, and cells comprising any one of such expression vectors, for example a cell is from a livestock, poultry, game, or aquatic species.

Exemplary Methods and Compositions

Provided herein are methods of increasing the efficiency of maintaining cells in culture.

In some embodiments, provided herein is a method of decreasing the concentration of ammonia in the culture medium of cells comprising increasing the expression of glutamine synthetase (GS) protein in the cells, wherein the cells are of livestock, poultry, game or aquatic animal species, and wherein the concentration of ammonia in the culture medium is decreased by at least 2.5%.

In some embodiments, provided herein is a method of increasing the production of glutamine in cells comprising increasing the expression of glutamine synthetase (GS) protein in the cells, wherein the cells are of livestock, poultry, game or aquatic animal species, and wherein the concentration of glutamine in the cells is increased by at least 2.5%.

In some embodiments, provided herein is a method of increasing the concentration of Insulin-like growth factor (IGF) in the medium of cells in culture comprising increasing the expression of IGF protein secreted by the cells, wherein the cells are of livestock, poultry, game or aquatic animal species, and wherein the concentration of IGF in the ambient medium, or within the cell, is increased by at least 2.5%.

In some embodiments, provided herein is a method of increasing the concentration of albumin in the medium of cells in culture comprising increasing the expression of albumin in the cells, wherein the cells are of livestock, poultry, game or aquatic animal species, and wherein the concentration of albumin in the ambient medium, or within the cell, is increased by increased by at least 2.5%.

In some embodiments, provided herein are methods for increasing the cell density of a culture comprising metazoan cells comprising introducing any combination of the following cellular modifications: increased expression of GS, increased expression of IGF, increased expression of albumin, increased expression of telomerase reverse transcriptase (TERT), loss-of-function mutations in cyclin-dependent kinase inhibitor (CKI) proteins, increased expression of YAP, increased expression of TAZ, increased expression of myogenic transcription factors.

In some embodiments, provided herein is a method for increasing the cell density of a culture comprising metazoan cells, the method comprising (a) introducing into the cells one or more polynucleotide sequences encoding glutamine synthetase (GS), insulin-like growth factor (IGF), and albumin; and (b) culturing the cells in a cultivation infrastructure.

In some embodiments, provided herein is a method for increasing the cell density of a culture comprising metazoan cells, the method comprising (a) introducing into the cells one or more polynucleotide sequences encoding glutamine synthetase (GS), insulin-like growth factor (IGF), albumin or combinations (GS+IGF; GS+albumin; IGF+albumin; GS+IGF+albumin) thereof; and (b) culturing the cells in a cultivation infrastructure.

In some embodiments, provided herein is a method for increasing the cell density of a culture comprising metazoan cells, the method comprising (a) introducing into the cells one or more polynucleotide sequences encoding glutamine synthetase (GS), insulin-like growth factor (IGF), albumin or combinations (GS+IGF; GS+albumin; IGF+albumin; GS+IGF+albumin) thereof; (b) introducing into the cells a polynucleotide sequence encoding a telomerase reverse transcriptase (TERT); and (c) culturing the cells expressing GS, IGF, albumin or combinations thereof and TERT in a cultivation infrastructure.

As provided herein, the density of cells in a culture or cultivation infrastructure is determined by calculating the cell number per unit volume of the cultivation infrastructure, by determining the biomass per unit volume of the cultivation infrastructure, by determining the biomass DNA content per unit volume of the cultivation infrastructure, by determining the biomass RNA content per unit volume of the cultivation infrastructure, by determining the biomass protein content per unit volume of the cultivation infrastructure, or by visual, electronic, metabolic, spectroscopic, or microscopic, measurement of the biomass density.

In some embodiments, an increase in the cell density of a culture using the methods described herein is about 1.025 fold, 1.05 fold, 1.10-fold, 1.15-fold, 1.20-fold, 1.25-fold, 1.30 fold, 1.35-fold, 1.40-fold, 1.45-fold, 1.5-fold, 2-fold, 2.5-fold, 3-fold, 3.5-fold, 4-fold, 4.5-fold, 5-fold, 7.5-fold, 10-fold, 15-fold, 20-fold, 25-fold, 30-fold, 40-fold, or even about 50-fold, 75-fold, 100-fold, 150-fold, or is even about 200-fold, compared to the density of a culture comprising cells that do not include one or more cellular modifications described herein.

In some embodiments, an increase in the density of cells in a culture using the methods described herein is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 150%, at least 200%, at least 250%, at least 300%, at least 350%, at least 400%, at least 450%, at least 500%, at least 550%, at least 600%, at least 650%, at least 700%, at least 750%, at least 800%, at least 850%, at least 900%, at least 950%, at least 1000%, compared to the cell density of a culture comprising cells that do not include one or more cellular modifications described herein.

In some embodiments, using the methods described herein, there is an increased yield of cellular biomass harvestable per unit volume of the cultivation infrastructure. In some embodiments, the increase is at least about 1.0-fold, 1.25-fold, 1.5-fold, 2-fold, 2.5-fold, 3-fold, 3.5-fold, 4-fold, 4.5-fold, 5-fold, 7.5-fold, 10-fold, 15-fold, 20-fold, 25-fold, 30-fold, 40-fold, or even about 50-fold, 75-fold, 100-fold, 150-fold, or is even about 200-fold compared to the yield of cellular biomass harvestable per unit volume of the cultivation infrastructure in the absence of one or more cellular modifications described herein.

In some embodiments, methods described herein increase the density of cells in a culture by increasing the rate of proliferation of cells in the culture. In some embodiments, the increase in the rate of cell proliferation is at least 2.5%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 150%, at least 200%, at least 250%, at least 300%, at least 350%, at least 400%, at least 450%, at least 500%, at least 550%, at least 600%, at least 650%, at least 700%, at least 750%, at least 800%, at least 850%, at least 900%, at least 950%, or at least 1000%, including values and ranges therebetween, compared to the rate of proliferation of cells that do not include one or more cellular modifications described herein. In some embodiments, the increase in the rate of cell proliferation is about 25-1000%, about 25-750%, about 25-500%, about 50-1000%, about 50-750%, about 50-500%, about 100-1000%, about 100-750%, or about 100-500%, including values and ranges therebetween, compared to the rate of proliferation of cells that do not include one or more cellular modifications described herein.

In some embodiments, methods described herein increase the cell density of a culture by decreasing cell death within the cellular biomass. In some embodiments, the decrease in cell death is at least 2.5%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, including values and ranges therebetween, compared to the rate of cell death in cells that do not include one or more cellular modifications described herein. In some embodiments, a decrease in the rate of cell death within the cellular biomass is about 2.5-10%, about 2.5-75%, about 2.5-50%, about 5.0-100%, about 5.0-75%, about 5.0-50%, about 10-100%, about 10-75%, or about 10-50%, including values and ranges therebetween, compared to the rate of cell death in cells that do not include one or more cellular modifications described herein.

In some embodiments, using the methods described herein, the density of cells in a culture may reach about $10^5$ cells/mL, about $10^6$ cells/mL, about $10^7$ cells/mL, about $10^8$ cells/mL, about $10^9$ cells/mL, or about $10^{10}$ cells/mL (cells in the cellular biomass/mL of cultivation infrastructure), including values and ranges therebetween.

In some embodiments, using the methods described herein, the density of cells in a culture may reach about 1 g/L, 5 g/L, 10 g/L, 25 g/L, 50 g/L, 75 g/L, 100 g/L, 150 g/L, 200 g/L, 250 g/L, 300 g/L, 350 g/L, 400 g/L, 450 g/L, 500 g/L, 550 g/L, 600 g/L, 650 g/L, 700 g/L, 750 g/L, 800 g/L, 850 g/L, 900 g/L, or 1000 g/L (g of cellular biomass/L of cultivation infrastructure), including values and ranges therebetween. In some embodiments, the density of cells in a culture may range from about 1 g/L to about 5 g/L, about 1 g/L to about 750 g/L, about 1 g/L to about 500 g/L, about 1 g/L to about 250 g/L, about 1 g/L to about 100 g/L, about 1 g/L to about 50 g/L, about 5 g/L to about 1000 g/L, about 5 g/L to about 750 g/L, about 5 g/L to about 500 g/L, about 5 g/L to about 250 g/L, about 5 g/L to about 100 g/L, about 5 g/L to about 50 g/L, about 25 g/L to about 1000 g/L, about 25 g/L to about 750 g/L, about 25 g/L to about 500 g/L, about 25 g/L to about 300 g/L, about 25 g/L to about 250 g/L, about 25 g/L to about 100 g/L, about 50 g/L to about 1000 g/L, about 50 g/L to about 750 g/L, about 50 g/L to about 500 g/L, about 50 g/L to about 300 g/L, about 50 g/L to about 250 g/L, about 100 g/L to 1000 g/L, about 100 g/L to about 750 g/L, about 100 g/L to about 500 g/L, about 200 g/L to about 1000 g/L, about 200 g/L to about 750 g/L, about 200 g/L to about 500 g/L, about 300 g/L to about 1000 g/L, about 300 g/L to about 800 g/L, about 400 g/L to about 1000 g/L, or about 500 g/L to about 1000 g/L including values and ranges therebetween.

In some embodiments, provided herein is an in vitro method for producing a cultured edible product (e.g. cultured poultry, cultured livestock, cultured game, cultured fish), the method comprising: (a) introducing one or more polynucleotide sequences encoding glutamine synthetase (GS), insulin-like growth factor (IGF), albumin or combinations (GS+IGF; GS+albumin; IGF+albumin; GS+IGF+albumin) thereof into myogenic metazoan cells; (b) optionally introducing a polynucleotide sequence encoding a telomerase reverse transcriptase (TERT) into the myogenic metazoan cells; (c) inducing myogenic differentiation of the cells, wherein the differentiated cells form myocytes and multinucleated myotubes; and (d) culturing the myocytes and myotubes to generate skeletal muscle fibers, thereby producing a cultured edible product. In one embodiment, myogenic cells are natively myogenic. In another embodiment, myogenic cells are not natively myogenic and are modified to become myogenic cells by expressing one or more myogenic transcription factors.

In some embodiments, provided herein is an in vitro method for producing a cultured edible product, the method comprising: (a) overexpressing GS, IGF, albumin, or a combination thereof in a self-renewing cell line, wherein the cell line is a myogenic transcription factor-modified cell line, and wherein the cell line is of a livestock, poultry, game or aquatic animal species; (b) inducing myogenic differentiation of the cell line, wherein the differentiated cell line forms myocytes and multinucleated myotubes; and (c) culturing the myocytes and myotubes to generate skeletal muscle fibers, thereby producing a cultured edible product.

In some embodiments, provided herein is cultured edible product produced by the in vitro methods.

In the methods for producing a cultured edible product provided herein, myogenic differentiation can be induced in a variety of ways. In some embodiments, cellular biomass with increased cell density can be differentiated into a phenotype of interest by contacting the cells with a differentiation agent. For example, if the phenotype of interest for the expanded cellular biomass is skeletal muscle and the cellular biomass comprises non-myogenic cells (e.g., non-myogenic stem cells or fibroblasts), the expanded cellular biomass can be contacted with a differentiation agent that would induce the skeletal muscle phenotype into the cells of the biomass. Exemplary differentiation agents that may induce skeletal muscle phenotype include myogenic transcription factors such as MYOD1, MYOG, MYF5, MYF6, PAX3, PAX7, paralogs, orthologs, and genetic variants thereof. A PCT publication, WO/2015/066377, discloses exemplary methods for differentiating cells into a skeletal muscle phenotype and is incorporated by reference herein in its entirety. Accordingly, in some embodiments, the expanded cellular biomass may be differentiated into the skeletal muscle phenotype using the methods described in WO/2015/066377.

In some embodiments, cells of the expanded biomass can be differentiated into a phenotype of interest without a differentiation agent. For example, if the phenotype of interest for the expanded biomass is a skeletal muscle and the cellular biomass comprises cells of the skeletal muscle lineage, then these cells may differentiate into the skeletal muscle phenotype on their own without a need for an external differentiation agent. However, in some embodiments, an external differentiation agent such as one or more myogenic transcription factors can be used to differentiate cells of the skeletal muscle lineage into the skeletal muscle phenotype.

Induction of myogenic differentiation in cells overexpressing any one of the cellular modifications described herein would result in the formation of differentiated myocytes and multinucleated myotubes. These myocytes and myotubes are cultured to generate skeletal muscle fibers thereby producing a cultured edible biomass or a cultured edible product.

The cultured edible biomass/product can be processed as a raw, uncooked edible product (cultured meat) or as a cooked edible product or as a cooked/uncooked food ingredient. In some embodiments, processing comprises withdrawal of the culture medium that supports the viability, survival, growth, expansion and differentiation of the cellular biomass. Withdrawal may comprise physical removal of the culture medium or altering the composition of the culture medium, for example, by addition of components that would reduce or prevent further expansion and/or differentiation of the biomass or by depletion of components that support expansion and/or differentiation of the biomass.

In some embodiments, processing comprises exposing the cultured edible biomass to sub-physiological temperatures that would not support the expansion and/or differentiation of the biomass. Sub-physiological temperatures include a temperature of about 15° C. (about 59° F.) or lower, about 10° C. (about 50° F.) or lower, about 0° C. to about 15° C. (about 32° F. to about 59° F.), about 0° C. to −15° C. (about 32° F. to about 5° F.), about −15° C. to about 15° C. (about 5° F. to about 59° F.), about 0° C. to −213° C. (about 32° F. to about −350° F.), about −30° C. to about −100° C. (about −22° F. to about −148° F.), about −50° C. to about −90° C. (about −58° F. to about −130° F.), or about −170° C. to about −190° C. (about −274° F. to about −310° F.). For example, in one embodiment, the expanded and/or differentiated biomass can be cooled to a temperature of about 2° C. to about 8° C. (about 35° F. to about 46.5° F.). In another embodiment, the expanded and/or differentiated biomass can be frozen, for example, by cooling to a temperature of about 32° F. or lower, e.g. about 32° F. to about 0° F., about 32° F. to about −10° F., about 32° F. to about −20° F., about 32° F. to about −30° F., about 32° F. to about −40° F., about 32° F. to about −50° F., about 32° F. to about −60° F., about 32° F. to about −70° F., about 32° F. to about −80° F., and the like. In some embodiments, the expanded and/or differentiated biomass can be exposed to sub-physiological temperatures as low as about −300° F. to about −350° F., such as the liquid nitrogen temperature of about −321° F.

In some embodiments, processing comprises exposing the biomass to superphysiological temperatures that would not support the viability, survival, expansion and/or differentiation of the biomass. In one embodiment, exposing the biomass to superphysiological temperatures comprises fully or partially cooking the biomass, for example, by heating the biomass to a temperature of about 100° F. to about 600° F., about 100° F. to about 550° F., about 100° F. to about 500° F., about 100° F. to about 450° F., about 100° F. to about 400° F., about 100° F. to about 350° F., about 100° F. to about 300° F., about 100° F. to about 250° F., about 100° F. to about 200° F. or about 100° F. to about 150° F.

In some embodiments, provided herein is an edible metazoan biomass product (cultured edible product) comprising cells having any combination of the following cellular modifications: increased expression of GS, increased expression of IGF, increased expression of albumin, increased expression of telomerase reverse transcriptase (TERT), loss-of-function mutations in cyclin-dependent kinase inhibitor (CKI) proteins, increased expression of YAP, increased expression of TAZ, increased expression of myogenic transcription factors.

Cultivation Infrastructure

As referred to herein, a cultivation infrastructure refers to the environment in which metazoan cells are cultured, i.e. the environment in which the cellular biomass is cultivated.

A cultivation infrastructure may be a tube, a cylinder, a flask, a petri-dish, a multi-well plate, a dish, a vat, an incubator, a bioreactor, an industrial fermenter and the like. A cultivation infrastructure may be a culture medium in which metazoan cells are cultured.

A cultivation infrastructure can be of any scale, and support any volume of cellular biomass and culturing reagents. In some embodiments, the cultivation infrastructure ranges from about 10 µL to about 100,000 L. In exemplary embodiments, the cultivation infrastructure is about 10 µL, about 100 µL, about 1 mL, about 10 mL, about 100 mL, about 1 L, about 10 L, about 100 L, about 1000 L, about 10,000 L, or even about 100,000 L.

In some embodiments, the cultivation infrastructure comprises a substrate. A cultivation infrastructure may comprise a permeable substrate (e.g. permeable to physiological solutions) or an impermeable substrate (e.g. impermeable to physiological solutions).

In some embodiments, the cultivation infrastructure comprises a primary substrate, which can be a flat, concave, or convex substrate. In some embodiments, the cultivation infrastructure further comprises a secondary substrate, either introduced, or autologous, to direct cellular growth between the substrates, e.g. to direct attachment, proliferation and hypertrophy of cells on a plane perpendicular to the primary substrate.

In some embodiments, the cultivation infrastructure comprises a hydrogel, a liquid cell culture media, or soft agar.

In some embodiments, the cultivation infrastructure does not comprise a substrate to which cells can adhere. In some embodiments, the cultivation infrastructure comprises a suspension culture, e.g. supporting the growth of a self-adhering biomass, or single-cell suspension in a liquid medium.

In some embodiments, the cultivation infrastructure comprises adherent cells (i.e. those cells that adhere to a substrate). In some embodiments, the cultivation infrastructure comprises non-adherent cells (i.e. those cells that do not adhere to a substrate). In some embodiments, the cultivation infrastructure comprises both adherent and non-adherent cells.

Kits and Articles of Manufacture

The present application also provides kits for engineering cells of interest to increase production of glutamine, increase production of IGF, increase production of albumin, and/or decrease the production of ammonia.

In some embodiments, the kits comprise a GS DNA construct, an IGF construct, and/or an albumin construct for transfection. The kits optionally may further comprise tools for immortalization or extending cell self-renewal capacity, activating YAP/TAZ pathways, and myogenic differentiation.

The present application also provides articles of manufacture comprising any one of the compositions or kits described herein.

It is to be understood that the terminology employed herein is used for the purpose of describing particular embodiments only and is not intended to be limiting since the scope of the present invention will be limited only by the appended claims and equivalents thereof. The following examples are for illustrative purposes. These are intended to show certain aspects and embodiments of the present invention but are not intended to limit the invention in any manner.

EXAMPLES

Example 1: The Effects of Ectopic Expression of Glutamine Synthetase (GS) in Primary Duck Fibroblasts and Myoblasts This example describes the effects of ectopic expression of GS on ammonia concentration in ambient media from primary duck fibroblast and myoblast cultures.

Methods

Measurement of Ammonia Concentration

Following the manufacturer's instructions (Sigma-Aldrich #AA0100), the absolute ammonia concentration (in μg/mL) was determined for each time point and treatment group (in biological triplicate). Results were reported as the mean of the treatment group bounded by the 95% confidence interval. Measurements of the ammonia detection assay were performed on a spectrophotometer (Spectramax 250). All statistical analyses and visualizations were performed in Microsoft Excel 2010.

Primary Duck Fibroblast and Myoblast Cultures

A peptide-coated (peptides mimicking extracellular matrix) T-150 flask was prepared for cell seeding by adding 10 mL of an aqueous peptide solution to the T-150 flask and incubated for at least 1 hour at 37° C. The aqueous peptide solution was aspirated from the T-150 flask and the flask washed with PBS. 25 mL of culture medium specific to the targeted cell type was added to the flask and the flask incubated and equilibrated at 37° C. in 5% atmospheric $CO_2$.

Under aseptic conditions the targeted tissue was excised with dissection instruments. Tissue sections were minced into approximately 2 mm×2 mm sections. 150 mg tissue sections were weighed and then transferred to a sterile 50 mL centrifuge tube containing 8 mL of enzymatic cell dissociation solution consisting of 0.17% trypsin and 0.085% collagenase in Hanks Balanced Salt Solution pH 7.4. The centrifuge tube was closed tightly and incubated on ice. Following overnight incubation, the tube was then incubated at 37° C. for 15 minutes. The enzymatic tissue digest was triturated with a sterile 5 mL serological pipet for 1 minute. The cell suspension was passed through a sterile 70 μm strainer into a sterile 50 mL centrifuge tube. 20 mL of cold basal medium was flowed through the strainer. The strainer was discarded and the tube capped. The centrifuge tube was centrifuged at 300×g for 5 minutes. The supernatant was aspirated, and the cell pellet was resuspended in culture medium before transfer to the T-150 flask prepared for seeding. The flask was incubated at 37° C. in 5% atmospheric $CO_2$. The cells were checked daily for growth and contamination. Culture medium was changed every two to three days. After the cultures reached a confluence of 70% to 90%, the cells were dissociated and either cryopreserved or passaged using standard cell culture technique.

Transfection

The primary duck fibroblast and myoblast cultures were routinely sub-cultured under 5% atmospheric $CO_2$ at 37° C. (i.e. incubation conditions) until 80% confluent on gelatin-coated dishes. Cells were dissociated to single cells and counted to determine the number of cells. In a gelatin-coated 12-well tissue culture plate, $5×10^4$ cells were seeded into each well. Growth culture medium was added to each well to a total final volume of 1 ml per well. The cells were incubated overnight at 37° C.

Cells were washed with PBS and transfection media added. 1 μg of plasmid DNA containing the murine GS coding sequence (pcDNA3.1+/C-(K)DYK (SEQ ID NO: 58), Genscript OMu19897D, Table 1A) driven by a CMV promoter was complexed using the Lipofectamine 3000 system (Thermo Fisher Scientific #L3000001). The complexed DNA was added dropwise to each well in biological triplicate. Vehicle control cells received an equivalent treatment absent the DNA. The cells were shaken gently and incubated for 48 hours; the media was then changed to proliferation media supplemented with 10% FBS and either the combination of 434 μg/mL (2 mM) L-alanyl-L-glutamine and 584 μg/mL (4 mM) L-glutamine or no supplemented glutamine (0 mM glutamine, "glutamine absent"). The cells were then returned to incubation conditions.

Conditioned Media Collection

Cells were washed with PBS, and 1 mL of either glutamine-supplemented or glutamine-absent proliferation medium was added to each well. Cells were then returned to incubation.

200 μL media samples were collected from each well and stored in sterile tubes at −80° C. In a gelatin-coated 12-well plate, proliferation medium was incubated in wells devoid of cells (i.e. acellular) in parallel experimental wells containing cells as a background control for ammonia accumulation.

Following each 24-hour period through day seven, 200 μL samples of media were collected from each well stored at −80° C. 200 μL of fresh medium were then added to each of the wells to a total volume of 1 mL. Following sample collection, the plates were then returned to incubation conditions.

Results

As demonstrated in FIG. 1, concentration of ammonia in media spontaneously increased in the absence of cells over the course of seven days. The rate at which ammonia increased differed between the three media conditions shown in the figure. Initial concentration of ammonia was largely dependent on whether or not the media had been supplemented with glutamine.

Figure 2B:
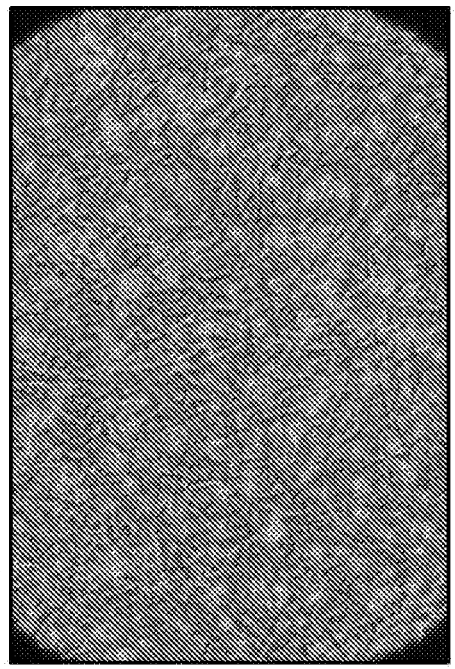
FIGS. 2A-D show morphology of wild type duck fibroblast cells following transfection with a glutamine synthetase (GS) gene.
Figure 2D:
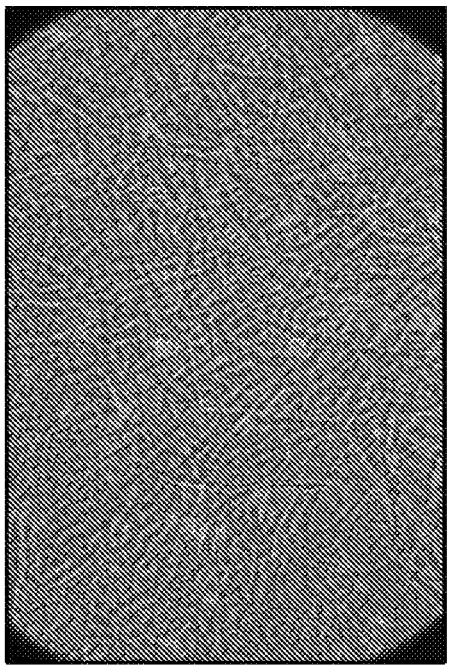
Figure 2A:
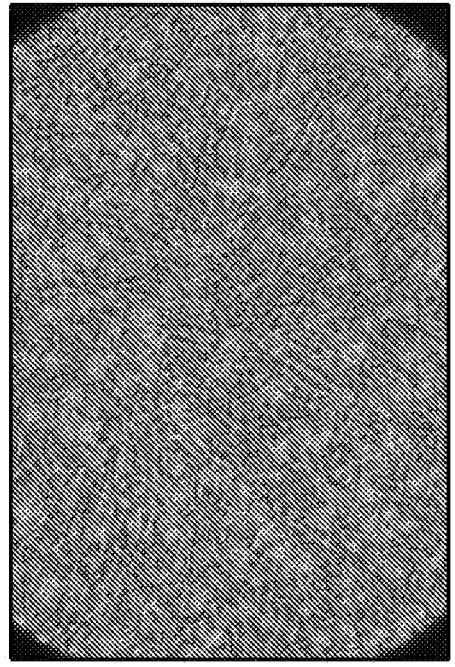
Figure 2C:
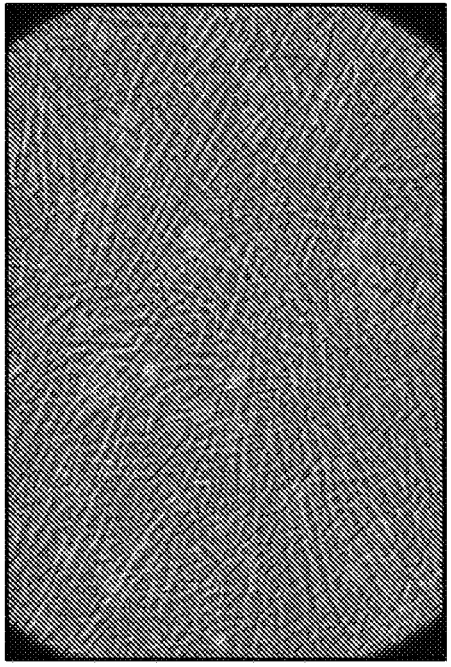

FIG. 2A-D shows that fibroblasts transfected with expression vectors coding for glutamine synthetase exhibited morphology similar to vehicle-only control transfected fibroblasts. Transfected fibroblasts remained viable and stable as evidenced by their continued adherence to substrate following a seven day incubation. FIG. 2A shows fibroblasts transfected with vehicle-only and grown in media with supplemented glutamine; FIG. 2B shows fibroblasts transfected with mouse GS and grown in media with supplemented glutamine; FIG. 2C shows fibroblasts transfected with vehicle-only and grown in media without supplemented glutamine; and FIG. 2D shows fibroblasts transfected with mouse GS and grown in media without supplemented glutamine.

Figure 3:
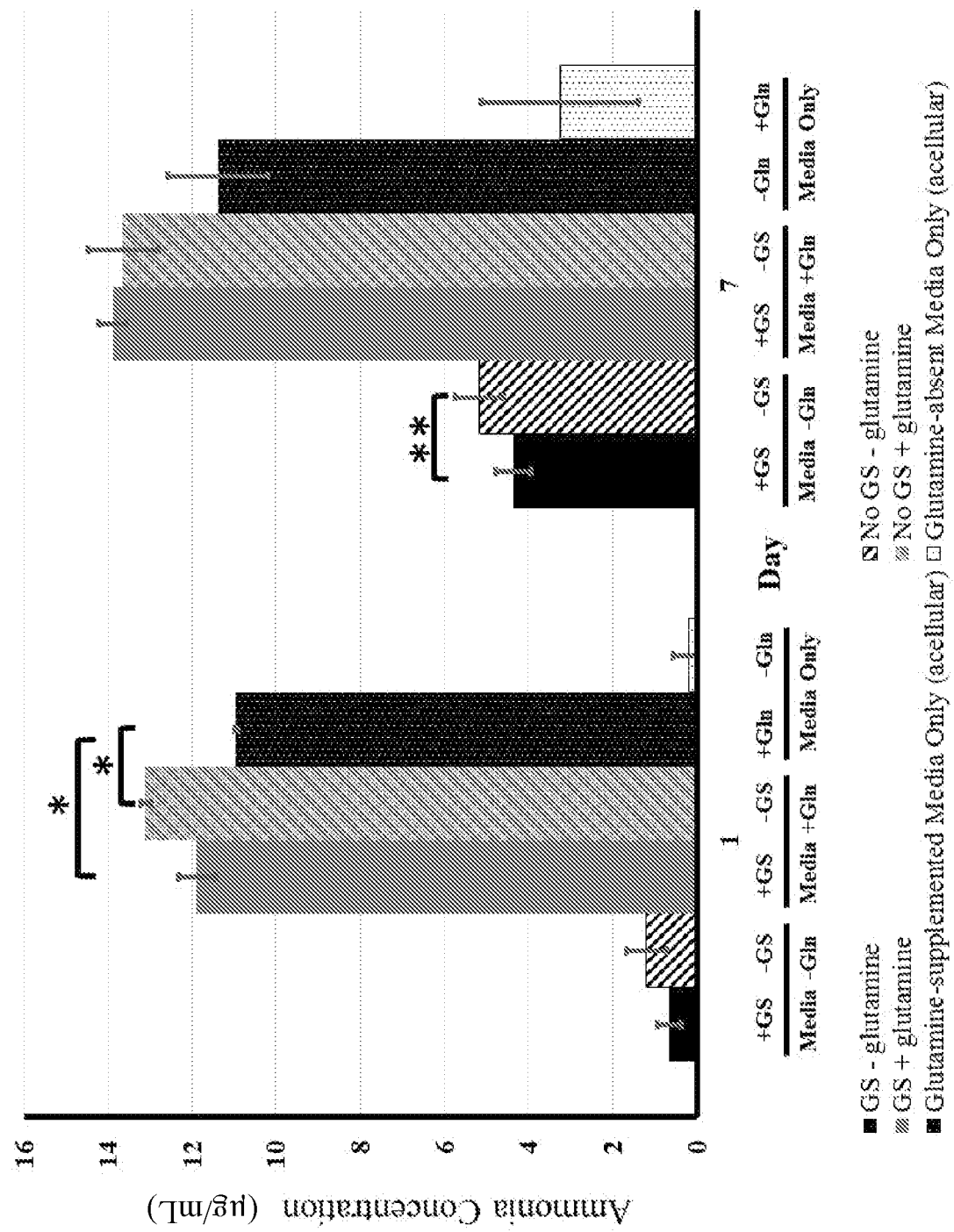
FIG. 3 demonstrates quantification of ammonia levels in media following transfection of wild type duck fibroblast cells with a GS gene.

As demonstrated in FIG. 3, following a one day incubation post transfection, fibroblasts expressing GS and grown in a culture medium supplemented with glutamine showed a smaller increase in extracellular ammonia than cells transfected with vehicle-only and grown in a culture medium supplemented with glutamine compared to a culture medium supplemented with glutamine in which no cells were grown. Within glutamine treatment groups, two-way ANOVA revealed a statistically significant difference ($p<0.001$) between ammonia concentration over time, dependent upon GS transfection and dependent on which day the measurement was made. The glutamine-supplemented culture medium in which no cells were grown showed an increase in ammonia concentration of 0.072 μg/mL/day, and the culture medium not supplemented with glutamine in which no cells were grown showed an increase in ammonia concentration of 0.51 μg/mL/day. It was observed on Day 3 that fibroblasts grown without supplemental ammonia and transfected with GS exhibited a statistically lower ammonia concentration compared to fibroblasts transfected with vehicle-only. Seven days following transfection, there was a significant difference ($p<0.001$, two-way ANOVA) in the amount of ammonia in glutamine absent growth media between cells transfected with GS and cells transfected with vehicle-only. Error bars in FIG. 3 indicate 95% confidence intervals. One asterisk indicates $p<0.05$; two asterisks indicate $p<0.01$.

Figure 4:
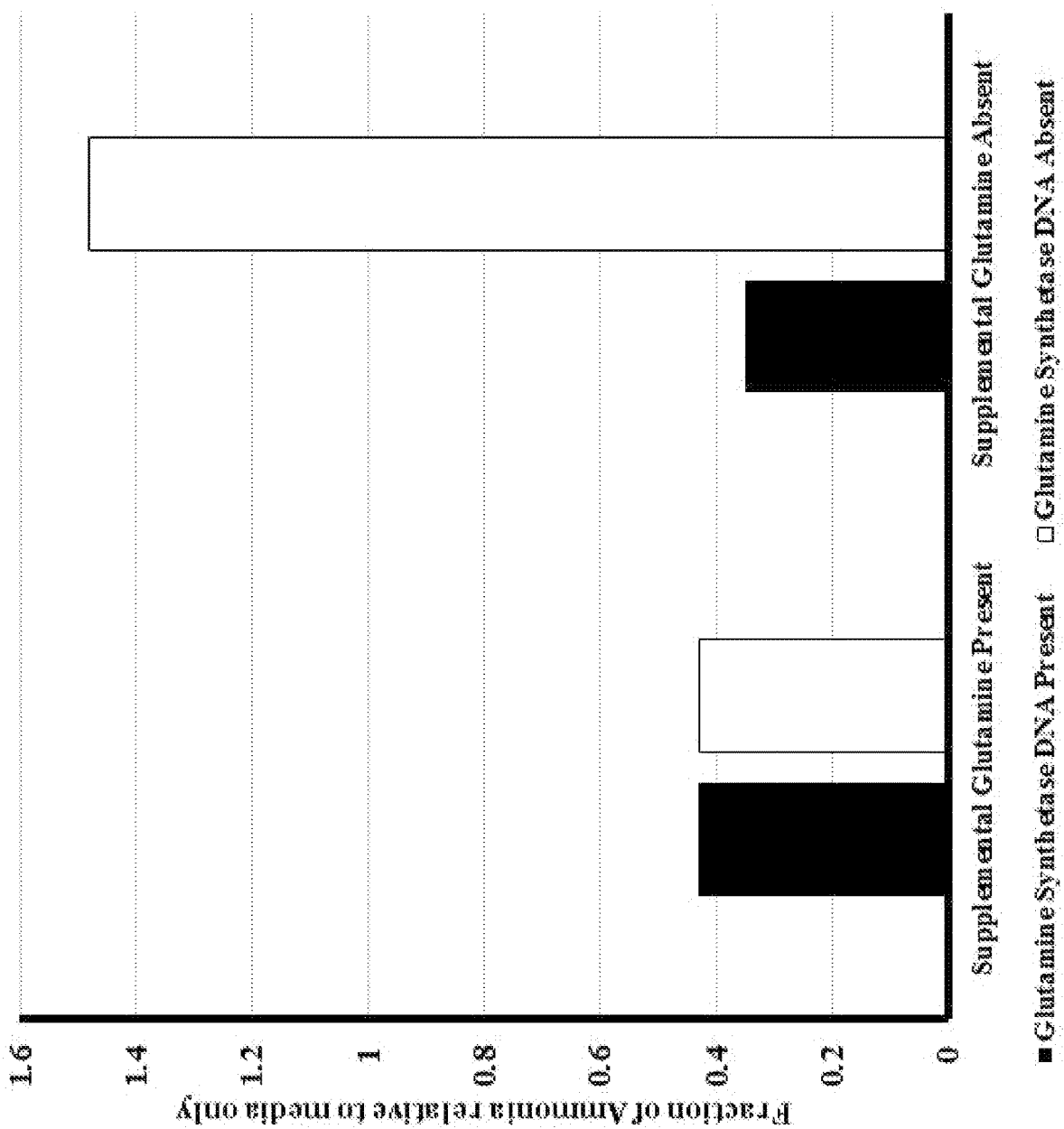
FIG. 4 shows an increase in glutamine in culture media from duck fibroblast cell cultures normalized to culture medium in which no cells were present.
Figure 5B:
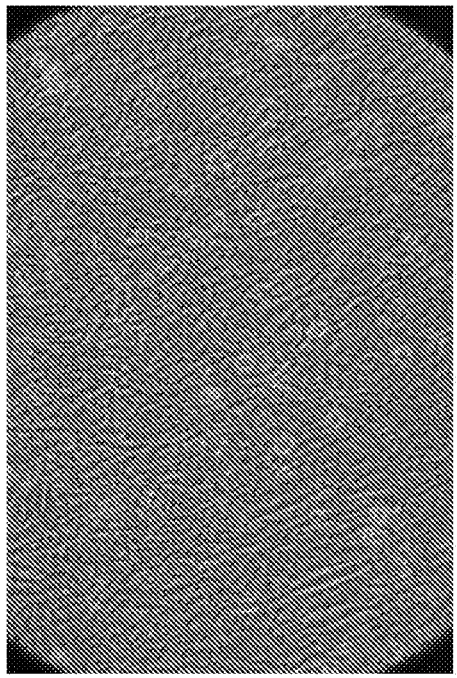
FIGS. 5A-D show morphology of wild-type duck myoblast cells following transfection with GS.
Figure 5D:
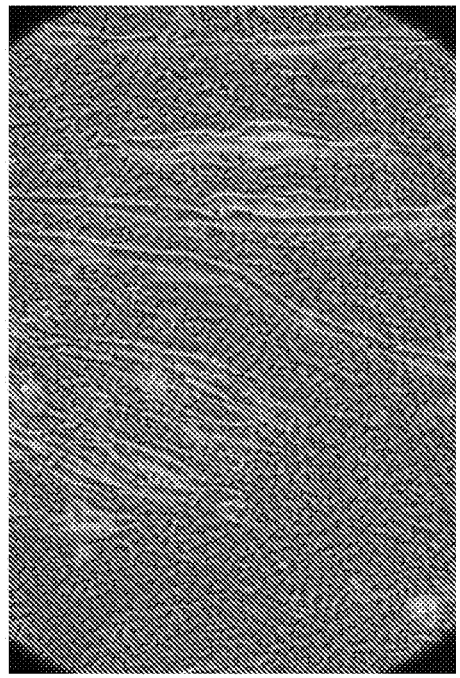
Figure 5A:
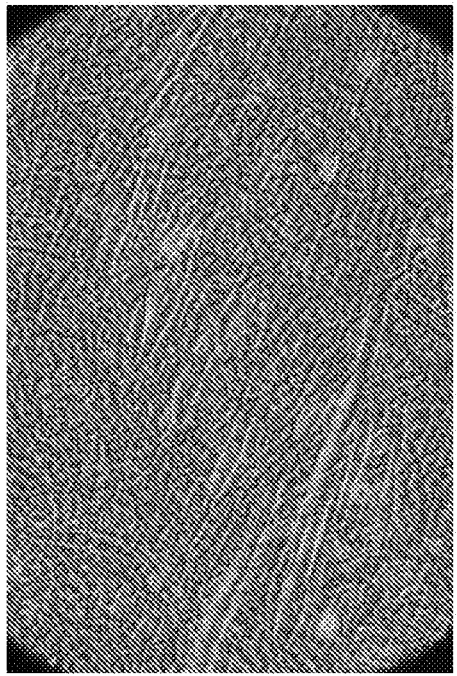
Figure 5C:
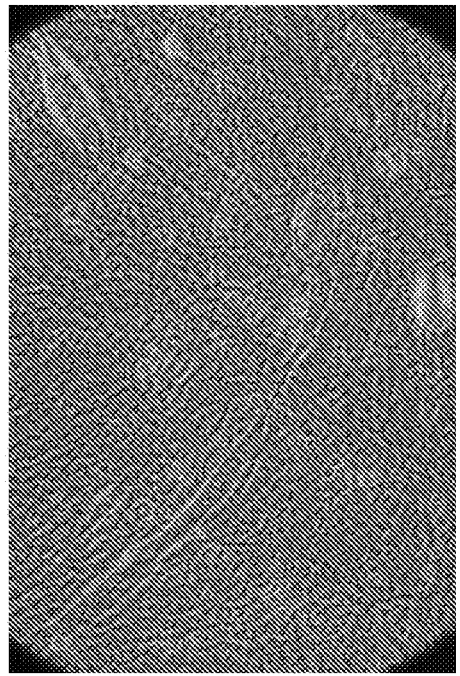

FIG. 4 and Table 2 show normalized data from FIG. 3 to present a percent increase in ammonia relative to the extracellular ammonia concentration. After seven days in media without supplemented glutamine, fibroblasts transfected with GS showed a smaller increase in ammonia than cells transfected with vehicle-only.

TABLE 2

Percent Increase of Ammonia Relative to Media-Only Ammonia Concentration

|  | +Glutamine Media | −Glutamine Media |
|---|---|---|
| Glutamine Synthetase | 43% | 35% |
| Vehicle | 43% | 148% |

As shown in FIG. 5, myoblasts transfected with expression vectors coding for GS exhibited morphology similar to vehicle treated myoblasts. Transfected cells remain viable and capable of normal differentiation as evidenced by spontaneous myotube formation. FIG. 5A shows myoblasts transfected with vehicle and grown in media with supplemented glutamine; FIG. 5B shows myoblasts transfected with a mouse GS gene and grown in a medium with supplemented glutamine; FIG. 5C shows myoblasts transfected with vehicle-only and grown in media without supplemented glutamine; and FIG. 5D shows myoblasts transfected with a mouse GS gene and grown in a medium without supplemented glutamine.

Figure 6:
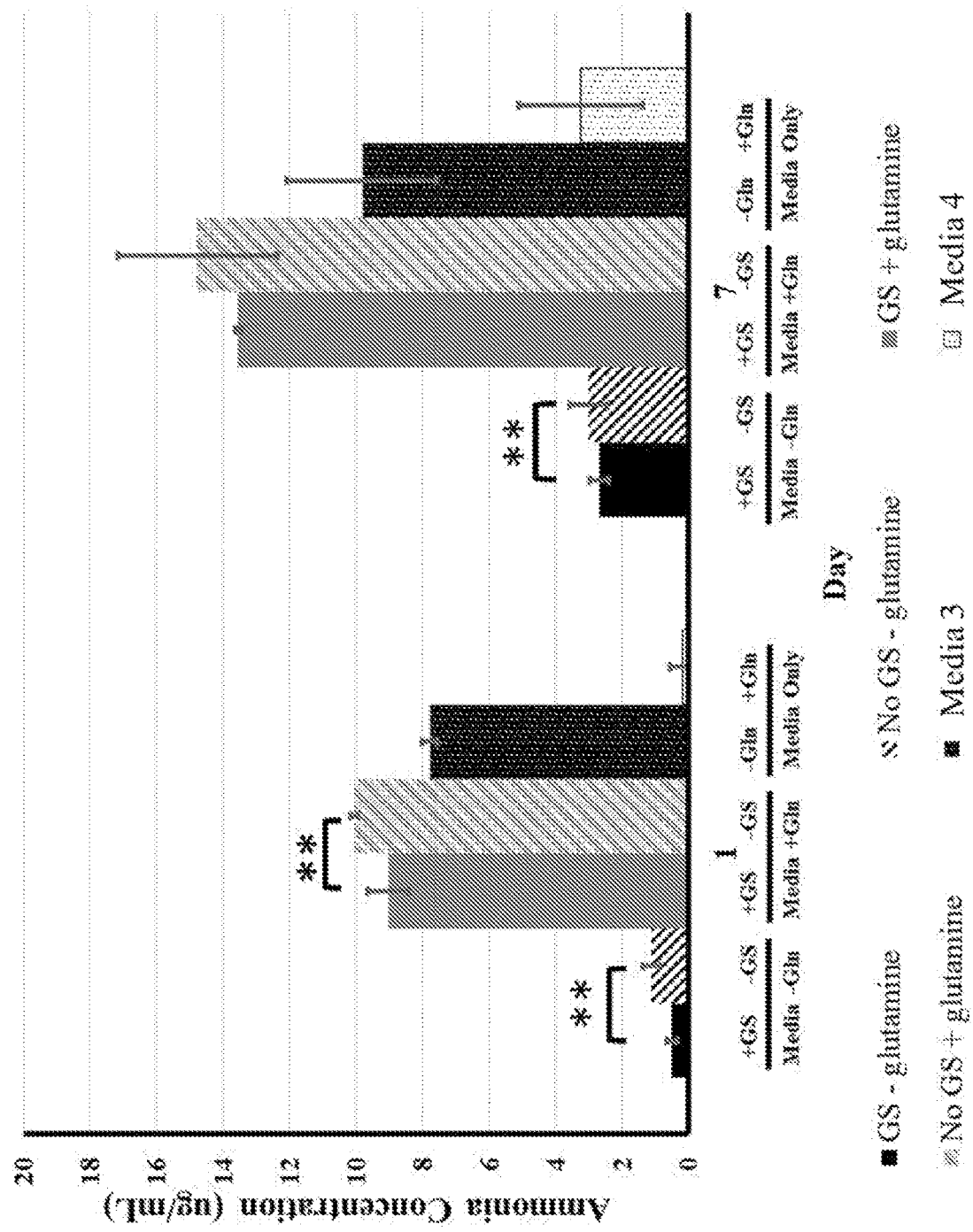
FIG. 6 demonstrates quantification of ammonia levels in media following transfection of wild type duck myoblast cells with a GS gene.
Figure 7:
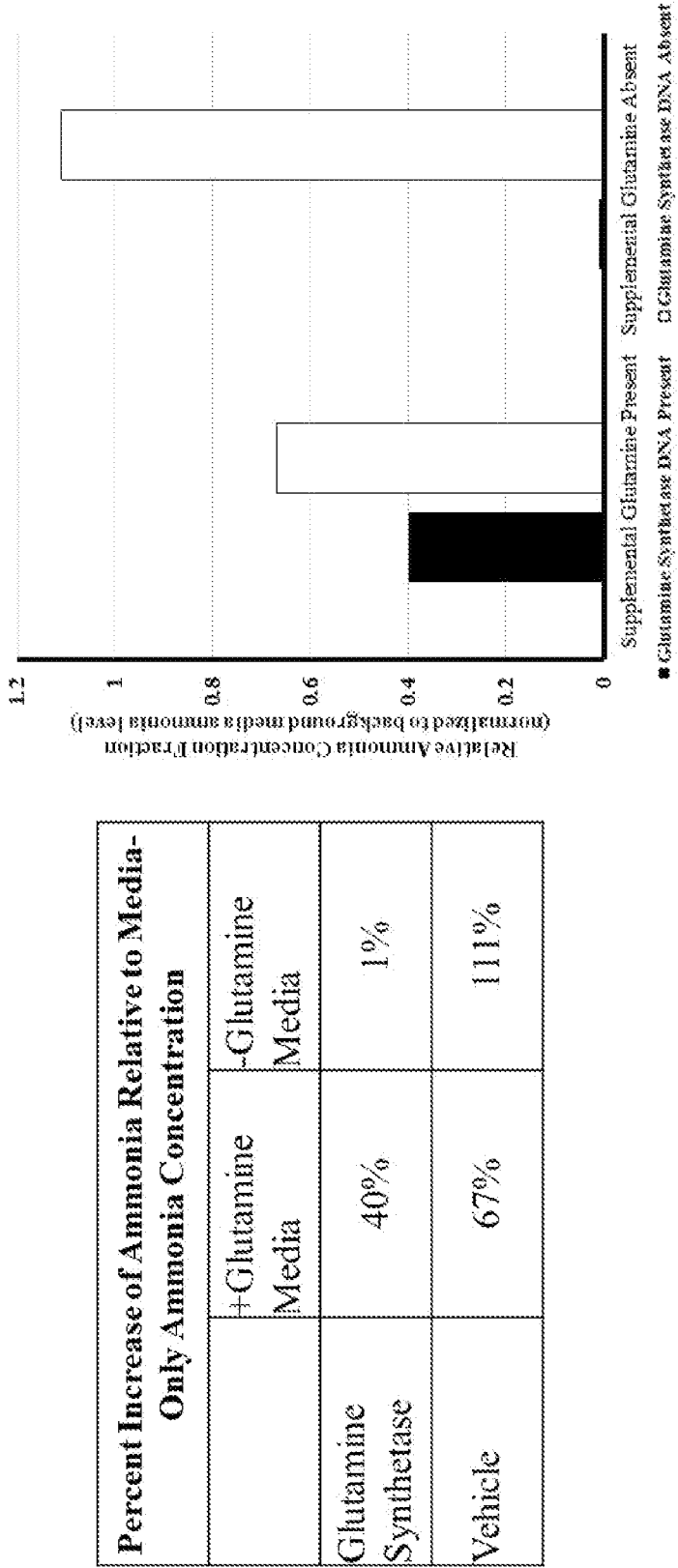
FIG. 7 shows an increase in glutamine in in culture media from myoblast cultures normalized to culture medium in which no cells were present.

As demonstrated in FIG. 6, following a one-day incubation post transfection, myoblasts expressing GS and grown in media not supplemented with glutamine show less increase in ammonia in the media than myoblasts transfected with vehicle and grown in media not supplemented with glutamine compared to acellular control medium supplemented with glutamine. Additionally, following a one-day incubation post transfection, myoblasts expressing GS and grown in media supplemented with glutamine show less increase in ammonia in the media than myoblasts transfected with vehicle and grown in a medium supplemented with glutamine compared to a medium supplemented with glutamine in which no cells were grown. Glutamine-supplemented medium in which no cells were grown showed an increase in ammonia concentration of 0.34 μg/mL/day, and medium in which no cells were grown and not supplemented with glutamine increased by 0.51 μg/mL/day. It was observed on Day 3 that myoblasts grown without supplemental ammonia and transfected with GS exhibited a statistically lower ammonia concentration compared to fibroblasts transfected with vehicle. Seven days following transfection, there is a significant difference in the amount of ammonia in growth media between myoblasts transfected with GS and myoblasts transfected with vehicle. Two-way ANOVA revealed a statistically significant difference ($p<0.001$) between ammonia concentrations over time, dependent upon the presence or absence of glutamine, revealing that the effect of GS was statistically significant ($p<0.001$) only when glutamine was absent. Error bars in FIG. 6 indicate 95% confidence intervals. One asterisk indicates $p<0.05$; two asterisks indicate $p<0.01$. FIG. 7 and Table 3 normalize the data from FIG. 6 to show a percent increase in ammonia relative to the medium-only (medium without cells—control) concentration of ammonia. After seven days in media with or without supplemented glutamine, myoblasts transfected with GS show a smaller increase in ammonia than myoblasts transfected with vehicle.

TABLE 3

Percent Increase of Ammonia Relative to Media-Only Ammonia Concentration

|  | +Glutamine Media | −Glutamine Media |
|---|---|---|
| Glutamine Synthetase | 40% | 1% |
| Vehicle | 67% | 111% |

Figure 8:
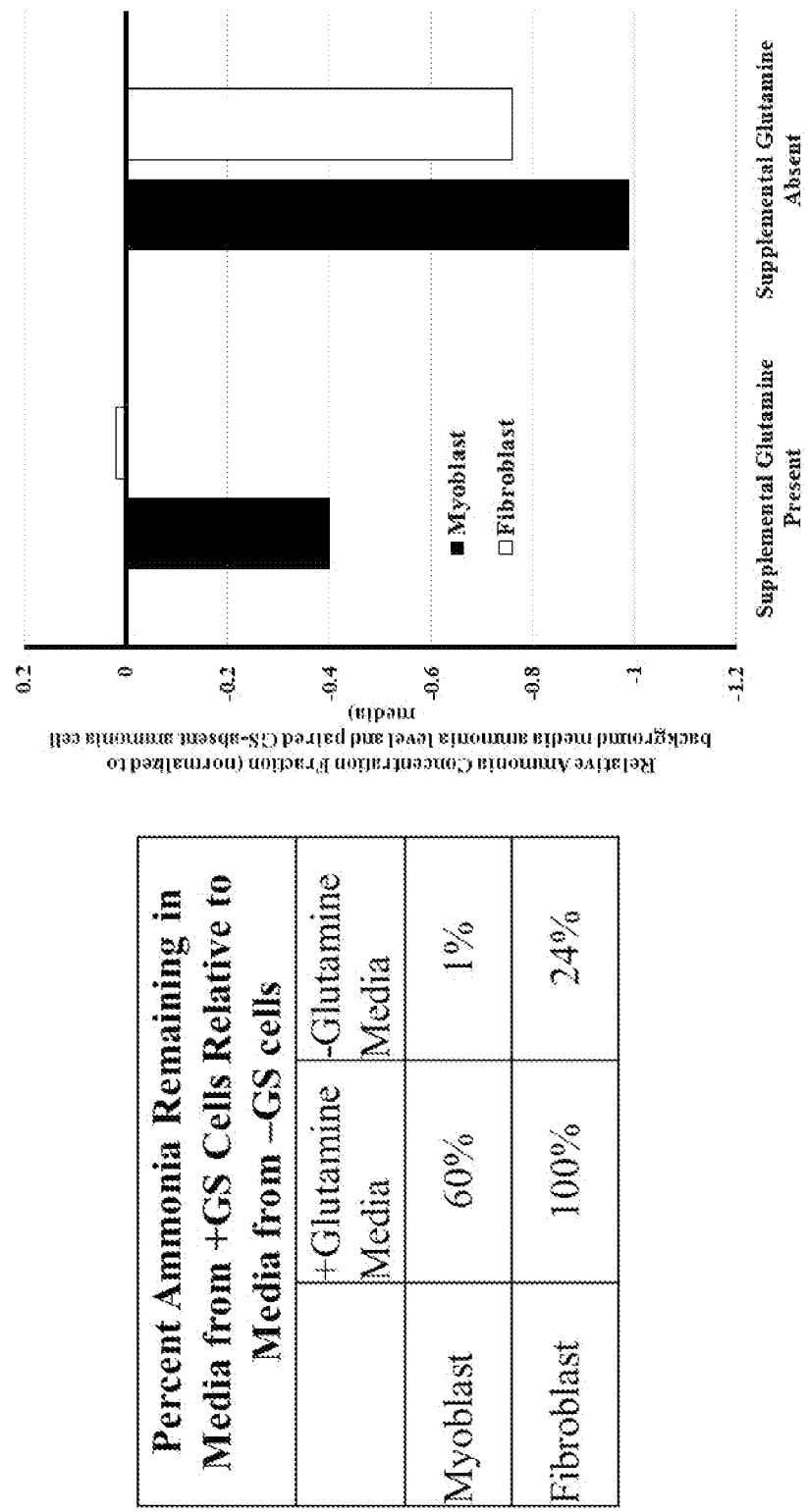
FIG. 8 shows a comparison of normalized ammonia levels between culture media from myoblast cultures and culture media from fibroblast cultures.

FIG. 8 and Table 4 demonstrate that myoblast cultures show a reduction in ammonia in glutamine supplemented medium and an even larger percentage decrease in medium not supplemented with glutamine. Fibroblast cultures do not show a decrease in ammonia in glutamine supplemented media, but do exhibit a decrease in ammonia in media without supplemented glutamine.

TABLE 4

Percent Ammonia Remaining in Media from +GS Cells Relative to Media from −GS cells

|  | +Glutamine Media | −Glutamine Media |
|---|---|---|
| Myoblast | 60% | 1% |
| Fibroblast | 100% | 24% |

In both fibroblasts and myoblasts, transfection of GS resulted in statistically significant reduction of observed ammonia concentration compared to background ammonia generation (p<0.001, two-way ANOVA). In both cell types, there was a significant difference between ammonia concentrations in groups that were supplemented with glutamine compared to those that were not supplemented with glutamine (P<0.001). There was a statistically significant difference in cells transfected with GS compared to those transfected with vehicle alone when media was not supplemented with glutamine (p<0.001). The presence or absence of glutamine in cell culture media exhibits a significantly different effect between treatment groups (p<0.01, two-way ANOVA). Regression analysis reveals that the presence or absence of glutamine accounts for 72-98% of the variance of the data (p<0.001). Covariance analysis reveals strong positive interactions between systems where glutamine is present (4-12 fold greater than without glutamine), and a moderate interaction when cells are transfected with a GS gene or vehicle-only control, regardless of whether glutamine is present or not.

Figure 9:
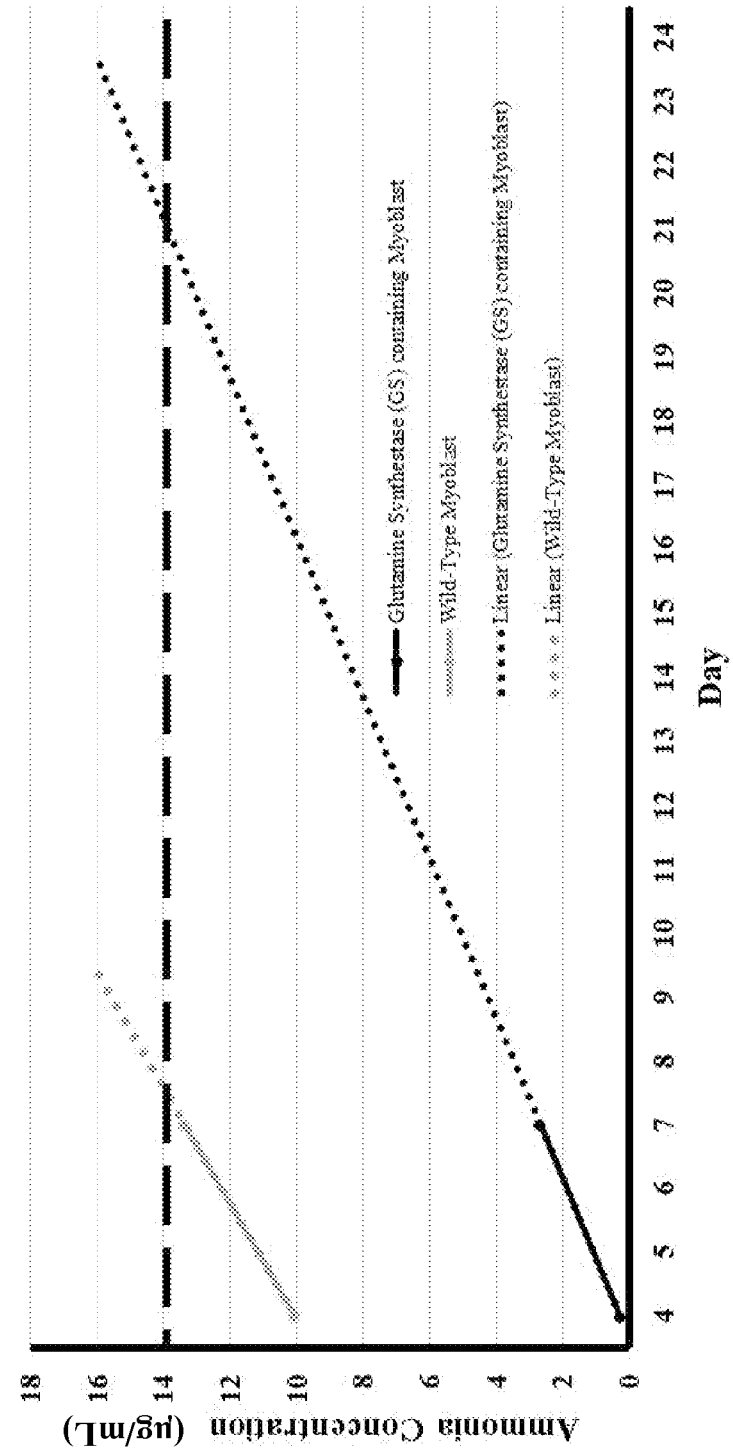
FIG. 9 depicts predicted extension of growth period before media reaches growth-limiting ammonia concentration.

Based on data presented in FIG. 3, FIG. 9 illustrates cells transfected with a GS gene demonstrate a 6.8-fold delay in the time to achieve wild-type, primary cell ammonia concentration (in this instance, 14 µg/mL was observed on average and is indicated by horizontal dashed line). When controlled for the absence of supplemented glutamine, transfection of a GS gene accounts for 31% of this delay. Solid lines depict experimental data while dotted lines are extrapolated values based on a linear fit of the experimental data.

Example 2: The Effects of Ectopic Expression of IGF-1 and Albumin Expression in Primary Duck Fibroblasts and Myoblasts This example describes the effects of ectopic expression of IGF-1 and albumin expression on the concentration of IGF-1 and albumin in media in primary duck fibroblasts and myoblasts.

Primary duck myoblast and fibroblast cells were isolated and cultured as described in Example 1. Cells were washed with PBS and transfection medium was added. 1 µg of plasmid DNA comprising a human serum albumin gene (Genscript OHu18744, Table 1A), a murine serum albumin gene (Genscript OMu21640, Table 1A) or human insulin-like growth factor 1 (IGF-1) (Origene RG212527, Table 1A) gene coding sequence fused to a nucleotide coding sequence encoding a FLAG-tag peptide (DYKDDDDK (SEQ ID NO: 57)) driven by a CMV promoter was complexed using the Lipofectamine 3000 system as a transfection vehicle (Thermo Fisher Scientific #L3000001). For transfection, the complexed DNA was added dropwise to each well in biological triplicate. Vehicle-only control cells received an equivalent treatment absent the DNA. The cell cultures were shaken gently and incubated for 48 hours; the transfection medium was then changed to growth medium and the cells were returned to incubation. Conditioned medium was collected as described in Example 1.

Figure 10B:
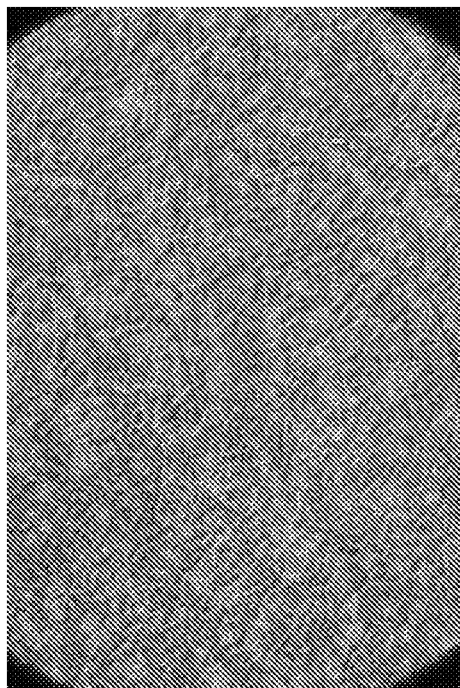
FIGS. 10A-D show morphology of wild type duck fibroblast cells following transfection with IGF-1, mouse albumin, or human albumin genes.
Figure 10D:
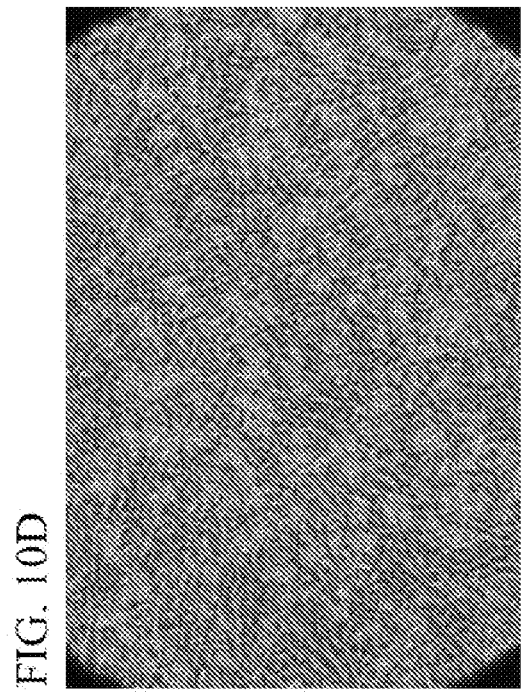
Figure 10A:
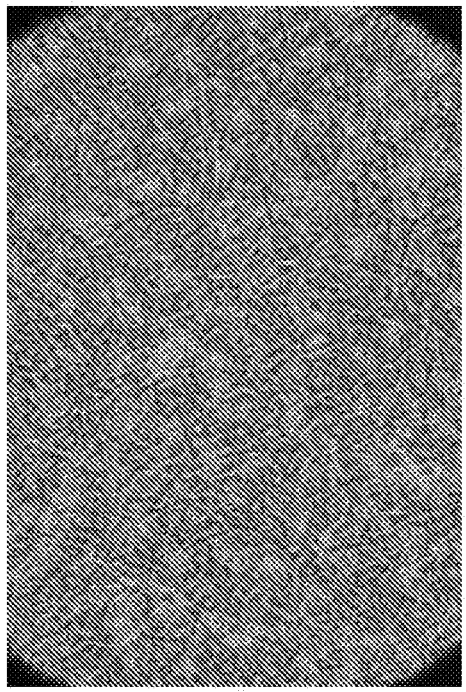
Figure 10C:
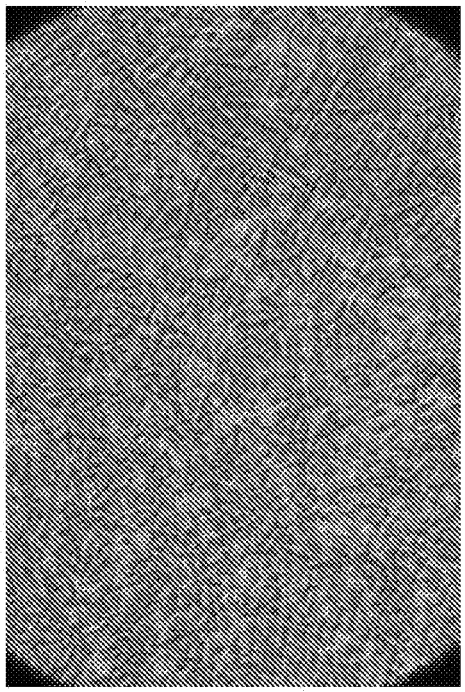

FIG. 10A-D show that fibroblasts transfected with a IGF-1 or albumin gene show morphology similar to cells transfected with vehicle-only (FIG. 10A Fibroblasts transfected with vehicle-only; FIG. 10B Fibroblasts transfected with a human IGF-1 gene; FIG. 10C Fibroblasts transfected with a mouse albumin gene; FIG. 10D Fibroblasts transfected with a human albumin gene).

Figure 11A:
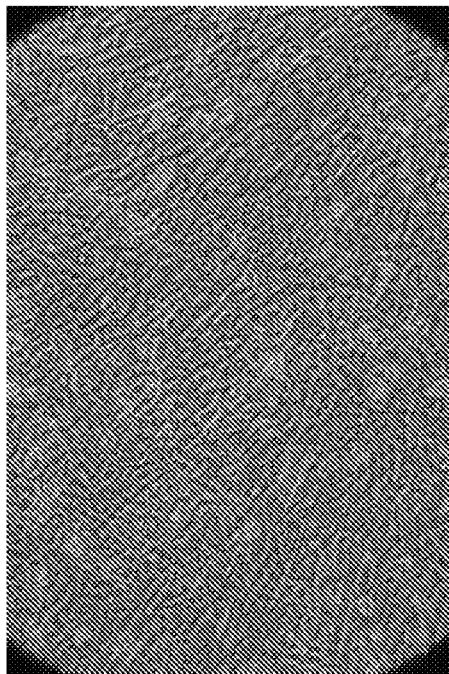
FIGS. 11A-D show morphology of duck myoblasts following transfection with IGF-1, mouse albumin, or human albumin genes.
Figure 11B:
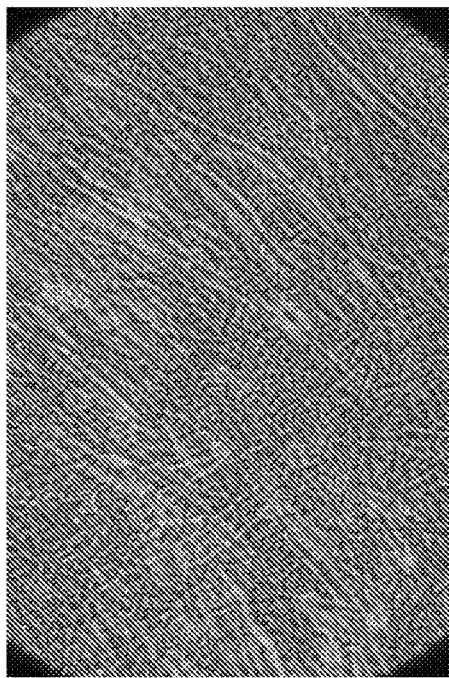
Figure 11C:
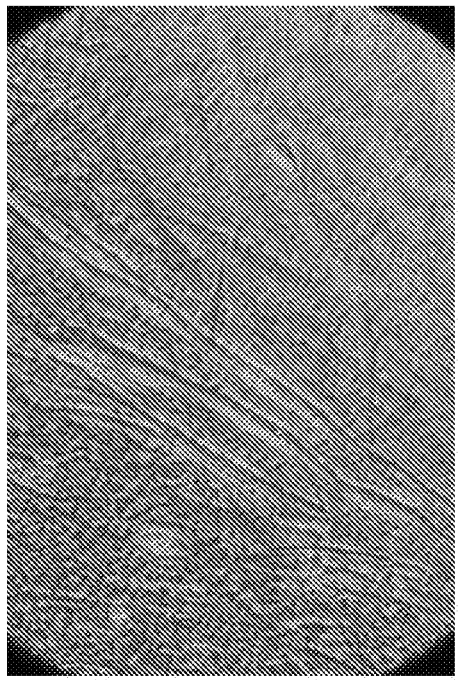
Figure 11D:

FIG. 11A-D show that myoblasts transfected with an IGF-1 or albumin gene show morphology similar to cells transfected with vehicle-only (FIG. 11A Myoblasts transfected with vehicle-only; FIG. 11B Myoblasts transfected with a human IGF-1 gene; FIG. 11C Myoblasts transfected with a mouse albumin gene; FIG. 11D Myoblasts transfected with a human albumin gene).

Figure 12:
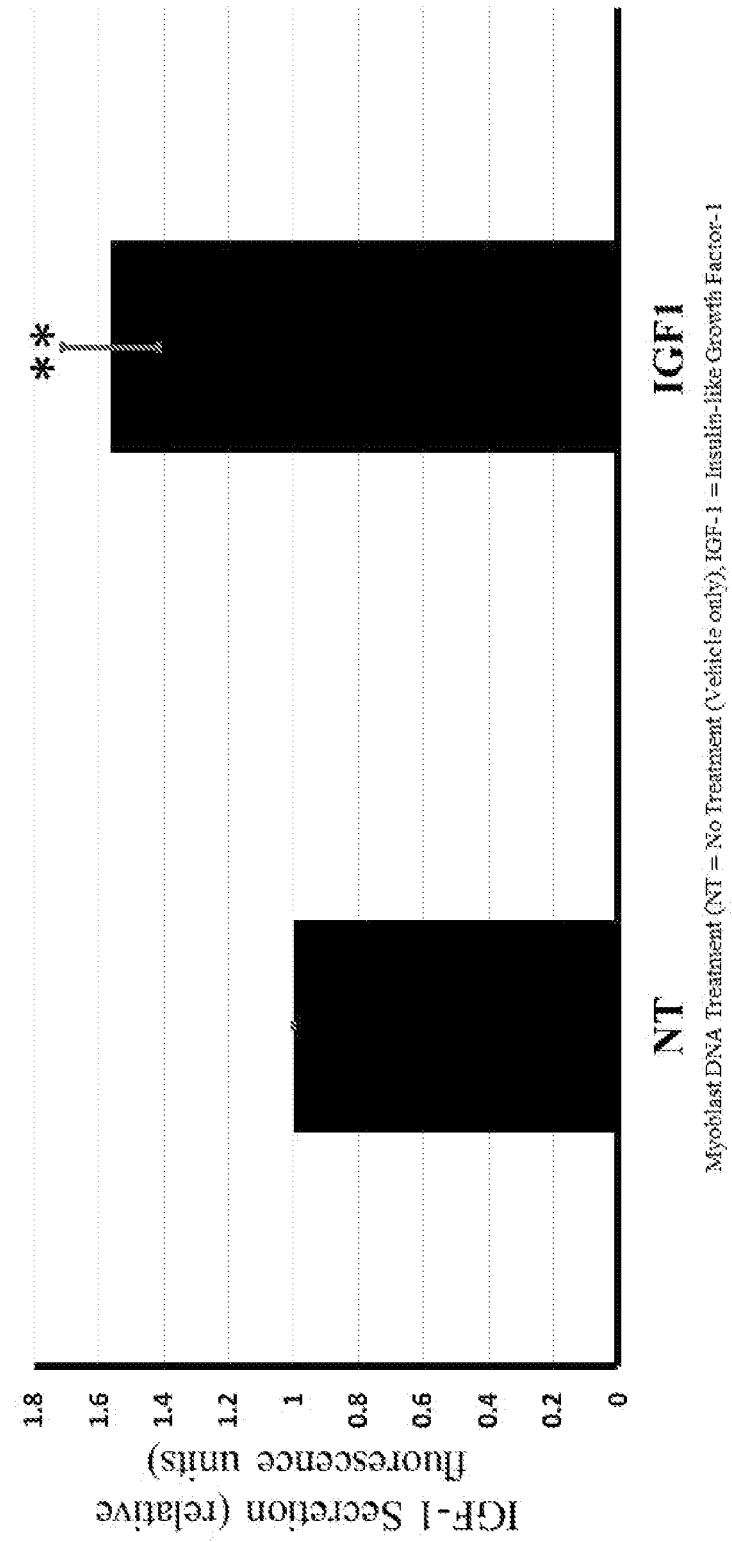
FIG. 12 shows IGF-1 levels secreted in myoblast cell culture media.

Indirect ELISA detection assays were used to measure the secretion of IGF-1 into the ambient medium by the cells. Ambient culture media samples were thawed and maintained on ice until use. Total protein concentration in media samples was determined by absorbance measurement on a spectrophotometer (Spectramax 250) using a BCA serial dilution method (Thermo Fisher Scientific #22325). Using untreated black walled, black-bottomed polystyrene 96-well plates, 1 µg of total protein from each treatment was adsorbed to the plate using 1× coating buffer (Abcam #ab210899). Following coating, the wells were washed and blocked using a 5% solution of non-fat dry milk (NFDM) in 1×PBS. Primary antibody (murine anti-DDK monoclonal, Origene #OTI4C5) was incubated at 1:5000 dilution in 5% NFDM/PBS at 4° C. for 18 hours. Wells were washed with PBS for three cycles of shaking for five minutes per cycle. Secondary antibody (goat anti-mouse-HRP conjugate, Sigma AP130P) was applied at a 1:10000 dilution in 5% NFDM/PBS for 1.5 hours at 22° C. A second PBS wash/shake cycle was applied to remove excess secondary antibody. QuantaRed kit detection was applied as per manufacturer's instructions (Thermo Fisher Scientific #15159). Fluorescence emission values were obtained by a fluorometer (Tecan Infinite F200). Data was analyzed and visualized using Microsoft Excel 2010. Transfection with a plasmid encoding an IGF-1 protein resulted in a statistically significant 53% increase in secretion of IGF-1 into the ambient medium (FIG. 12) compared to vehicle-only transfected cells (p<0.001, one-way ANOVA) as measured by ELISA.

Example 3: Edible Metazoan Biomass Manufacturing Methods

The manufacturing of an edible metazoan biomass, in one exemplary protocol, can comprise three steps:

Step 1 is expanding cell populations overexpressing containing a GS gene, an IGF gene, an albumin gene, or a combination thereof in a cell line capable of self-renewal, wherein the cell line is a myogenic transcription factor-modified cell line, and wherein the cell line is of from a livestock, poultry, game or an aquatic animal species. Selected cell populations overexpressing targeted genes are seeded onto a substrate consisting of peptide-coated tissue-culture treated plastic, in a standard growth medium at a density of $7.5 \times 10^3$ cells/cm$^2$ and cultured at 37° C. under 5% $CO_2$ atmospheric conditions. As cultures approach 80% confluence, cells are enzymatically dissociated and the expanded quantity of cells are seeded at $7.5 \times 10^3$ cells/cm$^2$. This process is repeated until the total number of cells harvested following dissociation exceeds $1.0 \times 10^8$ cells.

Step 2 is cryopreserving and storing the expanded cell populations in a cryopreserved cell bank. Cells harvested in quantities equal to or exceeding $1.0 \times 10^8$ following expansion of selected cells are pelleted by centrifugation for 5 minutes at 300×g. The cell pellet is suspended in a standard cryopreservation medium at $2.5 \times 10^6$ cells/mL and aliquoted at 1.0 mL per cryovial. Cryovials are cooled to −80° C. at −1° C./minute using an insulated container and transferred to a dewar containing liquid nitrogen for long-term storage. As cells stocks are depleted from this bank, remaining vials of cells are expanded and cryopreserved to replenish the cryopreserved cell bank inventory.

Step 3 is seeding and cultivating cells from a master cell bank in an ex vivo milieu: In accordance with the cultivation scale desired, one or more vials from the master cell bank is rapidly thawed to room temperature. The cryopreservation medium is removed from the cells by a 5 minute, 300×g centrifugation step. Cells are suspended in standard growth medium and seeded onto a gelatin-coated cultivation substrate in standard growth medium as before, except that, on the final passage prior to harvest, the cells are permitted to proliferate to 100% confluence on the cell culture substrate. The growth medium is next exchanged for differentiation medium specific to the myogenic transcription factor-modified cell line, and the cultures are permitted to differentiate for up to 6 days inducing myogenic differentiation of the cell line, wherein the differentiated cell line forms myocytes and multinucleated myotubes; and the myocytes and myotubes are cultured to generate skeletal muscle fibers.

The cultivation scale for proliferative biomass is outlined according to Table 5, where the predicted average cell mass is $2.0 \times 10^{-9}$ grams, and the predicted average cell doubling time is 24 hours (h).

projected biomass of the proliferative culture by four to account for biomass accumulation during cell differentiation.

Numbered Embodiments

1. A method for increasing the cell density of a culture comprising metazoan cells, the method comprising:
   a. introducing into the cells one or more polynucleotide sequences encoding glutamine synthetase (GS), insulin-like growth factor (IGF), and albumin; and
   b. culturing the cells in a cultivation infrastructure.
2. A method for increasing the cell density of a culture comprising metazoan cells, the method comprising:
   a. introducing into the cells one or more polynucleotide sequences encoding glutamine synthetase (GS), insulin-like growth factor (IGF), albumin or a combination thereof; and
   b. culturing the cells in a cultivation infrastructure.
3. A method for increasing the cell density of a culture comprising metazoan cells, the method comprising:
   a. introducing into the cells one or more polynucleotide sequences encoding glutamine synthetase (GS), insulin-like growth factor (IGF), albumin or a combination thereof;
   b. introducing into the cells a polynucleotide sequence encoding a telomerase reverse transcriptase (TERT); and
   c. culturing the cells in a cultivation infrastructure.
4. The method of any one of embodiments 1-3, wherein the cells comprise a loss-of-function mutation in one or more genes encoding cyclin-dependent kinase inhibitor (CKI) proteins.
5. The method of embodiment 1 or 2, comprising introducing into the cells a polynucleotide sequence encoding a telomerase reverse transcriptase (TERT).

TABLE 5

Biomass Production Scale Cultivation Estimates During Cell Proliferation.
Masses are shown in grams. 1 vial is equivalent to $2.5 \times 10^6$ cells.

| # hours | 1 vial | 2 vials | 3 vials | 4 vials | 5 vials | 6 vials | 7 vials | 8 vials | 9 vials | 10 vials |
|---|---|---|---|---|---|---|---|---|---|---|
| 0 h | 0.005 | 0.01 | 0.015 | 0.02 | 0.025 | 0.03 | 0.035 | 0.04 | 0.045 | 0.05 |
| 24 h | 0.01 | 0.02 | 0.03 | 0.04 | 0.05 | 0.06 | 0.07 | 0.08 | 0.09 | 0.1 |
| 48 h | 0.02 | 0.04 | 0.06 | 0.08 | 0.1 | 0.12 | 0.14 | 0.16 | 0.18 | 0.2 |
| 72 h | 0.04 | 0.08 | 0.12 | 0.16 | 0.2 | 0.24 | 0.28 | 0.32 | 0.36 | 0.4 |
| 96 h | 0.08 | 0.16 | 0.24 | 0.32 | 0.4 | 0.48 | 0.56 | 0.64 | 0.72 | 0.8 |
| 120 h | 0.16 | 0.32 | 0.48 | 0.64 | 0.8 | 0.96 | 1.12 | 1.28 | 1.44 | 1.6 |
| 144 h | 0.32 | 0.64 | 0.96 | 1.28 | 1.6 | 1.92 | 2.24 | 2.56 | 2.88 | 3.2 |
| 168 h | 0.64 | 1.28 | 1.92 | 2.56 | 3.2 | 3.84 | 4.48 | 5.12 | 5.76 | 6.4 |
| 192 h | 1.28 | 2.56 | 3.84 | 5.12 | 6.4 | 7.68 | 8.96 | 10.24 | 11.52 | 12.8 |
| 216 h | 2.56 | 5.12 | 7.68 | 10.24 | 12.8 | 15.36 | 17.92 | 20.48 | 23.04 | 25.6 |
| 240 h | 5.12 | 10.24 | 15.36 | 20.48 | 25.6 | 30.72 | 35.84 | 40.96 | 46.08 | 51.2 |
| 264 h | 10.24 | 20.48 | 30.72 | 40.96 | 51.2 | 61.44 | 71.68 | 81.92 | 92.16 | 102.4 |
| 288 h | 20.48 | 40.96 | 61.44 | 81.92 | 102.4 | 122.88 | 143.36 | 163.84 | 184.32 | 204.8 |
| 312 h | 40.96 | 81.92 | 122.88 | 163.84 | 204.8 | 245.76 | 286.72 | 327.68 | 368.64 | 409.6 |
| 336 h | 81.92 | 163.84 | 245.76 | 327.68 | 409.6 | 491.52 | 573.44 | 655.36 | 737.28 | 819.2 |

Step 4 is harvesting cultivated cell biomass for dietary consumption. After the cells have proliferated to confluence, the culture medium is removed, and the adherent cell cultures are rinsed with phosphate buffered saline. Next, the confluent biomass of adherent cells mechanically dissociated from the substrate by means of a scraping device. The dissociated biomass is collected into centrifuge tubes, pelleted at 400×g for 5 minutes to remove excess liquid, and processed for food product preparation. Harvested yield of differentiated cell biomass are estimated by multiplying the 6. The method of embodiment 4, wherein the CKI proteins are p15, p16, paralogs, orthologs, or genetic variants thereof.
7. The method of any one of embodiments 1-6, wherein the cells are from a self-renewing cell line.
8. The method of embodiment 7, wherein the self-renewing cell line is selected from the group consisting of an embryonic stem cell line, induced pluripotent stem cell line, extraembryonic cell line, and somatic cell line.

9. The method of any one of embodiments 1-8, wherein the cells are modified with a myogenic transcription factor.

10. The method of embodiment 9, wherein the myogenic transcription factor is MYOD1, MYOG, MYF5, MYF6, PAX3, PAX7, paralogs, orthologs, or genetic variants thereof.

11. The method of any one of embodiments 1-10, wherein:
   a. the concentration of glutamine in the culture medium is increased to at least 0.001 mM, to at least 0.0025 mM, to at least 0.005 mM, to at least 0.0075 mM, to at least 0.01 mM, to at least 0.025 mM, to at least 0.05 mM, to at least 0.075 mM, to at least 0.1 mM, to at least 0.25 mM, to at least 0.50 mM, to at least 0.75 mM, to at least 1.0 mM, to at least 1.5 mM, to at least 2.0 mM, to at least 3.0 mM, to at least 5.0 mM, to at least 10 mM, or to at least 20 mM;
   b. the concentration of IGF in the culture medium is increased to at least 0.00001 ng/mL, to at least 0.000025 ng/mL, to at least 0.000075 ng/mL, to at least 0.0005 ng/mL, to at least 0.001 ng/mL, to at least 0.0025 ng/mL, to at least 0.005 ng/mL, to at least 0.0075 ng/mL, to at least 0.01 ng/mL, to at least 0.025 ng/mL, to at least 0.05 ng/mL, to at least 0.1 ng/mL, to at least 0.25 ng/mL, to at least 0.5 ng/mL, to at least 1 ng/mL, to at least 2.5 ng/mL, to at least 5 ng/mL, to at least 7.5 ng/mL, to at least 10 ng/mL, to at least 25 ng/mL, to at least 50 ng/mL, to at least 75 ng/mL, to at least 125 ng/mL, to at least 250 ng/mL, to at least 500 ng/mL, to at least 750 ng/mL, to at least 1,000 ng/mL, to at least 1,500 ng/mL, to at least 2,000 ng/mL, to at least 2,500 ng/mL, to at least 3,000 ng/mL, to at least 3,500 ng/mL, to at least 4,000 ng/mL, to at least 4,500 ng/mL, to at least 5,000 ng/mL to at least 6,000 ng/mL, to at least 7,000 ng/mL, to at least 8,000 ng/mL, to at least 9,000 ng/mL, or even by at least 10,000 ng/mL; and/or
   c. the concentration of albumin in the culture medium is increased to at least 0.0001 mg/mL, to at least 0.0002 mg/mL, to at least 0.0004 mg/mL, to at least 0.0005 mg/mL, to at least 0.0006 mg/mL, to at least 0.0007 mg/mL, to at least 0.0008 mg/mL, to at least 0.0009 mg/mL, to at least 0.001 mg/mL, to at least 0.002 mg/mL, to at least 0.003 mg/mL, to at least 0.004 mg/mL, to at least 0.005 mg/mL, to at least 0.006 mg/mL, to at least 0.007 mg/mL, to at least 0.008 mg/mL, to at least 0.009 mg/mL, to at least 0.01 mg/mL, to at least 0.05 mg/mL, to at least 0.075 mg/mL, to at least 0.1 mg/mL, to at least 0.25 mg/mL, to at least 0.5 mg/mL, to at least 0.75 mg/mL, to at least 1 mg/mL, to at least mg/mL, to at least 1.5 mg/mL, to at least 1.5 mg/mL, to at least 1.75 mg/mL, to at least 2 mg/mL, to at least 3 mg/mL, to at least 5 mg/mL, to at least 10 mg/mL, to at least 20 mg/mL, to at least 25 mg/mL, to at least 50 mg/mL, to at least 75 mg/mL, or to at least 100 mg/mL,
   compared to cultures of cells in which the expression of GS, IGF, albumin or a combination thereof is not increased.

12. The method of any one of embodiments 1-11, comprising inhibiting the HIPPO signaling pathway.

13. The method of embodiment 12, wherein inhibiting the HIPPO signaling pathway comprises activating Yes-Associated Protein 1 (YAP1), Transcriptional co-Activator with PDZ-binding motif (TAZ), or a combination thereof in the cells.

14. The method of any one of embodiments 1-13, wherein the cells are the cells of livestock, poultry, game or aquatic animal species.

15. The method of any one of embodiments 1-14, wherein the cells are of a chicken, duck, or turkey.

16. The method of any one of embodiments 1-14, wherein the cells are of a fish.

17. The method of any one of embodiments 1-14, wherein the cells are of a livestock species.

18. The method of embodiment 17, wherein the livestock species is porcine or bovine.

19. The method of any one of embodiments 1-14, wherein the cells are from any animal species intended for human or non-human dietary consumption.

20. The method of any one of embodiments 1-6, wherein the cells are myogenic cells.

21. The method of embodiment 20, wherein the myogenic cells are myoblasts, myocytes, satellite cells, side population cells, muscle derived stem cells, mesenchymal stem cells, myogenic pericytes, or mesoangioblasts.

22. The method of any one of embodiments 1-6, wherein the cells are non-myogenic cells.

23. The method of any one of embodiments 1-6, wherein the cells are non-myogenic cells modified to express one or more myogenic transcription factors.

24. The method of embodiment 23, wherein the myogenic transcription factor is MYOD1, MYOG, MYF5, MYF6, PAX3, PAX7, paralogs, orthologs, or genetic variants thereof.

25. The method of any one of embodiments 1-24, wherein the polynucleotide sequence encoding GS comprises a GS gene sequence from Tables 1A and 1B.

26. The method of any one of embodiments 1-24, wherein the polynucleotide sequence encoding IGF comprises an IGF gene sequence from Tables 1A and 1B.

27. The method of any one of embodiments 1-24, wherein the polynucleotide sequence encoding albumin comprises an albumin gene sequence from Tables 1A and 1B.

28. An in vitro method for producing a cultured edible product, the method comprising:
   a. introducing one or more polynucleotide sequences encoding glutamine synthetase (GS), insulin-like growth factor (IGF), albumin or a combinations thereof into myogenic cells;
   b. optionally introducing a polynucleotide sequence encoding a telomerase reverse transcriptase (TERT) into the cells;
   c. inducing myogenic differentiation of the cells expressing GS, IGF, albumin or combinations thereof and optionally TERT, wherein the differentiated cells form myocytes and multinucleated myotubes;
   d. culturing the myocytes and myotubes to generate skeletal muscle fibers, thereby producing a cultured edible product.

29. The method of embodiment 28, wherein the myogenic cells are natively myogenic.

30. The method of embodiment 28, wherein the myogenic cells are not natively myogenic and are modified to express one or more myogenic transcription factors.

31. The method of embodiment 28 or 29, wherein the myogenic cells are myoblasts, myocytes, satellite cells, side population cells, muscle derived stem cells, mesenchymal stem cells, myogenic pericytes, or mesoangioblasts.

32. The method of embodiment 30, wherein the myogenic transcription factor is MYOD1, MYOG, MYF5, MYF6, PAX3, PAX7, paralogs, orthologs, or genetic variants thereof.
33. The method of any one of embodiments 28-32, wherein the step of inducing myogenic differentiation comprises activating the expression of one or more myogenic transcription factors.
34. The method of any one of embodiments 28-33, comprising inhibiting the HIPPO signaling pathway.
35. The method of embodiment 34, wherein inhibiting the HIPPO signaling pathway comprises activating Yes-Associated Protein 1 (YAP1) and/or Transcriptional co-Activator with PDZ-binding motif (TAZ) in the cells.
36. The method of any one of embodiments 28-35, wherein the cells comprise a loss-of-function mutation in one or more genes encoding cyclin-dependent kinase inhibitor (CKI) proteins.
37. The method of embodiment 36, wherein the CKI proteins are p15, p16, paralogs, orthologs, or genetic variants thereof.
38. The method of embodiment 30, wherein the myogenic cells are from an embryonic stem cell line, induced pluripotent stem cell line, extraembryonic cell line, or a somatic cell line, modified to express one or more myogenic transcription factors.
39. The method of any one of embodiments 28-38, wherein:
    a. the concentration of glutamine in the culture medium is increased to at least 0.001 mM, to at least 0.0025 mM, to at least 0.005 mM, to at least 0.0075 mM, to at least 0.01 mM, to at least 0.025 mM, to at least 0.05 mM, to at least 0.075 mM, to at least 0.1 mM, to at least 0.25 mM, to at least 0.50 mM, to at least 0.75 mM, to at least 1.0 mM, to at least 1.5 mM, to at least 2.0 mM, to at least 3.0 mM, to at least 5.0 mM, to at least 10 mM, or to at least 20 mM;
    b. the concentration of IGF in the culture medium is increased to at least 0.00001 ng/mL, to at least 0.000025 ng/mL, to at least 0.000075 ng/mL, to at least 0.0005 ng/mL, to at least 0.001 ng/mL, to at least 0.0025 ng/mL, to at least 0.005 ng/mL, to at least 0.0075 ng/mL, to at least 0.01 ng/mL, to at least 0.025 ng/mL, to at least 0.05 ng/mL, to at least 0.1 ng/mL, to at least 0.25 ng/mL, to at least 0.5 ng/mL, to at least 1 ng/mL, to at least 2.5 ng/mL, to at least 5 ng/mL, to at least 7.5 ng/mL, to at least 10 ng/mL, to at least 25 ng/mL, to at least 50 ng/mL, to at least 75 ng/mL, to at least 125 ng/mL, to at least 250 ng/mL, to at least 500 ng/mL, to at least 750 ng/mL, to at least 1,000 ng/mL, to at least 1,500 ng/mL, to at least 2,000 ng/mL, to at least 2,500 ng/mL, to at least 3,000 ng/mL, to at least 3,500 ng/mL, to at least 4,000 ng/mL, to at least 4,500 ng/mL, to at least 5,000 ng/mL to at least 6,000 ng/mL, to at least 7,000 ng/mL, to at least 8,000 ng/mL, to at least 9,000 ng/mL, or even by at least 10,000 ng/mL; and/or
    c. the concentration of albumin in the culture medium is increased to at least 0.0001 mg/mL, to at least 0.0002 mg/mL, to at least 0.0004 mg/mL, to at least 0.0005 mg/mL, to at least 0.0006 mg/mL, to at least 0.0007 mg/mL, to at least 0.0008 mg/mL, to at least 0.0009 mg/mL, to at least 0.001 mg/mL, to at least 0.002 mg/mL, to at least 0.003 mg/mL, to at least 0.004 mg/mL, to at least 0.005 mg/mL, to at least 0.006 mg/mL, to at least 0.007 mg/mL, to at least 0.008 mg/mL, to at least 0.009 mg/mL, to at least 0.01 mg/mL, to at least 0.05 mg/mL, to at least 0.075 mg/mL, to at least 0.1 mg/mL, to at least 0.25 mg/mL, to at least 0.5 mg/mL, to at least 0.75 mg/mL, to at least 1 mg/mL, to at least mg/mL, to at least 1.5 mg/mL, to at least 1.5 mg/mL, to at least 1.75 mg/mL, to at least 2 mg/mL, to at least 3 mg/mL, to at least 5 mg/mL, to at least 10 mg/mL, to at least 20 mg/mL, to at least 25 mg/mL, to at least 50 mg/mL, to at least 75 mg/mL, or to at least 100 mg/mL,
    compared to cultures of cells in which the expression of GS, IGF, albumin or a combination thereof is not increased.
40. The method of any one of embodiments 28-39, wherein the cells are from livestock, poultry, game or aquatic animal species.
41. The method of any one of embodiments 28-40, wherein the cells are from a chicken, duck, or turkey.
42. The method of any one of embodiments 28-40, wherein the cells are from a fish.
43. The method of any one of embodiments 28-40, wherein the cells are from a livestock species.
44. The method of embodiment 43, wherein the livestock species is porcine or bovine.
45. The method of any one of embodiments 28-44, wherein the cells are from any animal species intended for human or non-human dietary consumption.
46. The method of any one of embodiments 28-45, wherein the polynucleotide sequence encoding GS comprises a GS coding sequence from Tables 1A and 1B.
47. The method of any one of embodiments 28-45, wherein the polynucleotide sequence encoding IGF comprises an IGF coding sequence from Tables 1A and 1B.
48. The method of any one of embodiments 28-45, wherein the polynucleotide sequence encoding albumin comprises an albumin coding sequence from Tables 1A and 1B.
49. The method of any one of embodiments 1-48, wherein the cells express the GS protein at levels sufficient to decrease the ammonia production, increase the production of glutamine, or any combination thereof.
50. A method of decreasing the concentration of ammonia and/or ammonium hydroxide in the medium of cells in culture comprising increasing the expression of a glutamine synthetase (GS) protein in the cells, wherein the cells are of livestock, poultry, game or aquatic animal species, and wherein the concentration of ammonia (i.e. ammonium hydroxide) in the medium is decreased by at least 2.5%.
51. A method of increasing the production of glutamine in cells comprising increasing the expression of a glutamine synthetase (GS) protein in the cells, wherein the cells are of livestock, poultry, game or aquatic animal species, and wherein the concentration of glutamine in the cells is increased by at least 2.5%.
52. The method of any one of embodiments 50-51, wherein the cells are modified to overexpress a gene encoding the GS protein.
53. The method of any one of embodiments 50-52, wherein the cells overexpress the gene encoding the GS protein at levels sufficient to decrease the ammonia production, increase the production of glutamine, or any combination thereof.
54. A method of increasing the concentration of Insulin-like growth factor (IGF) in the medium of cells in culture comprising increasing the expression of an IGF protein in the cells, wherein the cells are of livestock, poultry, game or aquatic animal species, and wherein the concentration of the IGF protein in the medium is increased by at least 2.5% or is increased to at least 0.001 ng/mL.

55. The method of embodiment 54, wherein the cells are modified to overexpress a gene encoding the IGF protein.
56. The method of any one of embodiments 54-55, wherein the cells overexpress the gene encoding the IGF protein at levels sufficient to increase the concentration of IGF in the medium.
57. The method of any one of embodiments 54-56, wherein the IGF protein is an IGF-1 protein.
58. The method of any one of embodiments 54-56, wherein the IGF protein is an IGF-2 protein.
59. A method of increasing the concentration of albumin in the medium of cells in culture comprising increasing the expression of albumin in the cells, wherein the cells are of livestock, poultry, game or aquatic animal species, and wherein the concentration of albumin in the medium is increased at least 2.5% or is increased to at least 0.1 µg/mL.
60. The method of embodiment 59, wherein the cells are modified to overexpress a gene encoding the albumin protein.
61. The method of any one of embodiments 59-60, wherein the cells overexpress the gene encoding the albumin protein at levels sufficient to increase the concentration of albumin in the medium.
62. The method of any one of embodiments 50-61, wherein the cells are a self-renewing cell line.
63. The method of embodiment 62, wherein the self-renewing cell line is selected from the group consisting of an embryonic stem cell line, induced pluripotent stem cell line, extraembryonic cell lines, and somatic cell lines.
64. The method of any one of embodiments 50-63, wherein the cell line is a myogenic transcription factor-modified cell line.
65. The method of embodiment 64, wherein the myogenic transcription factor is MYOD1, MYOG, MYF5, MYF6, PAX3, PAX7, paralogs, orthologs, or genetic variants thereof.
66. The method of any one of embodiments 50-65, wherein the renewal capacity of the cells is extended.
67. The method of any one of embodiments 50-65, further comprising activating Telomerase reverse transcriptase (TERT) in the cells.
68. The method of any one of embodiments 50-67, wherein the cells comprise a loss-of-function mutation in one or more genes encoding cyclin-dependent kinase inhibitor (CKI) proteins.
69. The method of embodiment 68, wherein the CKI proteins are p15, p16, paralogs, orthologs, or genetic variants thereof.
70. The method of any one of embodiments 50-67, comprising inhibiting the HIPPO signaling pathway in the cells.
71. The method of embodiment 70, wherein inhibiting the HIPPO signaling pathway comprises activating Yes-Associated Protein 1 (YAP1), Transcriptional co-Activator with PDZ-binding motif (TAZ), or a combination thereof in the cells.
72. The method of any one of embodiments 50-71, wherein the cell line is of a game species.
73. The method of any one of embodiments 50-71, wherein the cell line is of a poultry species.
74. The method of embodiment 73, wherein the poultry species is a duck.
75. The method of any one of embodiments 50-71, wherein the cell line is of an aquatic species.
76. The method of any one of embodiments 50-71, wherein the cell line is of a livestock species.
77. The method of embodiment 76, wherein the livestock species is porcine or bovine.
78. The method of any one of embodiments 50-71, wherein the cell line is from any animal species intended for human or non-human dietary consumption.
79. An in vitro method for producing a cultured edible product, the method comprising:
   a. overexpressing a GS, IGF, albumin protein, or a combination thereof in a self-renewing cell line, wherein the cell line is a myogenic transcription factor-modified cell line, and wherein the cell line is of a livestock, poultry, game or aquatic animal species;
   b. inducing myogenic differentiation of the cell line, wherein the differentiated cell line forms myocytes and multinucleated myotubes; and
   c. culturing the myocytes and myotubes to generate skeletal muscle fibers, thereby producing a cultured edible product.
80. The method of embodiment 79, wherein the cell line is modified to overexpress a gene encoding the GS protein.
81. The method of embodiment 80, wherein the cell line is engineered to overexpress the gene encoding the GS protein at levels sufficient to decrease the ammonia production, increase the production of glutamine, or any combination thereof.
82. The method of embodiment 79, wherein the cell line is modified to overexpress a gene encoding the IGF protein.
83. The method of embodiment 82, wherein the cells overexpress the gene encoding the IGF protein at levels sufficient to increase the production of IGF by the cells.
84. The method of any one of embodiments 79-83, wherein the IGF protein is an IGF-1 protein.
85. The method of any one of embodiments 79-83, wherein the IGF protein is an IGF-2 protein
86. The method of embodiment 79, wherein the cell line is modified to overexpress a gene encoding the albumin protein.
87. The method of embodiment 86, wherein the cells overexpress the gene encoding the albumin protein at levels sufficient to increase the concentration of albumin in cells.
88. The method of any one of embodiments 79-87, wherein the self-renewing cell line is selected from the group consisting of embryonic stem cells, induced pluripotent stem cells, extraembryonic cell lines, and somatic cell lines.
89. The method of any one of embodiments 79-88, wherein the myogenic transcription factor is the MYOD1, MYOG, MYF5, MYF6, PAX3, PAX7, paralogs, orthologs, or genetic variants thereof.
90. The method of any one of embodiments 79-89, wherein the renewal capacity of the cells is extended.
91. The method of any one of embodiments 79-89, further comprising activating Telomerase reverse transcriptase (TERT) in the cells.
92. The method of any one of embodiments 79-91, wherein the cells comprise a loss-of-function mutation in one or more genes encoding cyclin-dependent kinase inhibitor (CKI) proteins.
93. The method of embodiment 92, wherein the CKI proteins are p15, p16, paralogs, orthologs, or genetic variants thereof.
94. The method of any one of embodiment 79-93, comprising inhibiting the HIPPO signaling pathway in the cells.
95. The method of embodiment 94, wherein the inhibition of the HIPPO signaling pathway comprises activating Yes-Associated Protein 1 (YAP1) and/or Transcriptional co-Activator with PDZ-binding motif (TAZ) in the cells.

96. The method of any one of embodiments 79-95, wherein the cell line is of a game species.
97. The method of any one of embodiments 79-95, wherein the cell line is of a poultry species.
98. The method of embodiment 97, wherein the poultry species is a duck.
99. The method of any one of embodiments 79-95, wherein the cell line is of an aquatic species.
100. The method of any one of embodiments 79-95, wherein the cell line is of a livestock species.
101. The method of embodiment 100, wherein the livestock species is porcine or bovine.
102. The method of any one of embodiments 79-95, wherein the cell line is from any animal species intended for human or non-human dietary consumption.
103. A cultured edible product produced by the in vitro method of any one of embodiments 28-49 and 79-102.
104. A cultured edible product comprising cells having increased expression of GS, increased expression of IGF, increased expression of albumin, and/or increased expression of TERT.
105. A construct comprising any one of the sequences selected from Table 1B.
106. An expression vector comprising any one of the sequences selected from Table 1B.
107. A cell comprising the expression vector of embodiment 106.
108. The cell of embodiment 107, wherein the cell is from a livestock, poultry, game, or aquatic species.
109. A method for increasing the secretion of glutamine by cells into a culture medium, the method comprising increasing the expression of a glutamine synthetase (GS) protein in the cells, wherein the cells are from livestock, poultry, game or aquatic animal species, and wherein the concentration of glutamine secreted into the culture medium is increased by at least 2.5%.
110. The method of embodiment 109, wherein the cells are modified to overexpress a gene encoding the GS protein.
111. The method of embodiment 109 or 110, comprising introducing into the cells a polynucleotide comprising a GS coding sequence from Table 1B.
112. The method of any one of embodiments 109-111, wherein the secretion of glutamine by cells into the culture medium is increased by at least 2.5% compared to cells in which the expression of GS is not increased.
113. A method for increasing the rate of proliferation of cells in a cultivation infrastructure, comprising:
  a. introducing into the cells one or more polynucleotide sequences encoding glutamine synthetase (GS), insulin-like growth factor (IGF), albumin or a combination thereof; and
  b. culturing the cells in a cultivation infrastructure, wherein the cells are from livestock, poultry, game or aquatic animal species.
114. The method of embodiment 113, wherein the polynucleotide sequence encoding GS comprises a GS coding sequence from Tables 1A and 1B.
115. The method of embodiment 113, wherein the polynucleotide sequence encoding IGF comprises an IGF coding sequence from Tables 1A and 1B.
116. The method of embodiment 113, wherein the polynucleotide sequence encoding albumin comprises an albumin coding sequence from Tables 1A and 1B.
117. The method of any one of embodiments 113-116, wherein the rate of proliferation of cells is increased by at least 5% compared to cells in which the expression of GS, IGF, albumin, or a combination thereof is not increased.
118. A method for decreasing death of cells in a cultivation infrastructure, comprising:
  a. introducing into the cells one or more polynucleotide sequences encoding glutamine synthetase (GS), insulin-like growth factor (IGF), albumin or a combination thereof; and
  b. culturing the cells in a cultivation infrastructure, wherein the cells are from livestock, poultry, game or aquatic animal species.
119. The method of embodiment 118, wherein the polynucleotide sequence encoding GS comprises a GS coding sequence from Tables 1A and 1B.
120. The method of embodiment 118, wherein the polynucleotide sequence encoding IGF comprises an IGF coding sequence from Tables 1A and 1B.
121. The method of embodiment 118, wherein the polynucleotide sequence encoding albumin comprises an albumin coding sequence from Tables 1A and 1B.
122. The method of any one of embodiment 118-121, wherein the cell death is decreased by at least 10% compared to cells in which the expression of GS, IGF, albumin, or a combination thereof is not increased.
123. A method for increasing protein production in cells in a cultivation infrastructure, comprising:
  a. introducing into the cells a polynucleotide sequence encoding insulin-like growth factor (IGF); and
  b. culturing the cells in a cultivation infrastructure, wherein the cells are from livestock, poultry, game or aquatic animal species.
124. The method of embodiment 123, wherein the polynucleotide sequence encoding IGF comprises an IGF coding sequence from Tables 1A and 1B.
125. The method of embodiment 123 or 124, wherein the IGF is IGF-1 or IGF-2.
126. The method of any one of embodiment 123-125, wherein the protein production measured as total cell protein per cell nucleus is increased by at least 5% compared to cells in which the expression of IGF is not increased.
127. The method of any one of embodiments 3, 28, 67, and 91, wherein the polynucleotide encoding TERT comprises a TERT coding sequence from Table 1B.

SEQUENCE LISTING

```
Sequence total quantity: 58
SEQ ID NO: 1           moltype = DNA  length = 465
FEATURE                Location/Qualifiers
misc_feature           1..465
                       note = bovine IGF1 and porcine albumin signal peptide
source                 1..465
                       mol_type = other DNA
                       organism = synthetic construct
SEQUENCE: 1
```

```
atgaagtggg tgactttat tcccttctc tttctcttca gctctgctta ttccttcttg    60
aagcaggtga agatgcccat cacatcctcc tcgcatctct tctatctggc cctgtgcttg   120
ctcgccttca ccagctctgc cacggcggga cccgagaccc tctgcggggc tgagttggtg   180
gatgctctcc agttcgtgtg cggagacagg ggcttttatt tcaacaagcc cacggggtat   240
ggctcgagca gtcggagggc gccccagaca ggaatcgtgg atgagtgctg cttccggagc   300
tgtgatctga ggaggctgga gatgtactgc gcgcctctca gcccgccaa gtcggccgcc   360
tcagtccgtg cccagcgcca caccgacatg cccaaggctc agaaggaagt acatttgaag   420
aacacaagta gagggagtgc aggaaacaag aactacagaa tgtag                   465
```

SEQ ID NO: 2          moltype = DNA  length = 462
FEATURE               Location/Qualifiers
misc_feature          1..462
                      note = chicken IGF1 and porcine albumin signal peptide
source                1..462
                      mol_type = other DNA
                      organism = synthetic construct
SEQUENCE: 2
```
atgaagtggg tgactttat tcccttctc tttctcttca gctctgctta ttccttcttg    60
aaggtgaaga tgcacactgt gtcctacatt catttcttct accttggcct gtgtttgctt   120
accttaacca gttctgctgc tgccggccca gaaacactgt gtggtgctga gctggttgat   180
gctcttcagt tcgtatgtgg agacagaggc ttctacttca gtaagcctac agggtatgga   240
tccagcagta gacgcttaca ccacaaggga atagtggatg aatgctgctt ccagagttgt   300
gacctgagga ggctggagat gtactgtgct ccaataaagc cacctaaatc tgcacgctct   360
gtacgtgctc agcgccacac tgtatatgcc aaagcacaaa aggaagtgca tttgaagaat   420
acaagtagag gaacacagg aaacagaaac tacagaatgt aa                      462
```

SEQ ID NO: 3          moltype = DNA  length = 414
FEATURE               Location/Qualifiers
misc_feature          1..414
                      note = porcine IGF1 and porcine albumin signal peptide
source                1..414
                      mol_type = other DNA
                      organism = synthetic construct
SEQUENCE: 3
```
atgaagtggg tgactttat tcccttctc tttctcttca gctctgctta ttccttggcc    60
ctgtgcttgc tctccttcac cagctctgcc acggctggac ctgagaccct ctgtggggct   120
gagctggtgg acgctcttca gttcgtgtgc ggagacaggg gctttatttt caacaagccc   180
acagggtacg gctccagcag tcggagggcg ccacagacgg catcgtgga tgagtgctgc   240
ttccggagct gtgatctgag gaggctggag atgtactgtg caccccctga gcctgccaag   300
tcggcccgct ccgtccgtgc ccagcgccac acggacatgc ccaaggctca gaaggaagta   360
catttgaaga acacaagtag agggagttca ggaaacaaga actacagaat gtag         414
```

SEQ ID NO: 4          moltype = DNA  length = 462
FEATURE               Location/Qualifiers
source                1..462
                      mol_type = other DNA
                      organism = Gallus gallus
SEQUENCE: 4
```
atggaaaaaa tcaacagtct tcaacacaa ttagttaagt gctgcttttg tgatttcttg    60
aaggtgaaga tgcacactgt gtcctacatt catttcttct accttggcct gtgtttgctt   120
accttaacca gttctgctgc tgccggccca gaaacactgt gtggtgctga gctggttgat   180
gctcttcagt tcgtatgtgg agacagaggc ttctacttca gtaagcctac agggtatgga   240
tccagcagta gacgcttaca ccacaaggga atagtggatg aatgctgctt ccagagttgt   300
gacctgagga ggctggagat gtactgtgct ccaataaagc cacctaaatc tgcacgctct   360
gtacgtgctc agcgccacac tgtatatgcc aaagcacaaa aggaagtgca tttgaagaat   420
acaagtagag gaacacagg aaacagaaac tacagaatgt aa                      462
```

SEQ ID NO: 5          moltype = DNA  length = 465
FEATURE               Location/Qualifiers
source                1..465
                      mol_type = other DNA
                      organism = Bos taurus
SEQUENCE: 5
```
atgggaaaaa tcagcagtct tccaacccaa ttatttaagt gctgcttttg tgatttcttg    60
aagcaggtga agatgcccat cacatcctcc tcgcatctct tctatctggc cctgtgcttg   120
ctcgccttca ccagctctgc cacggcggga cccgagaccc tctgcggggc tgagttggtg   180
gatgctctcc agttcgtgtg cggagacagg ggcttttatt tcaacaagcc cacggggtat   240
ggctcgagca gtcggagggc gccccagaca ggaatcgtgg atgagtgctg cttccggagc   300
tgtgatctga ggaggctgga gatgtactgc gcgcctctca gcccgccaa gtcggcccgc   360
tcagtccgtg cccagcgcca caccgacatg cccaaggctc agaaggaagt acatttgaag   420
aacacaagta gagggagtgc aggaaacaag aactacagaa tgtag                   465
```

SEQ ID NO: 6          moltype = DNA  length = 393
FEATURE               Location/Qualifiers
source                1..393
                      mol_type = other DNA
                      organism = Sus scrofa
SEQUENCE: 6
```
atgcacatca catcctcttc gcatctcttc tacttggccc tgtgcttgct ctccttcacc    60
```

```
agctctgcca cggctggacc tgagaccctc tgtggggctg agctggtgga cgctcttcag    120
ttcgtgtgcg gagacagggg cttttatttc aacaagccca cagggtacgg ctccagcagt    180
cggagggcgc cacagacggg catcgtggat gagtgctgct tccggagctg tgatctgagg    240
aggctggaga tgtactgtgc acccctcaag cctgccaagt cggcccgctc cgtccgtgcc    300
cagcgccaca cggacatgcc caaggctcag aaggaagtac atttgaagaa cacaagtaga    360
gggagttcag gaaacaagaa ctacagaatg tag                                 393
```

| SEQ ID NO: 7 | moltype = DNA length = 1824 |
|---|---|
| FEATURE | Location/Qualifiers |
| misc_feature | 1..1824 |
| | note = bovine albumin and porcine albumin signal peptide |
| source | 1..1824 |
| | mol_type = other DNA |
| | organism = synthetic construct |

SEQUENCE: 7
```
atgaagtggg tgacttttat ttcccttctc tttctcttca gctctgctta ttccaggggt     60
gtgtttcgtc gagatacaca caagagtgag attgctcatc ggtttaaaga tttgggagaa    120
gaacattta aaggcctggt actgattgcc ttttctcagt atctccagca gtgtccattt     180
gatgagcatg taaaattagt gaacgaacta actgagtttg caaaaacatg tgttgctgat    240
gagtcccatg ccggctgtga gaagtcactt cacactctct tggagatgaa ttgtgtaaa     300
gttgcatccc ttcgtgaaac ctatggtgac atggctgact gctgtgagaa acaagaacct    360
gagagaaatg aatgcttctt gtcacacaaa gatgatagcc ctgatctacc taaactcaaa    420
cctgacccca atactttgtg tgacgagttt aaggccgatg aaaagaagtt tggggaaaa     480
tacctatacg aaattgctag aagacatccc tactttatg caccagaact cctttactat    540
gctaataaat ataatggagt ttttcaagaa tgctgccaag ctgaagataa aggtgcctgc    600
ctgctaccaa agattgaaac tatgagggaa aaggtactga cttcatctgc cagacagaga    660
ctcaggtgtg ccagtattca aaaatttgga gaaagagctt taaaagcatg gtcagtagct    720
cgcctgagcc agaaatttcc caaggctgag tttgtagaag ttaccaagct agtgacagat    780
ctcacaaaag tgcacaagga atgctgccat ggagacctac ttgaatgcgc agatgacagg    840
gcggaccttg ccaagtacat atgtgataat caagataccat tctccagtaa actgaaggaa    900
tgctgtgata gccttttgtt ggaaaaatcc cactgcattg ctgaggtaga aaagatgcc     960
atacctgaaa acttgcccc attaactgct gactttgctg aagataagga tgtatgcaaa    1020
aactatcaag aagcaaagga tgccttcctg ggctcatttc tttatgaata ttcaagaagg   1080
catcctgaat atgctgtctc agtgctattg agacttggta aggaatatga agccacactg    1140
gaggaatgct gtgccaaaga tgatccacat gcatgctatt ccacagtgtt tgacaaactt   1200
aagcatcttg tggatgagcc tcagaattta attaaacaaa actgtgacca attcgaaaaa   1260
cttggagagt atggattcca aaatgcgctc atagttcgtt acaccaggaa agtacccaa    1320
gtgtcaactc caactctcgt ggaggtttca agaagcctag gaaagtggga tactaggtgt   1380
tgtacaaaac cggaatcaga aagaatgcc tgtacagaag acatatctgag cttgatcctg   1440
aaccggttgt gcgtgctgca tgaagagaca ccagtgagtg aaaaagtcac caagtgctgc   1500
acagagtcat tggtgaacag acggccatgt ttctctgctc tgacacctga tgaaacatat   1560
gtacccaaag cctttgatga gaaattgttc acccttcatg cagatatatg cacacttccc   1620
gatactgaga aacaaatcaa gaaacaaact gcacttgttg agctgttgaa acacaagccc   1680
aaggcaacag aggaacaact gaaaaccgtc atggagaatt tgtggctttt tgtagacaag   1740
tgctgcgcag ctgatgacaa agaagcctgc tttgctgtgg agggtccaaa acttgttgtt   1800
tcaactcaaa cagccttagc ctaa                                          1824
```

| SEQ ID NO: 8 | moltype = DNA length = 1848 |
|---|---|
| FEATURE | Location/Qualifiers |
| misc_feature | 1..1848 |
| | note = chicken albumin and porcine albumin signal peptide |
| source | 1..1848 |
| | mol_type = other DNA |
| | organism = synthetic construct |

SEQUENCE: 8
```
atgaagtggg tgacttttat ttcccttctc tttctcttca gctctgctta ttccaggaat     60
ctgcaaagat tgctcgtga tgcagagcac aagagtgaaa ttgcccatcg ctacaatgat    120
ttgaaagaag aaacatttaa ggcagttgcc atgatcacat ttgcccagta tctccagagg    180
tgctcttatg aaggactgtc taagcttgtg aaggatgttg gtgatcctggc acaaaaatgt    240
gtagccaatg aagatgctcc tgaatgctca aaaccactgc cttccattat cctggatgaa    300
atctgccaag tggaaaagct ccgtgactct tatggtgcaa tggccgactg ctgtagcaaa    360
gctgatcctg aaagaaatga gtgtttcctg tcatttaaag tttcccaacc agacttcgtt    420
cagccatacc aaagaccagc ttctgatgtg atatgccagg aataccagga caacagagtg    480
tcatttctgg gacatttcat ctattctgtt gcaagaagac accccttctt gtatgcccct    540
gcaatcctta gttttgctgt tgattttgaa catgcacttc aaagctgttg caaagagagt    600
gatgtcggtg cttgcctgga caccaaggaa attgttatga gagaaaaagc caaggagta     660
agtgtgaagc agcagtattt tgtgtggaatc ttgaagcagt tcggagatag agttttccaa    720
gcacgacaac ttatttacct aagccaaaaa taccccaagg ctccattctc agaggtttct    780
aaatttgtac atgattctat cggcgtccac aaagagtgct gtgaagggga catggtgaga    840
tgcatggatg acatggcacg tatgatgagc aatctgtgct ctcaacaaga tgttttctca    900
ggtaaaatca aagactgctg tgaaaagcct attgtggaac gaagccagtg cattatggag    960
gcagaatttg atgagaaacc tgcagatctt ccttcattag ttgaaagta catagaagat    1020
aaggaagtgt gtaaaagttt tgaagcaggc cacgatgcat tcatggcaga gttcgtttat   1080
gaatactcac gaagcacccc tagttctcc atacagctta ttatgagaat tgcaagga     1140
tatgaatcac ttctgaaaa gtgctgcaaa actgataacc ctgctgagtg ctacgcaaat   1200
gctcaagagc aactgaacca acatatcaaa gaaactcagg atgttgtgaa gacaaactgt   1260
gatcttctcc atgaccatgg cgaggcagac ttcctcaagt ccatcctgat ccgctacact   1320
aagaaaatgc ctcaagtacc aactgatctc tgcttgaaa ctgaagaa aatgacaact     1380
attggtacta agtgctgcca gcttcctgaa gacacagcga tggcttgttc tgagggttat    1440
```

```
ctgagcattg tgattcatga tacgtgcagg aaacaggaga ccacacctat aaatgacaac  1500
gtttcacaat gctgcagcag ctcctatgct aacagaagac catgtttcac tgctatggga  1560
gtagatacca aatatgttcc tccaccattt aatcctgata tgttcagctt tgatgaaaaa  1620
ttgtgcagtg ctcctgctga agaacgaaa gtaggccaga tgaaattgct aatcaacctc  1680
attaaacgca agccccagat gacagaagaa caaataaaga caattgctga tggtttcact  1740
gccatggttg acaagtgctg caagcagtcg gacatcaata catgctttgg agaagagggt  1800
gccaacctaa tagtccaaag cagagccaca ttaggaattg tgctttaa                1848

SEQ ID NO: 9           moltype = DNA  length = 1824
FEATURE                Location/Qualifiers
source                 1..1824
                       mol_type = other DNA
                       organism = Sus scrofa
SEQUENCE: 9
atgaagtggg tgactttat ttcccttctc tttctcttca gctctgctta ttccaggggt   60
gtgtttcgtc gagatacata caagagtgaa attgctcatc ggtttaaaga tttgggagaa  120
caatatttca aaggcctagt gctgattgcc ttttctcagc atctccagca atgcccatat  180
gaagagcatg tgaaattagt gagggaagta actgagttgt caaaaacatg tgttgctgat  240
gagtcagctg aaaattgtga caagtcaatt cacactctct tggagataaa attatgtgca  300
attccatccc ttcgtgaaca ctatggtgac ttggctgact gctgtgaaaa agaagagcct  360
gagagaaacg aatgcttcct ccaacacaaa atgataaccc ccgacatccc taaattgaaa  420
ccagaccctg ttgctttatg cgctgacttc caggaagatg aacagaagtt ttggggaaaa  480
tacctatatg aaattgccag aagacatccc tatttctacg ccccagaact cctttattat  540
gccattatat ataaagatgt tttttcagaa tgctgccaag ctgctgataa agctgcctgc  600
ctgttaccaa agattgagca tctgagagaa aaagtactga cttccgccgc caaacagaga  660
cttaagtgtg ccagtatcca aaaattcgga gagagagctt tcaaagcatg gtcattagct  720
cgcctgagcc agagatttcc caaggctgac tttacagaga tttccaagat agtgacagat  780
cttgcaaaag tccacaagga atgctgccat ggtgacctgc ttgaatgtgc agatgacagg  840
gcggatcttg ccaaatatat atgtgaaaat caagacacaa tctccactaa actgaaggaa  900
tgctgtgata agcctctgtt ggaaaaatcc cactgcattg gtgaggcaaa aagagataaa  960
ttgcctgcag acctgaaccc attagaacat gatttgttg aagataagga agtttgtaaa   1020
aactataaag aagcaaagca tgtcttcctg ggcacgtttt tgtatgagta ttcaagaagg  1080
cacccagact actctgtctc attgctgctg agaattgcca agatatatga gccacactg   1140
gaggactgct gtgccaaaga ggatcctccg gcatgctatg ccacagtgtt tgataaattt  1200
cagcctcttg tggatgagcc taagaattta atcaaacaaa actgtgaact ttttgaaaaa  1260
cttggagagt atggattcca aaatgcgctc atagttcgtt acaccaagaa agtaccccaa  1320
gtgtcaactc caactcttgt ggaggtcgca agaaaactag gactagtggg ctctaggtgt  1380
tgtaagcgtc ctgaagaaga aagactgtcc tgtgctgaag actatctgtc cctggtcctg  1440
aaccggttgt gcgtgttgca cgagaagaca ccagtgcagg aaaaagttac caaatgctgc  1500
acagagtcct tggtgaacag acggccttgc ttttctgctc tgacaccaga cgaaacatac  1560
aaacccaaag aatttgttga gggaaccttc accttccatg cagacctatg cacacttcct  1620
gaggatgaga aacaaatcaa gaagcaaact gcactcgttg agttgttgaa acacaagcct  1680
catgcaacag aggaacaact gagaactgtc ctgggcaact ttgcagcctt tgtacaaaag  1740
tgctgcgccg ctcctgacca tgaggcctgc tttgctgtgg agggtccgaa atttgttatt  1800
gaaattcgag ggatcttagc ctaa                                          1824

SEQ ID NO: 10          moltype = DNA  length = 1848
FEATURE                Location/Qualifiers
source                 1..1848
                       mol_type = other DNA
                       organism = Gallus gallus
SEQUENCE: 10
atgaagtggg taacattaat ttcattcatt ttcctcttca gttcagcaac atccaggaat   60
ctgcaaagat ttgctcgtga tgcagagcac aagagtgaaa ttgcccatcg ctacaatgat  120
ttgaaagaag aaacatttaa ggcagttgcc atgatcacat ttgcccagta tctccagagg  180
tgctctctatg aaggactgtc taagcttgtg aaggatgttg ttgatctggc acaaaaatgt  240
gtagccaatg aagatgctcc tgaatgctca aaaccactgc cttccattat cctggatgaa  300
atctgccaag tggaaaagct ccgtgactct tatggtgcaa tggccgactg ctgtagcaaa  360
gctgatctcg aaagaaatga gtgtttcctg tcatttaaag tttcccaacc agacttcgtt  420
cagccatacc aaagaccagc ttctgatgtg atatgccagg aataccagga caacagatga  480
tcatttctgg gacatttcat ctattctgtt gcaagaagac accccttctt gtatgcccct  540
gcaatcctta gttttgctgt tgattttgaa catgcacttc aaagctgttg caagagagt   600
gatgtcggtg cttgcctgga caccaaggaa attgttatga gagaaaagc caaggagta   660
agtgtgaagc agcagtattt ttgtggaatc ttgaagcagt tcggagatag agttttccaa  720
gcacgacaac ttatttacct aagccaaaaa taccccaagg ctccattctc agaggtttct  780
aaatttgtac atgattctat cggcgtccac aaagagtgct gtgaagggga catggtggag  840
tgcatggatg acatggcacg tatgatgagc aatctgtgct ctcaacaaga tgttttctca  900
ggtaaaatca aagactgctg tgaaaagcct atttgtggaac gaagcagtg cattatggag  960
gcagaatttg atgagaaacc tgcagatctt ccttcattag ttgaaaagta catagaagat 1020
aaggaagtgt gtaaaagttt tgaagcaggc cacgatgcat tcatggcaga gttcgtttat  1080
gaatactcac gaagacaccc tgagttctcc atacagctta ttatgagaat tgccaaagga  1140
tatgaatcac ttctggaaaa gtgctgcaaa actgataacc ctgctgagtg ctacgcaaat  1200
gctcaagagc aactgaacca acatatcaaa gaaactcagg atgttgtgaa gacaaactgt  1260
gatctttcta tgaccatgg cgaggcagac ttcctcactc catcctgat ccgctacact  1320
aagaaaatgc ctcaagtacc aactgatctc ctgcttgaaa ctgaaagaa aatgacaact  1380
attggtacta agtgctgcca gcttcctgaa gacagacgca tggcttgttc tgagggttat  1440
ctgagcattg tgattcatga tacgtgcagg aaacaggaga ccacacctat aaatgacaac  1500
gtttcacaat gctgcagcag ctcctatgct aacagaagac catgtttcac tgctatggga  1560
gtagatacca aatatgttcc tccaccattt aatcctgata tgttcagctt tgatgaaaaa  1620
```

```
ttgtgcagtg ctcctgctga agaacgagaa gtaggccaga tgaaattgct aatcaacctc 1680
attaaacgca agcccagat gacagaagaa caaataaaga caattgctga tggtttcact 1740
gccatggttg acaagtgctg caagcagtcg gacatcaata catgctttgg agaagagggt 1800
gccaacctaa tagtccaaag cagagccaca ttaggaattg gtgcttaa        1848
```

```
SEQ ID NO: 11          moltype = DNA  length = 1824
FEATURE                Location/Qualifiers
source                 1..1824
                       mol_type = other DNA
                       organism = Bos taurus
SEQUENCE: 11
atgaagtggg tgactttat ttctcttctc cttctcttca gctctgctta ttccagggt   60
gtgtttcgtc gagatacaca caagagtgag attgctcatc ggtttaaaga tttgggagaa 120
gaacatttta aaggcctggt actgattgcc ttttctcagt atctccagca gtgtccattt 180
gatgagcatg taaaattagt gaacgaacta actgagtttg caaaaacatg tgttgctgat 240
gagtcccatg ccggctgtga gaagtcactt cacactctct tggagatgaa attgtgtaaa 300
gttgcatccc ttcgtgaaac ctatggtgac atggctgact gctgtgagaa caagaacct  360
gagagaaatg aatgcttctt gtcacacaaa gatgatagcc ctgatctacc taaactcaaa 420
cctgacccca atactttgtg tgacgagttt aaggccgatg aaaagaagtt ttggggaaaa 480
tacctatacg aaattgctag aagacatccc tactttatg caccagaact cctttactat  540
gctaataaat ataatggagt ttttcaagaa tgctgccaag ctgaagataa aggtgcctgc 600
ctgctaccaa agattgaaac tatgagggaa aaggtactga cttcatctgc cagacagaga 660
ctcaggtgtg ccagtattca aaaatttgga gaaagagctt taaaagcatg gtcagtagct 720
cgcctgagcc agaaatttcc caaggctgag ttgtagaag ttaccaagct agtgacagat   780
ctcacaaaag tgcacaagga atgctgccat ggagacctac ttgaatgcgc agatgacagg 840
gcggaccttg ccaagtacat atgtgataat caagatcaaa tctccagtaa actgaaggaa 900
tgctgtgata agcctttgtt ggaaaaatcc cactgcattg ctgaggtaga aaagatgcc   960
ataccgtgaaa acttgccccc attaactgct gactttgctg aagataagga tgtatgcaaa 1020
aactatcaag aagcaaagga tgccttcctg ggctcatttc tttatgaata ttcaagaagg 1080
catcctgaat atgctgtctc agtgctattg agacttgaag atgaaatga agccacactg  1140
gaggaatgct gtgccaaaga tgatccacat gcatgctatt ccacagtgtt tgacaaactt 1200
aagcatcttg tggatgagcc tcagaattta attaaacaaa actgtgacca attcgaaaaa 1260
cttggagagt atggattcca aaatgcgctc atagttcgtt acaccaggaa agtaccccaa 1320
gtgtcaactc caactctcgt ggaggtttca agaagcctag gaaagtggg tactaggtgt   1380
tgtacaaaac cggaatcaga aagaatgccc tgtacagaag actatctgag cttgatcctg 1440
aaccggttgt gcgtgctgca tgaagagaca ccagtgagtg aaaaagtcac caagtgctgc 1500
acagagtcat tggtgaacag acggccatgt ttctctgctc tgacacctga tgaaacatat 1560
gtacccaaag cctttgatga gaaattgttc accttccatg cagatatatg cacacttccc 1620
gatactgaga aacaaatcaa gaaacaaact gcacttgttg agctgttgaa acacaagcca 1680
aaggcaacag aggaacaact gaaaaccgtc atggagaatt tgtggccttt tgtagacaag 1740
tgctgcgcag ctgatgacaa agaagcctgc tttgctgtgg agggtccaaa acttgttgtt 1800
tcaactcaaa cagccttagc ctaa                                       1824
```

```
SEQ ID NO: 12          moltype = DNA  length = 4041
FEATURE                Location/Qualifiers
misc_feature           1..4041
                       note = Gallus gallus telomerase reverse transcriptase
                       T2667C mutant
source                 1..4041
                       mol_type = other DNA
                       organism = synthetic construct
SEQUENCE: 12
atggagcgcg ggctcagcc gggagtcggt gtgcggcggc tccgcaatgt agcgcgggag   60
gagcccttcg ccgcggtcct gggcgcgctg cggggctgct acgccgaggc cacgccgctg  120
gaggccttcg tccggcgggct gcaggagggt ggcaccgggg aggtcgaggt gctgcgaggc 180
gacgacgctc agtgctaccg gaccttcgtg tcgcagtcgcg tggtgtgcgt ccccgcggtt 240
gctcgcgcca tccccggcc catctgcttc cagcagttat ccagtcagag cgaagtcatc  300
acaagaatcg ttcagaggct gtgtgaaaag aaaagaaga acatccttgc gtatggatac  360
tccttgctgg atgagaacag ttgtcacttc agagttttgc catcttcgtg tatatacagc 420
tatctgtcca atactgtaac agaaacgatt cgcatcagtg gcctctggga gatactgctg  480
agtaggatag gggacgacgt gatgatgtac ctgctggagc actgtgcact cttcatgctg  540
gttccccaa gtaactgtta ccaggtctgc gggcaaccaa tttatgaact tatttcgcgt   600
aacgtagggc catccccagg gtttgttaga cgacggtact caaggtttaa acataatagc  660
ttgctttgact atgtgcgaaa aagcttgtg tttcacaggc actatctttc caagtcgcag 720
tggtggaagt gcaggccgag acgtcgaggt cgtgtctcca gcaggagaaa aagaaggagc  780
catagggatac aaagcctaag gtctggttat cagccttctg caaaagtgaa cttcaagcca  840
ggtaggcaga tcagcacagt tactgcacgt ctggaaaaac agagctgctc cagtttatgt  900
ttgccagcta gagcaccatc tttaaaaagg aagcgtgatg gagaacaggt tgaaatcaca  960
gctaagagag tgaaaataat aggaaaagag atagaggaac aggctggtag atcgttcct  1020
gatgtaaacc aaagtagctc ccagaggcat ggaacctcct ggcatgtagc accacgtgct 1080
gtaggtctta ttaaagaaca ttacatttct gaaagaagta acgtgagat gtctggtcct  1140
tctgtagttc acagatctca ccctgggaag aggcctgtgg cagacaaaag ctcttttcca  1200
caaggagttc agggtaacaa acgcataaag accggtgcag aaaacgagc agaatccaat   1260
agaagggggca tagagatgta tataaaccca atccataaac ccaatagaag gggcatagag 1320
aggcgtataa atccaaccca caaacctgag ttgaattctg tacaaactga accaatggaa 1380
ggtgcttctt caggggacag aaagcaggaa atccccccag ctcatttggc aaagcagtta 1440
ccaaatacat tgtcgcgctc tacagtgtac tttgagaaga aatttcttct gtattcccgc 1500
agttaccaag aatattttcc taaatcgttc atactgagcc gcctgcaggg ttgtcaggca 1560
ggtggaaggc ggcttataga aactatattc ttaagccaaa acccattaaa ggaacagcag 1620
```

```
aaccaaagcc taccacagca aaagtggcga aagaagaggt tgcccaaacg ctactggcaa  1680
atgagagaga tatttcagaa gctggtaaag aaccatgaga agtgcccta tttagttttc    1740
ttgaggaaaa attgccctgt tttgctttct gaagcatgtt tgaaaaagac ggagctgacc   1800
ttgcaggcgg ctctgcctgg ggaagcaaag gttcacaagc acacagaaca tgggaaagag   1860
tccactgagg gtactgcacc gaacagcttc ctcgctcctc cctcagtgct agcatgtggg   1920
cagccagaga gagggaaca gcaccctgca gaggggagtg atccgctcct cagggagctg    1980
ctcaggcagc acagcagcca ctggcaggta tatggctttg tgagggagtg cctggagcgg   2040
gtgatccctc tgagctgtg gggttcaagc ataacaaat gccggttctt taaaaacgtg     2100
aaagcattca tttccatggg gaagtatgct aagctttcat tgcagcagct gatgtggaag   2160
atgagagtga atgactgcgt atggcttcgt ctggccaaag gtaatcactc tgttcctgcc   2220
tatgaacatt gttaccgtga agaaattctg gcaaaattcc tatactggct gatggattcc   2280
tatgttatcg agttgctcaa atcatttttc tatatcaccg agaccatgtt ccagaaaaac   2340
atgcttttct actaccgaaa gtttatctgg gcaagttac agaacattgg aattagagac    2400
cattttgcca aagtacatct acgtgccttg tcttcagagg agatgaagt gatccgtcaa    2460
aaaaagtatt ttcctattgc atcaaggctc cggttcattc ctaaaatgaa tggtttaaga   2520
cccgtagtaa gactaagccg tgttgttgaa ggacagaaac tcagcaagga aagcagagaa   2580
aagaagatac agcgctataa cactcagcta aaaaatctat ttagtgtttt aaactatgaa   2640
cgaactgtaa acaccagtat cattggctcc tcagtattcg ggagagatga tatctacagg   2700
aagtggaagg agtttgttac aaaggttttt gaatcaggtg gtgaaatgcc tcatttctac   2760
tttgtaaagg gtgatgtatc cagagctttt gataccattc ctcacaagaa acttgtggaa   2820
gtgatatcac aggtcttgaa acctgagagc caaactgtct atggaataag gtggtatgca   2880
gtgattatga ttaccccaac tggaaaagcc aggaaactct ataagagaca tgtttctact   2940
ttcgaggatt ttattccaga catgaagcag tttgtgtcca agcttcaaga gagaacttca   3000
ttacgaaatg caatagtagt tgaacagtgc ttaactttta tgagaacag ttccaccctg    3060
tttactttct ttcttcaaat gttacataat aacatcctgg agattgggca caggtactat   3120
atacagtgct ctggaatccc acagggctcc attttgtaca ccttacttg cagcttatgc    3180
tacgagacca tggaaaacaa attactctgt gggatccaga aggatggagt cctaatacgt   3240
cttattgatg acttttgct ggttacgcca catttaatgc aggcaagaac ttttctaagg    3300
actatagcag caggtattcc tgagtatggc ttttttaataa atgccaagaa gactgtggta   3360
aatttcctg ttgatgatat cccgggatgt tccaagttca aacatctgcc agattgtcgt    3420
ttgatctcat ggtgtggttt attattggat gtgcagacac ttgaggttta ttgtgattac    3480
tccagttatg cctttacttc tatcagatca agtcttcct tcaattcaag tagaatagct      3540
gggaaaaaca tgaaatgcaa attgactgca gtcctcaaac tgaaatgcca tcctttactt   3600
cttgacttaa agatcaacag ccttcagaca gttctaatta acatctacaa gatattttta   3660
cttcaggctt acaggttcca tgcctgtgtt cttcagcttc cattcaacca gaaagttagg   3720
aataatcctg atttcttcct aaggatcatc tctgatactg cttcatgctg ctattttatc   3780
ctgaaagcta aaaatccagg agtttcttta ggtagcaaag atgcatctgg catgttccct   3840
tttgaggcag cagaatggct gtgctaccat gccttcattg tcaaactgtc caaccacaaa   3900
gttatttaca aatgcttact taagcccctt aaagtctata agatgcatct gtttgggaag   3960
atcccaaggg atactatgga actgctgaag acggtgacgg aaccatcgct ttgtcaagat   4020
ttcaaaacta tactggacta a                                             4041
```

SEQ ID NO: 13            moltype = DNA   length = 1854
FEATURE                  Location/Qualifiers
misc_feature             1..1854
                         note = chicken cMyoDER
source                   1..1854
                         mol_type = other DNA
                         organism = synthetic construct SEQUENCE: 13
```
atggacttac tgggccccat ggaaatgacg gagggctccc tctgctcctt cacggccgcc   60
gatgacttct atgacgaccc gtgcttcaac acgtcggaca tgcacttctt cgaggacctg    120
gaccccggc tggtgcacgt gggcgggctg ctgaagcccg aggagcaccc gcaccaccac    180
gggcaccacc acgggaaccc acacgaggag gagcacgtgc gggcgccag tgggcaccac     240
caggccggcc gctgcctgct gtgggcgtgc aaggcctgca agaggaagac caccaacgct   300
gaccgccgca agccgccac catgagggaa cggcggcggc tcagcaaggt caacgaggcc     360
ttcgagaccc tcaagcgctg cacttccacc aaccccaacc agcgcctgcc caaggtggag   420
atcctgcgca cgccatccg ctacatcgag agcctgcagg ccctgctgcg tgagcaggag    480
ggcgattctt ctacagagct gcgagctcca accctttgga caagtccact ggtggttaaa   540
cataacaaga agaacagtcc ggctctgtct ctgacagaca acagcagtgt cagtgccttg   600
ctggaagctg agccacctat agtttattct gaatatgacc ccaatagacc attcaacgaa   660
gcatctatga tgaccctgtt gaccaacctt gcagacagaa attagtgca catgatcaac    720
tgggcaaaga gagttccagg atttgtggat ttaaacactc catgatcaggt ccatctgctg   780
gaatgtgcct ggttagagat attgatgatc ggcttatgct ggccgtccat ggaacaccca   840
ggaaagcttt tatttgcacc taatctatta ctggacagga atcaagggaa atgtgtagag   900
ggcatggtgg aaatctttga catgctactg gctactgctg ctcggtttcg gatgatgaac   960
cttcaagggg aggaatttgt gtgccttaag tccatcatcc tgctcaattc tggtgtgtac   1020
acttttcttt ctagcacctt gaaatctctg aagagaggg actatatcca ccgtgttctg   1080
gacaaaatca cagatactct gatacaccta atggcaaagt caggtctttc tctgcagcag   1140
caacaccggc gactagctca gctcctcctt atcctctctc acatcaggca tatgagcaac   1200
aaaggaatgg agcacctgta caatatgaag tgtaaaaatg tagttccgct ctacgacctc   1260
ttactggaga tgctggacgc tcaccgccta catgcaccgg cagccaggag tgctgcacca    1320
atggaagagg agaaccgaaa ccaactgaca accgcaccag cttcatctca ttccctgcag   1380
tccttttaca ttaacagcaa agaagaggag agtatgcaga atacagctat cgccgatgca   1440
tactacccag tgctggagca ctacagcggg gagtcagatg cctccagccc tcgctccaac   1500
tgctccgacg gcatgatgga gtacagcggg ccgcccgta gctctcgcag gagaaacagc    1560
tacgacagca gctactacac ggaatcacca aatgacccaa gcatgggaa gagttctgtt    1620
gtttccagcc tcgactgcct ctcaagcatt gtggagagga tttccacaga caactccaca   1680
tgtcccatac tgcctccagc tgaagctgta gctgaaggga gtccctgttc cccccaggaa   1740
```

```
ggagcaaacc tgagtgacag tggagcccag attccttccc ccaccaactg cacccctctt   1800
ccccaggaaa gcagcagcag cagcagcagc aatccaatct accaagtgct ataa         1854

SEQ ID NO: 14           moltype = AA  length = 8
FEATURE                 Location/Qualifiers
REGION                  1..8
                        note = FLAG-tag peptide
source                  1..8
                        mol_type = protein
                        organism = synthetic construct
SEQUENCE: 14
DYKDDDDK                                                            8

SEQ ID NO: 15           moltype = DNA  length = 540
FEATURE                 Location/Qualifiers
source                  1..540
                        mol_type = other DNA
                        organism = Bos taurus
SEQUENCE: 15
atggggatca cagcaggaaa gtcggtgctg gtgcttcttg ccttcttggc cttcgcctcg   60
tgctgctatg ctgcttaccg ccccagcgag actctgtgcg gcggggagct ggtggacacc   120
ctccagtttg tctgtgggga ccgcggcttc tacttcagcg gaccatccag ccgcataaac   180
cgacgcagcc gtggcatcgt ggaagagtgt tgcttccgaa gctgcgacct ggccctgctg   240
gagacttact gtgccacccc cgccaagtcc gagaggatg tgtctgcctc tacgaccgtg    300
cttccggacg acgtcaccgc ataccccgtg ggcaagttct ccaatatgac atctggaag    360
cagtccaccc agcgcctgcg caggggcctg cccgccttcc tgcgagcacg ccgggtcgc    420
acgctcgcca aggagctgga ggcgctcaga gaggccaaga gtcaccgtcc gctgatcgcc   480
ctgcccaccc aggaccctgc cacccacggg ggcgcctctt ccaaggcatc cagcgattag   540

SEQ ID NO: 16           moltype = DNA  length = 486
FEATURE                 Location/Qualifiers
source                  1..486
                        mol_type = other DNA
                        organism = Danio rerio
SEQUENCE: 16
atgtctagcg gtcatttctt ccaggggcat tggtgtgatg tctttaagtg taccatgcgc   60
tgtctcccga gtacccacac cctctcactg gtgctgtgcg tcctcgcgtt gactcccgcg   120
actctggagg cggggccgga gacgctgtgc ggggcggagc ttgtagacac gctgcagttt   180
gtgtgtggag acaggggctt ttatttcagc aaaccgacag gatatggagc tagttcaaga   240
aggtcacaca accgtggcat cgtggacgaa tgctgctttc agagctgtga gctacgcgc    300
ctcgagatgt attgtgcgcc tgtgaagaca ggcaaatctc cacgatctct acgagcacaa   360
cgacacacag atattcccag gacaccaaag aaacctatat ctgggcatag ccactcttcc   420
tgtaaggagg ttcatcagaa gaactcgagc cgaggaaaca caggggcag aaactatcgc    480
atgtag                                                              486

SEQ ID NO: 17           moltype = DNA  length = 312
FEATURE                 Location/Qualifiers
source                  1..312
                        mol_type = other DNA
                        organism = Oncorhynchus mykiss
SEQUENCE: 17
atgaggagac cctgtatcct ggccatccag cctgacacgg agttcatgcc cccagagctg   60
gatgccagca acttccacat gggccctgag ctctgcacca aggacagcaa ggagctgctg   120
ctctctggga gaaactact gtatggtgtg gtcagacata gaccaccat cactgaggag    180
cagctgaagt ccatctctac taaatatcac agtatgaagg agaagtgctg tgctgctgag   240
gaccaagcag catgcttcac tgaggaggca cccaagctgg ttgctgagag tgcagagctg   300
gtcaaggctt aa                                                       312

SEQ ID NO: 18           moltype = DNA  length = 1116
FEATURE                 Location/Qualifiers
source                  1..1116
                        mol_type = other DNA
                        organism = Oreochromis niloticus
SEQUENCE: 18
atggctacat ccgccagcgc cagcttgagt aaagctgtca agcagcagta catggagctc   60
cctcagggg acaaagtcca ggccatgtac atctggatcg acggaaccgg agaggggctc   120
cgatgcaaaa ccaggacgct tgattctgag cccaaaagca tcgaagatct tcctgaatgg   180
aactttgacg gatccagtac ctaccagtcc gaaggctcca acgacgacat gtatctgatc   240
ccctcagcca tgttccgcga tccattccgc aaagacccca caagctggt gctgtgtgaa   300
gtcctgaagt acaaccgtaa acctacgaa accaacttc ggctcacctg taagaaagtg     360
atggatatgg tggcggatca gcatccttgg tttggcatgg agcaggagta caccatcctt   420
ggaacgacg gcatccatt tggctggcca tctaatggtt tccccggacc acggggccg     480
tactactgtg gtgttggagc tgcaaaagcc tatggcaggg acgtagtcga ggccattac    540
aaagcttgtt gtacgctgga agtccagatt tgtggcacaa atgctgaagt aatgcctgcc   600
cagtgggagt ccaggtcgg accttgcgaa ggcattgaca tgggcgatca tttgtggta    660
gcgcgcttca tcctgcaccg tgtctgtgag gattttggcg tcgtcgcctc atttgatccc   720
aagccaatcc ctgaaactg gaacggtgct ggctgccata caaacttcag cacgaaagag    780
atgagggaag acggtggatt gaaagctatt gaggattcca ttgagaagct tggaaagagg   840
cacagctacc acattcgtgc ctacgacccc aaggggggc tcgacaacgc ccgccgtctc    900
```

```
actggccgcc atgaaacctc aaacatcaac gaattctctg ctggtgtggc caaccgtggt   960
gccagcattc gcattcctcg taatgttggt caggagaaga aaggctactt cgaagaccgt  1020
cgcccttcag ccaactgtga cccgtacagt gtgaccgagg ccctgatccg cacctgtctg  1080
ctgaacgagg aaggagatga acccgcggat tactaa                            1116

SEQ ID NO: 19            moltype = DNA   length = 645
FEATURE                  Location/Qualifiers
source                   1..645
                         mol_type = other DNA
                         organism = Oncorhynchus mykiss
SEQUENCE: 19
atggaaaccc agaaaagaca cgaataccac tcagtttgtc acacctgccg gagaacggaa    60
aacacaagaa tgaaggtcaa gatgatgtct tcgtcaaatc gagtgctggt cattgcgctg   120
gcacttactc tgtacattgt tgaagtggct tcggcagaaa cgctatgtgg aggagaactg   180
gtggacgcgc tgcagttcgt ctgtgaagat agaggattct atttcagtag gccaaccagc   240
aggtctaaca gcagacgctc ccagaaccgt ggtatcgtgg aggagtgttg tttccgtagc   300
tgtgacctca acctgttgga gcagtactgt gccaaacctg ccaagtcaga gagggacgtg   360
tcggccaccct ctctacagat cattcccatg gtgcccacaa tcaaacagga tgtcccaaga   420
aaacatgtga ctgtgaagta ttccaaatat gaggcgtggc agaggaaggc tgctcagcgg   480
ctccggaggg gcgtcccggc catcctcagg gcccggaagt tccggaggca ggcggtgaag   540
atcaaggccc aagagcaggc gatgttccac cggcctctga tcaccctgcc cagcaagctt   600
cccccagtcc tgcccccac ggacaactac gtcagccaca attga                    645

SEQ ID NO: 20            moltype = DNA   length = 462
FEATURE                  Location/Qualifiers
source                   1..462
                         mol_type = other DNA
                         organism = Xenopus tropicalis
SEQUENCE: 20
atggaaaaaa acaacagtct ttcaacacaa ttatttaagt gctacttttg tgatttctta    60
aagctgaaga tgcacaaaat gtcctacatt catctgctct acctggcttt gtgtttcctg   120
acttaaccc attcagcagc tgctggacca gagaccctct gtggagccga actggtagac   180
actcttcagt ttgtatgtgg agacagaggc ttctatttta gcaagccaac agggtacgga   240
tccagcaatc gaagatcgca tcacagagga atagtagagg aagtgctgtt ccaaagctgt   300
gatttcagaa ggctgggagat gtactgcgct cctgccaagc cagccaaatc agcacgttct   360
gtacgtgctc aacgtcacac tgacatgcca aaagcccaga aggaagtaca cctaaagaat   420
gcaagtcgag gaaacacagg gagtcgagga ttccgaatgt aa                      462

SEQ ID NO: 21            moltype = DNA   length = 1122
FEATURE                  Location/Qualifiers
source                   1..1122
                         mol_type = other DNA
                         organism = Xenopus tropicalis
SEQUENCE: 21
atggcaacct ccgccagtgc tcagttgagt aaggccataa agcagatgta tctggaactg    60
ccacagggag ataaggtgca ggctatgtac atctgggttg atgggaccgg ggagggtctt   120
cgctgcagca ctcgcactct ggacagtgaa cccaagacta tagaagatct tcctgaatgg   180
aacttcgatg gatctagcac ataccaatcc gagggttcca acagtgacat gtacctgatt   240
ccagttgcaa tgtttagaga ccctttttcga agggaccccca acaagctggt actctgcgag   300
gtgctcaaat acaaccgaaa aacagctgaa acaaacttgc gtcatacatg taaccagata   360
atggacatga tggccaatga gcatccatgg tttggcagga acaggaata cacattgctg   420
ggtatggatg gacaccccttt tggctggcct tcaaatggct tcccaggacc acaaggtccc   480
tattactgtg gagtgggtgc agataaggca tatggtcggg atattgtgga ggctcattat   540
cgggcttgcc tttatgctgg tgtgaaaatt gcaggaacaa atgcagaagt tatgccagca   600
cagtgggagt tccaaattgg gccatgtgag ggaataaaa tgggagatca cctttggatt   660
gctcgattta tactgcatag aatttgtgag gattttggga tcattgtttc gtttgtaccca   720
aagcccataa ctggaaactg gaatggagct ggatgtcaca ccaatttcag cacaaagtca   780
atgcgtgaag aaggaggcct taaggacata gaagaatcca ttgaacgtct aagcaaacgt   840
catgattatc acatcagaat gtatgaccca aggggtggta aagacaatgc ccgtcgtctc   900
acaggtttcc atgagacctc cagcatccat gagttctctg caggagtggc aaacctgget   960
gccagtatcc gcattcccg cagtgtaggc caggagaaga aaggctattt tgaagatcgt  1020
cgtccatcag ccaactgtga tccctatgct gtgacagaag ctatgatcag aacctgccta  1080
ctgaatgaaa ctggagacga acctcttgaa tacaagaact aa                     1122

SEQ ID NO: 22            moltype = DNA   length = 1719
FEATURE                  Location/Qualifiers
source                   1..1719
                         mol_type = other DNA
                         organism = Xenopus tropicalis
SEQUENCE: 22
atgaacgcgt tgatgcggcg tgcctgctgc ggggcgctat tcccctctc attccgactg    60
gccgcgctga gcctatgaa gggagctagt aactttagct gcggtaacgt gtgcgcctct   120
cctgccggat gtttgggcgcc accaagtgga cacgacacgg gataaaagt gtacaacagc   180
cttactagga ggaaggatcc acttattctg gcagatccga cagtagcgac atggtatagc   240
tgtggaccta cagtttatga ccatgcacat cttggacatg catgttctta tgttagatgt   300
gacataattc gaaggattct gctcaaggtt tttgggattg acagtcgt ggtgatggta   360
gtcacagaca ttgatgataa gataatcaag agagcaaagg agctcaatat atctcctgtg   420
gcctcagctc gtacttacga acaggatttt aaacaagaca tgactgcgtt gaaggtcctt   480
ccaccaacag tatacatgag agttactgaa atattccac agatcatatc atttattgaa   540
```

```
cacataattg ccaatggata tgcatatgct acctcacaag gaaatgttta ttttgatgtt    600
cagtcgattg gagagcgata tgggaaattt aatgattctt tcagtgatac agccagcgaa    660
tcagcatcac aagataaaag gcatatccga gattttgctt tgtggaaaac atccaagcct    720
gaggagcctt actgggcttc tccttggggc aagggaagac ctggctggca catagagtgt    780
tccacaattg caagttctgt atttggcaaa catctagaca ttcacactgg tgggattgac    840
cttgctttcc ctcatcatga aaatgaaatt gctcagtgtg aggcatatca ccagagcaca    900
cagtggggaa actatttcct tcatactgga catttacatt tgaaagggaa tgaagaaaaa    960
atgtcaaaat ccctgagaaa ctatctgaca gttaaggagt tttttaaagtc cttttcccct   1020
gaccagttta gaatgttttg tctgcgctca aaatataaat cagccgtgga atacagcaac   1080
gggtccatgc atgatgcagt aaatacccta cacaccatct cttcgtttgt cgatgatgca   1140
aaagcctata tgaaaggtca gctgatttgc caaccagtgc aggaggcttt actctggcaa   1200
aggctgaatg aaacaaaagt aaatgttaag gctgcgtttt cagatgactt tgacaccca    1260
cgagcagttg atgcagttat ggacctcatt ccatggca acagacagct taaggctgtt    1320
tccaaggagt caaactctcc caggagctct gtagtttatg gtgccatgat ctcttacatt   1380
gaacaatttc tggagatatt gggaaattcc ttgagccaaa accaggtcgc tgcagaagat   1440
agacactcgg ctgttctctt taatgtagta aagaaatga tcagttttag aagtaaggtg    1500
cggaattacg ccctggctgc agatgaatca ccaaatgcaa taggacaaga ggaaaaacag   1560
caatacaagg agaggagaag gcagttgtta ctggaaaggg aaccactcct acaggcttgt   1620
gacataatgc gccaacatct ggctgtatat ggcataaatg taaaggatcg tggaaataca   1680
tcaacatggg aactacttga ccgcaaagaa gaaacctag                          1719

SEQ ID NO: 23          moltype = DNA  length = 549
FEATURE                Location/Qualifiers
source                 1..549
                       mol_type = other DNA
                       organism = Xenopus tropicalis
SEQUENCE: 23
atgaggcatc tcctcctcct ctctatcacc ttcctggtat acacgctaga ctctgctaaa     60
gcctatggag caacggagac cctgtgcggt ggggagctgg tggacaccct gcagtttgtt    120
tgtgagacaa ggggcttcta tttcagcagg aataatggcc gctccaaccg cagggctaac    180
aggggggattg tggaagaatg ttgcttccgg agctgtgatt tggaactgtt ggaaacgtac    240
tgcgcaaagc cagctaagaa cgagagggat gtctccactg caccctccac agcaatacca    300
ccactgaaca agcaggacct gtaccacaaa catcaccaca aaagagctc caagtatgac    360
atttggcaga ggaagtctat ccatcggctg cggagaggag tccctgccat tgtacgtgct    420
aggcagtatc gattgctaat gcagcaggct gaagaatcag agcaggcact atcacatcgg    480
ccccttacca ccttaccccat aacgcggcct ctccatctgc aacaaacctc agaaccttcc    540
ctcaattga                                                            549

SEQ ID NO: 24          moltype = DNA  length = 1122
FEATURE                Location/Qualifiers
source                 1..1122
                       mol_type = other DNA
                       organism = Gallus gallus
SEQUENCE: 24
atggccacct cggcgagctc ccacctgagc aaagccatca agcacatgta catgaagctg     60
ccgcagggtg agaaggtcca agccatgtac atctggatcg acgggactgg ggagcacctc    120
cgctcgaaaa cccgcactct ggaccacgaa cccaagagcc tggaagatct ccccgagtyg    180
aactttgatg gctccagcac cttccaagcc gaaggctcca acagcgacat gtacctgcga    240
cctgctgcca tgttccggga ccctttttcgc aaggatccca caaaattagt tctctgtgag    300
gtcttcaaat acaaccgcca gtctgcagac acaaatcttc ggcacacctg taggcggatt    360
atggatatgg tgtccaacca gcaccccctgg ttttgggatg agcaggagta caccttccag    420
ggaacagatg gtcatccgtt tggctggcct tccaattgct tccctggacc caaggtccg    480
tactactgcg gtgtaggagc tgacaaagcc tatggcagag acattgtgga ggcccactac    540
cgagcgtgcc tgtatgctgg tgtgaaaatt ggaggaacca acgcagaagt gatgccagcc    600
cagtgggagt tccaggtggg accgtgcgaa gggattgaa tggggggatca cctctggata    660
gcacgtttca tcctccaccg ggtgtgcgaa gactttggtg tcattgtgtc cttcgatccc    720
aaacccatcc ctgggaactg aacggtgct ggctgtcaca ccaacttcag caccaagaac    780
atgagggaag atgaggtct caagcacatc gaggaggcca tcgagaagct gagcaagcgc    840
caccagtacc acatccgtgc ctacgacccc aaaggagggc tggacaacgc ccggcgcctg    900
acgggcttcc acgagacgtc cagcatccac gagttctccg ccggcgtggc caaccgcgg    960
gccagcatcc gcatcccacg caacgtgggc catgagaaga aaggctactt cgaggaccgc   1020
gggccttcag ccaactgcga tccctacgcc gtgacggagg ccctggtccg tacgtgtctc   1080
ctcaacgaaa ccggggacga gccttttgag tacaagaact aa                      1122

SEQ ID NO: 25          moltype = DNA  length = 564
FEATURE                Location/Qualifiers
source                 1..564
                       mol_type = other DNA
                       organism = Gallus gallus
SEQUENCE: 25
atgtgtgctg ccaggcagat actgctgcta ctgctggcct tcctggccta tgcgttggat     60
tcagctgcgc cgtatggcac ggcggagacc tctgcggtg gggagctggt ggacacactg    120
cagttcgtct gtgggacag gggcttctac ttcagtagac cagtgggacg aaataacagg    180
aggatcaacc gtggccattgt ggaggagtgc tgctttcgga gctgtgacct ggctctgctg    240
gaaacctact gtgccaagtc cgtcaagtca gagcgtgacc tctccgccac ctccctcgcg    300
ggcctcccag ccctcaacaa ggagagcttc agaagccat ctcatgccaa gtactccaag    360
tacaacgtgt ggcagaagaa gagctcgcag cggctgcagc gggaggtgcc aggcatcctg    420
cgtgcccgtc ggtaccggtg gcaggcggag gggctgcaag cagctgagga agccaggcg    480
atgcatcgtc ccctcatctc cttgcccagt cagcggccc cagcgccgcg ggcatcccct    540
```

```
gaagcgaccg gcccccagga atga                                           564

SEQ ID NO: 26         moltype = AA  length = 179
FEATURE               Location/Qualifiers
source                1..179
                      mol_type = protein
                      organism = Bos taurus
SEQUENCE: 26
MGITAGKSVL VLLAFLAFAS CCYAAYRPSE TLCGGELVDT LQFVCGDRGF YFSRPSSRIN     60
RRSRGIVEEC CFRSCDLALL ETYCATPAKS ERDVSASTTV LPDDVTAYPV GKFFQYDIWK    120
QSTQRLRRGL PAFLRARRGR TLAKELEALR EAKSHRPLIA LPTQDPATHG GASSKASSD    179

SEQ ID NO: 27         moltype = AA  length = 161
FEATURE               Location/Qualifiers
source                1..161
                      mol_type = protein
                      organism = Danio rerio
SEQUENCE: 27
MSSGHFFQGH WCDVFKCTMR CLPSTHTLSL VLCVLALTPA TLEAGPETLC GAELVDTLQF     60
VCGDRGYFS KPTGYGPSSR RSHNRGIVDE CCFQSCELRR LEMYCAPVKT GKSPRSLRAQ    120
RHTDIPRTPK KPISGHSHSS CKEVHQKNSS RGNTGGRNYR M                       161

SEQ ID NO: 28         moltype = AA  length = 103
FEATURE               Location/Qualifiers
source                1..103
                      mol_type = protein
                      organism = Oncorhynchus mykiss
SEQUENCE: 28
MRRPCILAIQ PDTEFMPPEL DASNFHMGPE LCTKDSKELL LSGKKLLYGV VRHKTTITEE     60
QLKSISTKYH SMKEKCCAAE DQAACFTEEA PKLVAESAEL VKA                     103

SEQ ID NO: 29         moltype = AA  length = 371
FEATURE               Location/Qualifiers
source                1..371
                      mol_type = protein
                      organism = Oreochromis niloticus
SEQUENCE: 29
MATSASASLS KAVKQQYMEL PQGDKVQAMY IWIDGTGEGL RCKTRTLDSE PKSIEDLPEW     60
NFDGSSTYQS EGSNSDMYLI PSAMFRDPFR KDPNKLVLCE VLKYNRKPTE TNLRLTCKKV    120
MDMVADQHPW FGMEQEYTIL GTDGHPFGWP SNGFPGPQGP YYCGVGADKA YGRDVVEAHY    180
KACLYAGVQI CGTNAEVMPA QWEFQVGPCE GIDMGDHLWV ARFILHRVCE DFGVVASFDP    240
KPIPGNWNGA GCHTNFSTKE MREDGGLKAI EDSIEKLGKR HSYHIRAYDP KGGLDNARRL    300
TGRHETSNIN EFSAGVANRG ASIRIPRNVG QEKKGYFEDR RPSANCDPYS VTEALIRTCL    360
LNEEGDEPAD Y                                                        371

SEQ ID NO: 30         moltype = AA  length = 214
FEATURE               Location/Qualifiers
source                1..214
                      mol_type = protein
                      organism = Oncorhynchus mykiss
SEQUENCE: 30
METQKRHEYH SVCHTCRRTE NTRMKVKMMS SSNRVLVIAL ALTLYIVEVA SAETLCGGEL     60
VDALQFVCED RGFYFSRPTS RSNSRRSQNR GIVEECCFRS CDLNLLEQYC AKPAKSERDV    120
SATSLQIIPM VPTIKQDVPR KHVTVKYSKY EAWQRKAAQR LRRGVPAILR ARKFRRQAVK    180
IKAQEQAMFH RPLITLPSKL PPVLPPTDNY VSHN                               214

SEQ ID NO: 31         moltype = AA  length = 153
FEATURE               Location/Qualifiers
source                1..153
                      mol_type = protein
                      organism = Xenopus tropicalis
SEQUENCE: 31
MEKNNSLSTQ LFKCYFCDFL KLKMHKMSYI HLLYLALCFL TLTHSAAAGP ETLCGAELVD     60
TLQFVCGDRG FYFSKPTGYG SSNRRSHHRG IVDECCFQSC DFRRLEMYCA PAKPAKSARS    120
VRAQRHTDMP KAQKEVHLKN ASRGNTGSRG FRM                                153

SEQ ID NO: 32         moltype = AA  length = 373
FEATURE               Location/Qualifiers
source                1..373
                      mol_type = protein
                      organism = Xenopus tropicalis
SEQUENCE: 32
MATSASAQLS KAIKQMYLEL PQGDKVQAMY IWVDGTGEGL RCKTRTLDSE PKTIEDLPEW     60
NFDGSSTYQS EGSNSDMYLI PVAMFRDPFR RDPNKLVLCE VLKYNRKTAE TNLRHTCNQI    120
MDMMANEHPW FGMEQEYTLL GMDGHPFGWP SNGFPGPQGP YYCGVGADKA YGRDIVEAHY    180
RACLYAGVKI AGTNAEVMPA QWEFQIGPCE GIEMGDHLWI ARFILHRICE DPGIIVSFDP    240
KPITGNWNGA GCHTNFSTKS MREEGGLKDI EESIERLSKR HDYHIRMYDP RGGKDNARRL    300
TGFHETSSIH EFSAGVANRG ASIRIPRSVG QEKKGYFEDR RPSANCDPYA VTEAMIRTCL    360
LNETGDEPLE YKN                                                      373
```

```
SEQ ID NO: 33            moltype = AA   length = 572
FEATURE                  Location/Qualifiers
source                   1..572
                         mol_type = protein
                         organism = Xenopus tropicalis
SEQUENCE: 33
MNALMRRACC GALFPLSFRL AALSPMKGAS NFSCGNVCAS PAGCWAPPSG HDTGIKVYNS   60
LTRRKDPLIL ADPTVATWYS CGPTVYDHAH LGHACSYVRF DIIRRILLKV FGIDTVVVMV  120
VTDIDDKIIK RAKELNISPV ALARTYEQDF KQDMTALKVL PPTVYMRVTE NIPQIISFIE  180
HIIANGYAYA TSQGNVYFDV QSIGERYGKF NDSFSDTASE SASQDKRHIR DPALWKTSKP  240
EEPYWASPWG KGRPGWHIEC STIASSVFGK HLDIHTGGID LAFPHHENEI AQCEAYHQST  300
QWGNYFLHTG HLHLKGNEEK MSKSLRNYLT VKEFLKSFSP DQFRMFCLRS KYKSAVEYSN  360
GSMHDAVNTL HTISSFVDDA KAYMKGQLIC QPVQEALLWQ RLNETKVNVK AAFSDDFDTP  420
RAVDAVMDLI HHGNRQLKAV SKESNSPRSS VVYGAMISYI EQFLEILGIS LSQNQVAAED  480
RHSAVLFNVV EEMISFRSKV RNYALAADES PNAIGQEEKQ QYKERRRQLL LEREPLLQAC  540
DIMRQHLAVY GINVKDRGNT STWELLDRKE ET                                572

SEQ ID NO: 34            moltype = AA   length = 182
FEATURE                  Location/Qualifiers
source                   1..182
                         mol_type = protein
                         organism = Xenopus tropicalis
SEQUENCE: 34
MRHLLLLSIT FLVYTLDSAK AYGATETLCG GELVDTLQFV CGDRGFYFSR NNGRSNRRAN   60
RGIVEECCFR SCDLELLETY CAKPAKNERD VSTAPSTAIP PLNKQDLYHK HHHTKSSKYD  120
IWQRKSIHRL RRGVPAIVRA RQYRLLMQQA EESEQALSHR PLTTLPITRP LHLQQTSEPS  180
LN                                                                 182

SEQ ID NO: 35            moltype = AA   length = 373
FEATURE                  Location/Qualifiers
source                   1..373
                         mol_type = protein
                         organism = Gallus gallus
SEQUENCE: 35
MATSASSHLS KAIKHMYMKL PQGEKVQAMY IWIDGTGEHL RCKTRTLDHE PKSLEDLPEW   60
NFDGSSTFQA EGSNSDMYLR PAAMFRDPFR KDPNKLVLCE VFKYNRQSAD TNLRHTCRRI  120
MDMVSNQHPW FGMEQEYTLL GTDGHPFGWP SNCFPGPQGP YYCGVGADKA YGRDIVEAHY  180
RACLYAGVKI GGTNAEVMPA QWEFQVGPCE GIEMGDHLWI ARFILHRVCE DFGVIVSFDP  240
KPIPGNWNGA GCHTNFSTKN MREDGGLKHI EEAIEKLSKR HQYHIRAYDP KGGLDNARRL  300
TGFHETSSIH EFSAGVANRG ASIRIPRNVG HEKKGYFEDR GPSANCDPYA VTEALVRTCL  360
LNETGDEPFE YKN                                                     373

SEQ ID NO: 36            moltype = AA   length = 615
FEATURE                  Location/Qualifiers
source                   1..615
                         mol_type = protein
                         organism = Gallus gallus
SEQUENCE: 36
MKWVTLISFI FLFSSATSRN LQRFARDAEH KSEIAHRYND LKEETFKAVA MITFAQYLQR   60
CSYEGLSKLV KDVVDLAQKC VANEDAPECS KPLPSIILDE ICQVEKLRDS YGAMADCCSK  120
ADPERNECFL SFKVSQPDFV QPYQRPASDV ICQEYQDNRV SFLGHFIYSV ARRHPFLYAP  180
AILSFAVDFE HALQSCCKES DVGACLDTKE IVMREKAKGV SVKQQYFCGI LKQFGDRVFQ  240
ARQLIYLSQK YPKAPFSEVS KFVHDSIGVH KECCEGDMVE CMDDMARMMS NLCSQQDVFS  300
GKIKDCCEKP IVERSQCIME AEFDEKPADL PSLVEKYIED KEVCKSFEAG HDAFMAEFVY  360
EYSRRHPEFS IQLIMRIAKG YESLLEKCCK TDNPAECYAN AQEQLNQHIK ETQDVVKTNC  420
DLLHDHGEAD FLKSILIRYT KKMPQVPTDL LLETGKKMTT IGTKCCQLPE DRRMACSEGY  480
LSIVIHDTCR KQETTPINDN VSQCCSSSYA NRRPCFTAMG VDTKYVPPPF NPDMFSFDEK  540
LCSAPAEERE VGQMKLLINL IKRKPQMTEE QIKTIADGFT AMVDKCCKQS DINTCFGEEG  600
ANLIVQSRAT LGIGA                                                   615

SEQ ID NO: 37            moltype = AA   length = 153
FEATURE                  Location/Qualifiers
source                   1..153
                         mol_type = protein
                         organism = Gallus gallus
SEQUENCE: 37
MEKINSLSTQ LVKCCFCDFL KVKMHTVSYI HFFYLGLCLL TLTSSAAAGP ETLCGAELVD   60
ALQFVCGDRG FYFSKPTGYG SSSRRLHHKG IVDECCFQSC DLRRLEMYCA PIKPPKSARS  120
VRAQRHTDMP KAQKEVHLKN TSRGNTGNRN YRM                               153

SEQ ID NO: 38            moltype = AA   length = 187
FEATURE                  Location/Qualifiers
source                   1..187
                         mol_type = protein
                         organism = Gallus gallus
SEQUENCE: 38
MCAARQILLL LLAFLAYALD SAAAYGTAET LCGGELVDTL QFVCGDRGFY FSRPVGRNNR   60
RINRGIVEEC CFRSCDLALL ETYCAKSVKS ERDLSATSLA GLPALNKESF QKPSHAKYSK  120
```

```
YNVWQKKSSQ RLQREVPGIL RARRYRWQAE GLQAAEEARA MHRPLISLPS QRPPAPRASP  180
EATGPQE                                                            187

SEQ ID NO: 39           moltype = DNA  length = 3378
FEATURE                 Location/Qualifiers
source                  1..3378
                        mol_type = other DNA
                        organism = Bos taurus
SEQUENCE: 39
atgccgcgcg cgcccaggtg ccggccgtg cgcgcccttc tgcgggccag ctaccggcag    60
gtgctgcccc tggccgcctt cgtacggcgc ctgcggcccc agggccaccg gcttgtgcgg  120
cgcggggacc cggcggcctt ccgcgcgctg gtggctcagt gcttggtgtg cgtgccctgg  180
gacgcgcagc cgcccctgc cgcccgtcc ttccgcagg tgtcctgcct gaaggagctg    240
gtggccagag tcgtgcagag gctctgcgag cgcggcgcga ggaacgtgct ggcctttcgg  300
ttcacgctgc tggccggggc ccgcggcggg ccgcccgtgg ccttcacgac cagcgtacgc  360
agctacctgc ccaacacggt aaccgacacg ctgcgcggca cgggcgcctg ggggctgctg  420
ctgcaccgcg tgggcgacga cgtgctcacc cacctgctgt cgcgctgcgc gctctacctg  480
ctggtgcccc cgacctgcgc ctaccaggtg tgtgggcgc cgctctatga cctccgcgcc  540
gccgccgccg ccgctcgtcg gcccacgcgc caagtgggcg ggacccgggc gggcttcgga  600
ctcccgcgcc cggcctcgtc gaacggcgga cacggggagg ccgaaggact cctggaggcg  660
cgggcccagg gcgcgaggcg cgtcgcagt agccgcgggg acgactgcc tccagccaag  720
aggccaggcc gcggcctgga gccgggcgg gatctcgaag ggcaggtgc cgcagccgcc  780
ccccgcgtgg tgacacctac ccgagacgct gcggaagcca agtctcggaa gggcgacgtg  840
cccgggccct gccgcctctt ccggggcgg gagcggggtg tcggctccgc gtcctggcgg  900
ctgtcaccct cggagggcga gccgggtgcc ggagcttgcg ctgagaccaa gaggttcctt  960
tactgctccg gcgtggcga acagctgcgc cgctccttcc tgctctgctc cctgcctcc  1020
agcctggccg gggcgcggac actcgtgaa accatctttc tggactcgaa gcccgggccg  1080
ccaggggctc ccgccggcc gcgccgcctg ccgcgcgct actggcagat gcggcccctg  1140
ttccggaaac tgcttgggaa ccacgcgcgg agccctatg gcgcgctgct cagggcgcac  1200
tgcccgctgc cggcctctgc gcccggggcg gggcagacc atcagaagtg cctggtgtt  1260
gggggctgcc cctctgagag gccgccgct gccccgagg gcgaggcgaa ctcagggcgc  1320
ctggtccagc tgctccgcca gcacagcagc ccctggcagg tgtacgggct cctgcgggcc  1380
tgtcttcgcc gcctggtgcc cgccggcctc tgggctcc ggcacaacga gcggcgcttc  1440
ctgcggaacg tgaagaagct cctctccctg gggaagacg gcaggctctc gcagcaggag  1500
ctcacgtgga agatgaaggt gcaggactgc gcctggctgc gcgagcc aggggctcgc  1560
tgcgtgcccg ccgcggagca ccgccagcgc gaggccgtcc tgggtcgctt cctgcactgg  1620
ctgatgggcg cctacgtggt ggagctgctc aggagcttct tctacgtcac agagaccacg  1680
ttccagaaga accggctctt cttcttccgg aagcgcatct ggagccagct gcagcgcctg  1740
ggcgtcagac aacacttaga ccgtgtgcgg cttcagaac tgtcagaagc agaggtcagg  1800
cagcaccagg aggccaggcc ggctctgctg acatccagg tccgtttcgt cccaagccc  1860
ggcgggctgc ggcccatcgt gaacgtgggc tgtgttgagg gcgcccggc accgccaga  1920
gacaagaagg tgcagcatct cagctcacgg gtcaagacg tgttcgcggt gctgaactac  1980
gagcgagctc gcgggcctgg cctcctgggg gcctcggtgc tggacatcca ggggcctggc  2040
gggccttcgt gctgcccctg agggccgggg gcccagcccc ccgctctac  2100
ttcgtcaagg tggacgtggt ggggcctac gatgccctcc cccaggataa gctggcagag  2160
gtgatcgcta acgtgctgca gccgcaggag aatacgtact gcgtgcgcca ctgcgccatg  2220
gtccggactg cgcgcgggcg catgccgaag tccttcaaga gacacgtgtc caccttctcg  2280
gacttccagc cgtacctgag gcagctcgtg gagcatctgc aggcgatggg ctccctgagg  2340
gacgccgtgg tcatcgagca gagctgctcc ctgaacgagc ctggcagcag cctcttcaac  2400
ctcttcctgc acctggtccg cagccacgtc atcaggatcg ggggcaggtc ctacatccag  2460
tgtcagggga tccccaggg ctccatcctg tccacctgc tctgcagctt ctgctatgag  2520
gacatggaga acaagctctt ccctggagtc cagcaggacg gggtgcttct cgcgcctggtg  2580
gacgacttcc tgctggtcac cccacacctg acgcgggcca gagacttcct caggacgctg  2640
gtgcgcggtg tgcctgagta tggctgccag gtgaacctgc ggaagacggt ggtgaacttc  2700
cccgtggagc ccgggggccct gggcggccgg gcgccccctg agctgccggc ccactgcttg  2760
ttccctggt gcggcctgct gctggatacc cgcaccctgg aggtgcatgg cgaccactcc  2820
agttatgccc ggacgtccat cagagcgagt ctcaccttca ccagggcatt caagcccggg  2880
aggaacatgc gtcgcaagct gttggcggtc ttgcagctca agtgccatgg gctcttcctg  2940
gacctgcagg tgaacagtct gcagacggtc ttcacaaacg ttacaagat attcctgctg  3000
caggcctaca ggttccacgc ctgcgtgctg cagctgccct tcagcagcc ggtcaggagc  3060
agccccgcgt tctttctcca ggtcatcgcc gacaccgcat cccgcggcta cgccctcctg  3120
aaagccagga acgcaggggc gtcactgggg ccaggggcg ccgccggcct gttcccgtct  3180
gaagctgcgc agtggctgtg tctccacgcc ttcctgctca gctggctcg ccaccgtgtc  3240
acctacagcc gcctgctggg gcccctccgg acagcccgag cacggctgca ccggcagctc  3300
ccggggccca cacgggccgc cctggaggcg gcggccgacc ccgccctgac cgcagacttc  3360
aagaccatct tggactga                                              3378

SEQ ID NO: 40           moltype = DNA  length = 3396
FEATURE                 Location/Qualifiers
source                  1..3396
                        mol_type = other DNA
                        organism = Sus scrofa
SEQUENCE: 40
atgccgcgcg cgccccggtg ccggccgtg cgctccctgc tccgggaccg ctacaggcag   60
gtgctgcccc tggccacctt cgtgcggcgc ctgggccctg agggccgcg gcttgttcgg  120
cgcggggacc cggcggccta ccgcgcgctg gtggcgcagt gctggtgtg cgtgccctgg  180
gacgcgcagc cgcctcctgc ctcccgtcc ttccgcagg tgtcctgcct gaaggagctg  240
gtggccaggg tcgtgcagag gctctgcgag cgcggcgcga ggaacgtgct ggcctttggc  300
ttcgcgctgc tggacggggc tcgcggcggg ccgcccgtgg ccttcacgac cagcgtcgc  360
```

```
agctacctgc caacaccgt gaccgacaca ctgcgcggga gcggcgcgtg ggggctgctg    420
ctgcgccgcg tgggcgacga cgtgctcacc cacctgttgg cgcgctgcgc gctgtacctg    480
ctggtgcccc cgagttgcgc ctaccaggtg tgcgggccgc cactctatga cctctacacc    540
gcagcggagg ctcggcccat gcgacacaag ggccagaccc cgactggcct cggactcacg    600
cgcccgtttt gcaatgggga agccgggcga ccccaggagc agaggcgca aggtgtgagg    660
cgacgtcggg gcagagcggg gggacatcca cttccagcca agaggcccag gcacgtcccg    720
gagcctgaac agggtcccga agggcaggcg tcccgggccc accagggcag ggcgcctggg    780
ccgagcgaca gcgaccccc cgtgatgaca cctaccagag ccgctgcgaa agccaagtct    840
cgggagggtg aggcgcccgg aacccggcac ctttccctc aagcaggcgg tgcgcggggt    900
acctgcccc catcctggtg gcagccacac ctccaggca agcccagtcc tcatgtgtgc    960
gctgccgaga ccaagcgctt cctctactgc tcggggagca aggaagggct gcgccgctcg    1020
ttcctgctct gctccctgcc gcccagcctg cggggggccg ggaggctcgt ggaggtcatc    1080
tttctggcct caaagcccgg gcagccaggg gcgcgccgc tgcccgcacg ctactggcgg    1140
atgaggcccc tgttccggga gctgcttaag aaccacgcgc ggtgccccta caaggcgctt    1200
ctcagggcgc actgcccgtt gcgggctgcg gcgaccctct cggggtccgg cggtcaggtg    1260
tgcgaccaca aagtgggccc cctcgctcca gagcggctgg cagcggccgc cgaggggac    1320
tcggcctcga ggcgcctagt ccagctgctc cgccagcaca gcagcccctg gcaggtgtac    1380
cgcctcctgc gggcctgtct tcaccggctg tgcccccgg gcctctgggg ctccccgcac    1440
aacaagcggc gctttctgaa gaatgtgaag aagctcgtct ccctggggaa gcacgccagg    1500
ctctcgctgc aggagctgat gtggaagatg aaagtgcaag actgcatctg gctgcgccgg    1560
agcccggacg ctcgccatgt ccaggccgcc gagcaccgtc tgagagaggc cattctggcc    1620
aagttcctgc gctggttgat gggcacgtac gtggtcgacgt tgctcaggtc gtttttttat    1680
gtcacggaga ccacgtttca gaagaaccgg ctcttcttct tccggaagcg catctggagc    1740
cggctgcaga gcgcaggcat caggcaacac ttagatcgtg tgcggcttcg agaactgtcg    1800
gaagcagaga tcaggcgacg ccgggaggcc aggcccgctg tactgacctc caagctccgc    1860
ttcgtcccca aacccgacgg gctgcggccc atcgtgaaca tggcgaacgt cgtgcgagcc    1920
aggacaggcc ccggagacaa gaaggtccgg cgtctcacgg ggcaggtcaa gacgctgttt    1980
gctgtgctga actacgagcg ggcgcggcgc ccgcgcctcc tgggggcctc cgtgctgggc    2040
gtgggtgaca tccacagggc ctggcgggcc tttgtgctgc ccctgcgggc ccaggacccg    2100
gccccccgc tgtactttgt caaggtggac gtgacggggg cctacgacgc cctccctcag    2160
gacaggctgc tggaggtggt cgccaacgtg atccggcccc acgagagcac gtactgcgtg    2220
cgccagtgcg ccgtgctccg gaggaccgcc cgcgggcacg tgcgcaagtc cttccaaacc    2280
cacgtgtcca ccttcgcaga cctccagcct tacatgagac agtttgtggc acacctgcag    2340
gcaaccggcc cgctgaggga cgccgtggtc atcgagcaga gctgctctct gaacgaggcc    2400
ggcagccgtc tcctggagct tttcctgagc ctgctgcgaa accacgtcat ccggatcggg    2460
ggcaggtcct acgtccagtg tcaggggatc ccacagggct ccattctgtc cacgctgctc    2520
tgcagcctgt gctacgggga catggaaaac agactcttcc ccgggatcca gcgtgacggg    2580
gtgctcctgc gcttggtgga cgacttcctg ctggtgaccc ctcacctgac acgagccaaa    2640
gccttttctca ggaccctggt ccgcggccgtg ccggagtacg gctgcctggc caacttgcgg    2700
aagacggccg tgaacttccc tgtgggaggac ggcgcccggg gcgcccggc cccactgcag    2760
ctgccggcac actgcctgtt cccctggtgc gggctgctgc tggacacccg cacgctggag    2820
gtgcactgcg actatgccag ttacgcccgg acctcgatca gagcgagtct caccttcaac    2880
cagggcttca gcccggggag gaacatgcgc cgcaagctct tggccgtctt gcggctaaag    2940
tgccacggga tccttctgga cctgcaggtg aacagtcttc cgacggtgct cgccaacgtt    3000
tacaagatct tcctgctgca ggcctacagg ttccacgcgt gtgtgctgca gctgcccttc    3060
cgtcagccgc ttgcgaggaa cccctcattt ttcctccggg ttgtctccga caccgcgtcc    3120
tgctgctact cgctcctgaa agccagaaac gcagggatgt ccctgggagc caggggcgcc    3180
tccggcccgt ttccctctga agccgcagag tggctctgcc tccacgcctt cctgctcaag    3240
ctggttcgtc accgcgttac ctacagctgt cttctggggc cgctccgggc agccagagag    3300
cgattgtgcc agcggctccc tggggccaca ctggccgccc tcgaggccgc cgccgaccca    3360
gccctgacta cagacttccg gaccatcctg gactga                             3396

SEQ ID NO: 41          moltype = DNA   length = 3297
FEATURE                Location/Qualifiers
source                 1..3297
                       mol_type = other DNA
                       organism = Danio rerio
SEQUENCE: 41
atgtctggac agtactcgac agatggcgga tttaggccgg ttttggagat tctgcgctcc    60
ttatatccgg tcgtgcagac tttggaggag ttcaccgacg gactgcaatt ccctgacggc    120
cgaaagccgg ttctgctgga ggaaacagac ggcgcgcgct ttaaaaagct cctcagtgga    180
cttattgtat gtgcgtacac gccgccgcag ctgcgcgtcc ccgcccagct cagcaccctg    240
ccggaggtct tggcgttcac tctgaaccac attaaacgta agaaactgag gaacgtcctg    300
ggcttcggtt atcaatgcag cgacgtgacg accagttcgg atcccttccg tttccatggc    360
gacgtttcgc agacggctgc ctccatcagc accagcgagg tctggaagcg tatcaaccag    420
cgtctgggca cggaggtaac gcggtacctg ctgcaggact gtgccgtttt caccaccgtc    480
ccgccatcgt gtgttctgca ggtgtgcgga gaacctgttt acgacttgct gatgccgcgc    540
tcatggtctg gcttttttcct cagtaactca gataatgaac gaatcagcgg cgcgatgcgg    600
aaattccctg ctgtccagaa gacagtcgca atttccaaaa agagaacaag agataacgaa    660
aaatatattt cggtaaagcg gcggagggta aaggaaactg tgaataataa taacggaaat    720
tacagatctc tgtgtttttgc aatttctaaa aagagagcga tagataatga agaaaatatt    780
tcgttaaagc gacggaggat ggaggaaact gaccaagtag cgaaaatacg taatgaaaat    840
cacgaatctc agagtttcgc aatttctaaa agagagcga gagataatga agaaaatatt    900
tcgttaaagc gacaaaggat ggaggaaatt gaccaagtag cgaaaatacg taacgaaaat    960
catggatctc agagttggaa accagcagat cagcgtcctc ctcgaccctc gcaatgttca    1020
atacgcgttc tgagcatgct ctacaatggg cggggcatga agaacttcct gctcaacagg    1080
aagttgaaag gagtgggcgg ggccaggcgc atgcaagggg aggatcttgt ccgcatgatt    1140
ttcctccaat cagaatccaa cgacagcaaa ccgaaaaaac ttcccaaacg attcttcgca    1200
atggtgccgc tattcagtcg gctgttgcgg cagcacagga agtgtccgta tcggctgttc    1260
```

```
ctgcagagga agtgtgcagg aaatccagac gtgaaggata tggagtctct gctgaagtca   1320
cactcgtctc catatagagt ttatctgttc gtcagggagt gtctgcgcca tattattccc   1380
cacgagctct ggggctgcca ggaaaaccag ctccacttcc tgtctaatgt aaagaacttc   1440
ctgcttctgg ggaagtttga gcgcctcacg ctggtccagc tgatgtggag gatgaaggtt   1500
caggcctgcc attggctggg gcccaagaaa cgtcagtgtg cgagcgagca ccgctaccgt   1560
gagtggatgt tgggtcagtg tatgggctgg atgttgagtg gttttgtggt cggtctggtc   1620
agagctcagt tctacatcac ggagagtatg gccacaaac acacactgcg cttctacagg    1680
ggagatgtct ggagcagact gcaggaccag gccttcaggg ctcatctgtg taagggccag   1740
tggaggcccc tgtctccatc ccaggcgctg aaggtccca atagtgcagt gacatcccgc    1800
atccgcttta ttcccaaaac cagcagcatg aggcccatca cacgcctcag cggcagcaga   1860
gacacactgc agtattttca gagctgtgtg cgtgtgctgc agaatgtgtt gagtgtgtgt   1920
gtgcgtgagg ccccggggcc catgggctcc accgtctggg gttggcagga cattcacaga   1980
cgcctgcaag acttcagccc tcagcagaag agctcgccac gaccgctcta cttcgtcaag   2040
gtggatgtga gcggagcgta tgacagtctc ccgcacctga agtggtgga ggtgctgaag    2100
gaagtgttgg gtccgtttgc agagcagagc ttcttcctgc gtcagtacag cagtgtgtgg   2160
agcgacccga cccgcggcct gcgcaaacgc ttctgcacca aagctgagat gtcagagccg   2220
ctcaacatga agggggtttgt tgtggatgaa caggtcagcg ggcgcctgca tgacgctata   2280
ttagtgggag ggcactcgtc tgaggtcaga ggtggagcag tcttccagtt cttccagaag   2340
atgctctgca gttacgtcat ccattacgac cagcagatgt tccggcaggt gtgtgggatc   2400
ccgcagggct cttcagtgtc ttctctgctg tgtaatctgt gttacggaca catggagaaa   2460
gccctgctga aggacatcgc taaaggaggg tgtctgatga ggctgattga tgattttttg   2520
ctcattactc ctcatctgag taaagccaca gagttcctga ccatccttct gtctggagtt   2580
ccagattacg gttgccagat taaccctcag aaggtggcgg tgaacttccc cgtgtgtgtg   2640
tcctgggtaa actcgggcgt ctctgtgctg ccgtccagct gcctgttccc ctggtgcggc   2700
ttgatgatac acacacacac gctggacgtc tataaagact actcacgta tgacggccta    2760
tcactgcgct acagcctgac tcttggctcc gcccactctc catctacagt catgaagaag   2820
ctgctgtcgg tgctcagcat caaaagcacg gacatcttct tagacctcag gctgaactct   2880
gtggaggccg tttacaggag tctgtataag ctgattctgc tgcaggcgct cagggtttcat  2940
gcgtgcgtga ggagtctgcc gttgggtcag agtgtgaaca gaaacccgtc gttcttcctg   3000
aagatgatct ggagaatgac tcgagtcacc aataaactcc tcacacacat taacaaaggt   3060
ctgcctgtgt gttctgtgga cagtggtggt gttctgcagt ctgaggcggt tcagcttta    3120
ttctgtttgg ccttcgagac gcttttcaga cggtttcgct cggttaccca ctgcctgatc   3180
cctgcactgc acaaacggaa gcgtgctctt cagcgtgagc tctgcgggat cactctggct   3240
cggggtccgtc aagcttcctc tcccagaatc ccctggatt tcagcatgcg ggtgtaa      3297

SEQ ID NO: 42           moltype = DNA   length = 3366
FEATURE                 Location/Qualifiers
source                  1..3366
                        mol_type = other DNA
                        organism = Oreochromis niloticus
SEQUENCE: 42
atgacgcggg cccttaaaag gtcaaacata gctaaatccc agtgtaaagt agctaacctc    60
cgtccaagtg ctccgaacac agtcggtatg tctgcgactg atatgtccgg tgtgctgagt   120
atccttcggt tactgtaccg gcacacgcag acactggagg agttttcgga cagcatcgtg   180
ttcagagaag gacagaaagc agctctcatt gagcagacag atacaaaccg attcaaatct   240
ttcgttagga gtgttttgt gtgctttgac aaggagctac agcaggtagc gagctgtaaa    300
cagatctgca gtctgcctga actactggcg tttgttctca aactctaaa aagaaaaaga   360
aaaaggaatg tcttggcaca tggctataac tttcagaccc tggctcagga ggatcgggat   420
gcagacttcc tcaaattcca aggcgacgta acacagagtg ctgcctacat ccacggcagt   480
gacctgtgga aaaagtcac aatgcgtctg ggcacagaca tcacgcaata tcttctggag    540
agtctgctcg tgtttgtggc agttcctcct tcgtgtgttt tccaggtgtg cggccctcgt   600
gtctatgaca gggtgtccat gaccatggcc tcgagtgggt tttttctcca gcctggagtc   660
aggaaacata atcgtaccaa gattgagagc tgtcgagggt cagtgagttt gaaacagaaa   720
cgcacagttt tgaatcctgc tgcaagcaag aagatgaaaa gaaggaataa aggagggaaa   780
aaagggaaaa gaaacgggaa aactggtgaa gaggagggg tggcggtttg ttcaagaaag   840
aggcggcgag tagcgtctat agaacatcaa caggcgatcc aaccagttgg ctctgaaaag   900
gaaggacagg ttgtgcctgt ggaatcagca ccgcctgcag ctttcaaaca gcctgttgaa   960
atgccaacat tggagggcgg tcctagttgg agatcaggga ttttccccc tttaccaccc    1020
tcgcaatgtt ttatccgcac cctgggattc ctgtatgggg gcagggcat gcgtggcttt    1080
cttcttaaca ggaggaagaa gactgctcat ggatccagaa ggcttcaagg acaagatctg   1140
gtaagaatag tcttcttcga gggactagcg tatttgaatg gagtagagag gaagcctaaa   1200
aaactccccc agaggttctt tggcatgtcc ccctgtttta ggcagctctt acaacaacac   1260
aggagctgtt cctacaccaa aatactacag aggttatgtc catcaataga ggagagcaat   1320
gcaggacagg gagaactaaa ctcactctta cctcagcact gtgcaccgca cagggtttca   1380
ctgtttgtcc gggaatgcct ctcttctgtg atcccgcaag aactgtgggg ctctgatcaa   1440
aaccggctgc atttctttgc cagggtcagg acttctttgc gaagtggcaa gtttgagagg   1500
ctctcactgg ctgaactgat gtggaagata aaggtgaatg actgtgattg gttgaagagg   1560
agtaaaacag gctgttttcc accggaggag cttgcgtatc ggacacaggt cctgggtcag   1620
ttcttggctt ggcttctgga tggatatgtt acaggccttg tgagagcctg tttctatgca   1680
acagagagta ttgggcaaaa aaacgccatc aggttctaca ggcaggaagt ctgggccaaa   1740
ctgcaagact tggccttcag aggtcaacctt tccaaaggcc agatggaaga gctgactcca   1800
gctcaggtgg catccctgcc caaaggcacc gtcatctccc gccttcgctt tattcccaag   1860
actgatggca tgaggcccat cacacagagt ataggagcag atgccaaaac aaggctctac   1920
cgaggccgtg tcagggactt gctgatatgt cgcggcgtc gtgtcgctgc cactccatca   1980
ctgctgggct ccacagtgtg gggggatgact gacatcccaca aggttttgtg ctcttttggca  2040
ccagcgcaga aggaaaaacc acaacccctc tattttgtta aggtggacgt gagtggagcc   2100
tatgagagtt tgccgcatga caaactcata gaggtgattg gccaagccct gtcacctgtc   2160
cacgatgaac tctttaccat ccgccgctat gccaagatct gggcggactc ccacgaaggc   2220
ctgaaaaagg ccttttgtcag acaggcagat ttcctggagg ataacatggg atccaccaac  2280
```

```
atgaagggct tttttgacgtc actgcagaga aaaggcaaag ttcatcacgc catcctggtt    2340
gagcagcact tttgctcaga tcttcatggc agagaggcat tgcagttctt tacccaaatg    2400
ctaactggca gtgttgttca gtatgggaaa aagacgtacc gtcagtgccg ggggattcct    2460
cagggatcgg ttgtgtctag tctgctctgc tgcctttgct acggccacat ggagaatctc    2520
ctgtttaaag atattcctgg acacaaaggg tgtttgatga gactggtgga tgacttcctt    2580
ctgatcacac cagaccaaca tgaagcacaa gcttttctca agatcttgct ggccggagtg    2640
ccacagtatg gtctggcggt caacccgcag aaggtggttt tgaactttca ggtatcggga    2700
agcgtggcct cctgtcccga cattcgcatc ctgccccctc actgcctctt ccctggtgt     2760
ggactgctgc tggacaccca caagctggac gtctataaag actattccag ctatgctgga    2820
ctgtctctgc gctacagcct tactctgggt tcatcccact ctgcaggaca gcaatgaaa    2880
aggaaactaa tggctatcct caggctcaag tgtcatgccc tgttcttcga cttgaagact    2940
aattctcttg aagcggtcta caagaacatc tacaagctgg tgctgctgca tgcgtgcagg    3000
tttcatgtct gtgcccaaag cttgcccttt ggtcagaccg tttccaagaa ccccgtcttc    3060
tttctgcagt tgatatggga gatggccag tactgcaaca agctcatcag acgcagcaac    3120
aaaggactga ttttaggtga taaggcccag acggggatcg tgcagtacga agcagtggag    3180
ctgcttttct gtctgtgctt cttgctggtg ctgtcacaac atcgtcttct ctataaagat    3240
ctgctcgcac acttgcacaa gcgaaagcgc agtctggagc ggcgtctggg ggacctgagg    3300
ctggccaggg tgcggcaggc tgctagcccc aggactccag tcgacttctt ggccattcag    3360
acataa                                                              3366

SEQ ID NO: 43           moltype = DNA   length = 3549
FEATURE                 Location/Qualifiers
source                  1..3549
                        mol_type = other DNA
                        organism = Oncorhynchus mykiss
SEQUENCE: 43
atgcccagtg gcgatatgac acgtgtgctc ggcatactcg gctctctgta tcggcacgtc    60
gagaccctgg aggagtttgc agaccatatt gtattcagag agggacagag agcggtgctc    120
atcgaaccga cagatacaac gcgcttcata tcgtttgtcc ggggagtgtt ggtctgcacg    180
gataaaaccc tacaggacgt ccccagctgc aatcagatca gcaacccgtc ctgagctgttg   240
gcgttcgtgt tgaacaacat caagaggaaa aagaaaagga atgtcctggc gcacaggttac    300
ggttacacgt tccaggaccg cgacgcagac cagtttaagt tcatggcga gatcactcag    360
agtgccatgt acatccactg cagcgactta tggaagaggg cctgccagcg cctcggcacg    420
gacatctcca agtacctcct ggagagctgt tcttttgttcg tgacggtgcc gccgtcgtcc    480
gcgttccagg tgtgcggcgt gcctgtgtac gaccgcgttt ccatgtcaac gggtatctct    540
aggttccacc tgggatacaa acggaatggt actactagga acagcagagg gagaagtaag    600
gaggtcagaa atgggggatg ggaatttcag ggttctgctg ggagaaatag gagaaaggat    660
ggaggtagag acactgggga aaggaaggga gacgaggtca gtttgggagg gaagaggaag    720
agggagaggg aggaggtgga aggagatgtg tgtttgcctg gaaaaaggag atgcactcaa    780
agagaagctc ccacagtctc cagtgggact agccgatcgta agcacagaac actgaaaaca    840
aatgggttca agagaccagt ggaggtcatt tctctcacca agggacccac acagagccta    900
caggttttca atggttctag caatgtggaa caggtgtcag cagaaatgga acgtctcagg    960
aagccagtgg agaaactggc tggacccgga agaccattgg aggctgtgat ggtcaccata    1020
gcacccgctg agagctctaa acaggtctcc aacggcacag gtaatatcga gcagatgtca    1080
atgaaaacag gacatagaag gccagcggct gtagtcccaa gaccagtaga agaacagtct    1140
ggacctgtat cggccaccgt ccatgtagag ggggccccta gttggagaac agggtcgttc    1200
ccaccgcttc cccactccca gtgtttcatc cgcacccttg gtgctctca cggagggcgg    1260
ggcatgcgcc gcttcctact aaacaggaag aggaaaagta gggacgaggg gcccaggcgt    1320
ctgcaggggc gagacttagt gagactggtc ttctttgaag gcgtgcccta tctgaacgga    1380
acagaaagga agcctgagag acttcccaga agattttttca ccttggtgcc tctgttttgt    1440
cagttgttac gtcgacacag gaggtgtccc tattctaaga tactgcagag ggtttgttca    1500
gcagtgggac agggggatat ggcctccctc ctgcccagc acagtgcacc tcaccgggtg    1560
tacctctttg tcagagagtg cctcaacgcg tggtcccct cggagttctg ggggtcggac    1620
cataaccgat tcaaattcct gtccgcagtc aggaacttcc tgtccatggg caagtttgag    1680
aggatgtcat tggctgagct gatgtggaag atgaaggtga atgactgtga ttggctgaag    1740
atcagcaaga caggccgctg cccgcccagt gagctgtcgt atcggacgcg ggtgctaggc    1800
cagctcctgg cttggctgct ggatggctat tgctaggcc tggtgagagc tatgttctac    1860
gtcacagaga gcatgggaca gaagaacgca ctgcgcttct acagatacca ggtctgggcc    1920
aagctgcaga agctggctct cagtggtcac ctctctaaag gtcagatgtc agagttgacc    1980
ctggcccagg tgacgtcgct cccccaaacc actgtccct cccgcctccg cttcatcccc    2040
aagaccgaag ggatgagacc catcacacgt gtcatagggg ctgacgccaa acaaggttg    2100
ttccagaccc gtgtgaagga gctgttagat gtgctaggtg tctgtgtacg gtcctctccc    2160
tctctcctgg gctctacagt gtgggggttg accgacatcc acagagtcct ctcttccatc    2220
accccctgct cagaaagacaa accacagcgg ctctactttg tcaaggtgga tgtgagtggg    2280
gcctatgaca gtctacccca cactcagctc ttggaggtga ttggtcaggt cctgtcacat    2340
gtgcagcaag agctttttctc ggtgcgacgc tatgccaagg tgtgggccga cacccacgag    2400
ggcctcaaga gacctttgt cagacaggca gacttcacgg aagacactgt gtcgtccacc    2460
aacatgaaag gctttgtgat gtcactgcag agagaggca aagttcacga tgccatactg    2520
gtgggacagc atttctccac agatattcat ggcaaagacg tcttggagtt cttcacccag    2580
atgctctcta gctgtgttgt ccagtttggg aagaaatcgt tccgtcagtg tcaggggatt    2640
cctcagggtt ccgcggtgtc gtctctgctg tgctgcctct gttacggcca catggagaac    2700
cttctgtttc ctaacgtcag tcggcgagga gggtgtctga tgagactggt tgacgatttc    2760
ctcctcatca ctcctgacct gagccaggca cagaccttcc tcaagaccct gatggcgggg    2820
gtaccacggt acgggtgtg ggtgaaccce cagaaggtgg tgttaactt ccctttggtg    2880
gagtgggggt cctgtcctgc tggggtacgc ctgctgcctt tacactgtct gttccctgg    2940
tgtggactat tgctgaatac acacaccctg acgtccaca caactacgc cagctacgct    3000
ggcctatccc tgcgctacag cctgacgcta ggctccgccc actgcgcggg gcagcaaatg    3060
aagaggaagc tcatgtccat ccttagattc aagtgccacg ccctcttcct ggacctcaaa    3120
accaactccc tggaggctgt ctatagcaac gtctacaagt tagtgttgct gcaggcgttc    3180
```

```
aggttccatg cctgtgcaca gagtttgccg tttggtcaga aagtgggcgg aaaccactcg 3240
tacttcctca atctgatctg ggacttggcg gagtacacca accatctagt cagactctgc 3300
aacaaaggtg tgtctctagg ctgtaaggct ttaacaggta gccttcagta tgaggcagta 3360
gaactgatat actgtctggc cttcctgttg gttctgtccc gtcatcgccc cctctactac 3420
catctcctcg ctccgctacg cacacgtaag aggaagctgg aggggaagct ggagggtttg 3480
agattggccc gaatcagaca ggctgccaca cccaaaatgc ctgaagactt caaggccatc 3540
caggcctag                                                      3549

SEQ ID NO: 44          moltype = DNA   length = 3645
FEATURE                Location/Qualifiers
source                 1..3645
                       mol_type = other DNA
                       organism = Xenopus tropicalis
SEQUENCE: 44
atgactctgt gtaccggagg agctgaacta ctgagcattt tgcacagcct ttatggccag 60
gtccttggga ttgtggaata tatcgactca ctgcatgttc ccgcgcggcat taaggtgcct 120
gtgctgcgag agggagaccc ggagaagttc aagtcatttg ttgcggaact gatgctgtgc 180
attccaagag gaacaaagtc gcttccgtcc cctgtctcct ttcttcagct atcaactcag 240
agagaagtag tggcgcgagt aattcagcgg atttgtgaaa agaaaagaaa aaatgttctt 300
gcttttggtt atggcttagt tgatgaaaaa agctctctga atattcgatt gactccaaat 360
atttgcagtt attttcctaa ttccacaaca acaacaatca gcacaagtat tctttgggaa 420
actctgctta ctagagtagg tgatgatgtt atgatgtatt ggctggaaca atgctcagtt 480
tttgtatttg tgccacctag ttgttgttat caaatcagtg ggcagccaat ctacacttta 540
ccctatgata gtatgtgttc atttcgatct cagtcattta tgcatagcaa tgttttgttg 600
cagtacatta aaagaaatgc cttttcttg cggaaaaaat atctgaagcc aaaaaagtgg 660
tggaaaacgg tgttaaacag caaagtagaa aaacattcaa aacttctca aatgctaaca 720
tggcaaaata aaaagtccac atcagcattg cctatttgta gtgagtcatc tatgaaagtt 780
accacaaaaa tacattccaa aaggaagatg tgtactacag atatttgtga cattccaact 840
aagaaacgca gagtcaactt ggacaaagat gataaaatgg accacgtttc ctttacgtct 900
gcatgtctttt cttcctctc aaatgtgtgc cctgaagcta aagtacaagc aacggaatttt 960
attacctcaa gatatggaaa aaaaacaaaa attcaatgtc caaaatcgac ttcatactca 1020
gttgatggtg aatttaatgt aactcttcaa aataatgcta atacgtttat taccaatgct 1080
tctgtcccta caatacaaag caaaacttca ttttcaaata tttttattga aattggaaga 1140
acattgtatt caagtattag tttcaagaag ggcttctctg aaagttttat attaacagt 1200
ttagactgta ccccttctgg gagccaaaaa ttagtggaaa ccatatttct aaacaacttt 1260
ttaactgagc aaaattttga ccagccaaaa cgggatgaaa actttagatc taaacttccc 1320
aaacgttatt ggagaatgag aaaatatttc caagaattaa tacagaacca taagaatttc 1380
ccttatctgg tatatttgaa taaacactgc cctgttaggc cttcaatggc ttgttcacac 1440
aaactgccgt tgcagaaaaa gaataaatgt aaaatgaata aatcaatttg tgacttaagt 1500
aataccctcag ttatgaaaaa caaaattgta aatgatgaaa agccgctaaa acatgttaca 1560
gccgaagcaa ctttttttacc tcttcttaaa caacacagca gcagttggca agtgtacatg 1620
tttgttagag aatgtttaaa tagtttagtg cctgatttca tatggggctc cagtcacaac 1680
aagtgccgtt tccttagaaa tgtaaaatct tttctttttt tttctggcaa atttggcaag 1740
gtctctttat tagagcttat gtggaagatg aaagtagaag actgctcttg gattcgtcta 1800
cgaaaaagtg atcactttgt tcctgcttca gaacacttgc tacgagagag aatccttgcc 1860
aaatttatct tttggctaat ggacacctat gtcatacagt tgctgaaatc attttttttt 1920
gtcacggaaa ccatgtttca gaagaataga cttttgttct acagaaaaag aatttggaag 1980
aaacttcaaa atttaggtct aagaaaacat ctagagaagg tgaaattgcg tccattgtcc 2040
tgcgatgaac tagaaaagat gcaacaatgg aaaaacattc cactggtttc caggctcaga 2100
ttcataccaa aaacaaatgg actacgtcca atatctagag tatccagtac tttgggtagc 2160
caacaaagca aagaaaacca agagaagaag attcaacatt ttacctctcg ggttcgaaac 2220
ctttttagtg ttcttaacta tgaatggaat agaaattgca gcctaattgg ctcatctgtt 2280
tttggcatgg atgatatata caaacagtgg aaaaaatttg tgctagattt tgaaaaatcg 2340
agagctgaaa aaggcaaatt ttactttgtg aagacagatg ttaagggagc atatgataccc 2400
attccacatt caaagctcga tgaagtgatc ttaaaagtaa ttaatccaaa tgcaaatgaa 2460
gtatattgca tacgacgtta tgcctcagtt tcagtggatt caactggacg cattataaaa 2520
tcttcaaaaa gacatgtatc tgcattagca gatgttcttc caaatatgaa acagtttgtt 2580
tcaaatcaac aagaaaaaaa cttgacacgt aacacaattc tagtggaaca gagccttta 2640
ttgaatgaga gctctgtcaa acttcttgct gttttttcaac aaatgatcag atcccatatt 2700
ttaagaatag aagatcgata ttacatgcag tgctgtgaaa taccacaggg ttcaatgtta 2760
tctacaatcc tatgcagttt atgctatgga gacatgaaa ataaactgtt tggcggaata 2820
cagcaaaatg gggtactaat gcgattgatt gatgattttt tgtttgtaac acctcatctt 2880
aaccaggcaa aaacatttttt aaggactctg gcagaaggaa ttccccaata tgggtgctcc 2940
atcagccctc aaaaaacagt ggtaaacttt cctgttagtg acatcccagc atgctgtgga 3000
gtggaacaat accagttca ctgcttgttc cggtggtgtg gtcttttgct ggacactcag 3060
actttgatg tttactatga ttattcaagc tatgcctgta cctcaatccg atcaagtatg 3120
acattttgtc acagttctgc agcaggaaaa acatgaaac aaaaacttct aagagtcctt 3180
aaattgaagt gccacagtct ctttcttgat ttacaggtaa acagttaag gacagttttc 3240
atcaatactt ataagatatt cttacttcaa gcttacagat tccatgcttg tgttgttcag 3300
cttccatttg gccagcgtgt aatgaataat ccaccttttt tcttactgt gatttctgat 3360
atggcacctt gcttacac tactttaag tccaaaaaca aagatgtcac acgtgggtac 3420
aaggatgtga gctgccagtt taactttgaa gcagtccagt ggctcagtta tcaagctttt 3480
cttactaagc ttcgcaatca aaaatatta tacaaatgtc ttattgggcc actgcagaac 3540
tgtaaaatgc agttatctag aagactttcg cagtatacta ttgatcttct aaaagctgtc 3600
acagattctt cccttcacaa agacttttca tgtataatgg attag         3645

SEQ ID NO: 45          moltype = DNA   length = 4041
FEATURE                Location/Qualifiers
source                 1..4041
```

```
                    mol_type = other DNA
                    organism = Gallus gallus
SEQUENCE: 45
atggagcgcg gggctcagcc gggagtcggc gtgcggcggc tccgcaatgt agcgcgggag    60
gagcccttcg ccgcggtcct gggcgcgctg cggggcgct acgccgaggc cacgccgctg   120
gaggccttcg tccggcggct gcaggagggt ggcaccgggg aggtcgaggt gctgcgaggc   180
gacgacgctc agtgctaccg gaccttcgtg tcgcagtgcg tggtgtgcgt ccccgcggt   240
gctcgcgcca tccccggcc catctgcttc cagcagttat ccagtcagag cgaagtcatc   300
acaagaatcg ttcagaggct gtgtgaaaag aaaaagaaga acatccttgc gtatggatac   360
tccttgctgg atgagaacag ttgtcacttc agagttttgc catcttcgtg tatatacagc   420
tatctgtcca atactgtaac agaaacgatt cgcatcagtg gcctctggga gatactgctg   480
agtaggatag gggacgacgt gatgatgtac ctgctggagc actgtgcact cttcatgctg   540
gttcccccaa gtaactgtta ccaggtctgc gggcaaccaa tttatgaact tatttcgcgt   600
aacgtagggc catcccccagg gtttgttaga cgacggtact caaggtttaa acataatagc   660
ttgcttgact atgtgcgaaa aaggcttgtg tttcacaggc actatctttc caagtcacag   720
tggtggaagt gcaggccgag acgtcgaggt cgtgtctcca gcaggagaaa agaaggagc   780
cataggatac aaagcctaag gtctggttat cagccttctg caaagtgaa cttcaagca    840
ggtaggcaga tcagcactgt tactgcacgt ctggaaaaac agagctgctc cagttttatgt   900
ttgccagcta gagcaccatc tttaaaaagg aagcgtgatg gagaacaggt tgaaatcaca   960
gctaagagag tgaaagtaat ggagaaagag atagaggaac aggcttgtag tatcgttcct  1020
gatgtaaacc aaagtagctc ccagaggcat ggaacctcct ggcatgtagc accacgtgct  1080
gtaggtctta ttaaagaaca ttacatttct gaaagaagta acagtgaagt gtctggtcct  1140
tctgtagttc gcagatctca ccctgggaag aggcctgtgg cagacaaaag ctctttccca  1200
caaggagttc agggtaacaa acgcataaag accggtgcag aaaaacgagc agaatccaat  1260
agaagggca tagagatgta tataaaccca atccataaac ccaatagaag gggcatagag  1320
aggcgtataa atccaaccca caaacctgag ttgaattcgt tacaaactga accaatggaa  1380
ggtgcttctt caggggacag aaagcaggaa aatcccccag ctcatttggc aaagcagtta  1440
ccaaatacat tgtcgcgctc tacagtgtac tttgagaaga aatttcttct gtattccgc  1500
agttaccaag aatattttcc taaatcgttc atactgagcc gcctgcaggg ttgtcaggca  1560
ggtggaaggc ggcttataga aactatattc ttaagcaaa acccattaaa ggaacagcag  1620
aaccaaagcc taccacagca aaagtggcga aagaagaggt tgcccaaacg ctactgcaa  1680
atgagagaga tatttcagaa gctggtaaag aaccatgaga agtgcccctta tttagttttc  1740
ttgaggaaaa attgccctgt tttgctttct gaagcatgtt tgaaaaagac ggagctgacc  1800
ttgcaggcgg ctctgcctgg ggaagcaaag gttcacaagc acacagaaca tgggaaagag  1860
tccactgagg gtactgcacc gaacagcttc ctcgctcctc cctcagtgct agcgtgtggg  1920
cagccagaga gaggggaaca gcaccctgca gaggggagtg atccgctcct cagggagcgg  1980
ctcaggcagc acagcagcca ctggcaggtg tatggctttg tgagggagtg cctggagcgg  2040
gtgatccctg ctgagctgtg gggttcaagc cataacaat gccggttctt taaaaacgtg  2100
aaagcattca tttccatggg gaagtatgct aagctttcat tgcagcagct gatgtggaag  2160
atgagagtga atgactgcgt atggcttcgt ctggccaaag gtaatcactc tgttcctgcc  2220
tatgaacatt gttaccgtga agaaattctg cgaaaattcc tatactggct gatggattcc  2280
tatgttatcg agttgctcaa atcatttttc tatatcaccg agaccatgtt ccagaaaaac  2340
atgcttttct actaccgaaa gtttatctgg ggcaagttac agaacattgg aattagagac  2400
cattttgcca agtacatctc acgtgccttg tcttcagagg gatggaagt gatccgtcaa  2460
aaaaagtatt ttcctattgc atcaaggctc cggttcattc ctaaaatgaa tggttaaga   2520
cccgtagtaa gactaagccg tgttgttgaa ggacagaaac tcagcaagga aagcagaaa  2580
aagaagatac agcgctataa cactcagcta aaaaatctat ttagtgtttt aaactatgaa  2640
cgaactgtaa acaccagtat cattggctct tcagtattcg ggagagatga tatctacagg  2700
aagtggaagg agtttgttac aaaggttttt gaatcaggtg gtgaaatgcc tcatttctac  2760
tttgtaaagg gtgatgtatc cagagctttt gataccattc ctcacaagaa acttgtgaa   2820
gtgatatcac aggtcttgaa acctgagagc caaactgtct atggaataag gtggtatgca  2880
gtgattatga ttaccccaac tggaaaagcc aggaaactct ataagagaca tgtttctact  2940
ttcgaggatt ttattccaga catgaagcag tttgtgtcca agcttcaaga gagaacttca  3000
ttacgaaatg caatagtagt tgaacagtgc ttaacttta tgagaacag ttccaccctg    3060
tttactttct ttcttcaaat gttacataat aacatcctgg agattgggca caggtactat  3120
atacagtgct ctggaatccc acagggctcc attttgtcaa ccttactttg cagcttatgc  3180
tacggagaca tggaaaacaa attactctgt gggatccaga aggatggagt cctaatacgt  3240
cttattgatg acttttgct ggttacgcca catttaatgc aggcaagaac ttttctaagg   3300
actatagcag caggtattcc tgagtatgc ttttaataa actgccaagaa gactgtggtg    3360
aattttcctg ttgatgatat cccgggatgt tccaagttca aacatctgcc agattgtcgt  3420
ttgatctcat ggtgtggttt attattggat gtgcagacac ttgaggttta ttgtgattac  3480
tccagttatg cctttacttc tatcagatca agtctttcct tcaattcaag tagaatagct  3540
ggaaaaaaca tgaaatgcaa attgactgca gtcctcaaac tgaaatgcca tccttttactt  3600
cttgacttaa agatcaacag ccttcagaca gttctaatta acatctacaa gatattttta  3660
cttcaggctt acaggttcca tgcctgtgtt cttcagcttc cattcaacca gaaagttagg  3720
aataatcctg atttcttcct aaggatcatc tctgatactg cttcatgctg ctatttatc   3780
ctgaaagcta aaaatccagg agtttcttta ggtagcaaag atgcatctgg catgttccct  3840
tttgaggcag cagaatggct gtgctaccat gccttcattg tcaaactgtc caaccacaaa  3900
gttatttaca aatgcttact taagcccctt aaagtctata agatgcatct gtttgggaag  3960
atcccaaggg atactatgga actgctgaag acggtgacgg aaccatcgct ttgtcaagat  4020
ttcaaaacta tactggacta a                                             4041

SEQ ID NO: 46          moltype = DNA   length = 3804
FEATURE                Location/Qualifiers
source                 1..3804
                       mol_type = other DNA
                       organism = Meleagris gallopavo
SEQUENCE: 46
atgtctgggg ctcgggggct cgtctggtgc gacgagcgag cgtggctgtt atccagtcag    60
```

```
agcgaagtca tcacaagaat cgttcagaga ctatgtgaaa agaaaaagaa gaacatcctt    120
gcgtatggat actccttgct ggatgaaaac agttgtcact tcaggatttt gccatcttcg    180
tgcatataca gctatctgcc caatactgta acagaaacga ttcgcatcag tggcctctgg    240
gagatactgc tgagcaggat aggggacgat gtgatgatgt acctgctgga gcactgtgca    300
ctcttcatgc tggttccccc aagtaactgt taccaggtct gcgggcaacc aatttatgaa    360
cttatttcgc gtaacatagg gccgtcccca gggttcgtta gacgacgata ttcaaggttt    420
aaacataata acttgcttaa ctatgtgcga aaaagacttg tgtttcatag gcactatctt    480
tccaagtcac agtggtggaa gtgcgggccg agacgtcaag gtcgtgtctc cagcagaaga    540
aaaagaagga cccataggat acaaagccca aggtctggtt accagtcttc tgcaaaagtg    600
aactttcaag caggcatgcg gatcagcaca gttactgcac atctggaaaa acagaactgc    660
tccagtttat gtttgccagc tagaacacca tctttaaaaa ggaagcgtga tggagaacag    720
gttgaaacca cagctaagag agtgaaagta atggagagag aggaacaggc ttgtagtatc    780
gttcctgatg taaatcgaag tagctcccgg aggcatggag tttggcatgt agcaccacgt    840
gctgtaggtc ttattaaaga acgttacgtt tctgaaagaa gttacagtga gatgtctgat    900
ccttctgtag ttcacagatc tcaccctggg aagaggcctg tagcagacaa aagctctttt    960
ccaagaggag ttcagggtaa caaacacata aagaccggtg cagaaaaacg agcagaatcc   1020
aataaaaggg gcatagagat gtatataaac ccaatctgta aacccaatag aagggggtata   1080
gagaggcata taaatccaac ccataaacct gggttgaatt ctgtacaaac tgaaccaatg   1140
gaaagtgctt cttcggggga cagaaagcag gaaaatcccc cagctcattt ggcaaagcag   1200
ttaccaaata cattcttgcg ctctgcagtg tactttgaga gaaaatttct tctgtattcc   1260
cgtagttacc aagaatattt tcctaaatcg ttcatactga gccgcctgca gggttgtcag   1320
gcaggtggaa ggcagcttat agaaactata ttttaagcc aaaacccatt aaaggaaaag   1380
cagaaccaaa gcctaaaaca gcaaagtgg agaagaaga ggttgcccaa acgctactgg   1440
caaatgagag agatatttca gaagctgtta aaaaaccacg agaagtgccc ttatttagtt   1500
ttcttgagaa aaaattgccc tgttttgctt tctgaagcat gtttgaaaa aacggagctg   1560
accttgcacg cagctctgcc tggggaagca aaggttcaca agcacacaga acatggggaa   1620
gagaccactg agggtactgc accgaacagc ttctacactc ctcccctcaat gccattgtgt   1680
gggcagacag agagagagga gcagcacctt cagagggga gtgatccgct cctcaggag   1740
ctgctcaggc agcacagcag ccactggcag gtgtatggct ttgtgaggga gtgcctggag   1800
cgggtgattc ctgccgagct gtggggttca agccataaca aatgccggtt ctttaaaaac   1860
gtgaaagcat tcatttccat gggaagtat gctaagcttt cattgcagca gctgatgtg    1920
aagatgagag tgaatgactg cgtatggctt cgtctggcca aagtaatca ttctgttcct    1980
gcctatgaac attgttaccg tgaagaaatt ttggcaaaat tcctatactg gctgatggat   2040
tccatgtta tcgagttgct caaatcattt ttctatatca ccgagaccat gttccagaaa   2100
aacatgcttt tctactaccg aaagtttatc tggggcaagt tacagaacat tggaattaga   2160
aaccattttg ccaaagtaca tctacgtgct ttatcttcag aggagatgga agtgatccat   2220
caaaaaaagt attttcctat tgcatcaagg ctccggttca ttcctaaaat caatggttta   2280
agacccgtag taagactaag ccgtgttgtt gaaggacaga aactcagcaa ggaaagcaga   2340
gaaaagaaga tacagcgcta taacactcag ctaaaaaatc tatttagtgt gttaaattat   2400
gaacgaactg taaacaccag tatcattggc tcttcagtat tcgggagaga tgatatctac   2460
aggaagtgga aggagttttgt tacaaaggtt tttgaatcag gtggtgaaat gcctcatttc   2520
tactttgtga agggtgatgt gtccagagct tttgatacta ttcctcacaa gaaacttgtg   2580
gaagtgatct cacaggtctt gaaacctgag agccaaactg tatatggaat aaggtggtaa   2640
gctgtgatta tgattacccc aactggaaaa gccaggaagc tctataagag acacgtttct   2700
acttttgagg attttattcc agacatgaag cagtttgtgt ccaagcttca agagagaact   2760
tcattacgaa atgcaatagt agttgaacag tgcttaactt ttaatgagaa cagttccacc   2820
ctgttactt tctttcttca aatgttacat aataacatcc tggagattgg cacaggtac    2880
tatatacagt gctctggaat cccacagggc tccattttgt caaccttact ttgcagctta   2940
tgctatggag acatggaaaa caaattactt tgtggaatcc agaaggatgg aatcctaata   3000
cgtcttattg atgactttt gctggttaca ccacatttaa tgcaggcaaa aacttttcta   3060
aggactataag cagcaggtat tcctgagtat ggcttttaa taaatgccaa gaagacagtg   3120
gtgaattttc ctgttgatga tattccggga tgttctaagt tcaaacagct gccagattgt   3180
cgtttgatct catggtgcgg tttattactg gatatgcaga cacttgaggt ttattgtgat   3240
tactccagtt atgcctttac ttctatcaga tcaagtctt ccttcaattc aagtagaata   3300
gctggaaaaa acatgaaatg caaattgact gcagtcctca aactgaaatg ccatcctta   3360
tttcttgact aaagatcaa cagccttaaa acagttttaa ttaacatcta caagatattt   3420
ttacttcagg cttacagatt ccatgcctgt gttcttcagc ttccattcaa ccagaaagtt   3480
aggaataatc cttatttctt tgtaaggatc atctctgata ctgcttcatg ctgctatttt   3540
atcctgaaag ctaaaaatcc aggggtttgt ttaggttgca aagatgcatc tggcatgttc   3600
cctttgagg cagcagaatg gctctgctac catgctttca ttgtcaaact gtccaaccac   3660
aaagttattt acaaatgctt acttaagccc cttaaagtct ataagatgca tctgtttggg   3720
aagataccaa gggatactat ggtactgctg aagacagtga cggaaccatc tctttgtcaa   3780
gatttcaaaa ctatactgga ctaa                                          3804
```

SEQ ID NO: 47        moltype = DNA  length = 3468
FEATURE              Location/Qualifiers
source               1..3468
                     mol_type = other DNA
                     organism = Anas platyrhynchos
SEQUENCE: 47

```
atgcagaggc tgtgtgggaa aaagaagaag aacatcctca cgtatggata ctccttgctg     60
gatgaaaaca gttctcactt ccaaatcatg ccgctctcaa acgtgtacag ctacctgccc    120
aacaccgcaa cagaaaccat gcgtatcagt ggcctctggg aaacgctgct gagcaggata    180
ggggatgacg tgatgatgta tttattggaa cactgtgcta tctttatgct ggttcccct    240
agtaactgtt accaagtctg tgggcaacca atttatgaac ttatttcgca aaatgtagaa    300
tcagccccag cgtttgttaa caacggcttt caaagcaca aacgtagtag cttgcttaag    360
tatcccagaa aaggctaac gtttcacaga cagtatcttt caaagtcacg tcagtcgaaa    420
cgcaggcaaa gacttgaagc taatgtctcc agcgtgagaa ataaaaccag caataatata    480
caaagcctag ggtccgctgc tctggaaaaa cagagtagcc ccaatgcagg tttgtcagct    540
```

```
acagcaccgt ccttaaaaag gaagcttgct agggagcaac tggaagtcac ggctaagaga     600
gcaagattag aagagaaaga gagggaggaa caggcatgta atactgctcc taatgtaaac     660
cagagcattc ccaagaggta tggaaccggc tgtgtagcat cacgttctgt aagtctgact     720
aaagaaaaaa acatttctca aagaagtaac agtgatatgc ctcgtccttc tttagttcac     780
aattctcatc gcgggaagaa gtctgtggca gacaaaagct ctttcctgca aggagctgag     840
agtaacagac atttaaagcc cagcattgaa atgcaagcag gatccagcag gaagggagtg     900
gagacacgca ggcctatacc tcggttggat tgggtaccaa tcgaaccggc ggaaagtagt     960
tcttcaggac acaaaagca ggaaggtccc ctagctcatc tggcagagga ggtaccaaat    1020
aggttttgc catctacaat atacattgac aggaagtttc tgtattctcg cagatactgg    1080
ggggagcgtt tcccgaaatc cttcctattg aatcgcctga agggtagcca ggcaggtgta    1140
aagcggctaa tagaaacgat attcttaagc caaaatccgt ttgggcaaaa gtgcaaccaa    1200
ggtctgccac agaaaaaacg gagaaagaag aagcttccca aacgcttctg agaatgaga    1260
agtatatttc aacaactctt aaagaatcat ggaaagttcc cttacgtagc tttcctgaga    1320
caaaattgcc ctcttcggat atctgacacc attttgggaa aagccaagct gctcagtcgg    1380
gcacctttgc ctgggcaagc agaggctcgc aagcaagcag aacagcttgg gaaggagcct    1440
gctgagcgtg tggcaagcag cagatgtgaa tctggtcaca ccaacgtgcc cagcagcgta    1500
cgcgctcctc tcgcagcatc tgcgtgtggg gagccggggg gtgaggagca gatccctgca    1560
gaggcgtctg attcagtcct cagggagctt ctcaaggagc actgcagcca cttccaggtg    1620
tacctctttg tgagggagtg cgtggagagg gtgatcccca ccgagctctg gggttcaaac    1680
cataacaagc gccggttctt caagaacgtg aaagcgttca tttccatggg gaagtacgct    1740
aagctttcct tgcaggtgtt gatgtggaag atgagagtaa atgactgcat gtggcttcgt    1800
ctggccaaag gtaatcactc tgttcctgcc tctgaaccacc tttaccgtga agaaattttg    1860
gctaaattcc tatactggct gatggatacg tatgttgttc agttgctcag atcatttttc    1920
tatgtcaccg agaccatgtt ccagaaaaac atgctcttct actaccgaaa gtgtatttgg    1980
ggcaagttac aggacattgg aattagaaag cattttccca aagtgaagct acgtccttta    2040
actgcagagg agatgaagc gatccatcaa aaaaaataacc ttcctatgcc gtcaaagctc    2100
cgtttcattc ccaaagtcac tggactaaga cccatcgtca gaatgagcgg tgttgttgaa    2160
gcacaaaacgt tgagcaagga aagcagagca agaaggccg atgtgtccag ggcttttgat    2220
agcattcctc acaataaact tgtggaagtg atttcacagg tcttaaaacc cgagaaaaaa    2280
actgtctact gcatacgcg ctatgcagtg gttatgatca ctggaagtgg aaaaaccagg    2340
aagttatata agagacatgt ttctactttc aaggatttta tgccagacat gaagcagttt    2400
gtgtcccggc ttcatgagag taccttcattg cgagatgcaa taatagttga acagagccta    2460
actttcaatg agacaagtgc cagtctattt aattttttttc ttcaaatgct aaataataac    2520
atcctggaaa ttgagcgcag ttactactta cagtgctctg gaattccaca gggctccctt    2580
ttgtcaacct tgctttgcag cttgtgctat ggagacatgg aaaacaaatt attcagtggg    2640
gtacagaagg atggagtcct gatccgtctc attgatgact ttttgctggt tacaccacat    2700
ttaatgcatg caagaacttt tctaaggact ctagcaatgg gcattcctga gtatggcttt    2760
ttgataaacc ccaaaaagac agtggtgaat ttttctgctg acgatatccc agaatgttct    2820
gaatttaaac agctgccaaa ctgtcgtttg atcccatggt gtggcttatt attggataca    2880
cagacacttg aggtttactg cgattactcc agctattcct gtacttctat cagatcaagt    2940
cttttccttca attcaaacag aacagctggg aaaaacatga acacaaatt gcttgcagtc    3000
cttaaactga aatgccatgg cttgtttctc gatttacaga tcaatagcct taaaacagtt    3060
ttcattaacg tctacaagat attttttactt caggcttaca ggttccatgc ctgtgttatt    3120
caacttccat tcaaccagaa agttaggaac aatcctgatt tcttcctcag agtcatcgct    3180
gagaatgcat cgtgctgcta ttctatgcta aaagctaaaa atccagggtt tactttaggt    3240
aacagaggtg catctggcat gtttccttct gaggcagcag agtggctctg ctatcatgcc    3300
ttcactgtca aactgtcaaa ccacaaagtt gtttacaaat gcttgctgaa gccccctgaag    3360
ttctgtatga tgcagctatt ccggaagatc ccaaaggata ctaaggcact actgaagaca    3420
gtgacagaac catctatttg taaagatttc aaatctatcc tggactga                 3468

SEQ ID NO: 48          moltype = AA  length = 1125
FEATURE                Location/Qualifiers
source                 1..1125
                       mol_type = protein
                       organism = Bos taurus
SEQUENCE: 48
MPRAPRCRAV RALLRASYRQ VLPLAAFVRR LRPQGHRLVR RGDPAAFRAL VAQCLVCPPW      60
DAQPPPAAPS FRQVSCLKEL VARVVQRLCE RGARNVLAFG FTLLAGARGG PPVAFTTSVR     120
SYLPNTVTDT LRGSGAWGLL LHRVGDDVLT HLLSRCALYL LVPPTCAYQV CGPPLYDLRA     180
AAAAARRPTR QVGGTRAGFG LPRPASSNGG HGEAEGLLEA RAQGARRRRS SARGRLPPAK     240
RPRRGLEPGR DLEGQVARSP PRVVTPTRDA AEAKSRKGDV PGPCRLFPGG ERGVGSASWR     300
LSPSEGEPGA GACAETKRFL YCSGGEQLR RSFLLCSLPP SLAGARTLVE TIFLDSKPGP      360
PGAPRRPRRL PARYWQMRPL FRKLLGNHAR SPYGALLRAH CPLPASAPRA GPDHQKCPGV     420
GGCPSERPAA APEGEANSGR LVQLLRQHSS PWQVYGLLRA CLRRLVPAGL WGSRHNERRF     480
LRNVKKLLSL GKHGRLSQQE LTWKMKVQDC AWLRASPGAR CVPAAEHRQR EAVLGRFLHW     540
LMGAYVVELL RSFFYVTETT FQKNRLFFFR KRIWSQLQRL GVRQHLDRVR LRELSEAEVR     600
QHQEARPALL TSRLRFVPKP GGLRPIVNVG CVEGAPAPPR DKKVQHLSSR VKTLFAVLNY     660
ERARRPGLLG ASVLGMDDIH RAWRAFVLPL RARGPAPPLY FVKVDVVGAY DALPQDKLAE     720
VIANVLQPQE NTYCVRHCAM VRTARGRMRK SFKRHVSTFS DFQPYLRQLV EHLQAMGSLR     780
DAVVIEQSCS LNEPGSSLFN LFLHLVRSHV IRIGGRSYIQ CQGIPQGSIL STLLCSFCYG     840
DMENKLFPGV QQDGVLLRLV DDFLLVTPHL TRARDFLRTL VRGVPEYGCQ VNLRKTVVNF     900
PVEPGALGGA APLQLPAHCL FPWCGLLLDT RTLEVHGDHS SYARTSIRAS LTFTQGFKPG     960
RNMRRKLLAV LQLKCHGLFL DLQVNSLQTV FTNVYKIFLL QAYRFHACVL QLPFSQPVRS    1020
SPAFFLQVIA DTASRGYALL KARNAGASLG ARGAAGLFPS EAAQWLCLHA FLLKLARHRV    1080
TYSRLLGALR TARARLHRQL PGPTRAALEA AADPALTADF KTILD                   1125

SEQ ID NO: 49          moltype = AA  length = 1131
FEATURE                Location/Qualifiers
source                 1..1131
```

```
                        mol_type = protein
                        organism = Sus scrofa
SEQUENCE: 49
MPRAPRCRAV  RSLLRDRYRQ  VLPLATFVRR  LGPEGRRLVR  RGDPAAYRAL  VAQCLVCVPW   60
DAQPPPASPS  FRQVSCLKEL  VARVVQRLCE  RGARNVLAFG  FALLDGARGG  PPVAFTTSVR  120
SYLPNTVTDT  LRGSGAWGLL  LRRVGDDVLT  HLLARCALYL  LVPPSCAYQV  CGPPLYDLYT  180
AAEARPMRHK  GQTPTGLGLT  RPVCNGEAGR  PQEQRAQGVR  RRRGRAGGHP  LPAKRPRHVP  240
EPEQGPEGQA  SRAHQGRAPG  PSDSDPPVMT  PTRAAAKAKS  REGEAPGTRH  LSPQAGGARG  300
TCPPSWWQPH  LQGKPSPHVC  AAETKRFLYC  SGSKEGLRRS  FLLCSLPPSL  AGAGRLVEVI  360
FLASKPGQPG  ARRVPARYWR  MRPLFRELLK  NHARCPYKAL  LRAHCPLRAA  ATLSGSGGQV  420
CDHKVGPLAP  ERLAAAAEGD  SASRRLVQLL  RQHSSPWQVY  RLLRACLHRL  VPPGLWGSPH  480
NKRRFLKNVK  KLVSLGKHAR  LSLQELMWKM  KVQDCIWLRR  SPDARHVQAA  EHRLREAILA  540
KFLRWLMGTY  VVELLRSFFY  VTETTFQKNR  LFFFRKRIWS  RLQSAGIRQH  LDRVRLRELS  600
EAEIRRRREA  RPAVLTSKLR  FVPKPDGLRP  IVNMANVVRA  RTGPGDKKVR  RLTGQVKTLF  660
AVLNYERARR  PRLLGASVLG  VGDIHRAWRA  FVLPLRAQDP  APPLYFVKVD  VTGAYDALPQ  720
DRLLEVVANV  IRPHESTYCV  RQCAVLRRTA  RGHVRKSFQT  HVSTFADLQP  YMRQFVAHLQ  780
ATGPLRDAVV  IEQSCSLNEA  GSRLLELFLS  LLRNHVIRIG  GRSYVQCQGI  PQGSILSTLL  840
CSLCYGDMEN  RLFPGIQRDG  VLLRLVDDFL  LVTPHLTRAK  AFLRTLVRGV  PEYGCLANLR  900
KTAVNFPVED  GARGGPAPLQ  LPAHCLFPWC  GLLLDTRTLE  VHCDYASYAR  TSIRASLTFN  960
QGFKPGRNMR  RKLLAVLRLK  CHGILLDLQV  NSLPTVLANV  YKIFLLQAYR  FHACVLQPLF  1020
RQPLARNPSF  FLRLVSDTAS  CCYSLLKARN  AGMSLGARGA  SGPFPSEAAE  WLCLHAFLLK  1080
LVRHRVTYSC  LLGPLRAARE  RLCQRLPGAT  LAALEAAADP  ALTTDFRTIL  D           1131

SEQ ID NO: 50           moltype = AA  length = 1098
FEATURE                 Location/Qualifiers
source                  1..1098
                        mol_type = protein
                        organism = Danio rerio
SEQUENCE: 50
MSGQYSTDGG  FRPVLEILRS  LYPVVQTLEE  FTDGLQFPDG  RKPVLLEETD  GARFKKLLSG   60
LIVCAYTPPQ  LRVPAQLSTL  PEVLAFTLNH  IKRKKLRNVL  GFGYQCSDVT  TSSDPFRFHG  120
DVSQTAASIS  TSEVWKRINQ  RLGTEVTRYL  LQDCAVFTTV  PPSCVLQVCG  EPVYDLLMPR  180
SWSGFFLSNS  DNERISGAMR  KFPAVQKTVA  ISKKRTRDNE  KYISVKRRRV  KETVNNNNGN  240
YRSLCFAISK  KRAIDNEENI  SLKRRRMEET  DQVAKIRNEN  HESQSFAISK  KRARDNEENI  300
SLKRQRMEEI  DQVAKIRNEN  HGSQSWKPAD  QRPPRPSQCS  IRVLSMLYNG  RGMKNFLLNR  360
KLKGVGGARR  MQGEDLVRMI  FLQSESNDSK  PKKLPKRFFA  MVPLFSRLLR  QHRKCPYRLF  420
LQRKCAGNPD  VKDMESLLKS  HSSPYRVYLF  VRECLRHIIP  HELWGCQENQ  LHFLSNVKNF  480
LLLGKFERLT  LVQLMWRMKV  QACHWLGPKK  RQCASEHRYR  EWMLGQCMGW  MLSGFVVGLV  540
RAQFYITESM  GHKHTLRFYR  GDVWSRLQDQ  AFRAHLCKGQ  WRPLSPSQAL  KVPNSAVTSR  600
IRFIPKTSSM  RPITRLSGSR  DTLQYFQSCV  RVLQNVLSVC  VREAPGPMGS  TVWGWQDIHR  660
RLQDFSPQQK  SSPRPLYFVK  VDVSGAYDSL  PHLKLVEVLK  EVLGPFAEQS  FFLRQYSSVW  720
SDPTRGLRKR  FCTKAEMSEP  LNMKGFVVDE  QVSGRLHDAI  LVERHSSEVR  GGDVFQFFQK  780
MLCSYVIHYD  QQMFRQVCGI  PQGSSVSSLL  CNLCYGHMEK  ALLKDIAKGG  CLMRLIDDFL  840
LITPHLSKAT  EFLTTLLSGV  PDYGCQINPQ  KVAVNFPVCV  SWVNSGVSVL  PSSCLFPWCG  900
LMIHTHTLDV  YKDYSRYDGL  SLRYSLTLGS  AHSPSTVMKK  LLSVLSIKST  DIFLDLRLNS  960
VEAVYRSLYK  LILLQALRFH  ACVRSLPLGQ  SVNRNPSFFL  KMIWRMTRVT  NKLLTHINKG  1020
LPVCSVDSGG  VLQSEAVQLL  FCLAFETLFR  RFRSVYHCLI  PALHKRKRAL  QRELCGITLA  1080
RVRQASSPRI  PLDFSMRV                                                  1098

SEQ ID NO: 51           moltype = AA  length = 1121
FEATURE                 Location/Qualifiers
source                  1..1121
                        mol_type = protein
                        organism = Oreochromis niloticus
SEQUENCE: 51
MTRALKRSNI  AKSQCKVANL  RPSAPNTVGM  SATDMSGVLD  ILRLLYRHTQ  TLEEFSDSIV   60
FREGQKAALI  EQTDTNRFKS  FVRSVFVCFD  KELQQVASCK  QICSLPELLA  FVLNTLKRKR  120
KRNVLAHGYN  FQTLAQEDRD  ADFLKFQGDV  TQSAAYIHGS  DLWKKVTMRL  GTDITQYLLE  180
SCSVFVAVPP  SCVFQVCGPP  VYDRVSMTMA  SSGFFLQPGV  RKHNRTKIES  CRGSVSLKQK  240
RTVVNPAASK  KMKRRNKGGK  KGKRKRETGE  EEEVAVCSRK  RRRVASIEHQ  QAIQPVGSEK  300
EGQVVPVESA  PPAAFKQPVE  MPTLEGGPSW  RSGIFPPLPP  SQCFIRTLGF  LYGGRGMRGF  360
LLNRRKKTAH  GSRRLQGQDL  VRIVFFEGLA  YLNGVERKPK  KLPQRFFGMV  PLFRQLLQQH  420
RSCSYTKILQ  RLCPSIEESN  AGQGELNSLL  PQHCAPHRVY  LFVRECLSSV  IPQELWGSDQ  480
NRLHFFARVR  TFLRSGKFER  LSLAELMWKI  KVNDCDWLKR  SKTGCFPPSE  LAYRTQVLGQ  540
FLAWLLDGYV  TGLVRACFYA  TESIGQKNAI  RFYRQEVWAK  LQDLAFRGHL  SKGQMEELTP  600
AQVASLPKGT  VISRLRFIPK  TDGMRPITRV  IGADAKTRLY  RGRVRDLLDM  LRACVRATPS  660
LLGSTVWGMT  DIHKVLCSLA  PAQKEKPQPL  YFVKVDVSGA  YESLPHDKLI  EVIGQALSPV  720
HDELFTIRRY  AKIWADSHEG  LKKAFVRQAD  FLEDNMGSTN  MKGFLTSLQR  KGKVHHAILV  780
EQHFCSDLHG  REALQFFTQM  LTGSVVQYGK  KTYRQCRGIP  QGSVVSSLLC  CLCYGHMENL  840
LFKDIPGHKG  CLMRLVDDFL  LITPDQHEAQ  AFLKILLAGV  PQYGLAVNPQ  KVVLNFQVSG  900
SVASCPDIRI  LPPHCLFPWC  GLLLDTHKLD  VYKDYSSYAG  LSLRYSLTLG  SSHSAGQQMK  960
RKLMAILRLK  CHALFFDLKT  NSLEAVYKNI  YKLVLLHACR  FHVCAQSLPF  GQTVSKNPVF  1020
FLQLIWEMAQ  YCNKLIRRSN  KGLILGDKAQ  TGIVQYEAVE  LLFCLCFLLV  LSQHRLLYKD  1080
LLAAHLHKRK  SLERRLGDLR  LARVRQAASP  RTPVDFLAIQ  T                      1121

SEQ ID NO: 52           moltype = AA  length = 1182
FEATURE                 Location/Qualifiers
source                  1..1182
                        mol_type = protein
```

```
                        organism = Oncorhynchus mykiss
SEQUENCE: 52
MPSGDMTRVL GILGSLYRHV ETLEEFADHI VFREGQRAVL IEPTDTTRFI SFVRGVLVCT    60
DKTLQDVPSC NQISTVPELL AFVLNNIKRK KKRNVLAHGY GYTFQDRDAD QFKFHGEITQ   120
SAMYIHCSDL WKRACQRLGT DISKYLLESC SLFVTVPPSS AFQVCGVPVY DRVSMSTGIS   180
RFHLGYKRNG TTRNSRGRSK EVRNGGWEFQ GSAGRNRRKD GGRDTGKRKG DEVSLGGKRK   240
REREEVEGDV CLPGKRRCTQ REAPTVSSGT SDRKHRTLET NGVKRPVEVI SLTKGPTQSL   300
QVFNGSSNVE QVSAEMERLR KPVEKLAGPG RPLEAVMVTI APAESSKQVS NGTGNIEQMS   360
MKTGHRRPAA VVPRPVEEQS GPVSATVHVE GGPSWRTGSF PPLPHSQCFI RTLGMLYGGR   420
GMRRFLLNRK RKSRDEGPRR LQGRDLVRLV FFEGVAYLNG TERKPERLPR RFFTLVPLFC   480
QLLRRHRRCP YSKILQRVCP AVGQGDMASL LPQHSAPHRV YLFVRECLNA VVPSEFWGSD   540
HNRFKFLSAV RNFLSMGKFE RMSLAELMWK MKVNDCDWLK ISKTGRCPPS ELSYRTRVLG   600
QLLAWLLDGY VLGLVRAMFY VTESMGQKNA LRFYRYQVWA KLQELAFSGH LSKGQMSELT   660
LAQVTSLPKT TVPSRLRFIP KTEGMRPITR VIGADAKTRL FQTRVKELLD VLGVCVRSSP   720
SLLGSTVWGL TDIHRVLSSI TPAQKDKPQR LYFVKVDVSG AYDSLPHTQL LEVIGQVLSH   780
VQQELFSVRR YAKVWADTHE GLKKTFVRQA DFTEDTVSST NMKGFVMSLQ REGKVHDAIL   840
VEQHFSTDIH GKDVLEFFTQ MLSSCVVQFG KKSFRQCQGI PQGSAVSSLL CCLCYGHMEN   900
LLFPNVSRRG GCLMRLVDDF LLITPDLSQA QTFLKTLMAG VPRYGCVVNP QKVAVNFPLG   960
EWGSCPAGVR LLPLHCLFPW CGLLLNTHTL DVHNNYASYA GLSLRYSLTL GSAHCAGQQM  1020
KRKLMSILRF KCHALFLDLK TNSLEAVYSN VYKLVLLQAF RFHACAQSLP FGQKVGGNHS  1080
YFLNLIWDLA EYTNHLVRLC NKGVSLGCKA LTGSLQYEAV ELIYCLAFLL VLSRHRPLYY  1140
HLLAPLRTRK RLEGKLEGL RLARIRQAAT PKMPEDFKAI QA                     1182

SEQ ID NO: 53           moltype = AA  length = 1214
FEATURE                 Location/Qualifiers
source                  1..1214
                        mol_type = protein
                        organism = Xenopus tropicalis
SEQUENCE: 53
MTLCTGGAEL LSILHSLYGQ VLGIVEYIDS LHVPGGIKVP VLREGDPEKF KSFVAELMLC    60
IPRGTKSLPS PVSFLQLSTQ REVVARVIQR ICEKKRKNVL AFGYGLVDEK SSLNIRLTPN   120
ICSYFPNSTT TTISTSILWE TLLTRVGDDV MMYWLEQCSV FVFVPPSCCY QISGQPIYTL   180
PYDSMCSFRS QSFMHSNVLL QYIKRNAFFL RKKYLKPKKW WKTVLNSKVE KHSKTSQMLT   240
WQNKKSTSAL PICSESSMKV TTKIHSKRKM CTTDICDIPT KKRRVNLDKD DKMDHVSFTS   300
ACLSSFSNVC PEAKVQATEF ITSRYGKKTK IQCPKSTSYS VDGEFNVTLQ NNANTFITNA   360
SVPTIQSKTS FSNIFIEIGR TLYSSISFKK GFSESFILNS LDCTPSGSQK LVETIFLNNF   420
LTEQNFDQPK RDENFRSKLP KRYWRMRKYF QELIQNHKNF PYLVYLNKHC PVRPSMACSH   480
KLALQKKNKC KMDKSICDLS NTSVMKNKIV NDEKPLKHVT AEATFLPLLK QHSSSWQVYM   540
FVRECLNSLV PDFIWGSSHN KCRFLRNVKS FLFFSGKFGK VSLLELMWKM KVEDCSWIRL   600
RKSDHFVPAS EHLLRERILA KFIFWLMDTY VIQLLKSFFF VTETMFQKNR LLFYRKRIWK   660
KLQNLGLRKH LEKVKLRPLS CDELEKMQQW KNIPLVSRLR FIPKTNGLRP ISRVSSTLGS   720
QQSKENQEKK IQHFTSRVRN LFSVLNYEWN RNCSLIGSSV FGMDDIYKQW KKFVLDFEKS   780
RAEKGKFYFV KTDVKGAYDT IPHSKLDEVI LKVINPNANE VYCIRRYASV SVDSTGRIIK   840
SFKRHVSALA DVLPNMKQFV SNQQEKNLTR NTILVEQSLL LNESSVKLLA VFQQMIRSHI   900
LRIEDRYYMQ CCGIPQGSML STILCSLCYG DMENKLFGGI QQNGVLMRLI DDFLFVTPHL   960
NQAKTFLRTL AEGIPQYGCS ISPQKTVVNF PVDDIPACSE VEQLPVHCLF RWCGLLLDTQ  1020
TLDVVYDYSS YACTSIRSSM TFCHSSAAGK NMKQKLLRVL KLKCHSLFLD LQVNSLRTVF  1080
INTYKIFLLQ AYRFHACVVQ LPFGQRVMNN PPFFLTVISD MAPCFYTTFK SKNKDVTRGY  1140
KDVSCQFNFE AVQWLSYQAF LTKLRNHKIL YKCLIGPLQN CKMQLSRRLS QYTIDLLKAV  1200
TDSSLHKDFS CIMD                                                   1214

SEQ ID NO: 54           moltype = AA  length = 1346
FEATURE                 Location/Qualifiers
source                  1..1346
                        mol_type = protein
                        organism = Gallus gallus
SEQUENCE: 54
MERGAQPGVG VRRLRNVARE EPFAAVLGAL RGCYAEATPL EAFVRRLQEG GTGEVEVLRG    60
DDAQCYRTFV SQCVVCVPRG ARAIPRPICF QQLSSQSEVI TRIVQRLCEK KKKNILAYGI   120
SLLDENSCHF RVLPSSCIYS YLSNTVTETI RISGLWEILL SRIGDDVMMY LLEHCALFML   180
VPPSNCYQVC GQPIYELISR NVGPSPGFVR RRYSRFKHNS LLDYVRKRLV PHRHYLSKSQ   240
WWKCRPRRRG RVSSRRKRRS HRIQSLRSGY QPSAKVNFQA GRQISTVTAR LEKQSCSSLC   300
LPARAPSLKR KRDGEQVEIT AKRVKVMEKE IEEQACSIVP DVNQSSSQRH GTSWHVAPRA   360
VGLIKEHYIS ERSNSEMSGP SVVRRSHPGK RPVADKSSFP QGVGNKRIK TGAEKRAESN   420
RRGIEMYINP IHKPNRRGIE RRINPTHKPE LNSVQTEPME GASSGDRKQE NPPAHLAKQL   480
PNTLSRSTVY FEKKFLLYSR SYQEYFPKSF ILSRLQGCQA GGRRLIETIF LSQNPLKEQQ   540
NQSLPQQKWR KKRLPKRYWQ MREIFQKLVK NHEKCPYLVF LRKNCPVLLS EACLKKTELT   600
LQAALPGEAK VHKHTEHGKE STEGTAPNSF LAPPSVLACG QPERGEQHPA EGSDPLLREL   660
LRQHSSHWQV YGFVRECLER VIPAELWGSS HNKCRFFKNV KAFISMGKYA KLSLQQLMWK   720
MRVNDCVWLR LAKGNHSVPA YEHCYREEIL AKFLYWLMDS YVIELLKSFF YITETMFQKN   780
MLFYRKFIW GKLQNIGIRD HFAKVHLRAL SSEEMEVIRQ KKYFPIASRL RFIPKMNGLR   840
PVVRLSVVE GQKLSKESRE KKIQRYNTQL KNLFSVLNYE RTVNTSIIGS SVFGRDDIYR   900
KWKEFVTKVF ESGGEMPHFY FVKGDVSRAF DTIPHKKLVE VISQVLKPES QTVYGIRWYA   960
VIMITPTGKA RKLYKRHVST FEDFIPDMKQ FVSKLQERTS LRNAIVVEQC LTFNENSSTL  1020
FTFFLQMLHN NILEIGHRYY IQCSGIPQGS ILSTLLCSLC YGDMENKLLC GIQKDGVLIR  1080
LIDDFLLVTP HLMQARTFLR TIAAGIPEYG FLINAKKTVV NFPVDDIPGC SKFKHLPDCR  1140
LISWCGLLLD VQTLEVYCDY SSYAFTSIRS SLSFNSSRIA GKNMKCKLTA VLKLKCHPLL  1200
LDLKINSLQT VLINIYKIFL LQAYRFHACV LQLPFNQKVR NNPDFFLRII SDTASCCYFI  1260
LKAKNPGVSL GSKDASGMFP FEAAEWLCYH AFIVKLSNHK VIYKCLLKPL KVYKMHLFGK  1320
```

-continued

```
IPRDTMELLK TVTEPSLCQD FKTILD                                           1346

SEQ ID NO: 55              moltype = AA  length = 1267
FEATURE                    Location/Qualifiers
source                     1..1267
                           mol_type = protein
                           organism = Meleagris gallopavo
SEQUENCE: 55
MSGARGLVWC DERAWLLSSQ SEVITRIVQR LCEKKKKNIL AYGYSLLDEN SCHFRILPSS        60
CIYSYLPNTV TETIRISGLW EILLSRIGDD VMMYLLEHCA LFMLVPPSNC YQVCGQPIYE       120
LISRNIGPSP GFVRRRYSRF KHNNLLNYVR KRLVFHRHYL SKSQWWKCGP RRQGRVSSRR       180
KRRTHRIQSP RSGYQSSAKV NFQAGMRIST VTAHLEKQNC SSLCLPARTP SLKRKRDGEQ       240
VETTAKRVKV MEREEQACSI VPDVNRSSSR RHGVWHVAPR AVGLIKERYV SERSYSEMSG       300
PSVVHRSHPG KRPVADKSSF PRGVQGNKHI KTGAEKRAES NKRGIEMYIN PICKPNRRGI       360
ERHINPTHKP GLNSVQTEPM ESASSGDRKQ ENPPAHLAKQ LPNTFLRSAV YFEKKFLLYS       420
RSYQEYFPKS FILSRLQGCQ AGGRQLIETI FLSQNPLKEK QNQSLKQQKW RKKRLPKRYW       480
QMREIFQKLL KNHEKCPYLV FLRKNCPVLL SEACLKKKTEL TLQAALPGEA KVHKHTEHGE       540
ETTEGTAPNS FYTPPSMPLC GQTEREEQHL AEGSDPLLRE LLRQHSSHWQ VYGFVRECLE       600
RVIPAELWGS SHNKCRFFKN VKAFISMGKY AKLSLQQLMW KMRVNDCVWL RLAKGNHSVP       660
AYEHCYREEI LAKFLYWLMD SYVIELLKSF FYITETMFQK NMLFYYRKFI WGKLQNIGIR       720
NHFAKVHLRA LSSEEMEVIH QKKYFPIASR LRFIPKINGL RPVVRLSRVV EGQKLSKESR       780
EKKIQRYNTQ LKNLFSVLNY ERTVNTSIIG SSVFGRDDIY RKWKEFVTKV FESGGEMPHF       840
YFVKGDVSRA FDTIPHKKLV EVISQVLKPE SQTVYGIRWY AVIMITPTGK ARKLYKRHVS       900
TFEDFIPDMK QFVSKLQERT SLRNAIVVEQ CLTFNENSST LFTFFLQMLH NNILEIGHRY       960
YIQCSGIPQG SILSTLLCSL CYGDMENKLL CGIQKDGILI RLIDDFLLVT PHLMQAKTFL      1020
RTIAAGIPEY GFLINAKKTV VNFPVDDIPG CSKFKQLPDC RLISWCGLLL DMQTLEVYCD      1080
YSSYAFTSIR SSLSFNSSRI AGKNMKCKLT AVLKLKCHPL FLDLKINSLK TVLINIYKIF      1140
LLQAYRFHAC VLQLPFNQKV RNNPYFFVRI ISDTASCCYF ILKAKNPGVC LGCKDASGMF      1200
PFEAAEWLCY HAFIVKLSNH KVIYKCLLKP LKVYKMHLFG KIPRDTMVLL KTVTEPSLCQ      1260
DFKTILD                                                               1267

SEQ ID NO: 56              moltype = AA  length = 1155
FEATURE                    Location/Qualifiers
source                     1..1155
                           mol_type = protein
                           organism = Anas platyrhynchos
SEQUENCE: 56
MQRLCGKKKK NILTYGYSLL DENSSHFQIM PLSNVYSYLP NTATETMRIS GLWETLLSRI        60
GDDVMMYLLE HCAIFMLVPP SNCYQVCGQP IYELISQNVE SAPAFVKQRL SKHKRSSLLK       120
YTQKRLTFHR QYLSKSRQSK RRQRLEANVS SVRNKTSNNI QSLGSAALEK QSSSNAGLSA       180
TAPSLKRKLA REQLEVTAKR ARLEEKEREE QACNTAPNVN QSIPKRYGTG CVASRSVSLT       240
KEKNISQRSN SDMPRPSLVH NSHRGKKSVA DKSSFLQGAE SNRHLKPSIE MQAGSSRKGV       300
ETRRPIPRLD WVPIEPAESS SSGHKKQEGP LAHLAEEVPN RVLPSTIYID RKFLYSRRYW       360
GERFPKSFLL NRLKGSQAGV KRLIETIFLS QNPFGQKCNQ GLPQKKRRKK KLPKRFWRMR       420
SIFQQLLKNH GKFPYVAFLR QNCPLRISDT ILGKAKLLSR APLPGQAEAR KQAEQLGKEP       480
AERVASSRCE SGHTNVPSSV RAPLAASACG EPGGEEQIPA EASDSVLREL LKEHCSHFQV       540
YLFVRECVER VIPTELWGSN HNKRRFFKNV KAFISMGKYA KLSLQVLMWK MRVNDCMWLR       600
LAKGNHFVPA SEHLYREEIL AKFLYWLMDT YVVQLLRSFF YVTETMFQKN MLFYYRKCIW       660
GKLQDIGIRK HFSKVKLRPL TAEEMEAIHQ KKYLPMASKL RFIPKVTGLR PIVRMSGVVE       720
AQTLSKESRA KKADVSRAFD SIPHNKLVEV ISQVLKPEKK TVYCIRRYAV VMITGSGKTR       780
KLYKRHVSTF KDFMPDMKQF VSRLHESTSL RDAIIVEQSL FNFETSASLF NFFLQMLNNN       840
ILEIERSYYL QCSGIPQGSL LSTLLCSLCY GDMENKLFSG VQKDGVLIRL IDDFLLVTPH       900
LMHARTFLRT LAMGIPEYGF LINPKKTVVN FSADDIPECS EFKQLPNCRL IPWCGLLLDT       960
QTLEVYCDYS SYSCTSIRSS LSFNSNRTAG KNMKHKLLAV LKLKCHGLFL DLQINSLKTV      1020
FINVYKIFLL QAYRFHACVI QLPFNQKVRN NPDFFLRVIA ENASCCYSML KAKNPGFTLG      1080
NRGASGMFPS EAAAEWLCYHA FTVKLSNHKV VYKCLLKPLK FCMMQLFRKI PKDTKALLKT      1140
VTEPSICKDF KSILD                                                       1155

SEQ ID NO: 57              moltype = AA  length = 8
FEATURE                    Location/Qualifiers
REGION                     1..8
                           note = synthetic sequence
source                     1..8
                           mol_type = protein
                           organism = synthetic construct
SEQUENCE: 57
DYKDDDDK                                                                  8

SEQ ID NO: 58              moltype = AA  length = 4
FEATURE                    Location/Qualifiers
REGION                     1..4
                           note = Synthetic sequence
source                     1..4
                           mol_type = protein
                           organism = synthetic construct
SEQUENCE: 58
KDYK                                                                      4
```

What is claimed is:

1. A method for manufacturing an edible metazoan biomass comprising cells having myogenic or fibroblastic capacity, the method comprising:
a) obtaining the cells from a master cell bank, wherein the cells are suspended in a cryopreservation media in a cryovial, and further wherein the cells:
are capable of renewal,
overexpress a Glutamine Synthase (GS) gene, an Insulin-like Growth Factor (IGF) gene, an albumin gene, or a combination thereof,
overexpress one or more myogenic transcription factors, and
are from a livestock, poultry, or game animal species;
b) removing the cryopreservation media;
c) suspending the cells in a cell culture media;
d) culturing the cells on a cultivation substrate in the cell culture media;
e) permitting cells to proliferate until the cells reach confluence;
f) inducing the cells to at least partially differentiate into myocytes and multinucleated myotubes using a differentiation medium;
g) forming the myocytes and multinucleated myotubes into skeletal muscle fibers; and
h) processing the skeletal muscle fibers to form the edible metazoan biomass.

2. The method of claim 1, wherein the cryovial is rapidly thawed to room temperature.

3. The method of claim 1, wherein the cryopreservation media is removed from the cryovial using 300×g centrifugation for 5 minutes.

4. The method of claim 1, wherein the cultivation substrate is gelatin-coated.

5. The method of claim 1, wherein inducing the at least partial differentiation comprises at least partially differentiating the cells for up to 6 days.

6. The method of claim 1, wherein the one or more myogenic transcription factors are selected from MYOD1, MYOG, MYF5, MYF6, PAX3, and PAX7.

7. The method of claim 1, wherein the cells are derived from a duck.

8. A method for manufacturing an edible metazoan biomass comprising cells having myogenic or fibroblastic capacity, the method comprising:
a) obtaining the cells suspended in a cryopreservation medium, wherein the cells:
are capable of renewal,
overexpress a Glutamine Synthase (GS) gene, an Insulin-like Growth Factor (IGF) gene, an albumin gene, or a combination thereof,
overexpress one or more myogenic transcription factors, and
are from a livestock, poultry, or game animal species;
b) removing the cryopreservation media and collecting the cells;
c) adding growth media to the cells;
d) culturing the cells in adherent culture for a growth period;
e) inducing the cells to at least partially differentiate into skeletal muscle cells using a differentiation medium; and
f) harvesting the skeletal muscle cells after the growth period to form the edible metazoan biomass.

9. The method of claim 8, wherein the cells comprise anchorage-dependent cells and are grown on a substrate.

10. The method of claim 8, wherein differentiation comprises at least partially differentiating the cells for up to 6 days.

11. The method of claim 8, wherein the one or more myogenic transcription factors are selected from MYOD1, MYOG, MYF5, MYF6, PAX3, and PAX7.

12. The method of claim 8, wherein the cells are derived from a duck.

13. A method for manufacturing an edible metazoan biomass comprising stem cells, the method comprising:
a) obtaining the stem cells that are suspended in a cryopreservation media,
wherein the cells:
are capable of renewal,
overexpress a Glutamine Synthase (GS) gene, an Insulin-like Growth Factor (IGF) gene, an albumin gene, or a combination thereof,
overexpress one or more myogenic transcription factors, and
are from a livestock, poultry, or game animal species; and
b) removing the cryopreservation media and collecting the stem cells;
c) adding growth media to the stem cells;
d) culturing the stem cells in adherent culture after a growth period;
e) inducing the stem cells to at least partially differentiate into myocytes and multinucleated myotubes using a differentiation medium;
f) forming the myocytes and multinucleated myotubes into skeletal muscle fibers; and
g) processing the skeletal muscle fibers after the growth period to form the edible metazoan biomass.

14. The method of claim 13, wherein the stem cells are mesenchymal stem cells.

15. The method of claim 13, wherein inducing the stem cells to at least partially differentiate into myocytes and multinucleated myotubes comprises at least partially differentiating the cells for up to 6 days.

16. The method of claim 13, wherein the one or more myogenic transcription factors are selected from MYOD1, MYOG, MYF5, MYF6, PAX3, and PAX7.

17. The method of claim 13, wherein the cells are derived from a poultry or a game species.

* * * * *